US010738087B2

(12) United States Patent
Vandenberghe et al.

(10) Patent No.: US 10,738,087 B2
(45) Date of Patent: Aug. 11, 2020

(54) ANCESTRAL VIRUS SEQUENCES AND USES THEREOF

(71) Applicants: Massachusetts Eye and Ear Infirmary, Boston, MA (US); Schepens Eye Research Institute, Boston, MA (US)

(72) Inventors: Luk H. Vandenberghe, Weston, MA (US); Eric Zinn, Cambridge, MA (US)

(73) Assignees: Massachusetts Eye and Ear Infirmary, Boston, MA (US); Schepens Eye Research Institute, Boston, MA (US)

( * ) Notice: Subject to any disclaimer, the term of this patent is extended or adjusted under 35 U.S.C. 154(b) by 113 days.

(21) Appl. No.: 15/748,738

(22) PCT Filed: Jul. 29, 2016

(86) PCT No.: PCT/US2016/044819
§ 371 (c)(1),
(2) Date: Jan. 30, 2018

(87) PCT Pub. No.: WO2017/019994
PCT Pub. Date: Feb. 2, 2017

(65) Prior Publication Data

US 2019/0100560 A1 Apr. 4, 2019

Related U.S. Application Data

(60) Provisional application No. 62/203,002, filed on Aug. 10, 2015, provisional application No. 62/199,059, filed on Jul. 30, 2015.

(51) Int. Cl.

| | |
|---|---|
| ***C07K 14/00*** | (2006.01) |
| ***C07K 14/005*** | (2006.01) |
| ***C07K 14/015*** | (2006.01) |
| ***C12N 15/00*** | (2006.01) |
| ***C12N 15/79*** | (2006.01) |
| ***C12N 15/86*** | (2006.01) |
| ***C12Q 1/70*** | (2006.01) |

(52) U.S. Cl.
CPC ............ *C07K 14/005* (2013.01); *C12N 15/86* (2013.01); *C12Q 1/701* (2013.01); *C12N 2750/14122* (2013.01); *C12N 2750/14143* (2013.01); *C12N 2750/14151* (2013.01)

(58) Field of Classification Search
CPC .... C07K 14/00; C07K 14/005; C07K 14/015; C12N 15/00; C12N 15/79; C12N 15/86; C12N 15/8645; C12N 2750/00; C12N 2750/14111; C12N 2750/14122; C12N 2750/14141; C12N 2750/14143
See application file for complete search history.

(56) References Cited

U.S. PATENT DOCUMENTS

| | | | |
|---|---|---|---|
| 5,037,384 | A | 8/1991 | Chang |
| 7,906,111 | B2 | 3/2011 | Wilson et al. |
| 2004/0216750 | A1 | 11/2004 | Snyder et al. |
| 2007/0028928 | A1 | 2/2007 | Peyman |

FOREIGN PATENT DOCUMENTS

| | | |
|---|---|---|
| JP | 2007-500518 | 1/2007 |
| WO | WO 2005/033321 | 4/2005 |
| WO | WO 2006/110689 | 10/2006 |
| WO | WO 2014/160092 | 10/2014 |
| WO | WO 2015/054653 | 4/2015 |

OTHER PUBLICATIONS

Vandenberghe et al, GenBank EU368925.1, 2008.*
Gao et al, GenBank AY242997; 2003.*
Extended European Search Report in Application No. 16831443.3, dated Nov. 26, 2018, 20 pages.
Santiago-Ortiz et al., "AAV ancestral reconstruction library enables selection of broadly infectious viral variants," gene Therapy, Jul. 2015, 22: 934-946.
Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).
Zinn and Vandenberghe, "Adeno-associated virus: fit to serve," Current Opinion in virology, Oct. 2014, 8: 90-97.
Zinn et al., "In Silico Reconstruction of the Viral Evolutionary Lineage Yields a Potent Gene Therapy Vector," Cell reports, Aug. 2015, 12: 1056-1068.
European Search Report in Application No. 16790158.6, dated Jan. 3, 2019, 5 pages.
Schon et al., "Retinal gene delivery by adeno-associated virus (AAV) vectors: Strategies and applications," European Journal of Pharmaceutics and Biopharmaceutics, Jan. 2015, 95: 343-352.
Adachi et al., "Molphy: Programs for Molecular Phylogenetics based on Maximum Likelihood," Tokyo Institute of Statistical Mathematics, 1996, 150 pages.
Altschul et al., "Gapped BLAST and PSI-BLAST: A new generation of protein database search programs," Nucleic Acids Res., 1997, 25:3389-3402.
Anisimova and Gascuel, "Approximate likelihood-ratio test for branches: A fast, accurate, and powerful alternative," Systematic Biology, 2006, 55:539-52.
Ausar et al., "Conformational stability and disassembly of Norwalk virus-like particles. Effect of pH and temperature," J. Biol. Chem., 2006, 281:19478-88.

(Continued)

*Primary Examiner* — Kevin K Hill
(74) *Attorney, Agent, or Firm* — Fish & Richardson P.C.

(57) ABSTRACT

Methods are described for predicting ancestral sequences for viruses or portions thereof. Also described are predicted ancestral sequences for adeno-associated virus (AAV) capsid polypeptides. The disclosure also provides methods of gene transfer and methods of vaccinating subjects by administering a target antigen operably linked to the AAV capsid polypeptides.

10 Claims, 40 Drawing Sheets

Specification includes a Sequence Listing.

(56) References Cited

OTHER PUBLICATIONS

Balazs et al., "Antibody-based protection against HIV infection by vectored immunoprophylaxis," Nature, 2012, 481:81-4.
Balazs et al., "Broad protection against influenza infection by vectored immunoprphylaxis in mice," Nat. Biotechnol., 2013, 31:647-52.
Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12.
Calcedo et al. "Worldwide Epidemiology of Neutralizing Antibodies to Adeno-Associated Viruses," J. Infect. Dis., 2009, 199:381-90.
Cao et al., "Phylogenetic relationships among eutherian orders estimated from inferred sequences of mitochondrial proteins: instability of a tree based on a single gene," J. Mol. Evol., 1994, 39:519-27.
Darriba et al., "ProTest3: Fast selection of best-fit models of protein evolution," Bioinformatics, 2011, 27(8):1164-5.
Deal et al., "Vectored antibody gene delivery protects against plasmodium falciparum sporozoite challenge in mice," PNAS USA, 2014, 111:12528-32.
Edgar, "MUSCLE: A multipole swquence alignment method with reduced time and space complexity," BMC Bioinform., 2004, 5:113.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Gao et al., "Adeno-associated viruses undergo substantial evolution in primates during natural infections," PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus-2]," Feb. 24, 1998, 1 page.
GenBank Accession No. AAD13756.1, "capsid protein [Adeno-associated virus-5]," Feb. 10, 1999, 1 page.
GenBank Accession No. AAD27757.1, "capsid protein [Adeno-associated virus-1]," Apr. 27, 1999, 1 page.
GenBank Accession No. AAN03857.1, "capsid protein [Adeno-associated virus-8]," Sep. 2, 2002, 1 page.
GenBank Accession No. AAO88201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.
GenBank Accession No. EU368910.1, "Adeno-associated virus isolate AAV6.2 capsid protein VP1 gene, partial cds," Jul. 31, 2008, 1 page.
GenBank Accession No. EU368926, "Adeno-associated virus isolate rh32.33 capsid protein VP1 gene, partial cds," Jul. 31, 2008, 1 page.
Guindon et al., "New algorithms and methods to estimate maximum-likelihood phylogenies: assessing the performance of PhyML 3.0," System. Biol., 2010, 59:307-21.
Guindon and Gascuel, "A simple, fast, and accurate algorithm to estimate large phylogenies by maximum likelihood," Systematic Biology, 2003, 52:696-704.
Henikoff and Henikoff, "Amino acid substitution matrices from protein blocks," PNAS, 1992, 89:10915-9.
International Preliminary Report on Patentability in International Application No. PCT/US2016/031218, dated Nov. 16, 2017, 7 pages.
International Preliminary Report on Patentability in International Application No. PCT/US2016/044819, dated Feb. 8, 2018, 5 pages.
International Search Report and Written Opinion in International Application No. PCT/US2014/060163, dated Jul. 13, 2015, 19 pages.
International Search Report and Written Opinion in International Application No. PCT/US2016/031218, dated Aug. 8, 2016, 12 pages.
International Search Report and Written Opinion in International Application No. PCT/US2016/044819, dated Oct. 31, 2016, 5 pages.
Jones et al., "The rapid generation of mutation data matrices from protein sequences," 1992, Comp. Appl. Biosci., 8:275-82.
Katoh et al., "MAFFT version 5: Improvement in accuracy of multiple sequence alignment," Nuc. Acids Res., 2005, 33:511-8.
Lassmann et al., "Kalign, Kalignvu and Mumsa: Web servers for multiple sequence alignment," Nuc. Acids Res., 2006, 34:W596-99.
Limberis et al., "Intranasal antibody gene transfer in mice and ferrets elicits broad protection against pandemic influenza," Sci. Transl. Med., 2013, 5:187ra72.
Lock et al., "Rapid, simple, and versatile manufacturing of recombinant adeno-associated viral vectors at scale," Hum. Gene Ther., 2010, 21:1259-71.
Loytynoja et al., "An Algorithm for progressive multiple alignment of sequences with insertions," PNAS USA, 2005, 102:10557-62.
Loytynoja et al., "Phylogeny-Aware Gap Placement Prevents Errors in Sequence Alignment and Evolutionary Analysis," Science, 2008, 320:1632-5.
Manning et al., "Transient immunosuppression allows transgene expression following readministration of adeno-associated viral vectors," 1998, Human Gene Ther., 9:477-85.
Mao et al., "Persistent Suppression of Ocular Neovascularization with intravitreal administration of AAVrh.10 coding for Bevacizumab," Hum. Gene Ther., 2011, 22:1525-35.
Nakai et al., "A limited number of transducible hepatocytes restricts a wide-range linear vector dose response in recombinant adeno-associated virus-mediated liver transduction," J. Virol., 2002, 76:11343-9.
Nakai et al., "Unrestricted hepatocyte transduction with adeno-associated virus serotype 8 vectors in mice," J. Virol., 2005, 79:214-24.
Notredame et al., "T-Coffee: A novel method for fast and accurate multiple sequence alignment," J. Mol. Biol., 2000, 302:205-17.
Paul et al., "Determination of hepatitis E virus seroprevalence by using recombinant fusion proteins and synthetic peptides," 1994, J. Infect. Dis., 169:801-6.
Pettersen et al., "UCSF Chimera—a visualization system for exploratory research and analysis," 2004, J. Comp. Chem., 25:1605-12.
Reeves, "Heterogeneity in the substitution process of amino acid sites of proteins coded for by mitochondrial DNA," 1992, J. Mol. Evol., 35:17-31.
Sakhria et al., "Co-Circulation of Toscana. Virus and Punique Virus in Northern Tunisia: A microneutralisation-based seroprevalence study," PLOS Negl. Trop. Dis., 2013, 7:e2429.
Sauerbrei et al. "Seroprevalence of herpes simplex virus type 1 and type 2 in Thuringia, Germany, 1999 to 2006," Euro Survell., 2011, 16(44):3).
Schneider et al., "Empirical codon substitution matrix," BMC Bioinform., 2005, 6:134.
Schwarz, "Estimating the Dimension of a Model," Ann. Statist. 1978, 6:461-4.
Thompson et al., "CLUSTAL W: improving the sensitivity of progressive multiple sequence alignment through sequence weighting, position-specific gap penalties and weight matrix choice," Nuc. Acids Res., 1994, 22:4673-90.
Wang et al., "Systematic Evaluation of AAV Vectors for Liver directed Gene Transfer in Murine Models," Mol. Ther., 2010, 18:118-25.
Watanabe et al., "AAVrh 10-mediated genetic delivery of bevacizumab to the pleura to provide local anti-VEGF to suppress growth of metastatic lung tumors," Gene Ther., 2010, 17:1042-51.
Whelan et al., "A general empirical model of protein evolution derived from multiple protein families using a maximum-likelihood approach," Mol. Biol. Evol., 2001, 18:691-9.

(56) References Cited

OTHER PUBLICATIONS

Xie et al., "AAV-mediated persistent bevacizumab therapy suppresses tumor growth of ovarian cancer," Gynecol. Oncol. 2014, 135: 325-32.
Xu et al., "Seroprevalence of herpes simplex virus types 1 and 2 in pregnant women in the United States," Am. J. Obstet. Gynecol., 2007, 196:43.e1-6.
Yang, "PAML 4: phylogenetic analysis by maximum likelihood," Mol. Biol. Evol., 2007, 24:1586-91.
Yang, "Maximum-likelihood estimation of phylogeny from DNA sequences when substitution rates differ over sites," Mol. Biol. Evol., 1993, 10:1396-1401.
Yang, "PAML: A program package for phylogenetic analysis by maximum likelihood," Comp. Applic. BioSci., 1997, 13:555-6.
"American Society of Gene & Cell Therapy 17th Annual Meeting," Molecular Therapy, May 2014, 22(Supplement 1): S1-S305.
Bartel et al., "Directed evolution of novel adeno-associated viruses for therapeutic gene delivery," Gene Therapy, Mar. 2012, 19: 694-700.
Carvalho et al., "Abstract #: 120: Retinal Tropism of in Silico Reconstructed Ancestral Adeno-Associated Viruses," Molecular Therapy, May 2014, 22(Supplement 1): S45.
EBI Accession No. GSP:ANJ81137, "Adeno-associated viral capsid protein, AAV-8," Dec. 13, 2007.
European Search Report in Application No. 18190809.6, dated Dec. 19, 2018, 5 pages.
Koerber et al., "DNA Shuffling of Adeno-associated Virus Yields Functionally Diverse Viral Progeny," Molecular Therapy, Aug. 2008, 16: 1703-1709.
Maheshri et al., "Directed evolution of adeno-associated virus yields enhanced gene delivery vectors," Nature Biotechnology, Jan. 2006, 24: 198-204.
Sarkar et al., "Abstract #: 194: Seroprevalence Assessment of Novel, Ancestrally Derived AAV Vectors," Molecular Therapy, May 2014, 22(Supplement 1): S74.
Zinn et al., "Abstract #: 237: In Silico, Ancestral Reconstruction of AAV Particles Circumvents Pre-Existing Immunity in Humans," Molecular Therapy, May 2014, 22(Supplement 1): S90.
Dayhoff et al., "22 a model of evolutionary change in proteins." Atlas of protein sequence and structure. vol. 5. National Biomedical Research Foundation Silver Spring, 1978. 345-352.
AU Office Action in Australian Appln. No. 2019201986, dated Mar. 13, 2020, 7 pages.
Sen et al., "Improved adeno-associated virus (AAV) serotype 1 and 5 vectors for gene therapy", Scientific Reports, May 2013, 3(1):1-6.

* cited by examiner

```
                10        20        30        40        50        60        70        80        90       100
L0065 MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADAEF
L0027 ....................................................................................................
L0033 ....................................................................................................
L0036 ....................................................................................................
L0044 ....................................................................................................
L0059 ....................................................................................................
L0060 ....................................................................................................
L0062 ....................................................................................................

               110       120       130       140       150       160       170       180       190       200
L0065 QERLQEDTSFGGNLGRAVFQAKKRVLEPLGLVEEGAKTAPGKKRPVEQSPQEPDSSSGIGKKGQQPARKRLNFGQTGDSESVPDPQPLGEPPAAPSGVGS
L0027 ....................................................................................................
L0033 ...................................................................K................................
L0036 ...................................................................K................................
L0044 ...................................................................K................................
L0059 ...................................................................K................................
L0060 ....................................................................................................
L0062 ....................................................................................................

               210       220       230       240       250       260       270       280       290       300
L0065 NTMAAGGGAPMADNNEGADGVGNASGNWHCDSTWLGDRVITTSTRTWALPTYNNHLYKQISSQSGGSTNDNTYFGYSTPWGYFDFNRFHCHFSPRDWQRL
L0027 ....................................................................................................
L0033 ....................................................................................................
L0036 ....S...............................................................................................
L0044 ....S...............................................................................................
L0059 ....S............................................................A..................................
L0060 ....................................................................................................
L0062 ....S...............................................................................................

               310       320       330       340       350       360       370       380       390       400
L0065 INNNWGFRPKKLNFKLFNIQVKEVTTNDGTTTIANNLTSTVQVFTDSEYQLPYVLGSAHQGCLPPFPADVFMIPQYGYLTLNNGSQAVGRSSFYCLEYFP
L0027 ..........R.........................................................................................
L0033 ....................................................................................................
L0036 ....................................................................................................
L0044 ....................................................................................................
L0059 ..........R.........................................................................................
L0060 ..........R.........................................................................................
L0062 ....................................................................................................
```

FIG. 4

```
               410       420       430       440       450       460       470       480       490       500
      ....|....|....|....|....|....|....|....|....|....|....|....|....|....|....|....|....|....|....|....|
L0065 SQMLRTGNNFQFSYTFEDVPFHSSYAHSQSLDRLMNPLIDQYLYYLSRTQTTSGTAGNRTLQFSQAGPSSMANQAKNWLPGPCYRQQRVSKTTNQNNNSN
L0027 ..........E.................................................................................A.......
L0033 ..........E.................................................................................A.......
L0036 ..........E.................................................................................A.......
L0044 ...........................................................E........................................
L0059 ...........................................................E........................................
L0060 ..........E................................................E........................................
L0062 ..........E................................................E........................................
               510       520       530       540       550       560       570       580       590       600
      ....|....|....|....|....|....|....|....|....|....|....|....|....|....|....|....|....|....|....|....|
L0065 FANTGATKYHLNGRDSLVNPGPAMATHKDDEDKFFPMSGVLIFGKQGAGNSNVDLDNVMITNEEEIKTTNPVATEEYGTVATNLQSANTAPATGTVNSQG
L0027 ...........................................................................Q........................
L0033 .............................................................S.............Q..........S.............
L0036 .............................................................S........................S.............
L0044 ...........................................................................Q........................
L0059 ....................................................................................................
L0060 .............................................................S........................S.............
L0062 .............................................................S......................................
               610       620       630       640       650       660       670       680       690       700
      ....|....|....|....|....|....|....|....|....|....|....|....|....|....|....|....|....|....|....|....|
L0065 ALPGMVWQDRDVYLQGPIWAKIPHTDGHFHPSPLMGGFGLKHPPPQILIKNTPVPANPPTTFSPAKFASFITQYSTGQVSVEIEWELQKENSKRWNPEIQ
L0027 ....................................................................................................
L0033 ........N...........................................................................................
L0036 ........N...........................................................................................
L0044 ....................................................................................................
L0059 ........N...........................................................................................
L0060 ........E...........................................................................................
L0062 ....................................................................................................
               710       720       730
      ....|....|....|....|....|....|....|..
L0065 YTSNYNKSTNVDFAVDTNGVYSEPRPIGTRYLTRNL*
L0027 ....................................*
L0033 ....................................*
L0036 ....................................*
L0044 ....................................*
L0059 ....................................*
L0060 ....................................*
L0062 ....................................*
```

FIG. 4 (Cont.)

| VP1 seq. Δ | AAV5 | AAV2 | AAV8 | rh10 | Anc80L65 | Anc80Lib |
|---|---|---|---|---|---|---|
| AAV5 | ID | 43.0% | 42.6% | 43.0% | 40.5% | 39.9-40.5% |
| AAV2 | 320 | ID | 17.1% | 15.9% | 12.2% | 12.0-12.8% |
| AAV8 | 317 | 127 | ID | 6.5% | 9.1% | 8.7-10.1% |
| rh10 | 320 | 118 | 48 | ID | 8.6% | 7.8-8.9% |
| L0065 | 301 | 91 | 68 | 64 | | 0-1.5% |
| Anc80Lib | 297-302 | 89-95 | 65-75 | 58-66 | 0-11 | ID |

FIG. 8

| | L0065 | Anc81 | Anc126 | Anc127 | Anc82 | Anc83 | Anc84 | Anc110 | AAV8 | Anc113 | AAV7 | AAV3 | AAV1 | AAV2 | AAV9 |
|---|---|---|---|---|---|---|---|---|---|---|---|---|---|---|---|
| L0065 | ID | 97.8% | 97.2% | 95.5% | 95.5% | 94.0% | 92.1% | 94.0% | 90.7% | 93.4% | 90.7% | 90.5% | 89.5% | 87.9% | 86.1% |
| Anc81 | | ID | 95.9% | 93.6% | 97.4% | 95.6% | 93.9% | 95.1% | 92.1% | 94.7% | 91.4% | 88.6% | 88.3% | 86.7% | 86.5% |
| Anc126 | | | ID | 97.4% | 93.4% | 92.0% | 90.7% | 92.5% | 89.1% | 91.8% | 88.8% | 91.9% | 91.5% | 89.2% | 85.8% |
| Anc127 | | | | ID | 91.7% | 90.7% | 89.7% | 90.7% | 88.3% | 89.8% | 87.3% | 94.4% | 89.4% | 90.7% | 86.0% |
| Anc82 | | | | | ID | 98.2% | 96.2% | 97.4% | 94.7% | 92.8% | 89.7% | 86.8% | 86.4% | 85.2% | 87.8% |
| Anc83 | | | | | | ID | 97.8% | 95.6% | 96.0% | 91.7% | 89.3% | 86.1% | 85.3% | 84.8% | 87.1% |
| Anc84 | | | | | | | ID | 93.7% | 94.5% | 91.3% | 89.1% | 85.5% | 85.0% | 84.1% | 86.3% |
| Anc110 | | | | | | | | ID | 92.5% | 90.5% | 88.2% | 86.3% | 86.5% | 85.6% | 89.0% |
| AAV8 | | | | | | | | | ID | 89.7% | 87.8% | 85.3% | 84.0% | 82.9% | 85.2% |
| Anc113 | | | | | | | | | | ID | 96.4% | 85.9% | 86.7% | 83.8% | 83.3% |
| AAV7 | | | | | | | | | | | ID | 84.2% | 85.0% | 82.3% | 81.8% |
| AAV3 | | | | | | | | | | | | ID | 86.4% | 87.3% | 83.7% |
| AAV1 | | | | | | | | | | | | | ID | 83.2.% | 82.4% |
| AAV2 | | | | | | | | | | | | | | ID | 81.9% |
| AAV9 | | | | | | | | | | | | | | | ID |

FIG. 11A

| | L0065 | Anc81 | Anc126 | Anc127 | Anc82 | Anc83 | Anc84 | Anc110 | AAV8 | AAV3 | Anc113 | AAV7 | AAV2 | AAV1 | AAV9 |
|---|---|---|---|---|---|---|---|---|---|---|---|---|---|---|---|
| L0065 | ID | 97.3% | 96.6% | 94.9% | 94.3% | 92.1% | 90.2% | 92.1% | 88.5% | 90.6% | 92.1% | 88.7% | 88.7% | 86.8% | 84.1% |
| Anc81 | | ID | 94.7% | 92.7% | 96.6% | 94.3% | 92.7% | 93.6% | 90.4% | 88.4% | 93.4% | 89.7% | 87.4% | 85.2% | 84.4% |
| Anc126 | | | ID | 97.5% | 91.5% | 89.7% | 88.7% | 89.9% | 86.7% | 92.6% | 89.9% | 86.5% | 90.8% | 89.5% | 83.3% |
| Anc127 | | | | ID | 90.2% | 88.7% | 88.0% | 88.5% | 86.3% | 94.9% | 88.2% | 85.2% | 92.1% | 87.6% | 83.1% |
| Anc82 | | | | | ID | 97.7% | 95.7% | 97.0% | 93.8% | 86.1% | 90.6% | 87.1% | 85.6% | 82.8% | 86.3% |
| Anc83 | | | | | | ID | 97.7% | 94.7% | 95.5% | 85.0% | 89.3% | 86.3% | 84.8% | 81.4% | 85.6% |
| Anc84 | | | | | | | ID | 92.8% | 93.4% | 84.8% | 88.4% | 85.8% | 84.4% | 81.6% | 84.6% |
| Anc110 | | | | | | | | ID | 91.4% | 85.0% | 88.0% | 85.6% | 85.7% | 82.4% | 87.8% |
| AAV8 | | | | | | | | | ID | 84.5% | 86.7% | 84.5% | 82.4% | 80.1% | 83.5% |
| AAV3 | | | | | | | | | | ID | 85.4% | 82.8% | 88.9% | 85.7% | 80.9% |
| Anc113 | | | | | | | | | | | ID | 95.8% | 84.1% | 83.5% | 80.5% |
| AAV7 | | | | | | | | | | | | ID | 82.4% | 81.8% | 78.9% |
| AAV2 | | | | | | | | | | | | | ID | 83.3% | 81.4% |
| AAV1 | | | | | | | | | | | | | | ID | 79.6% |
| AAV9 | | | | | | | | | | | | | | | ID |

FIG. 11B

| Viral Production Relative to AAV8 (%) | |
|---|---|
| Anc80-L0065 | 21.75% |
| Anc81 | 54.14% |
| Anc82 | 100.99% |
| Anc83 | 76.86% |
| Anc84 | 91.20% |
| Anc110 | 118.97% |
| Anc113 | 183.10% |
| Anc126 | 2.71% |
| Anc127 | 25.34% |
| AAV2 | 32.56% |
| Neg | 0.27% |

FIG. 13

| Viral Infectivity Relative to AAV8 (%) | |
|---|---|
| Anc80-L0065 | 850.83% |
| Anc81 | 102.26% |
| Anc82 | 28.31% |
| Anc83 | 47.36% |
| Anc84 | 68.78% |
| Anc110 | 24.56% |
| Anc113 | 117.12% |
| Anc127 | 113.78% |
| AAV2 | 5225.61% |
| Neg | 0.35% |

FIG. 16

| | AAV8 | AAV2 | Anc80-L0065 | Anc81 | Anc82 | Anc83 | Anc84 | Anc110 | Anc113 | Anc126 | Anc127 |
|---|---|---|---|---|---|---|---|---|---|---|---|
| Infectivity | = | +++ | +++ | = | - | - | - | -- | = | ND | = |
| Production | = | - | -- | - | = | = | = | = | ++ | -- | - |

Key

+++ : > 225%
++ : 175% - 224.5%
+ : 125 - 174.9%
= : 75% - 124.9%
- : 25-74.9%
-- : 0-24.9%
ND : Not Determined

FIG. 17

| | AAV5 | AAV2 | AAV8 | rh10 | Anc80L65 | Anc80Lib |
|---|---|---|---|---|---|---|
| AAV5 | | 43.0% | 42.6% | 43.0% | 40.5% | 39.9-40.5% |
| AAV2 | 320 | | 17.1% | 15.9% | 12.2% | 12.0-12.8% |
| AAV8 | 317 | 127 | | 6.5% | 9.1% | 8.7-10.1% |
| rh10 | 320 | 118 | 48 | | 8.6% | 7.8-8.9% |
| L0065 | 301 | 91 | 68 | 64 | | 0-1.5% |
| Anc80Lib | 297-302 | 89-95 | 65-75 | 58-66 | 0-11 | |

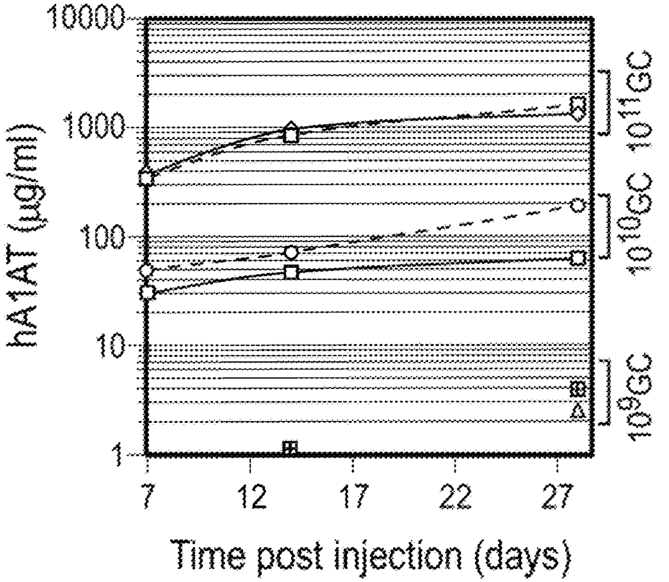
FIG. 21C
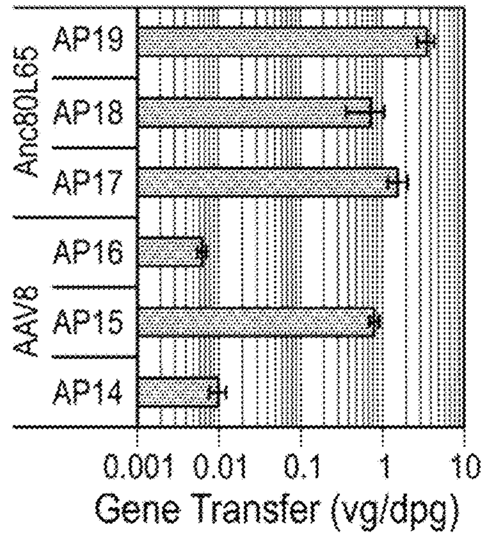
FIG. 21D
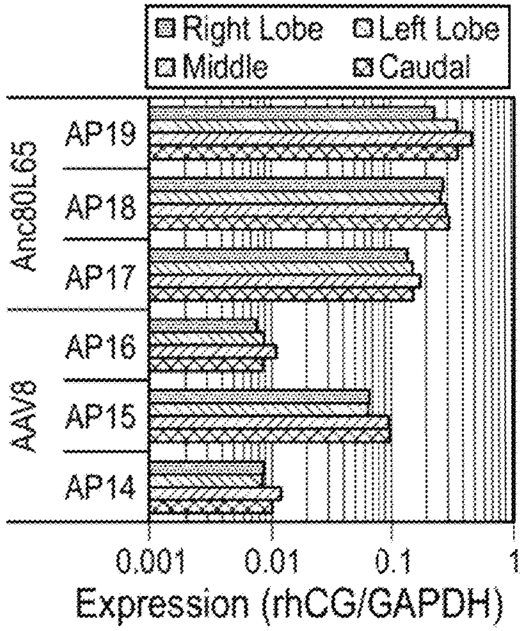
FIG. 21E
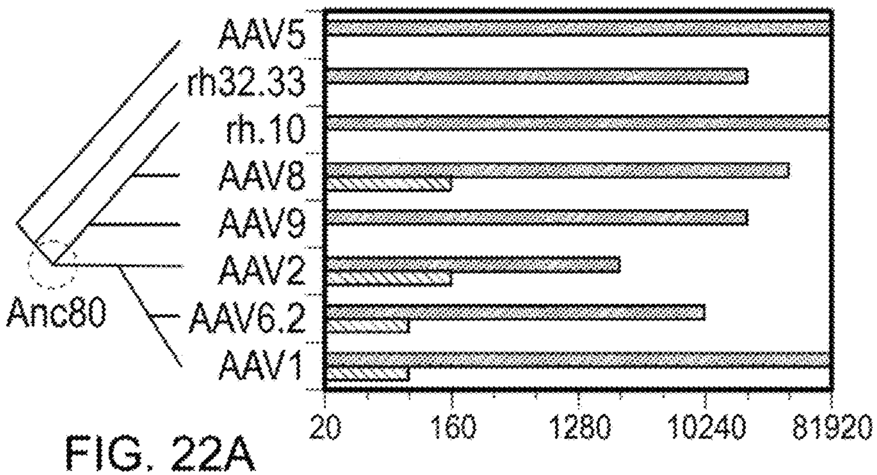
FIG. 22A
| AAV8>AAV8 | | | AAV8>Anc80 | | |
|---|---|---|---|---|---|
| % control | NAB8 | NAB80 | % control | NAB8 | NAB80 |
| <0.2% | 64 | <8 | 116% | 128 | <8 |
| <0.2% | 128 | <8 | 66% | 64 | <8 |
| <0.2% | 512 | <8 | <0.2% | 512 | <8 |
| <0.2% | 512 | <8 | <0.2% | 512 | <8 |
| <0.2% | 256 | <8 | 117% | 512 | <8 |
FIG. 22B

ANCESTRAL VIRUS SEQUENCES AND USES THEREOF

CROSS-REFERENCE TO RELATED APPLICATIONS

This application is a § 371 U.S. National Phase Application of International Application No. PCT/US2016/044819, filed on Jul. 29, 2016, which claims the benefit of U.S. Application No. 62/203,002, filed on Aug. 10, 2015 and U.S. Application No. 62/199,059, filed on Jul. 30, 2015. The entire contents of the foregoing are incorporated herein by reference.

TECHNICAL FIELD

This disclosure generally relates to viruses.

BACKGROUND

Circumventing and avoiding a neutralizing or toxic immune response against a gene therapy vector is a major challenge with all gene transfer vector types. Gene transfer to date is most efficiently achieved using vectors based on viruses circulating in humans and animals, e.g., adenovirus and adeno-associated virus (AAV). However, if subjects have been naturally infected with a virus, a subsequent treatment with a vector based on that virus leads to increased safety risks and decreased efficiency of gene transfer due to cellular and humoral immune responses. Capsid antigens are primarily responsible for the innate and/or adaptive immunity toward virus particles, however, viral gene-encoded polypeptides also can be immunogenic.

SUMMARY

This disclosure describes methods of predicting and synthesizing ancestral viral sequences or portions thereof, and also describes virus particles containing such ancestral viral sequences. The methods described herein were applied to adeno-associated virus (AAV); thus, this disclosure describes predicted ancestral AAV sequences and AAV virus particles containing such ancestral AAV sequences. This disclosure also describes the seroprevalance exhibited by virus particles containing ancestral sequences relative to virus particles containing contemporary sequences.

In one aspect, an adeno-associated virus (AAV) capsid polypeptide having the amino acid sequence shown in SEQ ID NO: 42 is provided. In some embodiments, such an AAV capsid polypeptide, or a virus particle comprising such an AAV capsid polypeptide, exhibits about the same or a lower seroprevalence than does an AAV9 capsid polypeptide or a virus particle comprising an AAV9 capsid polypeptide. In some embodiments, such an AAV capsid polypeptide, or a virus particle comprising the AAV capsid polypeptide, is neutralized to a similar or lesser extent by human serum than is an AAV9 capsid polypeptide or a virus particle comprising an AAV9 capsid polypeptide. In some embodiments, such an AAV capsid polypeptide is purified. In some embodiments, such an AAV capsid polypeptide is encoded by the nucleic acid sequence shown in SEQ ID NO: 43.

Also provided is a purified virus particle that includes such an AAV capsid polypeptide. In some embodiments, such a purified virus particle further includes a transgene.

In another aspect, a nucleic acid molecule encoding an adeno-associated virus (AAV) capsid polypeptide having the nucleic acid sequence shown in SEQ ID NO: 43 is provided.

In some embodiments, a vector is provided that includes such a nucleic acid molecule. In some embodiments, a host cell is provided that includes such a vector.

In another aspect, a method of gene transfer and/or vaccination with a transgene is provided. Such a method typically includes administering a virus particle as described herein to a subject in need of gene transfer or vaccination, wherein the virus particle exhibits about the same or a lower seroprevalence than does an AAV9 virus particle. In some embodiments, such a virus particle is neutralized to the same or to a lesser extent by human serum than is an AAV9 virus particle.

In another aspect, a method of vaccinating a subject is provided. Such a method typically includes administering a target antigen operably linked to an AAV capsid polypeptide as described herein to a subject in need of vaccination, wherein the AAV capsid polypeptide exhibits about the same or a lower seroprevalence than does an AAV9 capsid polypeptide. In some embodiments, such an AAV capsid polypeptide is neutralized to the same or to a lesser extent by human serum than is an AAV9 capsid polypeptide.

Thus, the present disclosure provides ancestral viruses or portions thereof that exhibit reduced susceptibility to pre-existing immunity in current day human populations than do contemporary viruses or portions thereof. Generally, the reduced susceptibility to pre-existing immunity exhibited by the ancestral viruses or portions thereof in current day human populations is reflected as a reduced susceptibility to neutralizing antibodies.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 4 illustrates an alignment of ancestral AAV VP1 polypeptides.

FIG. 8 is a graph showing the sequence comparison (% up from diagonal, # of aa differences below) between the Anc80 library and Anc80L65.

FIGS. 11A and 11B are sequence identity matrices producing using MAFFT that show the amino acid sequences of the VP1 proteins of ancestral vectors aligned with those of representative extant AAVs (FIG. 11A), and the amino acid sequences of the VP3 proteins of ancestral vectors aligned with those of representative extant AAVs (FIG. 118).

FIG. 13 is a table showing the titers of each vector, averaged and compared, to those of AAV8.

FIG. 16 is a table showing the luminescence of cells transduced by each vector, which were averaged and compared to those of AAV8.

FIG. 17 is a chart that provides a summary of in vitro experiments to determine the relative production and infectivity of the ancestral AAV vectors described herein.

DETAILED DESCRIPTION

Gene transfer, either for experimental or therapeutic purposes, relies upon a vector or vector system to shuttle genetic information into target cells. The vector or vector system is considered the major determinant of efficiency, specificity, host response, pharmacology, and longevity of the gene transfer reaction. Currently, the most efficient and effective way to accomplish gene transfer is through the use of vectors or vector systems based on viruses that have been made replication-defective.

Seroprevalence studies, however, indicate that significant proportions of worldwide human populations have been pre-exposed (e.g., by natural infection) to a large number of the viruses currently used in gene transfer and, therefore, harbor pre-existing immunity. Neutralizing antibodies toward the viral vector in these pre-exposed individuals are known to limit, sometimes significantly, the extent of gene transfer or even re-direct the virus away from the target. See, for example, Calcedo et al. (2009, J. Infect. Dis., 199:381-90) and Boutin et al. (2010, Human Gene Ther., 21:704-12). Thus, the present disclosure is based on the recognition that ancestral viruses or portions thereof exhibit reduced susceptibility to pre-existing immunity (e.g., reduced susceptibility to neutralizing antibodies) in current day human populations than do contemporary viruses or portions thereof.

Figure 1:
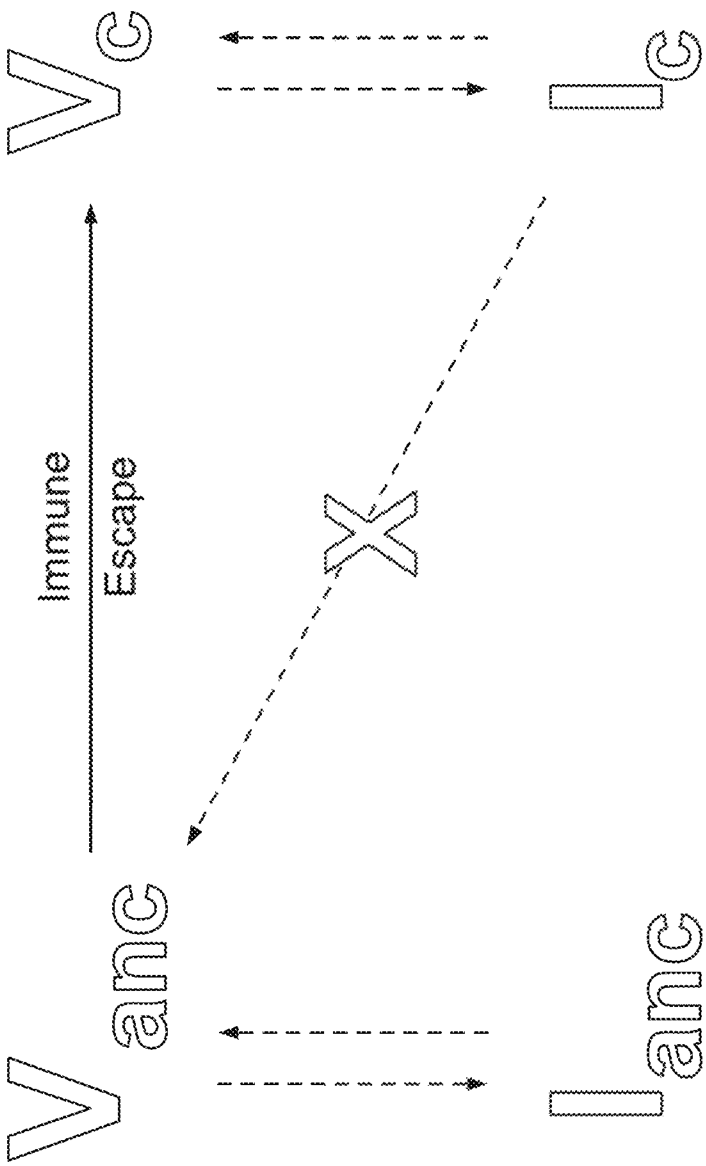
FIG. 1 is a schematic showing the relationships between ancestral/contemporary viral infections and ancestral/contemporary host immune response.
Figure 2A:
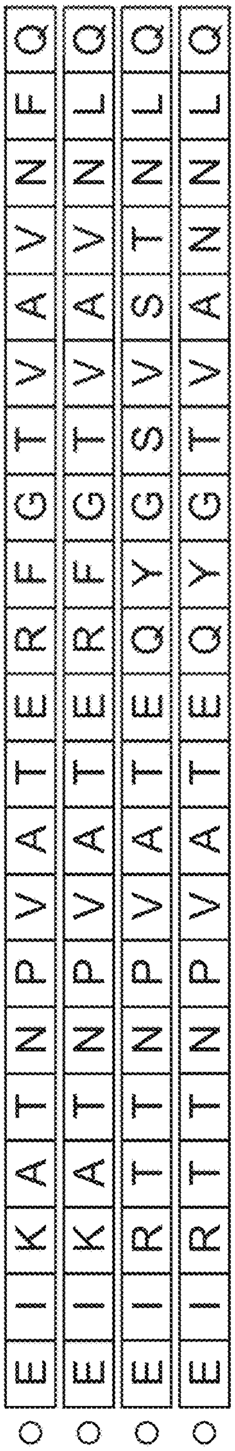
FIGS. 2A to 2D are a series of schematics showing an example of an ancestral reconstruction procedure. Data shown are excerpted from a full dataset and represent residues 564-584 (AAV2-VP1 numbering).
Figure 2B:
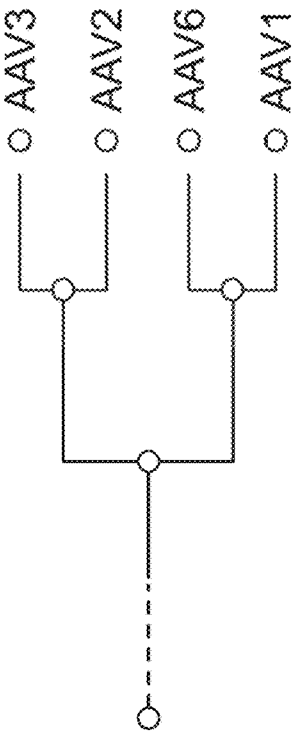
Figure 2C:
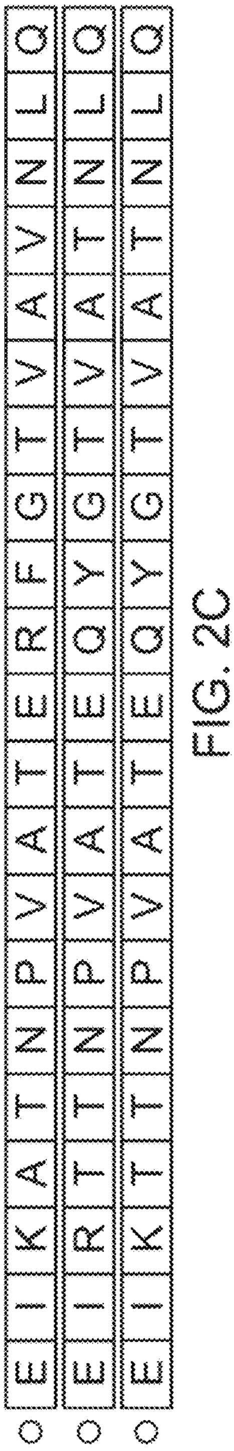
Figure 2D:
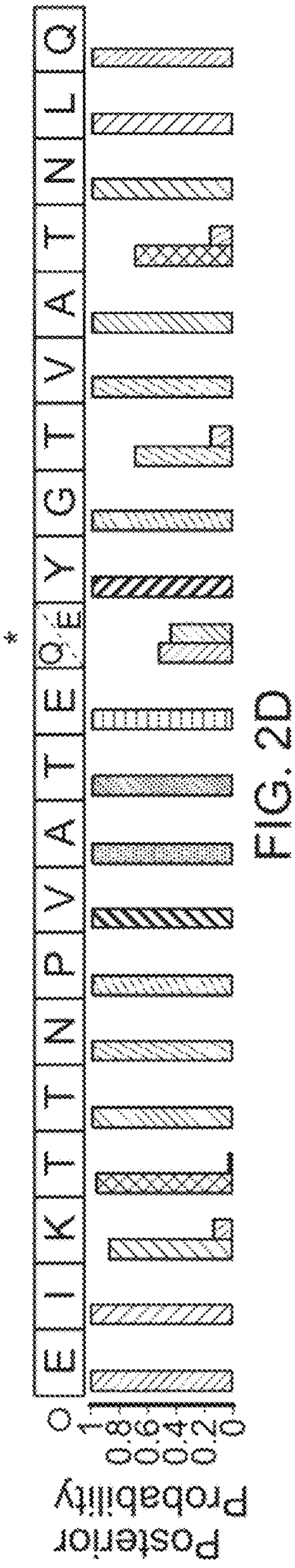

FIG. 1 is a schematic showing the relationships between ancestral and contemporary viral infections and ancestral and contemporary host immune response. FIG. 1 shows how ancestral AAVs can be refractory to contemporary pre-existing immunity. A contemporary, extant virus (Vc) is presumed to have evolved from an ancestral species (Vanc), primarily under evolutionary pressures of host immunity through mechanisms of immune escape. Each of these species, Vanc and Vc, have the ability to induce adaptive immunity including B and T cell immunity (Ianc and Ic, respectively). It was hypothesized, and confirmed herein, that immunity induced by contemporary viruses does not necessarily cross-react with an ancestral viral species, which can be substantially different in terms of epitope composition than the extant virus.

This disclosure provides methods of predicting the sequence of an ancestral virus or a portion thereof. One or more of the ancestral virus sequences predicted using the methods described herein can be generated and assembled into a virus particle. As demonstrated herein, virus particles assembled from predicted ancestral viral sequences can exhibit less, sometimes significantly less, seroprevalence than current-day, contemporary virus particles. Thus, the ancestral virus sequences disclosed herein are suitable for use in vectors or vector systems for gene transfer.

Methods of Predicting and Synthesizing an Ancestral Viral Sequence

To predict an ancestral viral sequence, nucleotide or amino acid sequences first are compiled from a plurality of contemporary viruses or portions thereof. While the methods described herein were exemplified using adeno-associated virus (AAV) capsid sequences, the same methods can be applied to other sequences from AAV (e.g., the entire genome, rep sequences, ITR sequences) or to any other virus or portion thereof. Viruses other than AAV include, without limitation, adenovirus (AV), human immunodeficiency virus (HIV), retrovirus, lentivirus, herpes simplex virus (HSV), measles, vaccinia virus, pox virus, influenza virus, respiratory syncytial virus, parainfluenza virus, foamy virus, or any other virus to which pre-existing immunity is considered a problem.

Sequences from as few as two contemporary viruses or portions thereof can be used, however, it is understood that a larger number of sequences of contemporary viruses or portions thereof is desirable so as to include as much of the landscape of modern day sequence diversity as possible, but also because a larger number of sequences can increase the predictive capabilities of the algorithms described and used. For example, sequences from 10 or more contemporary viruses or portions thereof can be used, sequences from 50 or more contemporary viruses or portions thereof can be used, or sequences from 100 or more contemporary viruses or portions thereof can be used.

Such sequences can be obtained, for example, from any number of public databases including, without limitation, GenBank, UniProt, EMBL, International Nucleotide Sequence Database Collaboration (INSDC), or European Nucleotide Archive. Additionally or alternatively, such sequences can be obtained from a database that is specific to a particular organism (e.g., HIV database). The contemporary sequences can correspond to the entire genome, or only a portion of the genome can be used such as, without limitation, sequences that encode one or more components of the viral capsid, the replication protein, or the ITR sequences.

Next, the contemporary sequences are aligned using a multiple sequence alignment (MSA) algorithm. FIG. 2(*a*) is a schematic showing an alignment of multiple sequences. MSA algorithms are well known in the art and generally are designed to be applied to different size datasets and different inputs (e.g., nucleic acid or protein), and to align the sequences in a particular manner (e.g., dynamic programming, progressive, heuristic) and apply different scoring schemes in the alignment (e.g., matrix-based or consistency-based, e.g., minimum entropy, sum of pairs, similarity matrix, gap scores). Well known MSA algorithms include, for example, ClustalW (Thompson et al., 1994, Nuc. Acids Res., 22:4673-90), Kalign (Lassmann et al., 2006, Nuc. Acids Res., 34:W596-99), MAFFT (Katoh et al., 2005, Nuc. Acids Res., 33:511-8), MUSCLE (Edgar, 2004, BMC Bioinform., 5:113), and T-Coffee (Notredame et al., 2000, J. Mol. Biol., 302:205-17).

As described herein, one of the main features when selecting a MSA algorithm for use in the methods described herein is the manner in which the algorithm treats a gap in the alignment. Gaps in a sequence alignment can be assigned a penalty value that is either dependent or independent on the size of the gap. In the present methods, it is preferred that the MSA algorithm used in the methods described herein apply phylogenetic information to predict whether a gap in the alignment is a result of a deletion or an insertion as opposed to a biased. non-phylogenetic treatment of gaps due to, e.g., insertions and/or deletions. A suitable method of treating gaps in alignments and evolutionary analysis is described in Loytynoja and Goldman, 2008, Science, 320: 1632-5, and commercially available algorithms that apply gaps in alignments in a manner that is suitable for use in the methods described herein is a Probabilistic Alignment Kit (PRANK; Goldman Group Software; Loytynoja and Goldman, 2005, PNAS USA, 102:10557-62), and variations of the PRANK algorithm.

An evolutionary model is then applied to the resulting alignment to obtain a predicted ancestral phylogeny (see FIG. 2(*b*)). There are a number of evolutionary models available in the art, each of which apply slightly different matrices of replacement rates for amino acids. Without limitation, algorithms for applying models of evolution include the Dayhoff models (e.g., PAM120, PAM160, PAM250; Dayhoff et al., 1978, In Atlas of Protein Sequence and Structure (ed. Dayhoff), pp. 345-52, National Biomedical Research Foundation, Washington D.C.), the JTT model (Jones et al., 1992, Comp. Appl. Biosci., 8:275-82), the WAG model (Whelan and Goldman, 2001, Mol. Biol. Evol., 18:691-9), and the Blosum models (e.g., Blosum45, Blosum62, Blosum80; Henikoff and Henikoff, 1992, PNAS USA, 89:10915-9).

In addition, the constraints that structure and function impose on an evolutionary model can themselves be modeled, for example, by considering that some positions are invariant ("+I"; Reeves, 1992, J. Mol. Evol., 35:17-31), that some positions undergo different rates of change ("+G"; Yang, 1993, Mol. Biol. Evol., 10:1396-1401), and/or that equilibrium frequencies of nucleotides or amino acids are the same as those in the alignment ("+F"; Cao et al., 1994, J. Mol. Evol., 39:519-27).

The fitness of one or more models of evolution can be evaluated using the Aikake Information Criterion (AIC; Akaike, 1973, In *Second International Symposium on Information Theory*, Petrov and Csaki, eds., pp 267-81, Budapest, Akademiai Kiado), the Bayesian Information Criterion (BIC; Schwarz, 1978, Ann. Statist. 6:461-4), or variations or combinations thereof. In addition, AIC, BIC, or variations or combinations thereof can be used to evaluate the relative importance of including one or more parameters (e.g., the constraints discussed above) in the evolutionary model.

As explained in the Example section below, ProTest3 (Darriba et al., 2011, Bioinformatics, 27(8):1164-5) can be used to determine, based on the lowest AIC, that a JTT+G+F algorithm was the most suitable model for AAV evolution. It would be understood by a skilled artisan that a JTT+G+F algorithm also may be used to predict ancestral viral sequences other than AAV capsid polypeptides, however, it also would be understood by a skilled artisan that, depending on the dataset and the fitness score, a different model of evolution may be more suitable.

Once a model of evolution has been selected and its fitness determined, a phylogenetic tree of the virus sequences or portions thereof can be constructed. Constructing phylogenetic trees is known in the art and typically employs maximum likelihood methods such as those implemented by PhyML (Guindon and Gascuel, 2003, Systematic Biology, 52:696-704)), MOLPHY (Adachi and Hasegawa, 1996, ed. Tokyo Institute of Statistical Mathematics), BioNJ (Gascuel, 1997, Mol. Biol. Evol., 14:685-95), or PHYLIP (Felsenstein, 1973, Systematic Biology, 22:240-9). A skilled artisan would understand that a balance between computational complexity and the goodness of fit is desirable in a model of amino acid substitutions.

If desired, the phylogenetic tree can be assessed for significance. A number of statistical methods are available and routinely used to evaluate the significance of a model including, without limitation, bootstrap, jackknife, cross-validation, permutation tests, or combinations or variations thereof. Significance also can be evaluated using, for example, an approximate likelihood-ratio test (aLRT; Anisimova and Gascuel, 2006. Systematic Biology, 55:539-52)).

At any phylogenetic node of the phylogeny (e.g., an interior phylogenetic node), the sequence can be reconstructed by estimating the evolutionary probability of a particular nucleotide or amino acid residue at each position of the sequence (FIG. 2(*c*)). A phylogenic node refers to an intermediate evolutionary branch point within the predicted ancestral phylogeny. As used herein, "evolutionary probability" refers to the probability of the presence of a particular nucleotide or amino acid at a particular position based on an evolutionary model as opposed to a model that does not take into account, for example, an evolutionary shift in the codon usage. Exemplary models that take into account the evolutionary probability of a particular nucleotide or amino acid residue at a particular position can be estimated using, for example, any number of maximum likelihood methods including, without limitation, Phylogenetic Analysis by Maximum Likelihood (PAML; Yang. 1997, Comp. Applic. BioSci., 13:555-6) or Phylogenetic Analysis Using Parsimony (PAUP; Sinauer Assoc., Inc., Sunderland, Mass.).

Based on the estimated evolutionary probability of a particular nucleotide or amino acid residue at each position, the predicted sequence of an ancestral virus or portion thereof can be assembled to form a complete or partial synthetic nucleic acid or polypeptide sequence. If desired, the likelihood that any residue was in a given state at a given node along the node can be calculated, and any position along the sequence having a calculated posterior probability beneath a particular threshold can be identified (FIG. 2(*d*)). In this manner, an ancestral scaffold sequence can be generated, which can include variations at those positions having a probability below the particular threshold.

If the ancestral sequence that is predicted using the methods herein is a nucleic acid sequence, the sequence then can be codon optimized so that it can be efficiently translated into an amino acid sequence. Codon usage tables for different organisms are known in the art. Optionally, however, a codon usage table can be designed based on one or more contemporary sequences that has homology (e.g., at least 90% sequence identity) to the ancestral scaffold sequence, and an ancestral sequence as described herein can be codon optimized toward mammalian (e.g., human) codon usage.

Any or all of the steps outlined herein for predicting an ancestral viral sequence can be performed or simulated on a computer (e.g., in silico) using a processor or a microprocessor.

Ancestral Adeno Associated Virus (AAV) Scaffold Sequences

Figure 3:
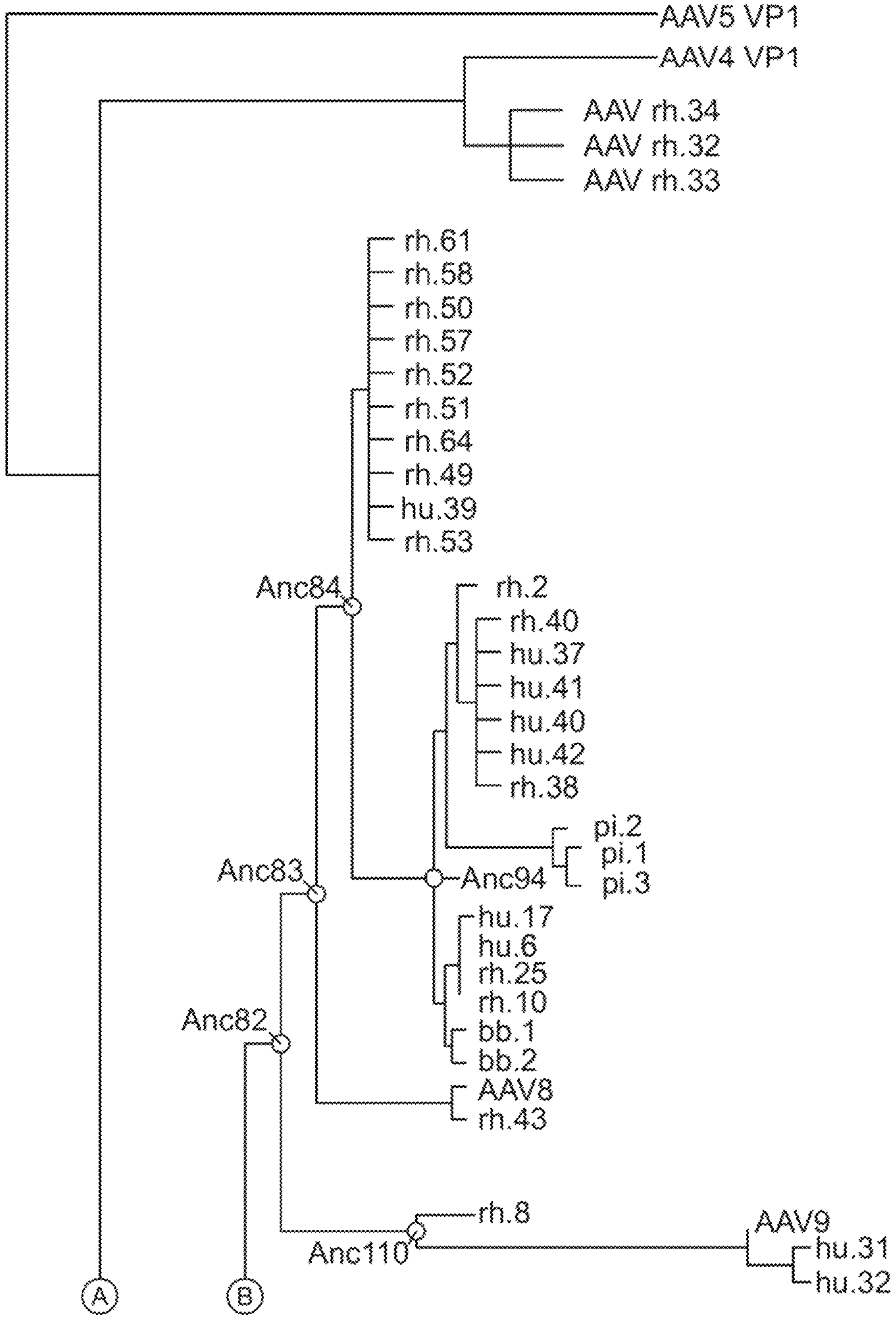
FIG. 3 illustrates a phylogenetic tree of AAV contemporary sequences generated using the methods described herein.

The methods described herein were applied to adeno-associated virus (AAV) using contemporary capsid sequences (described in detail in the Examples below). AAV is widely considered as a therapeutic gene transfer vector and a genetic vaccine vehicle, but exhibits a high seroprevalence in human populations. Using the methods described herein, a phylogenetic tree was assembled using contemporary AAV sequences (see FIG. 3) and predicted ancestral scaffold sequences were obtained at the designated phylogenic node (Table 1). As used herein, an ancestral scaffold sequence refers to a sequence that is constructed using the methods described herein (e.g., using evolutionary probabilities and evolutionary modeling) and is not known to have existed in nature. As used herein, the ancestral scaffold sequences are different from consensus sequences, which are typically constructed using the frequency of nucleotides or amino acid residues at a particular position.

TABLE 1

| Node | Polypeptide (SEQ ID NO) | Nucleic Acid (SEQ ID NO) |
|---|---|---|
| Anc80 | 1 | 2 |
| Anc81 | 3 | 4 |
| Anc82 | 5 | 6 |
| Anc83 | 7 | 8 |
| Anc84 | 9 | 0 |
| Anc94 | 11 | 12 |
| Anc113 | 13 | 14 |
| Anc126 | 15 | 16 |
| Anc127 | 17 | 18 |
| Anc110 | 42 | 43 |

The sequences of the scaffold polypeptide and nucleic acid, as well as the set of possible nucleotides or residues at positions of probability, are shown in the Sequence Listing. For example, the scaffold sequence of the Anc80 polypeptide is shown in SEQ ID NO:1, which is encoded by the scaffold sequence of the Anc80 nucleic acid shown in SEQ ID NO:2. As shown in the Sequence Listing, the scaffold sequence of Anc80 contains 11 positions at which either of two residues were probable. Therefore, the Anc80 scaffold sequence represents 2048 ($2^{11}$) different sequences. Additional scaffold sequences of the Anc81, Anc82, Anc83, Anc84, Anc94, Anc113, Anc126, Anc127, and Anc110 polypeptides are shown in SEQ ID NOs: 3, 5, 7, 9, 11, 13, 15, 17, and 42; these polypeptides are encoded by the scaffold sequence of the Anc81, Anc82, Anc83, Anc84, Anc94, Anc113, Anc126, Anc127, and Anc110 nucleic acids, respectively, shown in SEQ ID NOs: 4, 6, 8, 10, 12, 14, 16, 18, and 43. For each ancestral sequence, the set of possible nucleotides or residues at each position of probability is indicated.

To demonstrate the effectiveness of the methods described herein for predicting the ancestral sequence of a virus or portion thereof, a library of the 2048 predicted ancestral sequences at the AAV Anc80 node was generated and, as described herein, demonstrated to form viable virus particles exhibiting less seroprevalence, in some instances, significantly less seroprevalance, than virus particles assembled with contemporary capsid polypeptides.

Methods of Making Ancestral Virus Particles

After the predicted ancestral sequence of a virus or portion thereof has been obtained, the actual nucleic acid molecule and/or polypeptide(s) can be generated. Methods of generating a nucleic acid molecule or polypeptide based on a sequence obtained, for example, in silico, are known in the art and include, for example, chemical synthesis or recombinant cloning. Additional methods for generating nucleic acid molecules or polypeptides are known in the art and are discussed in more detail below.

Once an ancestral polypeptide has been produced, or once an ancestral nucleic acid molecule has been generated and expressed to produce an ancestral polypeptide, the ancestral polypeptide can be assembled into an ancestral virus particle using, for example, a packaging host cell. The components of a virus particle (e.g., rep sequences, cap sequences, inverted terminal repeat (ITR) sequences) can be introduced, transiently or stably, into a packaging host cell using one or more vectors as described herein. One or more of the components of a virus particle can be based on a predicted ancestral sequence as described herein, while the remaining components can be based on contemporary sequences. In some instances, the entire virus particle can be based on predicted ancestral sequences.

Such ancestral virus particles can be purified using routine methods. As used herein, "purified" virus particles refer to virus particles that are removed from components in the mixture in which they were made such as, but not limited to, viral components (e.g., rep sequences, cap sequences), packaging host cells, and partially- or incompletely-assembled virus particles.

Once assembled, the ancestral virus particles can be screened for, e.g., the ability to replicate; gene transfer properties; receptor binding ability; and/or seroprevalence in a population (e.g., a human population). Determining whether a virus particle can replicate is routine in the art and typically includes infecting a host cell with an amount of virus particles and determining if the virus particles increase in number over time. Determining whether a virus particle is capable of performing gene transfer also is routine in the art and typically includes infecting host cells with virus particles containing a transgene (e.g., a detectable transgene such as a reporter gene, discussed in more detail below). Following infection and clearance of the virus, the host cells can be evaluated for the presence or absence of the transgene. Determining whether a virus particle binds to its receptor is routine in the art, and such methods can be performed in vitro or in vivo.

Determining the seroprevalence of a virus particle is routinely performed in the art and typically includes using an immunoassay to determine the prevalence of one or more antibodies in samples (e.g., blood samples) from a particular population of individuals. Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Immunoassays are well known in the art and include, without limitation, an immunodot, Western blot, enzyme immunoassays (EIA), enzyme-linked immunosorbent assay (ELISA), or radioimmunoassay (RIA). As indicated herein, ancestral virus particles exhibit less seroprevalence than do contemporary virus particles (i.e., virus particles assembled using contemporary virus sequences or portions thereof). Simply by way of example, see Xu et al. (2007, Am. J. Obstet. Gynecol., 196:43.e1-6); Paul et al. (1994, J. Infect. Dis., 169:801-6); Sauerbrei et al. (2011, Eurosurv., 16(44): 3); and Sakhria et al. (2013, PLoS Negl. Trop. Dis., 7:e2429), each of which determined seroprevalence for a particular antibody in a given population.

As described herein, ancestral virus particles are neutralized to a lesser extent than are contemporary virus particles. Several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, Nature Med., 3:306-U) and Manning et al. (1998, Human Gene Ther., 9:477-85).

With respect to the ancestral AAV capsid polypeptides exemplified herein, the seroprevalence and/or extent of neutralization can be compared, for example, to an AAV8 capsid polypeptide or virus particle that includes an AAV8 capsid polypeptide, or an AAV2 capsid polypeptide or virus particle that includes an AAV2 capsid polypeptide. It is generally understood in the art that AAV8 capsid polypeptides or virus particles exhibit a seroprevalance, and a resulting neutralization, in the human population that is considered low, while AAV2 capsid polypeptide or virus particles exhibit a seroprevalance, and a resulting neutralization, in the human population that is considered high. Obviously, the particular seroprevalence will depend upon the population examined as well as the immunological methods used, but there are reports that AAV8 exhibits a seroprevalence of about 22% up to about 38%, while AAV2 exhibits a seroprevalence of about 43.5% up to about 72%. See, for example, Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12. See, also, Calcedo et al., 2009, J. Infect. Dis., 199:381-90.

Predicted Adeno Associated Virus (AAV) Ancestral Nucleic Acid and Polypeptide Sequences A number of different clones from the library encoding predicted ancestral capsid polypeptides from the Anc80 node were sequenced, and the amino acid sequences of representative AAV predicted ancestral capsid polypeptides are shown in SEQ ID NO: 19 (Anc80L27); SEQ ID NO: 20 (Anc80L59); SEQ ID NO: 21 (Anc80L60); SEQ ID NO: 22 (Anc80L62); SEQ ID NO: 23 (Anc80L65); SEQ ID NO: 24 (Anc80L33); SEQ ID NO: 25 (Anc80L36); and SEQ ID NO: 26 (Anc80L44). Those skilled in the art would appreciate that the nucleic acid sequence encoding each amino acid sequence readily can be determined.

In addition to the predicted ancestral capsid polypeptides having the sequences shown in SEQ ID NOs: 19, 20, 21, 22, 23, 24, 25 or 26, polypeptides are provided that have at least 95% sequence identity (e.g., at least 96%, at least 97%, at least 98%, at least 99% or 100% sequence identity) to the predicted ancestral capsid polypeptides having the sequences shown in SEQ ID NOs: 19, 20, 21, 22, 23, 24, 25 or 26. Similarly, nucleic acid molecules are provided that have at least 95% sequence identity (e.g., at least 96%, at least 97%, at least 98%, at least 99% or 100% sequence identity) to the nucleic acid molecules encoding the ancestral capsid polypeptides.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (basic local alignment search tool) programs, available at ncbi.nlm.nih-.gov on the World Wide Web. BLAST searches can be performed to determine percent sequence identity between a sequence (nucleic acid or amino acid) and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

Figure 5A:
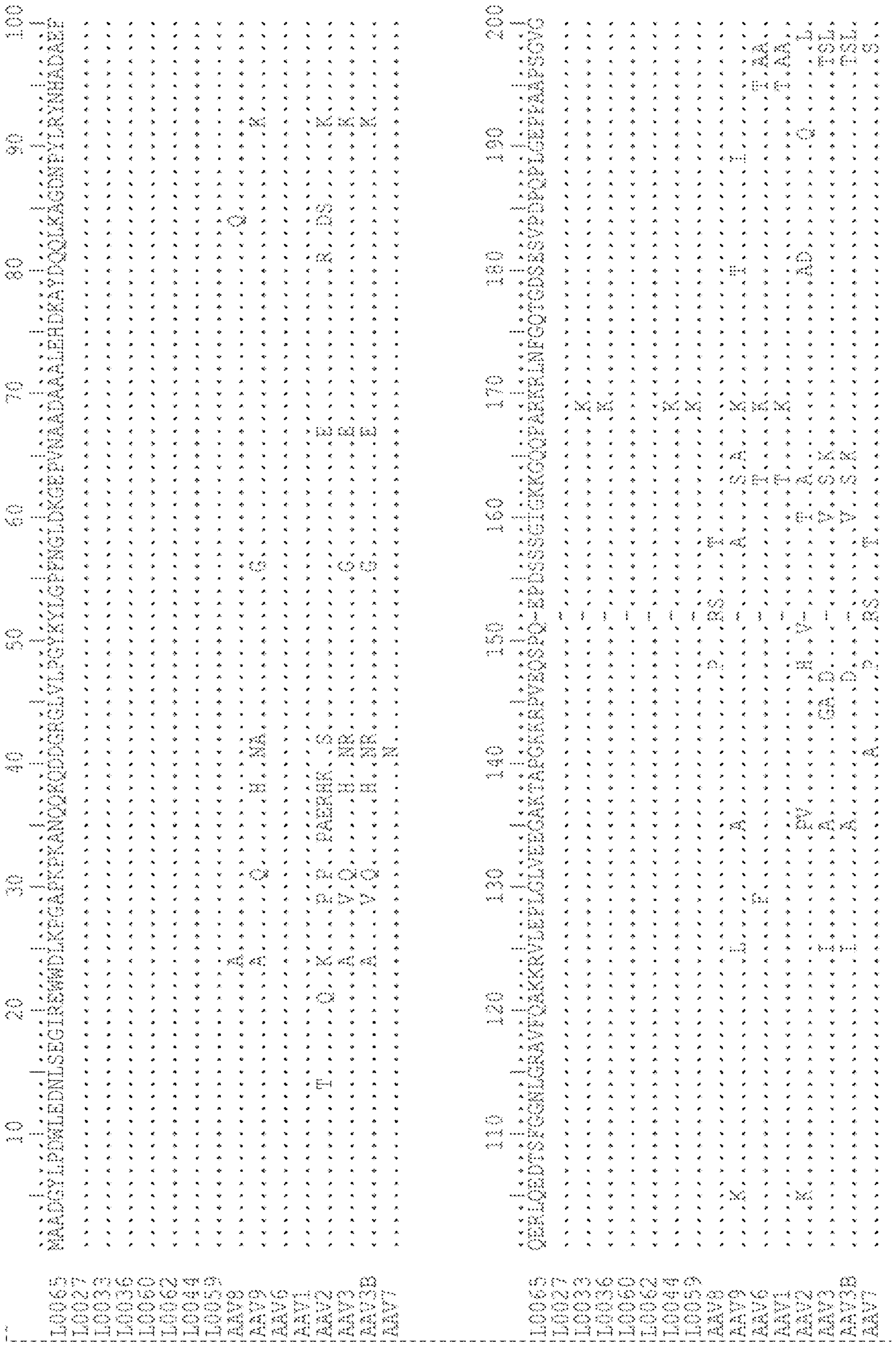
FIGS. 5A and 5B together illustrate an alignment of functional ancestral AAV VP1 polypeptides and contemporary AAV VP1 polypeptides.
Figure 5A:
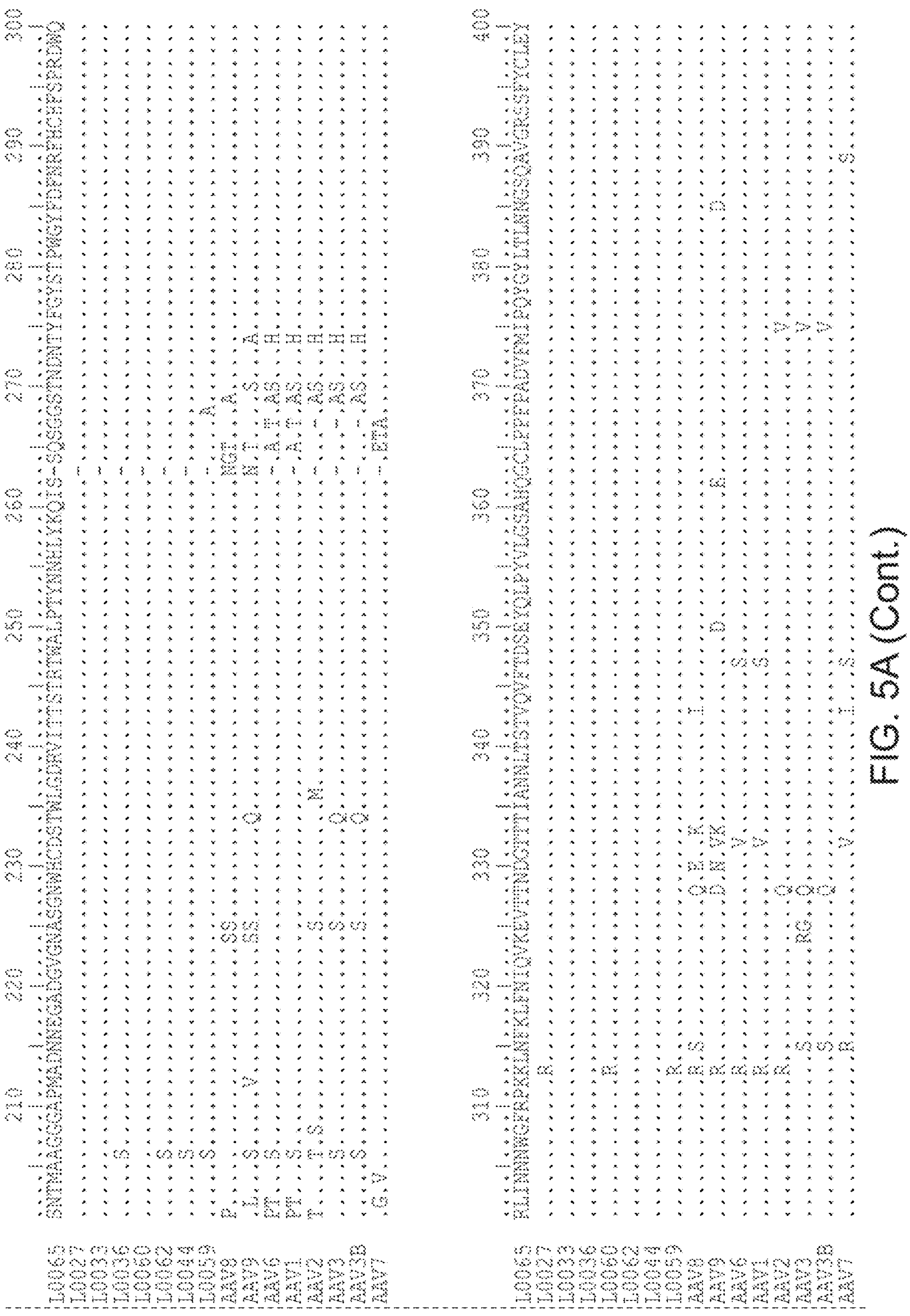
Figure 5B:
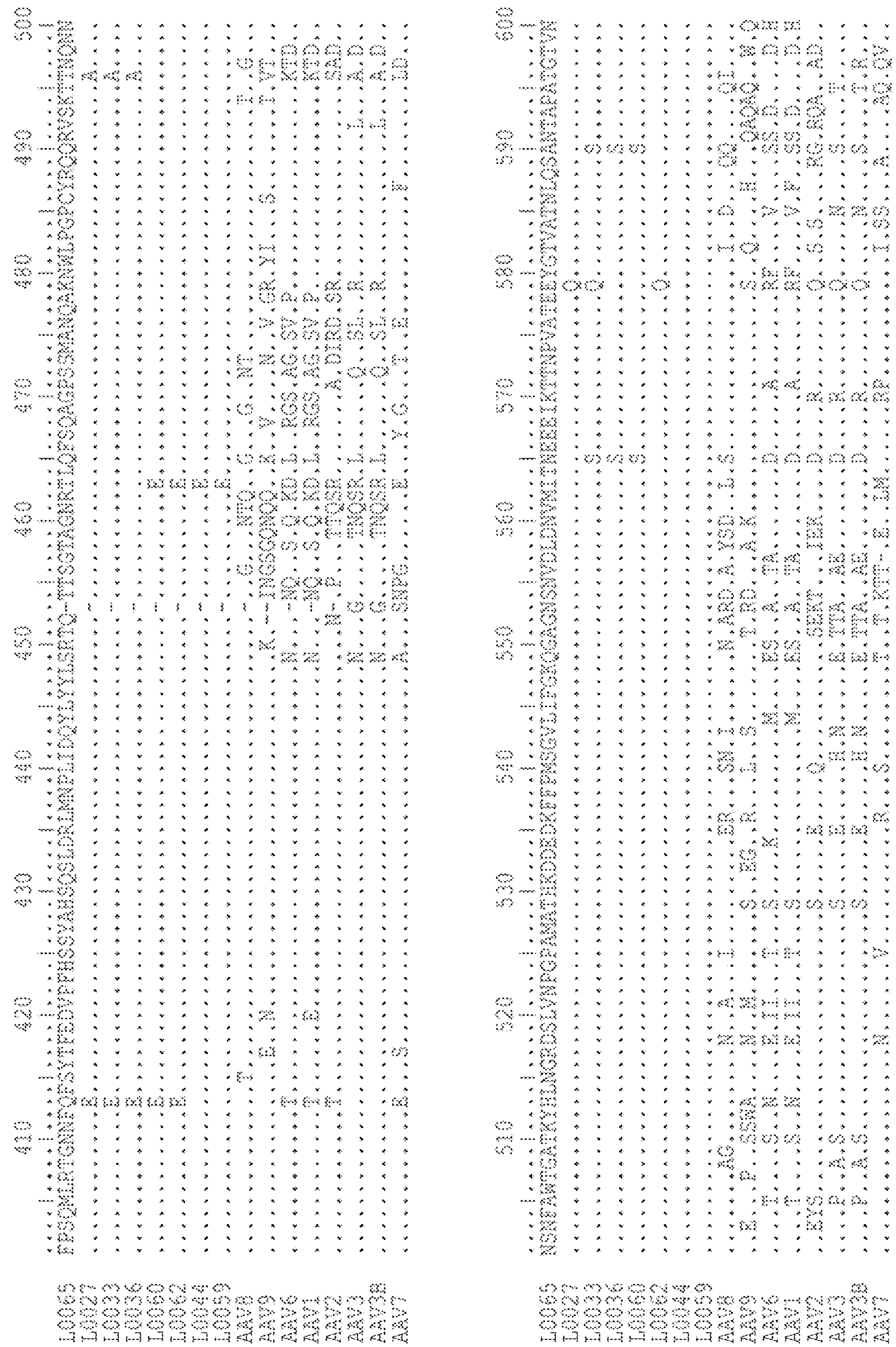
Figure 5B:
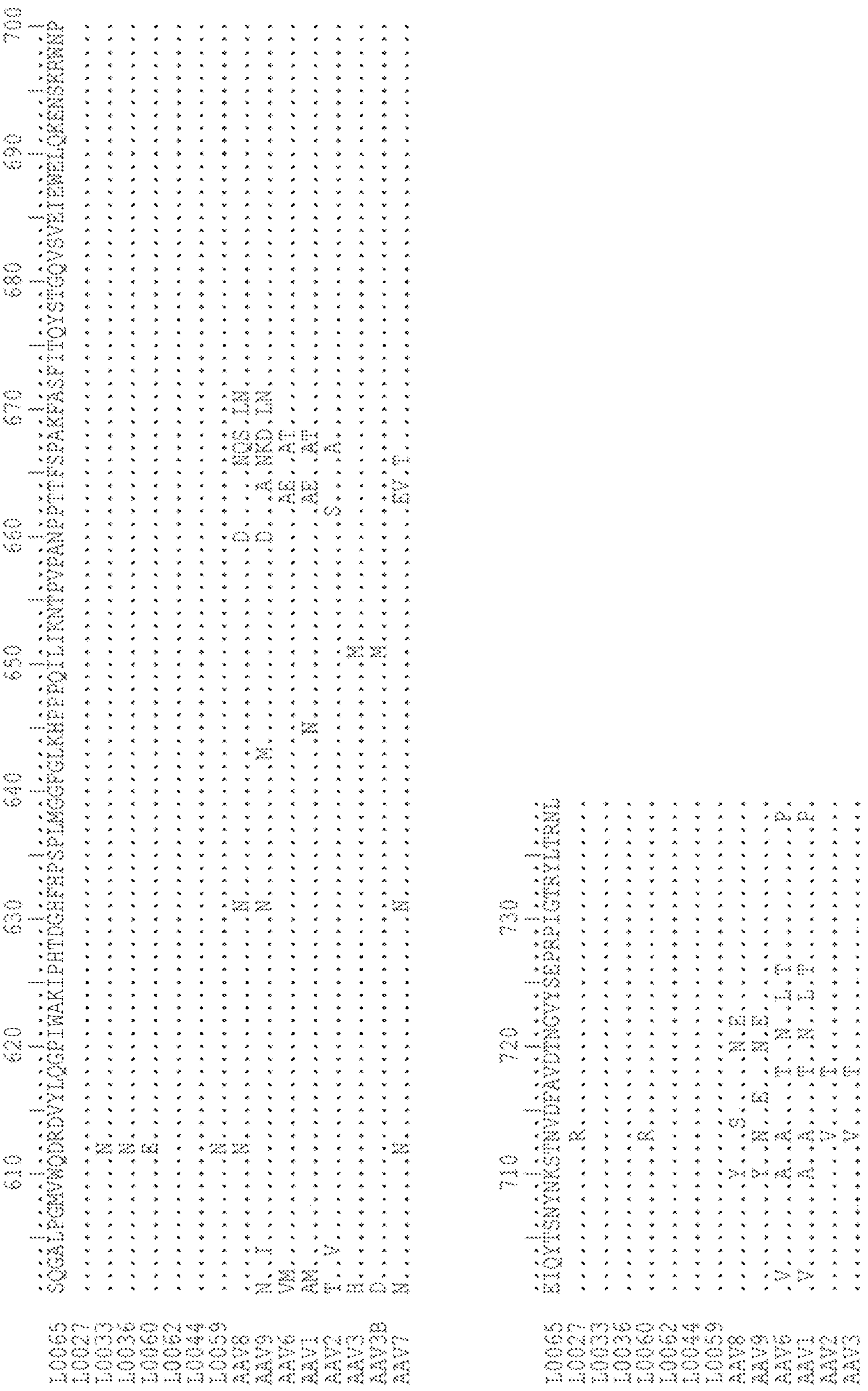

Representative alignments are shown in FIGS. 4A and 4B and FIGS. 5A and 5B. FIGS. 4A and 4B show an alignment of ancestral AAV VP1 capsid polypeptides, designated Anc80L65 (SEQ ID NO: 23), Anc80L27 (SEQ ID NO: 19), Anc80L33 (SEQ ID NO: 24), Anc80L36 (SEQ ID NO: 25), Anc80L44 (SEQ ID NO: 26), Anc80L59 (SEQ ID NO: 20), Anc80L60 (SEQ ID NO: 21), and Anc80L62 (SEQ ID NO: 22). The alignment shown in FIGS. 4A and 4B confirms the predicted variation at each of the 11 sites, and a single non-synonymous mutation at position 609E of Anc80L60 (SEQ ID NO: 21), which may be a cloning artifact. FIGS. 5A and 5B shows an alignment between ancestral AAV VP1 capsid polypeptides (Anc80L65 (SEQ ID NO: 23), Anc80L27 (SEQ ID NO: 19), Anc80L33 (SEQ ID NO: 24), Anc80L36 (SEQ ID NO: 25), Anc80L60 (SEQ ID NO: 21), Anc80L62 (SEQ ID NO: 22), Anc80L44 (SEQ ID NO: 26), and Anc80L59 (SEQ ID NO: 20)) and contemporary AAV VP1 capsid polypeptides (AAV8 (SEQ ID NO: 27), AAV9 (SEQ ID NO: 28), AAV6 (SEQ ID NO: 29), AAV1 (SEQ ID NO: 30), AAV2 (SEQ ID NO: 31), AAV3 (SEQ ID NO: 32), AAV3B (SEQ ID NO: 33), and AAV7 (SEQ ID NO: 34)). The alignment in FIGS. 5A and 5B shows that the ancestral AAV sequences have between about 85% and 91% sequence identity to contemporary AAV sequences.

Vectors containing nucleic acid molecules that encode polypeptides also are provided. Vectors, including expression vectors, are commercially available or can be produced by recombinant technology. A vector containing a nucleic acid molecule can have one or more elements for expression operably linked to such a nucleic acid molecule, and further can include sequences such as those encoding a selectable marker (e.g., an antibiotic resistance gene), and/or those that can be used in purification of a polypeptide (e.g., 6×His tag). Elements for expression include nucleic acid sequences that direct and regulate expression of nucleic acid coding sequences. One example of an expression element is a promoter sequence. Expression elements also can include one or more of introns, enhancer sequences, response elements, or inducible elements that modulate expression of a nucleic acid molecule. Expression elements can be of bacterial, yeast, insect, mammalian, or viral origin and vectors can contain a combination of expression elements from different origins. As used herein, operably linked means that elements for expression are positioned in a vector relative to a coding sequence in such a way as to direct or regulate expression of the coding sequence.

A nucleic acid molecule, e.g., a nucleic acid molecule in a vector (e.g., an expression vector, a viral vector) can be introduced into a host cell. The term "host cell" refers not only to the particular cell(s) into which the nucleic acid molecule has been introduced, but also to the progeny or potential progeny of such a cell. Many suitable host cells are known to those skilled in the art; host cells can be prokaryotic cells (e.g., *E. coli*) or eukaryotic cells (e.g., yeast cells, insect cells, plant cells, mammalian cells). Representative host cells can include, without limitation, A549, WEHI, 3T3, 10T1/2, BHK, MDCK, COS 1, COS 7, BSC 1, BSC 40, BMT 10, VERO, WI38, HeLa, 293 cells, Saos, C2C12, L cells, HT1080, HepG2 and primary fibroblast, hepatocyte and myoblast cells derived from mammals including human, monkey, mouse, rat, rabbit, and hamster. Methods for introducing nucleic acid molecules into host cells are well known in the art and include, without limitation, calcium phosphate precipitation, electroporation, heat shock, lipofection, microinjection, and viral-mediated nucleic acid transfer (e.g., transduction).

With respect to polypeptides, "purified" refers to a polypeptide (i.e., a peptide or a polypeptide) that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is considered "purified," but further can be removed from the components used to synthesize the polypeptide (e.g., amino acid residues). With respect to nucleic acid molecules, "isolated" refers to a nucleic acid molecule that is separated from other nucleic acid molecules that are usually associated with it in the genome. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and/or hydroxyapatite chromatography. A purified polypeptide also can be obtained, for example, by expressing a nucleic acid molecule in an expression vector or by chemical synthesis. The extent of purity of a polypeptide can be measured using any appropriate method, e.g., column chromatography, polyacrylamide gel electrophoresis, or HPLC analysis. Similarly, nucleic acid molecules can be obtained (e.g., isolated) using routine methods such as, without limitation, recombinant nucleic acid technology (e.g., restriction enzyme digestion and ligation) or the polymerase chain reaction (PCR; see, for example, PCR Primer: A Laboratory Manual, Dieffenbach & Dveksler, Eds., Cold Spring Harbor Laboratory Press, 1995). In addition, isolated nucleic acid molecules can be chemically synthesized.

Methods of Using Ancestral Viruses or Portions Thereof

An ancestral virus or portion thereof as described herein, particularly those that exhibit reduced seroprevalence relative to contemporary viruses or portions thereof, can be used in a number of research and/or therapeutic applications. For example, an ancestral virus or portion thereof as described herein can be used in human or animal medicine for gene therapy (e.g., in a vector or vector system for gene transfer) or for vaccination (e.g., for antigen presentation). More specifically, an ancestral virus or portion thereof as described herein can be used for gene addition, gene augmentation, genetic delivery of a polypeptide therapeutic, genetic vaccination, gene silencing, genome editing, gene therapy, RNAi delivery, cDNA delivery, mRNA delivery, miRNA delivery, miRNA sponging, genetic immunization, optogenetic gene therapy, transgenesis, DNA vaccination, or DNA immunization.

A host cell can be transduced or infected with an ancestral virus or portion thereof in vitro (e.g., growing in culture) or in vivo (e.g., in a subject). Host cells that can be transduced or infected with an ancestral virus or portion thereof in vitro are described herein; host cells that can be transduced or infected with an ancestral virus or portion thereof in vivo include, without limitation, brain, liver, muscle, lung, eye (e.g., retina, retinal pigment epithelium), kidney, heart, gonads (e.g., testes, uterus, ovaries), skin, nasal passages, digestive system, pancreas, islet cells, neurons, lymphocytes, ear (e.g., inner ear), hair follicles, and/or glands (e.g., thyroid).

An ancestral virus or portion thereof as described herein can be modified to include a transgene (in cis or trans with other viral sequences). A transgene can be, for example, a reporter gene (e.g., beta-lactamase, beta-galactosidase (LacZ), alkaline phosphatase, thymidine kinase, green fluorescent polypeptide (GFP), chloramphenicol acetyltransferase (CAT), or luciferase, or fusion polypeptides that include an antigen tag domain such as hemagglutinin or Myc) or a therapeutic gene (e.g., genes encoding hormones or receptors thereof, growth factors or receptors thereof, differentiation factors or receptors thereof, immune system regulators (e.g., cytokines and interleukins) or receptors thereof, enzymes, RNAs (e.g., inhibitory RNAs or catalytic RNAs), or target antigens (e.g., oncogenic antigens, autoimmune antigens)).

The particular transgene will depend, at least in part, on the particular disease or deficiency being treated. Simply by way of example, gene transfer or gene therapy can be applied to the treatment of hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS).

A transgene also can be, for example, an immunogen that is useful for immunizing a subject (e.g., a human, an animal (e.g., a companion animal, a farm animal, an endangered animal). For example, immunogens can be obtained from an organism (e.g., a pathogenic organism) or an immunogenic portion or component thereof (e.g., a toxin polypeptide or a by-product thereof). By way of example, pathogenic organisms from which immunogenic polypeptides can be obtained include viruses (e.g., picornavirus, enteroviruses, orthomyxovirus, reovirus, retrovirus), prokaryotes (e.g., Pneumococci, Staphylococci, *Listeria, Pseudomonas*), and eukaryotes (e.g., amebiasis, malaria, leishmaniasis, nematodes). It would be understood that the methods described herein and compositions produced by such methods are not to be limited by any particular transgene.

An ancestral virus or portion thereof, usually suspended in a physiologically compatible carrier, can be administered to a subject (e.g., a human or non-human mammal). Suitable carriers include saline, which may be formulated with a variety of buffering solutions (e.g., phosphate buffered saline), lactose, sucrose, calcium phosphate, gelatin, dextran, agar, pectin, and water. The ancestral virus or portion thereof is administered in sufficient amounts to transduce or infect the cells and to provide sufficient levels of gene transfer and expression to provide a therapeutic benefit without undue adverse effects. Conventional and pharmaceutically acceptable routes of administration include, but are not limited to, direct delivery to an organ such as, for example, the liver or lung, orally, intranasally, intratracheally, by inhalation, intravenously, intramuscularly, intraocularly, subcutaneously, intradermally, transmucosally, or by other routes of administration. Routes of administration can be combined, if desired.

The dose of the ancestral virus or portion thereof administered to a subject will depend primarily on factors such as the condition being treated, and the age, weight, and health of the subject. For example, a therapeutically effective dosage of an ancestral virus or portion thereof to be administered to a human subject generally is in the range of from about 0.1 ml to about 10 ml of a solution containing concentrations of from about $1\times10^{1}$ to $1\times10^{12}$ genome copies (GCs) of ancestral viruses (e.g., about $1\times10^{3}$ to $1\times10^{9}$ GCs).

Transduction and/or expression of a transgene can be monitored at various time points following administration by DNA, RNA, or protein assays. In some instances, the levels of expression of the transgene can be monitored to determine the frequency and/or amount of dosage. Dosage regimens similar to those described for therapeutic purposes also may be utilized for immunization.

The methods described herein also can be used to model forward evolution, so as to modify or ablate one or more immunogenic domains of a virus or portion thereof.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Computational Prediction of Ancestral Sequences

A set of 75 different amino acid sequences of AAV capsids was obtained from a number of public databases including GenBank, and the sequences were aligned using the PRANK-MSA algorithm, version 121002, with the option "-F".

ProtTest3 (see, for example, Darriba et al., 2011, Bioinformatics, 27(8):1164-5; available at darwin.uvigo.es/software/prottest3 on the World Wide Web) was used to evaluate different models of polypeptide evolution (e.g., those included in ProTest3, namely, JTT, LG, WAG, VT, CpRev, RtRev, Dayhoff, DCMut, FLU, Blosum62, VT, HIVb, MtArt, MtMam) under different conditions (e.g., those included in ProTest3, namely, "+I", "+F", "+G", and combinations thereof). The JTT model (Jones et al., 1992, Comp. Appl. Biosci., 8:275-82) with +G and +F (Yang, 1993, Mol. Biol. Evol., 10:1396-1401; and Cao et al., 1994, J. Mol. Evol., 39:519-27) was selected based on its Aikake Information Criterion (AIC; Hirotugu, 1974, IEEE Transactions on Automatic Control, 19:716-23) score as implemented in ProTest3.

A phylogeny of AAV evolution was constructed using PhyML (Guindon and Gascuel, 2003, Systematic Biology, 52:696-704)). See FIG. 3. The tree was generated using the JTT+F substitution model with 4 discrete substitution categories and an estimated Gamma shape parameter. The resultant trees were improved via Nearest Neighbor Interchange (NNI) and Subtree Pruning and Re-Grafting (SPR), and assessed for significance via bootstrap and approximate likelihood-ratio test (aLRT; Anisimova and Gascuel, 2006, Systematic Biology, 55:539-52)) using the "SH-Like" variant.

The phylogenic tree constructed above was then used to estimate the ancestral states of the AAV capsid at every node interior to the phylogeny. The ancestral capsid sequences were reconstructed using maximum likelihood principles through the Phylogenetic Analysis by Maximum Likelihood (PAML) software (Yang, 1997, Comp. Applic. BioSci., 13:555-6; available at abacus.gene.ucl.ac.uk/software/paml.html on the World Wide Web) wrapped in Lazarus (Sourceforge at sf.net). More specifically, the Lazarus/PAML reconstruction was set to generate an amino acid reconstruction using the JTT+F substitution model using 4 gamma-distributed categories. AAV5 was used as an outgroup. Finally, the "I" option was added to place indels (i.e., coded binarily and placed via Maximum Parsimony using Fitch's algorithm) after the PAML reconstruction was done.

Because the reconstruction was done in a maximum-likelihood fashion, the likelihood that any residue was in a given position at a given node can be calculated. To do this, an additional script was written to identify all positions along the sequence with a calculated posterior probability beneath a certain threshold. A threshold of 0.3 was selected, meaning that any amino acid with a calculated posterior probability of greater than 0.3 was included in the synthesis of the library. These residues were selected to be variants of interest in the library.

To finalize the sequence, an additional utility had to be coded to select codons. A script was written to derive codons similar to those of another AAV sequence (AVVRh10, which has about 92% sequence identity to the Anc80 scaffold sequence) and apply a novel algorithm to substitute codons where there were sequence mismatches based on a codon-substitution matrix. The novel algorithm is shown below:

Given: amino acid sequence, Pt; with corresponding nucleotide sequence, Nt, where Nt codes for Pt; and protein sequence, Pi, where Pi exhibits strong homology to Pt.

Align Pi with Pt using Needleman-Wunsch using the Blosum62 table for scoring. Generate a new nucleotide sequence, Ni, by stepping through the protein alignment, using the corresponding codon from Nt,

- where the amino acid in Pt exactly matches that in Pi,
- the "best scoring" codon from the Codon-PAM matrix (Schneider et al., 2005, BMC Bioinform., 6:134) where there is a substitution,
- a gap where there exists a gap in Pi aligned against an amino-acid in Pt, and
- the most frequently occurring nucleotide in the Nt (coding for a given amino acid) where there exists an amino-acid in Pi aligned against a gap in Pt.

In addition, two single nucleotide changes were made to ablate transcription of assembly-activating protein (AAP), which is encoded out of frame within the AAV capsid gene in the wild type AAV. Since the coding of AAP (contemporary or ancestral) was not a part of this reconstruction, the expression of AAP was ablated by making a synonymous mutation in the cap sequence, and the AAP sequence was provided in trans during viral production.

Example 2—Expression of Ancestral AAV VP1 Sequences

Experiments were performed to determine whether predicted ancestral AAV capsid sequences can be used to make viral vectors.

A number of the predicted ancestral AAV capsid sequences were cloned. The library of ancestral capsids was transferred to a rep-cap expression plasmid to enable viral particle formation in transient transfection. To maintain appropriate expression levels and splicing of VP1, VP2, and VP3, library cap genes were cloned by cutting HindIII, located 5' of cap in the rep coding sequence, and SpeI, which was engineered between the cap stop codon and the polyadenylation signal. Consequently, to clone the ancestral capsids into a more conventional "REP/CAP" construct, the passaging-plasmid was digested with HindIII and SpeI, gel purified, and ligated into a similarly digested rep/cap plasmid.

Figure 6:
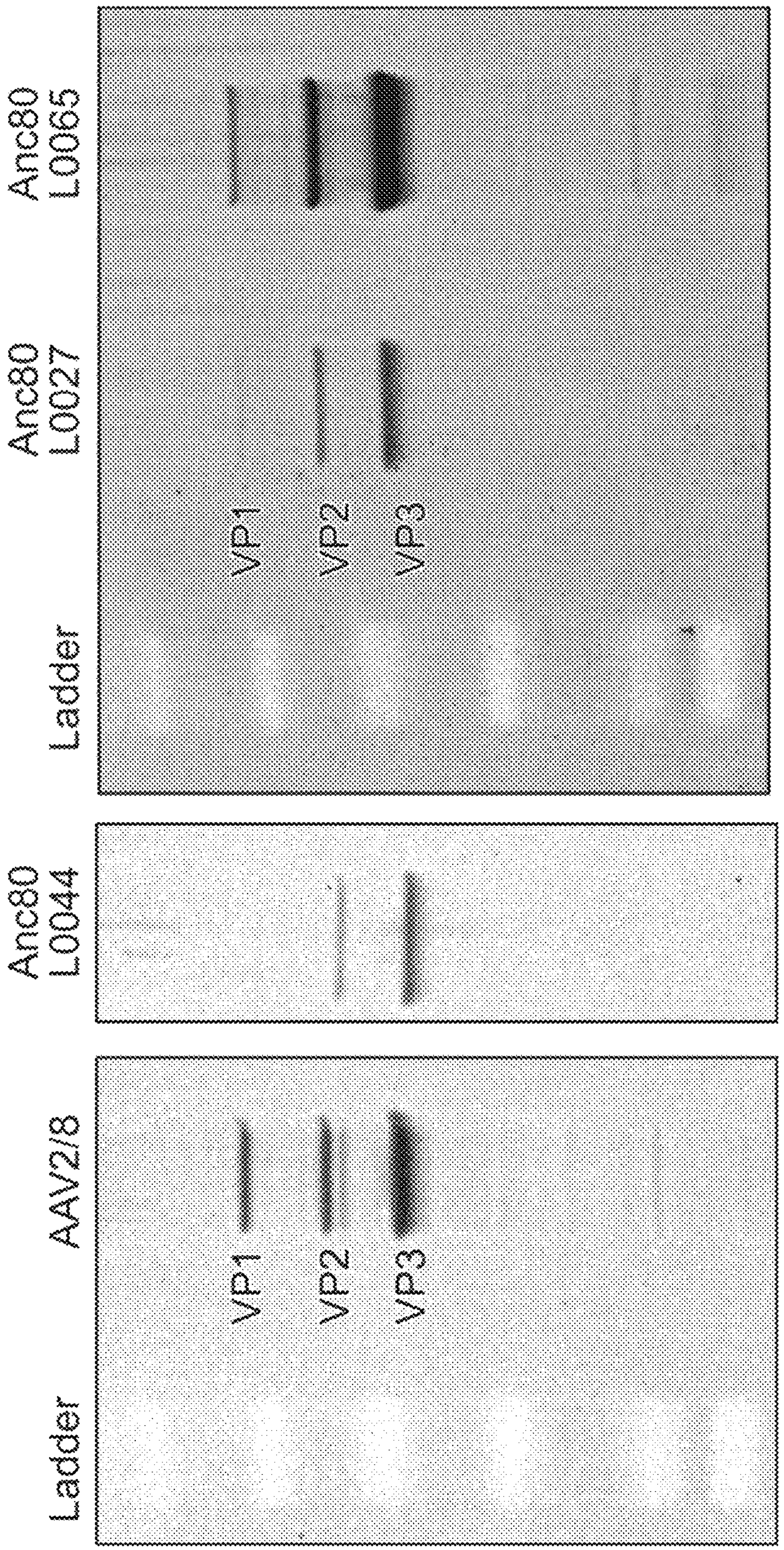
FIG. 6 is an electrophoretic gel demonstrating that ancestral AAV VP1 sequences are transcribed and alternately spliced in a manner similar to that for contemporary AAV VP1 sequences.

The expressed polypeptides were resolved on a 10% SDS gel. As shown in FIG. 6, the capsid polypeptides were appropriately expressed and spliced into VP1, VP2, and VP3 from a number of ancestral AAV sequences (Anc80L44, Anc80L27, and Anc80L65) as well as from a contemporary AAV sequence, AAV2/8.

Example 3—Viral Titration

AAV was produced in HEK293 cells via transient co-transfection of plasmids encoding all elements required for viral particle assembly. Briefly, HEK293 cells were grown to 90% confluency and transfected with (a) the viral genome plasmid encoding the luciferase transgene (expressed by the CMV promoter) flanked by AAV2 ITRs, (b) the AAV packaging plasmid encoding AAV2 rep and the synthesized capsid proteins disclosed herein, (c) AAV2-AAP expressing capsid, and (d) adenoviral helper genes needed for AAV packaging and assembly. Cells were incubated at 37° C. for 2 days, and cells and media were harvested and collected.

The cell-media suspension was lysed by 3 consecutive freeze-thaw cycles. Next, the lysate was cleared by centrifugation and treated with an enzyme under conditions to perform exhaustive DNA digestion, here Benzonase™, to digest any DNA present outside of the virus particle. The AAV preparation was diluted to fall within the linear measurement range of a control DNA template, in this case linearized plasmid with identical TaqMan™ primer and probe binding sequence as compared to the vector genome. TaqMan™ PCR was performed with primers and probe annealing to the viral vector genome of choice. Titer was calculated based on the TaqMan™ measurement in genome copies (GC) per milliliter (ml) as shown in Table 2 below.

TABLE 2

| Titers (GC/ml) | Small scale #1 | Small scale #2 |
|---|---|---|
| AAV2/2 | $1.12 \times 10^{9}$ | $1.99 \times 10^{9}$ |
| AAV2/8 | $4.17 \times 10^{10}$ | $5.91 \times 10^{10}$ |
| Anc80L27 | $8.01 \times 10^{8}$ | $1.74 \times 10^{9}$ |
| Anc80L44 | $1.52 \times 10^{9}$ | $1.43 \times 10^{9}$ |
| Anc80L65 | $1.42 \times 10^{9}$ | $2.05 \times 10^{9}$ |
| No capsid control | $5.23 \times 10^{5}$ | $7.25 \times 10^{5}$ |

Small scale vector production results on ancestrally reconstructed AAV capsid particles demonstrated yields that were similar to AAV2, but reduced relative to AAV8, both of which are vector preparations based on contemporary AAVs.

Example 4—In Vitro Viral Transduction

In vitro viral transductions were performed to evaluate the ability of viruses containing the predicted ancestral AAV sequences to infect cells.

Following high throughput vector production using the Anc80 library of sequences, HEK293 cells were transduced with each viral vector. In addition to an Anc80 sequence, each viral vector contained a luciferase transgene. Luciferase was measured by quantification of bioluminescence in a 96 well plate reader following addition of luciferin substrate to the transduced cells or cell lysate. Following quantification, a heat map of luciferase expression in four concatenated 96-well plates was produced (excluding a column of controls in each plate). Due to the large number of insertions, deletions, and transitions associated with the process of high throughput vector production, many of the vectors were non-functional. For purposes herein, only viruses that were functional in this assay (i.e., able to transduce HEK293 cells and express the transgene) were evaluated further.

Figure 7:
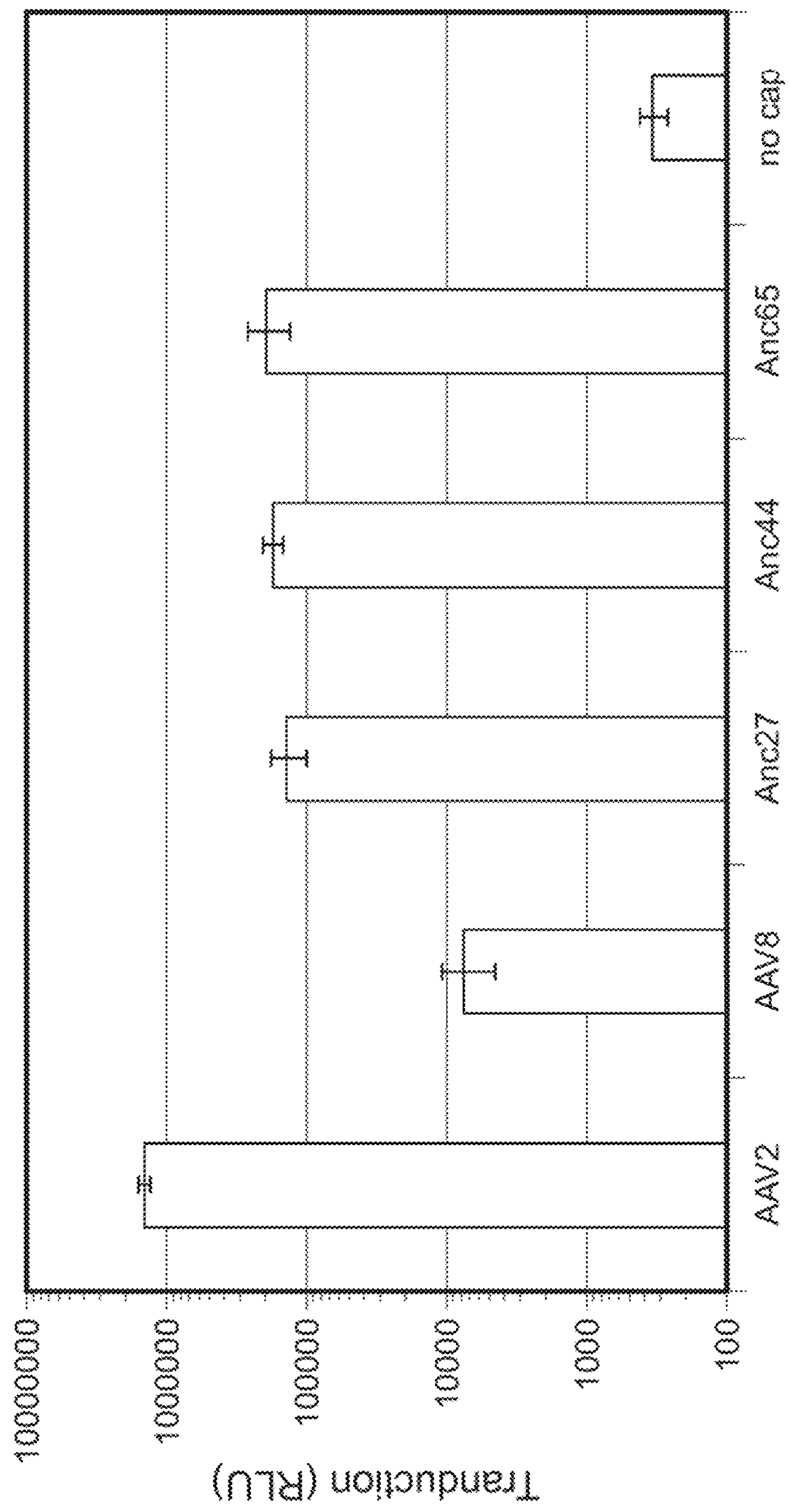
FIG. 7 is a graph showing the luciferase activity in HEK293 cells transduced with ancestral AAV vectors.

HEK293 cells were transduced, at equal multiplicity of infection (MOI) of $1\times10^{4}$ genome copies (GC) per cell, with two contemporary AAV vectors (AAV2/2 and AAV2/8) and three predicted ancestral AAV vectors (Anc80L27, Anc80L44, and Anc80L65). Each vector contained either a luciferase-encoding transgene or an eGFP-encoding transgene. Cells were imaged 60 hours later using the GFP channel of an AMG EvosFl Optical Microscope. FIG. 7 shows the luciferase expression following the in vitro transduction. Each of the ancestral AAV viruses demonstrated efficient transduction of HEK293 cells.

Example 5—In Vivo Retinal Transduction

Retinal transductions were performed to determine whether or not the ancestral AAV vectors are able to target murine retinal cells in vivo.

Murine eyes were transduced with $2\times10^{8}$ genome copies (GC) of three different ancestral AAVs (Anc80L27, Anc80L44, and Anc80L65) and a contemporary AAV (AAV2/8), all of which included an eGFP-encoding transgene. For transductions, each AAV vector was surgically delivered below the retina by generating a space between the photoreceptor and retinal pigment epithelium layer through delivery of a vector bolus with an injection device. The vector bolus was left in the sub-retinal space and the sub-retinal detachment resolved over time. GFP expression was monitored non-invasively by fundus photography of the retina of the animal following pupil dilation with Tropicamide™. All of the presented retinas demonstrated varying degrees of successful targeting of ancestral AAVs to the retina.

Retinal histology also was performed and visualized under fluorescent microscopy to identify the transduced cell type(s). Histology was performed on a murine retina transduced with the Anc80L65 ancestral AAV vector as described above. Anc80L65-mediated eGFP expression was evident in the outer nuclear layer (ONL), the inner segments (IS), and the retinal pigment epithelium (RPE), indicating that the ancestral Anc80L65 vector targets murine photoreceptors and retinal pigment epithelial cells.

Example 6—Neutralizing Antibody Assay

Neutralizing antibody assays are performed to evaluate whether or not an ancestral AAV virus is more resistant to antibody-neutralization than a contemporary AAV virus. Neutralizing antibody assays measure the antibody concentration (or the titer at which an experimental sample contains an antibody concentration) that neutralizes an infection by 50% or more as compared to a control in the absence of the antibody.

Serum samples or IVIG stock solution (200 mg/ml) are serially diluted by 2-fold, and undiluted and diluted samples are co-incubated with an ancestral AAV virus, Anc80L65, and a contemporary AAV virus, AAV2/8, at a MOI of $10^{4}$ for about 30 minutes at 37° C. Each virus includes a luciferase transgene. The admixed vector and an antibody sample then are transduced into HEK293 cells. For these experiments, the antibody sample used is intravenous immunoglobulin (IVIG), pooled IgGs extracted from the plasma of over one thousand blood donors (sold commercially, for example, as Gammagard™ (Baxter Healthcare; Deerfield, Ill.) or Gamunex™ (Grifols; Los Angeles, Calif.)). 48 hours following initiation of transduction, cells are assayed by bioluminescence to detect luciferase. Neutralizing antibody titer is determined by identifying the dilution of sample for which 50% or more neutralization (transduction of sample/transduction of control virus in absence of sample) is reached.

Example 7—Characterization of Anc80

Based on the methods described herein, the most probable Anc80 sequence (as determined through posterior probability) was obtained and designated Anc80L1 (SEQ ID NO:35 shows the nucleic acid sequence of the Anc80L1 capsid and SEQ ID NO:36 shows the amino acid sequence of the Anc80L1 VP1 polypeptide). The Anc80 probabilistic library also was synthesized using the sequences described herein by a commercial company and sub-cloned into expression vectors.

The Anc80 library was clonally evaluated for vector yield and infectivity in combined assays. Out of this screening, Anc80L65 (SEQ ID NO:23), as well as several other variants, were further characterized.

The Anc80 library and Anc80L65 were compared in terms of sequence difference (FIG. 8; % up from diagonal, # of amino acid differences below). Using NCBI-BLAST, the closest publically available sequence to Anc80L65 is rh10 (GenBank Accession No. AAO88201.1).

FIG. 9 shows that Anc80L65 produced vector yields equivalent to AAV2 (Panel A), generated virus particles under Transmission Electroscopy (TEM) (Panel B), and biochemically produced the AAV cap and the VP1, 2 and 3 proteins based on SDS page under denaturing conditions (Panel C) and Western Blotting using the AAV capsid antibody, B1 (Panel D). These experiments are described in more detail in the following paragraphs.

Figure 9A:
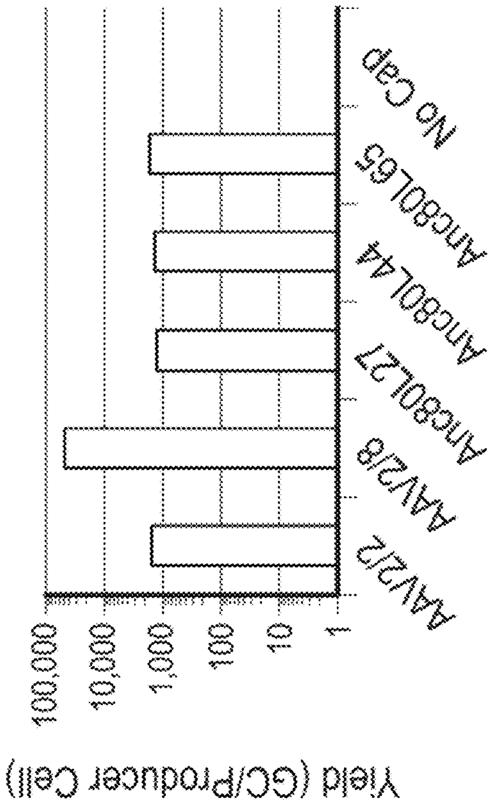
FIGS. 9A-D are images of experimental results demonstrating that Anc80L65 is capable of assembling and yielding particles of high titer. Panel A shows that Anc80L65 is able to produce vector yields equivalent to AAV2; Panel B is a TEM image of virus particles that include Anc80L65; Panel C shows that virus particles that include Anc80L65 are able to produce AAV cap VP1, 2 and 3 proteins based on SDS-PAGE gel under denaturing conditions; and Panel D shows a Western blot of Anc80L65 using the AAV capsid antibody, BI.

Briefly, AAV2/8, AAV2/2, AAV2/Anc80L27, AAV2/Anc80L44, and AAV2/Anc80L65 vectors were produced in small scale containing a reporter construct comprised of eGFP and firefly luciferase under a CMV promoter were produced in small scale. Titers of these small scale preparations of viruses were then obtained via qPCR. Based on these experiments, Anc80L27, Anc80L44, and Anc80L65 vectors were found to produce viral levels comparable to that of AAV2 (FIG. 9A).

Figure 9B:
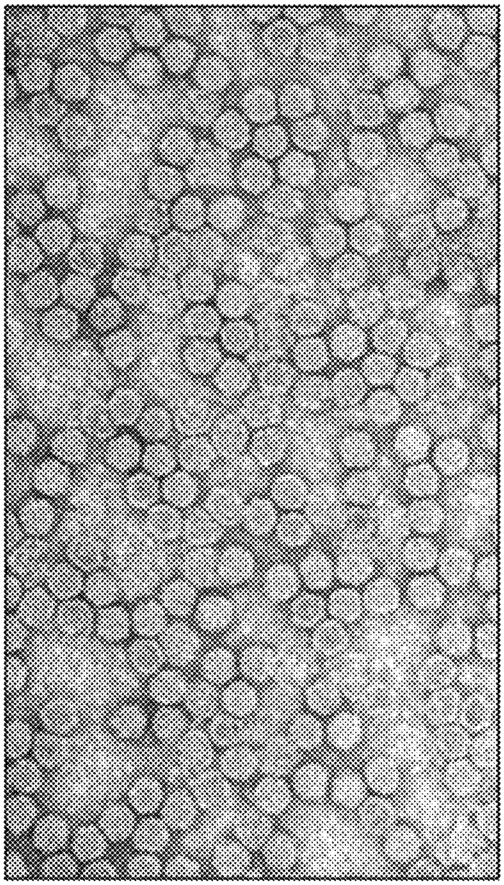

To confirm that the Anc80L65 capsid proteins assembled into intact virus-like-particles of the proper size and conformation, micrographs were obtained using transmission electron microscopy (TEM). A large scale, purified preparation of Anc80-L065 was loaded onto formvar coated copper grids and was then stained with uranyl acetate. Micrographs revealed intact, hexagonal particles with diameters between 20 and 25 nm (FIG. 9B).

Figure 9C:
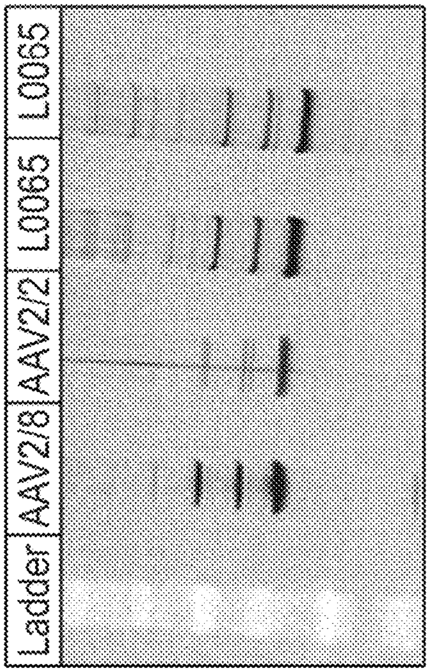
Figure 9D:
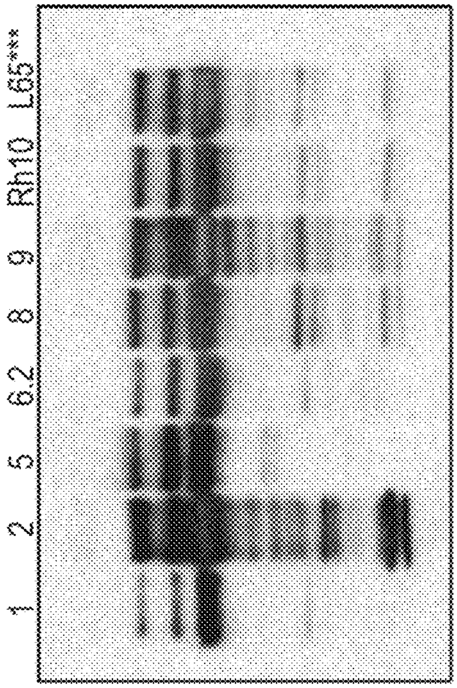

In order to determine whether the synthetic ancestral capsid genes were properly processed (i.e. spliced and expressed), large-scale purified preparations of AAV2/8, AAV2/2, and AAV2/Anc80L65 vectors were loaded onto an SDS-PAGE gel (1E10 GC/well) under denaturing conditions. Bands representing viral capsid proteins VP1, VP2, and VP3 were clearly present for each vector preparation (FIG. 9C). Western blotting with the AAV capsid antibody B1 further confirmed that these bands represented the predicted proteins (FIG. 9D).

In addition, FIG. 10 shows that Anc80L65 infected mammalian tissue and cells in vitro on HEK293 cells at MOI 10E4 GC/cell using GFP as readout (Panel A) or luciferase (Panel B) versus AAV2 and/or AAV8 controls. Anc80L65 also was efficient at targeting liver following an IV injection of the indicated AAV encoding a nuclear LacZ transgene (top row, Panel C), following direct intramuscular (IM) injection of the indicated AAV encoding GFP (middle row, Panel C), and following subretinal injection with the indicated AAV encoding GFP (bottom row, Panel C). These experiments are described in more detail in the following paragraphs.

Figure 10A:
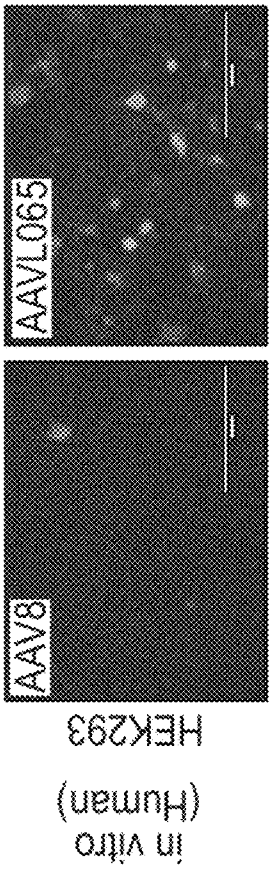
FIGS. 10A-C are images of experimental results demonstrating that Anc80L65 is able to infect cells in vitro on HEK293 cells using GFP as readout (Panel A) or luciferase (Panel B) versus AAV2 and/or AAV8 controls and also is efficient at targeting liver following an IV injection of AAV encoding a nuclear LacZ transgene (top row, Panel C: liver), following direct IM injection of an AAV encoding GFP (middle row, Panel C: muscle), and following sub-retinal injection with AAV encoding GFP (bottom row, Panel C: retina).
Figure 10B:
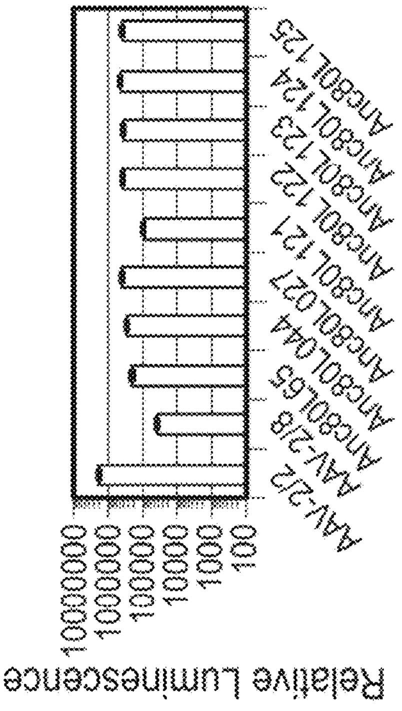

To obtain a relative measure of the infectivity of ancestral virions, crude preparations of AAV2/2, AAV2/8, AAV2/Anc80L65, AAV2/Anc80L44, AAV2/Anc80L27, AAV2/Anc80L121, AAV2/Anc80L122, AAV2/Anc80L123, AAV2/Anc80L124, and AAV2/Anc80L125 containing a bicistronic reporter construct that includes an eGFP and firefly luciferase sequences under control of a CMV promoter were produced. 96-well plates confluent with HEK293 cells were then subjected to transduction with each vector at an MOI of 1E4 GC/cell (titers obtained via qPCR as above). 48 hours later, fluorescent microscopy confirmed the presence of GFP in transduced cells (FIG. 10A). Cells were then assayed for the presence of luciferase (FIG. 10B), which determined that expression of luciferase in cells transduced with Anc80-derived vectors was in-between that of cells transduced with AAV8 (lower level of transduction) and AAV2 (higher level of transduction).

Figure 10C:
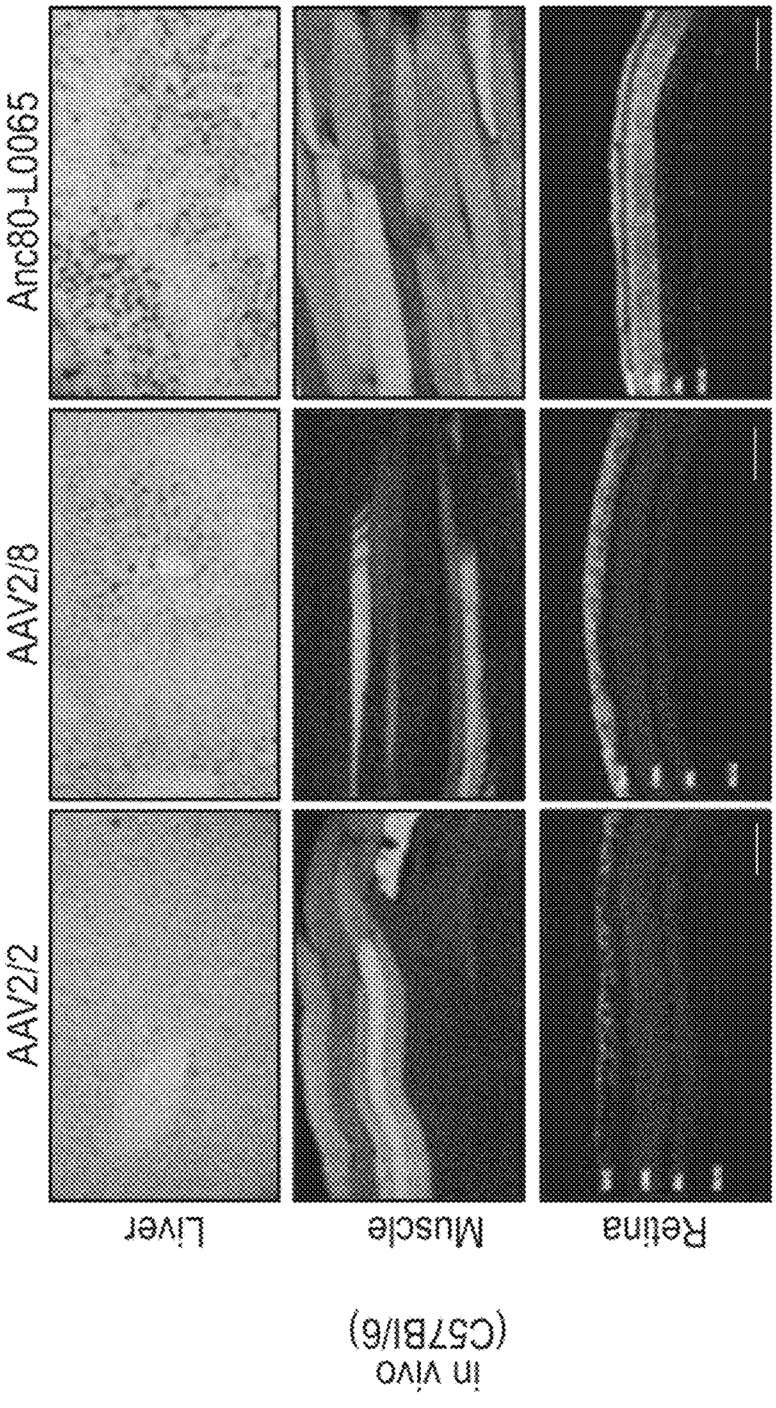

To assess the relative efficiency of gene transfer in an in vivo context, purified high-titer preparations of AAV2/2, AAV2/8, and AAV2/Anc80L65 were obtained. 3.9E10 GC of each vector, encapsidating a transgene encoding nuclear LacZ under control of a TBG promoter, were injected into C57BL/6 mice (3 mice per condition) via IP injection following general anesthetization. 28 days post-injection, mice were sacrificed and tissues were collected. Livers were sectioned via standard histological techniques and stained for beta-galactosidase. Sections were then imaged under a microscope and representative images are shown in FIG. 10C, top row.

Vectors of the same serotypes were then obtained containing a bicistronic transgene encoding eGFP and hA1AT under control of a pCASI promoter. To assess the ability of Anc80L65 to transduce murine skeletal muscle, 1E10 GC of each vector was injected into skeletal muscle of C57BL/6 mice (5 mice per condition) following general anesthetization. 28 days post-injection, mice were sacrificed, tissues were cryosectioned, and the presence of eGFP was assessed using fluorescent confocal microscopy (blue is DAPI, green is eGFP). Representative images are shown in FIG. 10C, middle row. These experiments demonstrated that Anc80L65 vectors were capable of transducing murine skeletal muscle via intramuscular injection.

Vectors of the same serotypes were obtained, this time encapsidating constructs encoding only an eGFP transgene under control of a CMV promoter. 2E9 particles were injected sub-retinally into C57BL/6 mice following general anesthetization. 28 days post-injection, mice were sacrificed and the eyes were collected, cryosectioned, and the presence of eGFP was assessed using fluorescent confocal microscopy (blue is DAPI, green is eGFP). Representative images are shown in FIG. 10C, bottom row. These experiments demonstrate that Anc80L65 vectors are able to transduce murine retina at a level that is comparable to AAV8 vectors.

Briefly, purified, high titer preparations of AAV2/8, AAV2/2, AAV2/rh32.33, and AAV2/Anc80L65 viral vectors encapsidating a bicistronic transgene that includes eGFP and firefly luciferase under control of a CMV promoter are obtained. These vectors are then either incubated with two-fold serial dilutions of IVIG (10 mg, 5 mg, 2.5 mg, etc.) or incubated without IVIG (1E9 GC per condition). Following incubation, vectors are used to transduce HEK293 cells at an MOI of 1E4 per well (one dilution per well). 48 hours later, the relative amounts of luciferase is assayed via luminescence assay.

Example 8—Generation of Additional Ancestral AAV Capsids

The most probable ancestral AAV capsid sequences (as determined through posterior probability) were then synthesized through a commercial lab (Gen9) and provided as linear dsDNA. These amino acid sequences were then compared to those of extant AAVs in order to ascertain the degree to which they differ (FIG. 11). Each ancestral VP1 protein differs from those of selected representative extant AAVs by between 3.6% and 9.3% (FIG. 11A), while the ancestral VP3 proteins differ by between 4.2 and 9.4% (FIG. 11B). At 89% sequence identity for VP1, And 110 is the closest reconstructed ancestral vector to AAV9, a potent CNS transducing vector. These capsids were each subcloned into AAV production plasmids (pAAVector2/Empty) via restriction enzyme digestion (HindIII & SpeI) and T4 ligation. These clones were confirmed via restriction digestion and Sanger sequencing, and medium scale preparations of plasmid DNA were then produced.

Figure 12:
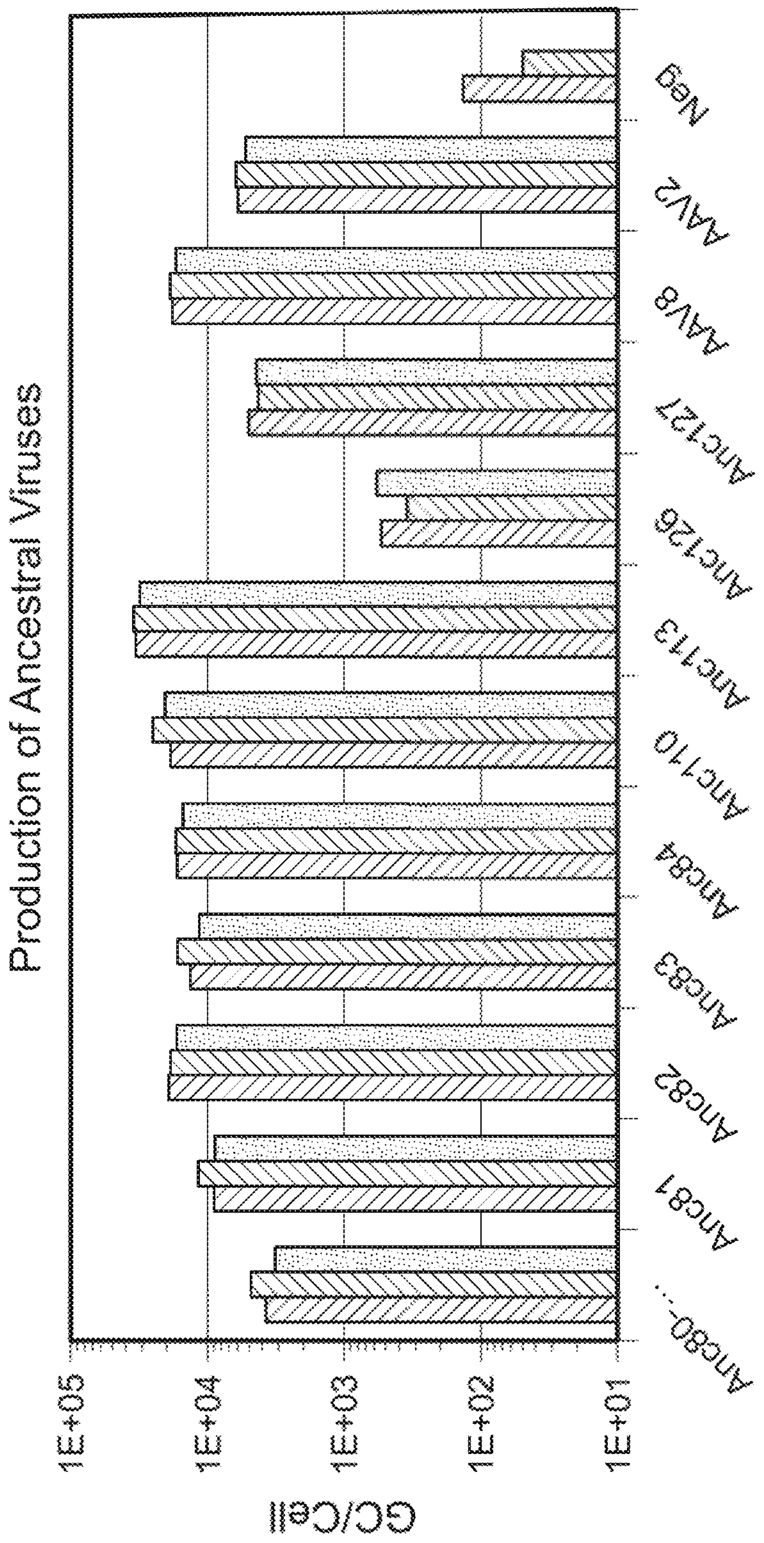
FIG. 12 is a graph that demonstrates that AAV vectors were produced in triplicate in small scale (6-well dishes). Crude viruses were assessed via qPCR to determine the absolute production of each vector.

Each of these plasmids were then used to produce AAV vectors containing a reporter gene encoding both eGFP and firefly luciferase. These vectors were produced in triplicate in small scale as previously described. Crude preparations of the virus were then titered via qPCR and were found to produce between 2.71% and 183.1% viral particles relative to AAV8 (FIGS. 12 and 13). The production and infectivity numbers of Anc110 are similar to those reported for AAV9. These titers were then used to set up a titer controlled experiment to assess relative infectivity. Anc126 was not titer controlled due to its significantly depressed production, and consequently, the data regarding the infectivity of Anc126 cannot be accurately compared to the infectivity of the other viruses in the experiment. The other vectors were used to transduce HEK293 cells at a multiplicity of infection (MOI) of 1.9E3 GC/cell.

Figure 14:
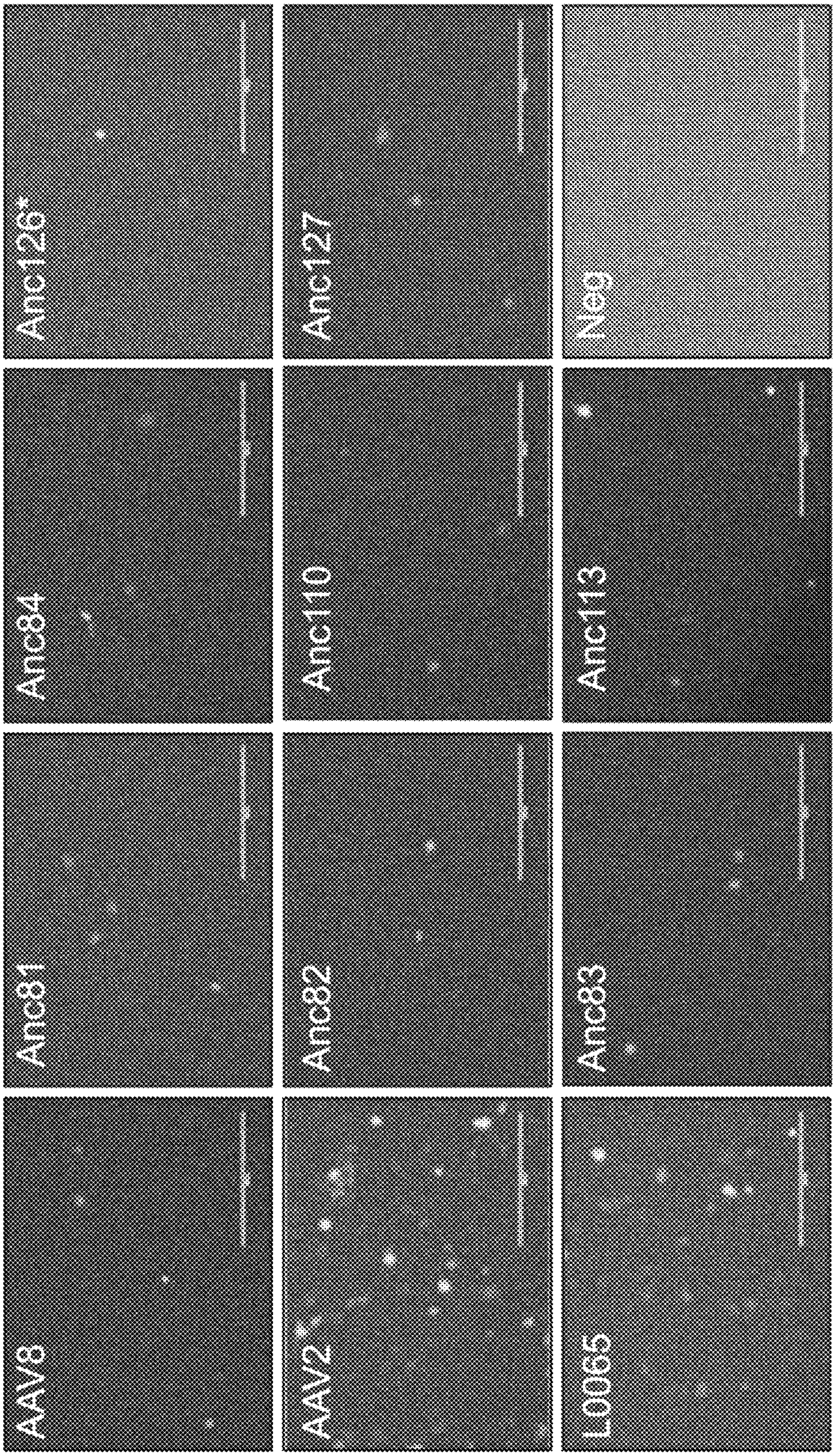
FIG. 14 are photographs that show the results of experiments in which 1.9E3 GC/cell of each vector was added to HEK293 cells (except for Anc126, in which case MOIs of 2.5E2-3.1E2 GC/cell were achieved). Sixty hours later, infectivity was assessed using fluorescence microscopy.
Figure 15:
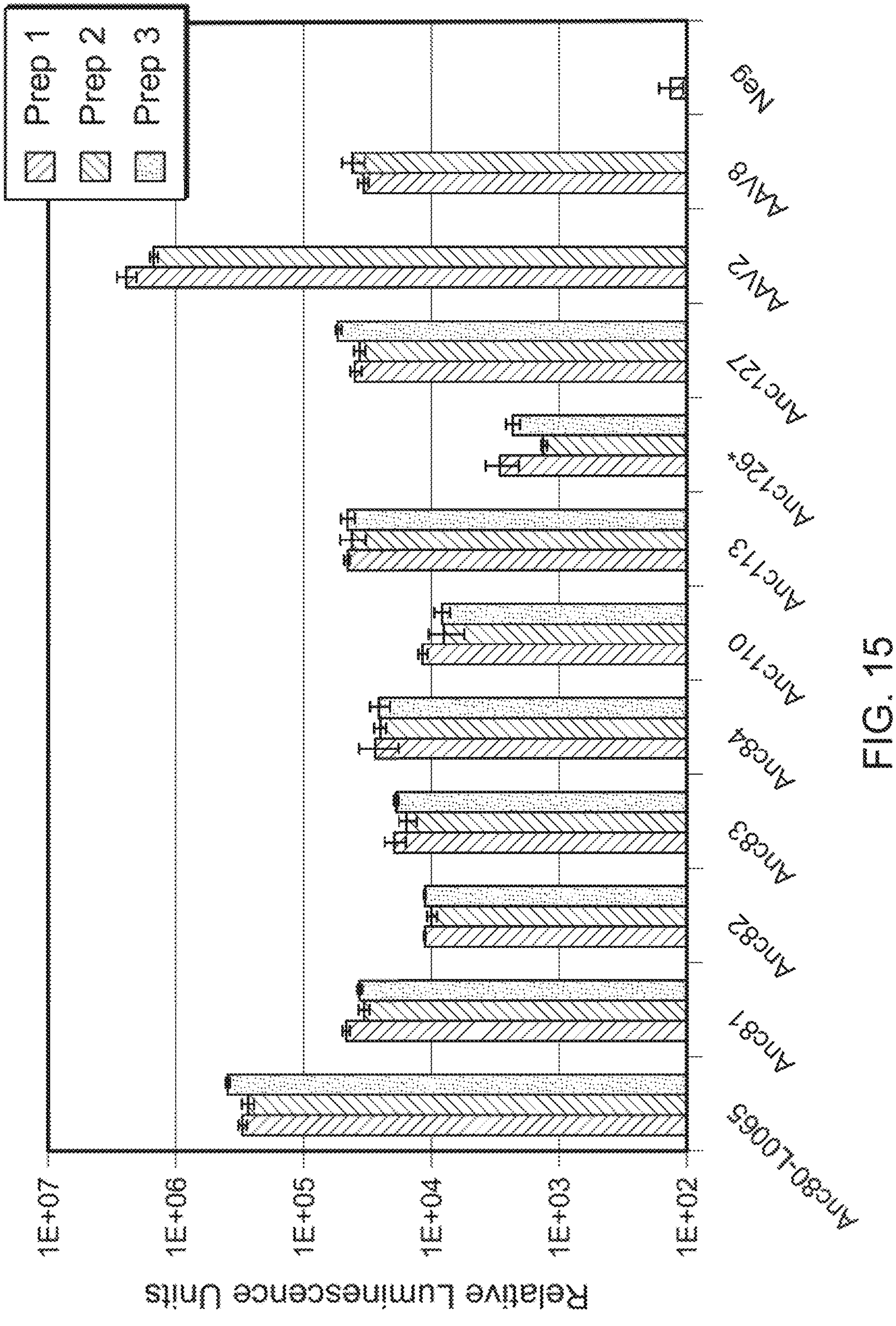
FIG. 15 is a graph showing the results of experiments in which the same cells from FIG. 14 were lysed and assayed for luciferase expression. As in FIG. 14, Anc126 was not titer controlled with the other vectors, but rather ranged from an MOI of 2.5E2-3.1E2 GC/cell.

60 hours post transduction, cells were assessed for GFP expression via fluorescence microscopy. eGFP positive cells were detected under each of the conditions except for the negative control (FIG. 14). This indicates that each of the ancestral sequences that were predicted, synthesized, and cloned, including Anc110, is capable of producing viable, infectious virus particles. To get an idea of the relative levels of infectivity, luciferase assays also were performed on the same cells. The results indicate that each of the ancestral vectors is capable of transducing HEK293 cells between 28.3% and 850.8% relative to AAV8 (FIGS. 15 and 16). It is noted that the transduction efficiency of Anc110 is similar to that reported for AAV9. Anc126 was excluded from the analysis of relative transduction since it was not titer-controlled.

In summary, eight novel ancestral AAV capsid genes were synthesized and used in the production of functional viral vectors along with AAV8, AAV2, Anc110, and the previously described Anc80L65 vectors. Production and infectivity were assessed in vitro and a summary of those findings is shown in FIG. 17. The in vitro production and infectivity of Anc110 was within the range that would be expected for AAV9 and other viruses that are able to pass through the blood-brain barrier.

Example 9—Vectored Immunoprophylaxis

In vectored immunoprophylaxis, gene therapy vehicles (such as AAV) are used to deliver transgenes encoding broadly neutralizing antibodies against infectious agents. See, for example, Balazs et al. (2013, Nat. Biotechnol., 31:647-52); Limberis et al. (2013, Sci. Transl. Med., 5:187ra72); Balazs et al. (2012, Nature, 481:81-4); and Deal et al. (2014, PNAS USA, 111:12528-32). One advantage of this treatment is that the host produces the antibodies in their own cells, meaning that a single administration has the potential to confer a lifetime of protection against etiologic agents.

Example 10—Drug Delivery Vehicles

LUCENTIS (ranibizumab) and AVASTIN (bevacizumab) are both anti-angiogenesis agents based on the same humanized mouse monoclonal antibodies against vascular endothelial growth factor A (VEGF-A). Although bevacizumab is a full antibody and ranibizumab is a fragment (Fab), they both act to treat wet age-related macular degeneration through the same mechanism—by antagonizing VEGF. See, for example, Mao et al. (2011, Hum. Gene Ther., 22:1525-35); Xie et al. (2014, Gynecol. Oncol., doi: 10.1016/j.ygyno.2014.07.105); and Watanabe et al. (2010, Gene Ther., 17:1042-51). Because both of these molecules are proteins, they can be encoded by DNA and produced in cells transduced with vectors containing a transgene, and are small enough to be packaged into AAV vectors.

Example 11—Ancestral Sequence Reconstruction of AAV Capsids

Figure 25:
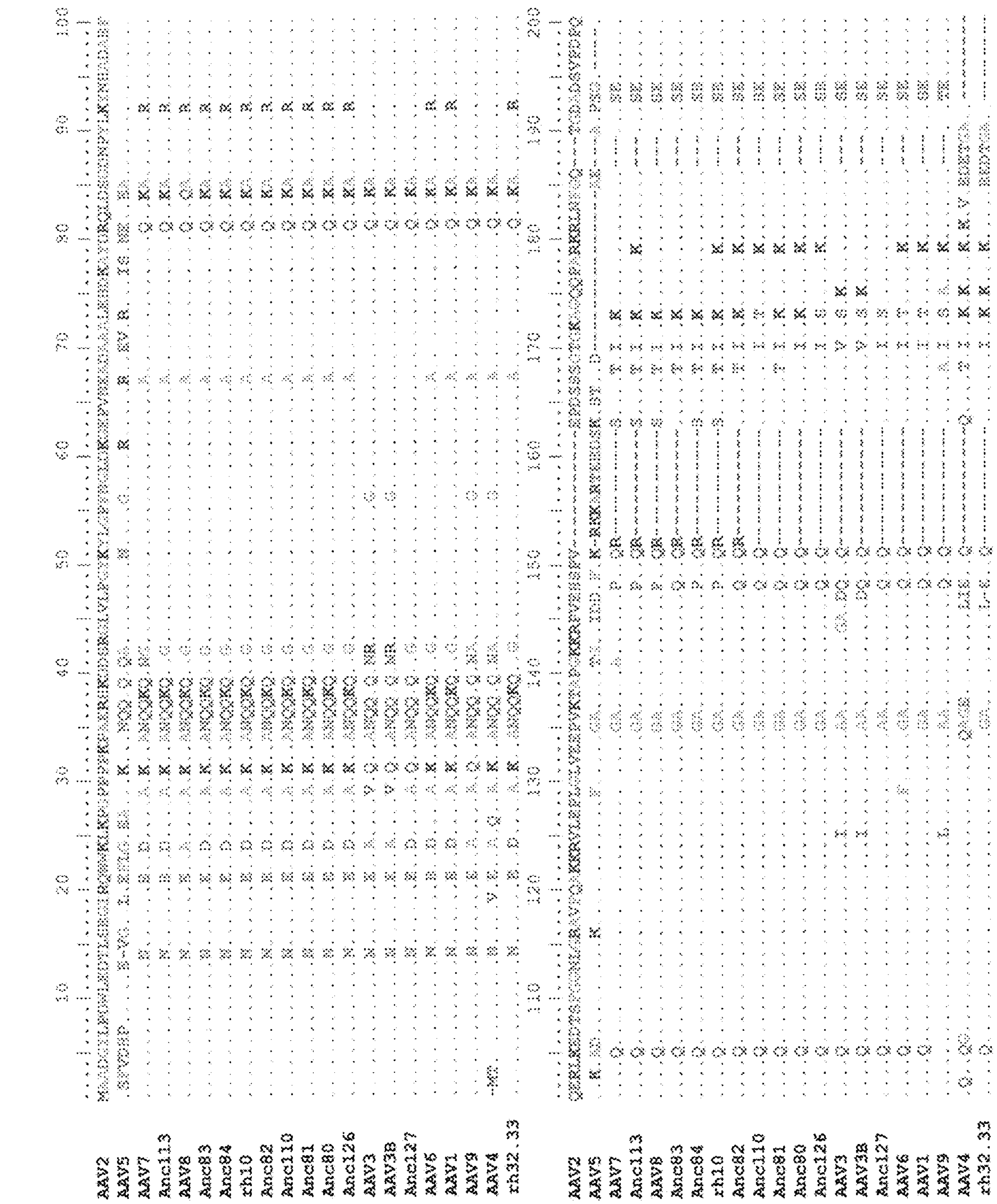
FIG. 25 is a multiple sequence alignment of the VP1 polypeptides from AAV isolates used in the ancestral sequence reconstruction (see, also, FIGS. 18 and 23 above). AAV2 (SEQ ID NO:31); AAV5 (SEQ ID NO:40); AAV7 (SEQ ID NO:34); Anc113 (SEQ ID NO:13); AAV8 (SEQ ID NO:27); Anc83 (SEQ ID NO:7); Anc84 (SEQ ID NO:9); rh10 (SEQ ID NO:41); Anc82 (SEQ ID NO:5); Anc110 (SEQ ID NO:42); Anc81 (SEQ ID NO:3); Anc80 (SEQ ID NO:1); Anc126 (SEQ ID NO:15); AAV3 (SEQ ID NO:32); AAV3B (SEQ ID NO:33); Anc127 (SEQ ID NO:17); AAV6 (SEQ ID NO:29); AAV1 (SEQ ID NO:30); AAV9 (SEQ ID NO:28); AAV4 (SEQ ID NO:44); rh32.33 (SEQ ID NO:45).
Figure 25:
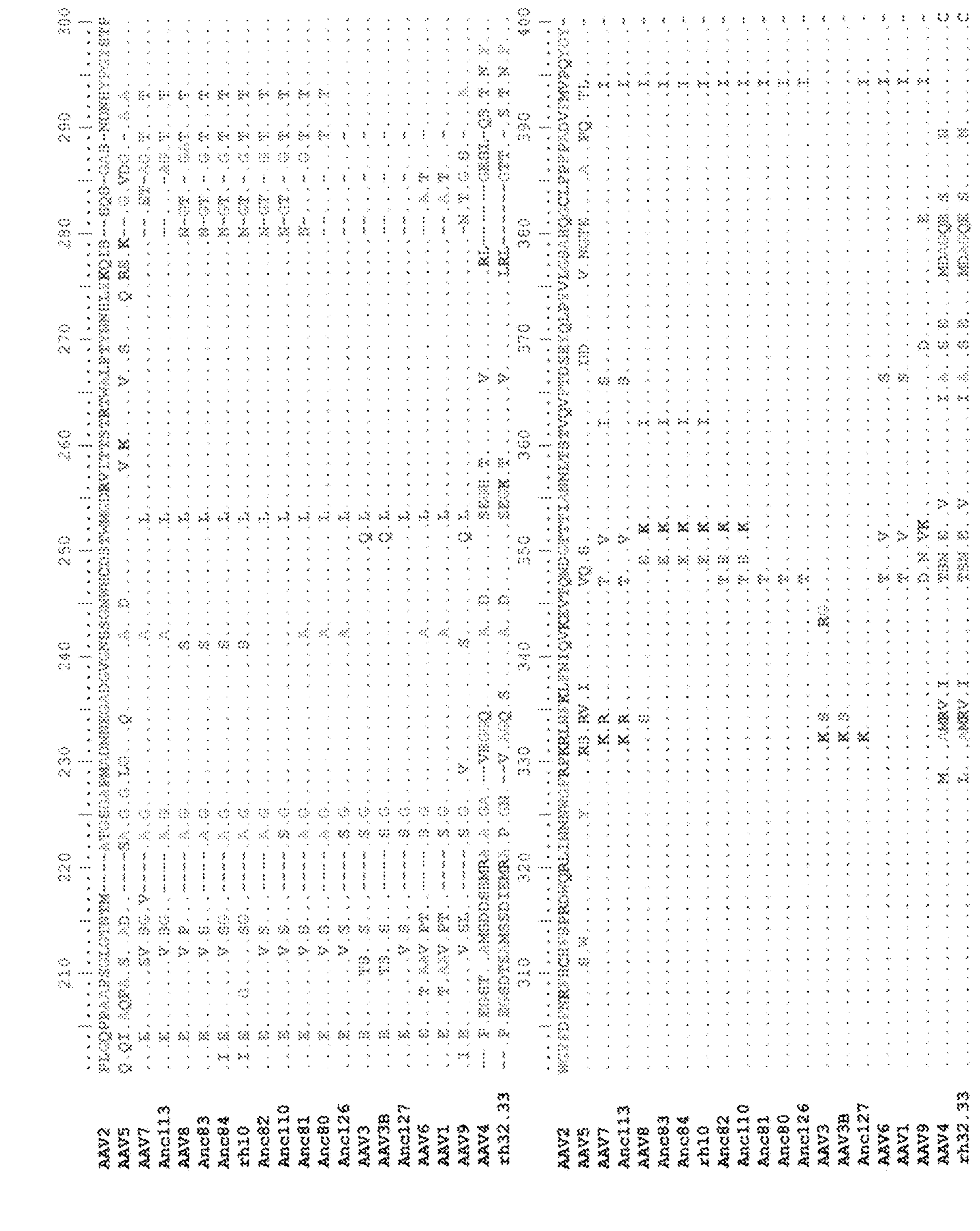
Figure 25:
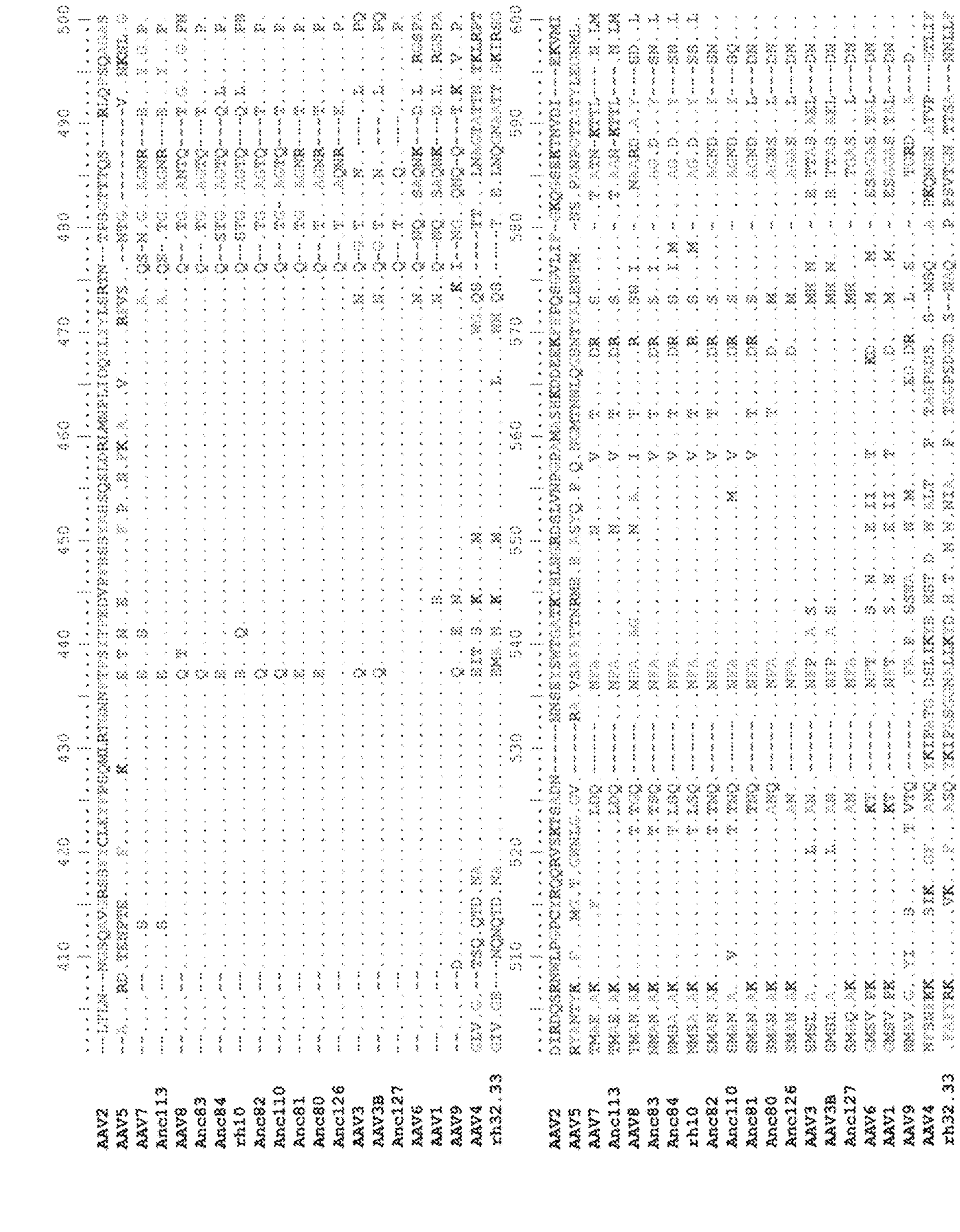
Figure 25:
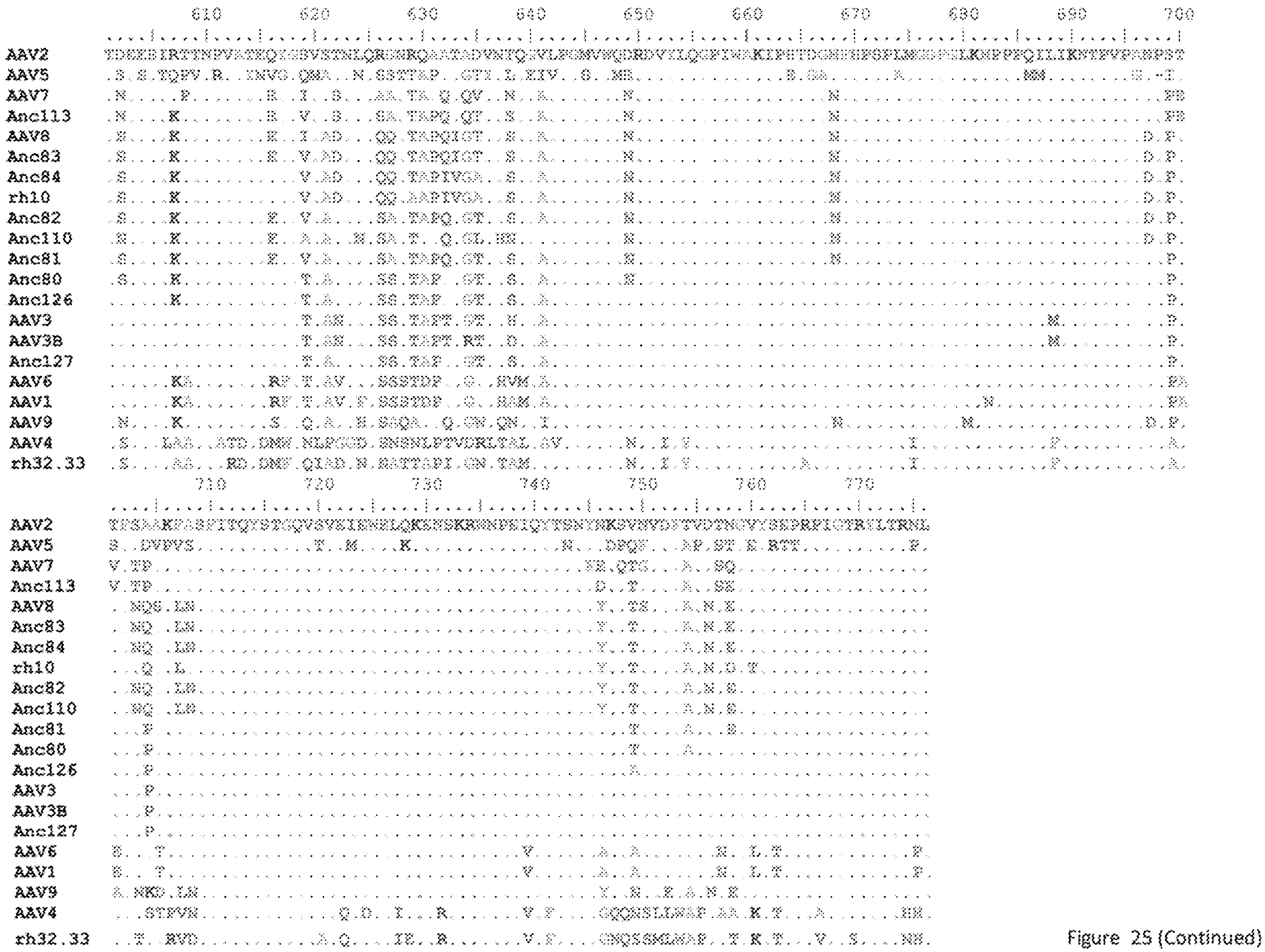
Figure 26:
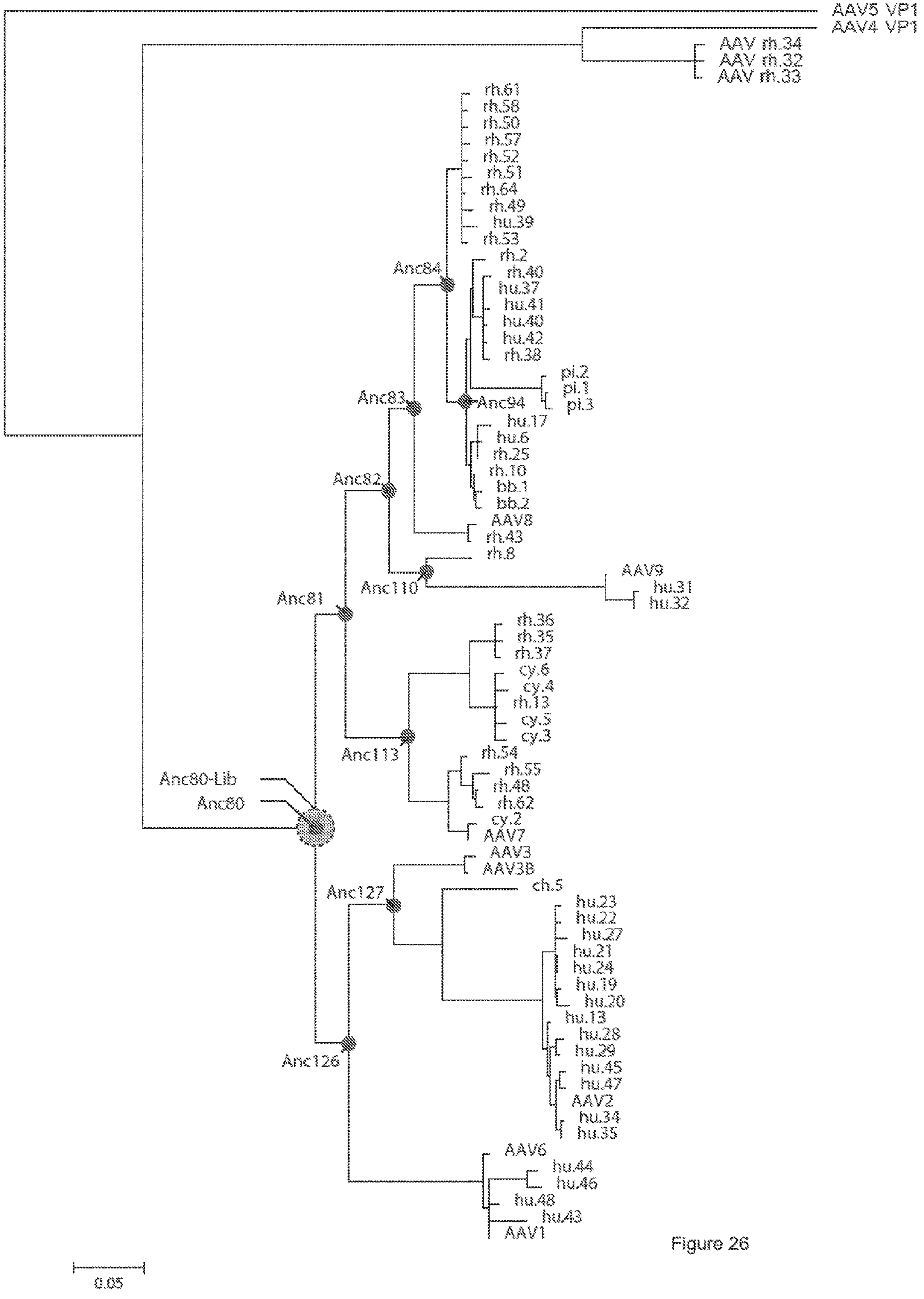
FIG. 26 shows a full phylogeny and reconstructed nodes of the AAV evolutionary lineage (see, also, FIG. 18 above). Maximum-likelihood phylogeny relating 75 isolates of AAV. Red circles represent evolutionary intermediates reconstructed through ASR. Blue circle represents a library of probabilistic space built around Anc80.

Ancestral capsid sequences were reconstructed using maximum-likelihood methods as in Finnigan et al. (2012, Nature, 481:360-4). An alignment of 75 AAV capsids (GenBank Accession Numbers provided herein) was generated using PRANK v.121002 using the -F option (Loytynoja & Goldman, 2005, PNAS USA, 102:10557-62; Loytynoja & Goldman, 2008, Science, 320:1632-5) and the JTT+F+G model was determined to be the phylogenetic model of best fit through the Aikake Information Criterion as implemented in ProtTest3 (Darriba et al., 2011, Bioinform., 27:1164-5). The full alignment can be seen in FIG. 25. The alignment and best-fit model were then used to infer a phylogeny through PhyML 3.0 (Guindon et al., 2010, System. Biol., 59:307-21), which was evaluated through the approximate likelihood-ratio test (aLRT) (Anismova & Gascuel, 2006, Syst. Biol., 55:539-52) as implemented in PhyML. A detailed version of the phylogeny with all AAVs included in the analysis is shown in FIG. 26. Ancestral capsid sequences were then inferred using PAML 4.6 (Yang, 2007, Mol. Biol. Evol., 24:1586-91) through the Lazarus package developed by the Thornton group. As indicated herein, the Anc110 reconstructed ancestral vector is evolutionarily close to AAV9 and Rh.8, both of which are known to be potent CNS transducing vectors.

In order to compensate for the uncertainty inherent to the reconstruction, a script was written to assess the computed posterior probabilities to identify ambiguously reconstructed sites. All positions along the ancestrally reconstructed capsid having more than one amino acids with posterior probabilities greater than 0.3 were included. Eleven such sites were identified, each with two probable amino acids. These eleven dimorphic sites were then incorporated into a DNA library using the codons from a modern virus (rh.10). Because the reconstruction did not consider the coevolution of AAP and the capsid, the AAP open-reading frame was ablated by changing the non-canonical CTG start codon to CAG during library design. In addition, another downstream ATG also in the AAP ORF was ablated by changing the codon to AAG. These modifications did not alter the amino acids in the cap ORF. The DNA library was then synthesized by DNA2.0 and subsequently sub-cloned into expression vectors via restriction enzyme digest and ligation.

Example 12—Vectors and Sequences

Adeno-associated viral vectors were pseudotyped with either extant or ancestral viral capsids. Extant capsids include AAV1 (GenBank Accession No. AAD27757.1), AAV2 (GenBank Accession No. AAC03780.1), AAV5 (GenBank Accession No. AAD13756.1), AAV6.2 (GenBank Accession No. EU368910), Rh.10 (GenBank Accession No. AA088201.1), AAV8 (GenBank Accession No. AAN03857.1), AAV9 (GenBank Accession No. AAS99264.1), and Rh32.33 (GenBank Accession No. EU368926). Ancestral AAV capsids include Anc80L65, Anc81, Anc82, Anc83, Anc84, Anc110, Anc113, Anc126, and Anc127 (submissions to GenBank pending). Vector transgene cassettes included CMV.eGFP.T2A.ffLuciferase.SVPA, CMV.ffLucifease.SVPA.(in vitro studies), TBG.LacZ.RBG (liver), TBG.eGFP.WPRE.bGH (liver and muscle immunization study), CASI.hA1AT.FF2A.eGFP.RBG (liver, muscle), and CMV.eGFP.WPRE (retina).

Example 13—Sequence-Structure Analysis

A pseudoatomic model of Anc80L65 VP3 was generated with the SWISS-MODEL structure homology modeling server (Biasini et al., 2014, Nucl. Acids Res., 42:W252-8), using AAV8 crystal structure (PDB 2QA0) as a template. AAV2 (PDB 1LP3), AAV8 (PDB 2QA0) and Anc80 VP3 structures were further superimposed and color-coded according to residue conservation, using the UCSF Chimera package (Pettersen et al., 2004, J. Comp. Chem., 25:1605-12). A structural alignment of Anc80, AAV2 and AAV8 VP3 was then generated and completed by a non-structural alignment of the VP1/2 domains of these three serotypes, generated with the T-coffee alignment package (Notredame et al., 2000, J. Mol. Biol., 302:205-17). The spatial distribution of the mutations separating Anc80L65 and AAV8 was also visualized at the inner and outer surface of AAV8 trimer structure, where the variable residues in the structural alignment of Anc80L65 and AAV8 VP3 were represented in blue, and polymorphic residues in red.

Example 14—In Vitro Characterization of AAV Ancestral Lineage Vectors

To identify and characterize functional AAV capsids within the Anc80Lib, individual clones from the subcloned DNA library were isolated and used to produce luciferase-containing vectors in either 6-well or 96-well with AAP2 provided in trans. Crude vector was isolated by filtering cell lysate through a 0.4 μm filter after 48 hours had elapsed since transfection. Next, equal volumes of this crude vector preparation were added to 96-well plates confluent with HEK293 cells which were evaluated for their luciferase activity an additional 48 hours later. In total, 776 clones were evaluated. Crude preparations of vector containing a CMV driven luciferase were produced by triple transfection in a 6-well format, supplementing AAP in trans to ancestral AAV vectors. In total, three different independent biologic replicates were produced per vector. DNAseI resistant transgenes were quantified as above. These crude preparations of virus were each then evaluated for their ability to transduce HEK293 cells in technical triplicates at an MOI of $1.9\times10^3$ GC/cell with the exception of Anc126, which was added at MOIs between $2.1\times10^2$ and $3.5\times10^2$ GC/cell. After 48 hours had elapsed, the transduced cells were assessed for luciferase via luminescence assay.

Example 15—AAV Vector Preparation

Large-scale polyethylenimine (PEI) transfections of AAV cis, AAV trans, and adenovirus helper plasmid were performed in a 10-layer hyperflask (Corning) with near confluent monolayers of HEK 293 cells. Plasmids were transfected at a ratio of 2:1:1 (260 μg of adenovirus helper plasmid/130 μg of cis plasmid/130 μg of trans plasmid). Transfections for production of Anc vectors were supplemented with pAAP2 in equivalent amounts as the AAV cis plasmid. PEI Max (Polysciences, Warrington, Pa.)/DNA ratio was maintained at 1.375:1 (w/w). The transfection and downstream purification process were performed as previously described (Lock et al., 2010, Hum. Gene Ther., 21:1259-71). DNAseI-resistant vector genomes copies were used to titrate AAV preparations by TaqMan qPCR amplification (Applied Biosystems 7500, Life Technologies) with primers and probes detecting promoter, transgene, or polyadenylation signal coding regions of the transgene cassette. The purity of the large-scale preparations was evaluated by SDS-PAGE gel electrophoresis.

Example 16—Structural and Biophysical Vector Characterization

Anc80L65 particle morphology was assessed by transmission electron microscopy loading 5 μL of a purified preparation of Anc80L65 vector onto formvar-coated 400-mesh copper grids and staining with uranyl acetate. Empty/Full particle ratios were determined through analytical ultracentrifugation. The content of a 500 μL of 10-30 μg/mL, glycerol-free Anc80L65 sample was analyzed using the Beckman Coulter ProteomeLab XL-I analytical ultracentrifuge available at the MIT biophysical facility. The experiment was conducted at 20° C., 15,000 rpm, using an eight-hole (50 Ti) rotor. Sedimentation profiles were acquired at regular time points by refractive index optical measurements. The Lamm equation was solved using the software SEDFIT (Schuck et al., 2002, Biophys. J., 82:1096-111), and a sedimentation coefficient distribution analysis was run to identify the different species contained in the AAV sample. The thermal stability of Anc80L065 was evaluated by UV fluorescence spectroscopy and Differential Scanning Fluorescence (DSF). For tryptophan fluorescence (Ausar et al., 2006, J. Biol. Chem., 281:19478-88) each serotype, six 4.5 μL aliquots were prepared in 200 μg Eppendorf tubes, incubated for 5 min at 30° C., 45° C., 60° C., 75° C., 90° C. or 99° C., spun down, cooled down at room temperature for 5 min and loaded in duplicates (2 μL each) onto a Take 3™ Micro Volume Plate (Bio-Tek). Samples were irradiated at 293 nm and emission spectra were acquired from 323 to 400 nm with a resolution of 1 nm, using a Synergy HI Hybrid Plate Reader (Bio-Tek). Sample and blank emission spectra were further smoothed using a moving average filter (span: 15). After background subtraction, the maximum emission wavelength was determined for each serotype and for each temperature condition. These wavelength values were subsequently plotted as a function of the temperature to derive the thermal stability profiles of the different AAV serotypes. For differential scanning fluorescence (Rayaprolu et al., 2013, J. Virol., 87:13150-60), 25 μL of each AAV was supplemented with 5× SYPRO® Orange (Life Technologies) were loaded into a 96-well PCR plate (Denville Scientific Inc.) and spun down for 2 min at 2000 rpm, exposed to a temperature gradient (30-99° C., 0.1° C./6 s) while monitoring the fluorescence of the SYPRO® Orange dye, using a Reaplex 2S MasterCycler Real-Time PCR machine (Eppendorf) (excitation: 450 nm; emission: 550 nm). In each assay, 25 μL FFB (21-031, Corning) and 25 μL of a 0.25 mg/mL lysozyme solution (Sigma-Aldrich), both supplemented with 5× SYPRO® Orange, were used as negative and positive controls, respectively. The fluorescence of 254 AAV vectors was also monitored in the absence of the dye for fluorescence background subtraction. Fluorescence intensity was further normalized between 0 and 100% and plotted as a function of the temperature.

Example 17—Murine Experiments

C57BL/6 male mice (6-8 weeks old) were purchased from Charles River Laboratories (Wilmington, Mass.) and kept at the Schepens Eye Research Institute (SERI) Animal Facility. All animal procedures were performed in accordance with protocols approved by the Institute of Animal Care and Use Committees at SERI. For liver-targeted gene transfer studies received 100 μl single intraperitoneal injection or a single retro-orbital sinus vein injection in 150 For muscle-targeted eGFP experiments, 50 μl was injected into the rear-right gastrocnemius. GoldenRod animal lancets (MEDIpoint, Inc.) were used for submandibular mouse bleed. Brown capped tubes (Micro tube 1.1 ml Z-Gel, Sarstedt) were used for serum collections. Vector biodistribution studies were performed on tissues including liver, heart, kidney, lung, and spleen from mice sacrificed at 28 dpi of vector administration. To visualize eGFP expression in liver, tissues were fixed overnight in 4% Para-formaldehyde (PFA), washed in phosphate-buffered saline PBS for 30 min, sequentially incubated in 10%, 20% and 30% sucrose gradients and frozen in O.C.T compound (Sakura Finetek USA, Torrance, Calif.). Mouse liver expression of lacZ was measured using β-Gal Staining kit (Life Technologies). 4% Para-formaldehyde fixed liver tissue was sectioned at 10 μm. Tissue sections were washed with PBS to remove residual fixative and stained at 37° C. using commercial staining solutions (400 mM Potassium ferricyanide, 400 mM Potassium ferrocyanide, 200 mM magnesium chloride, X-gal 95-bromo-4-chloro-3-indolyl-β-D-galactopyranoside)) for 0.5-2 h. Cryosections were prepared at 10 μm. To visualize eGFP expression in muscle, tissues were mounted on cork disks holding 10% Gum Tragacanth (Sigma-Aldrich Cat. No. G1128) and flash frozen using liquid nitrogen—150 c cooled Isopentane (Sigma-Aldrich 27,034-2). Muscle cryosections were prepared at 10 μm. Subretinal injections were performed with a volume of 2 μl and absolute dose per animal of $2\times10^9$GC. Each vector was injected in a total of 4 eyes per serotype analysed. Animals were euthanized at 4 weeks post injection and eyes were collected for histological analysis. Enucleated eyes were fixed in 4% paraformaldehyde (PFA) for 1 hour on ice and then embedded in OCT and frozen prior to cryosectioning. Retinal sections were stained with DAPI (1 μg/ml) for 10 minutes and slides mounted for confocal imaging.

Example 18—Non-Human Primates Models

Experiments with rhesus monkeys were performed at New England Primate Research Center (Harvard Medical School). All experimental procedures were approved by the Office for Research Subject Protection, Harvard Medical Area (HMA) Standing Committee on Animals, the Harvard Medical School Institutional Animal Care and Use Committee. Animals were sedated with ketamine or telazol in combination with dexdomitor. Viral vectors expressing a secreted rhCG were administered intravenously in a 20 ml volume at a rate of 1 ml/min. After recovering from the injection, the animals were monitored clinically for general wellbeing and followed for 2 months. During this time, phlebotomies were performed at regular intervals to evaluate immune response to AAV and toxicity. After 70 days monkeys were euthanized, and liver samples were harvested.

Example 19—Quantification of Human Alpha1-Antitrypsin (hA1AT)

The expression level of hA1AT in the serum samples was quantified using ELISA. Plates were coated with primary coating rabbit anti-A1AT antibody (Sigma) at 1000 ng/well and incubated at 4° C. overnight. Plates were washed and blocked for 2 hours. Serum samples were diluted five-fold and incubated at 4° C. overnight. HRP-conjugated goat anti-human A1AT antibody (Abcam) was incubated for 2 hours. ABTS peroxidase substrate was added; $OD_{405\ nm}$ values were measured using a spectrophotometer plate-reader within 1 hour.

Example 20—Tissue Biodistribution

Snap frozen tissue was proteinase K digested and genomic DNA (gDNA) was extracted using Blood & Cell Culture DNA Mini kit (Qiagen) as indicated. Isolated gDNA was quantified using the BioTek plate reading spectrophotometer (Biotek Instruments, Inc. Winooski, Vt.). Viral genome (vg) distribution in diploid cells were detected and quantified by QPCR using Applied Biosystems® 7500 Real-Time PCR Systems with TaqMan®PCR master mix reagents (Applied Biosystems®) and transgene-specific primer/probes as previously described (Wang et al., 2010, Mol. Ther., 18:118-25).

Example 21—mRNA Expression

Total RNA was isolated using Qiagen RNeasy mini kit (Qiagen). Total RNA (1 μg) was DNase treated and reverse-transcribed into cDNA using Qiagen QuantiTect Reverse Transcription Kit (Qiagen). Real-time mRNA expression was detected and quantified using Applied Biosystems® 7500 Real-Time PCR Systems with TaqMan®PCR master mix reagents with specific primer/probe reaction mixtures; GAPDH (Rh02621745_g1), rhesus Chorionic Gonadotropin (Rh02821983_g1). TaqMan custom primer/probe suggested reaction conditions were applied.

Example 22—Neutralizing Antibody Assay

NABs were assessed in vitro as previously described (Calcedo et al., 2009, J. Infect. Dis., 199:381-90) with the following modifications. Serum from rabbits pre-immunized with AAV1, AAV2, AAV5, AAV6, AAV8, AAV9, rh.10 and rh32.33 (a kind gift from Dr. Roberto Calcedo and James M. Wilson, UPenn) (Gao et al., 2004, J. Virol., 78:6381-88) was serially diluted 1:40 to 1:20,971,520 and incubated with $10^9$ GC particles of either matching serotype or Anc80L65 carrying a CMV./uciferase2.SVPA transgenic construct for 1 h at 37° C. The mixture was then added to HEK-293 cells on a 96-well plate infected with MOI (multiplicity of infection)=20 of human adenovirus 5 (hAd5) 24 h prior. The cells were incubated for 48 h after which D-luciferin containing buffer was added and luminescence was measured using Synergy H1 microplate reader (BioTek; Winooski, Vt.). Luminescence was normalized against control cells infected with AAV incubated without serum. A neutralizing titer was determined at the dilution at which luminescence was <50% compared with control wells.

Example 23—in Silico Ancestral Sequence Reconstruction of AAV Capsid Protein

In lieu of attempting to isolate an intact ancestral viral sequence from proviral DNA or archeological samples, contemporary AAV sequence data was integrated through phylogenetic analysis and maximum-likelihood ASR in order to infer the putative ancestral amino-acid sequence for the AAV Cap. A total of 75 sequences AAV serotype isolates and variants from previous biomining efforts (Gao et al., 2003, PNAS USA. 100:6081-6; Gao et al., 2004, J. Virol., 78:6381-8; Gao et al., 2005, Current Gene Ther., 5:285-97) led to a robust AAV Cap phylogeny generated with PHYML (Guindon et al., 2010, System. Biol., 59:307-21) with AAV5 as an outlier. Only full length AAV capsids were included in this analysis that were (a) naturally occurring in primate populations, (b) previously demonstrated to assemble and infect efficiently, and (c) not known to have arisen through recombination events in its natural history, as traditional phylogenic analysis and ASR do not account for horizontal evolutionary events. The dendrogram in FIG. 18 models the evolutionary path of AAV with early speciation of AAV4, and 5 serotypes, parallel to a single node, named Anc80, from which most known contemporary AAVs evolved. These serotypes include AAV1, 2, 8 and 9, currently under clinical development in gene therapy trials. Nodes in this phylogeny were named Anc and numbered sequentially. To validate the approach described herein of ASR on AAV, Anc80 was chosen as a node to develop into a recombinant virus for possible use as a gene therapy vector.

Figure 18:
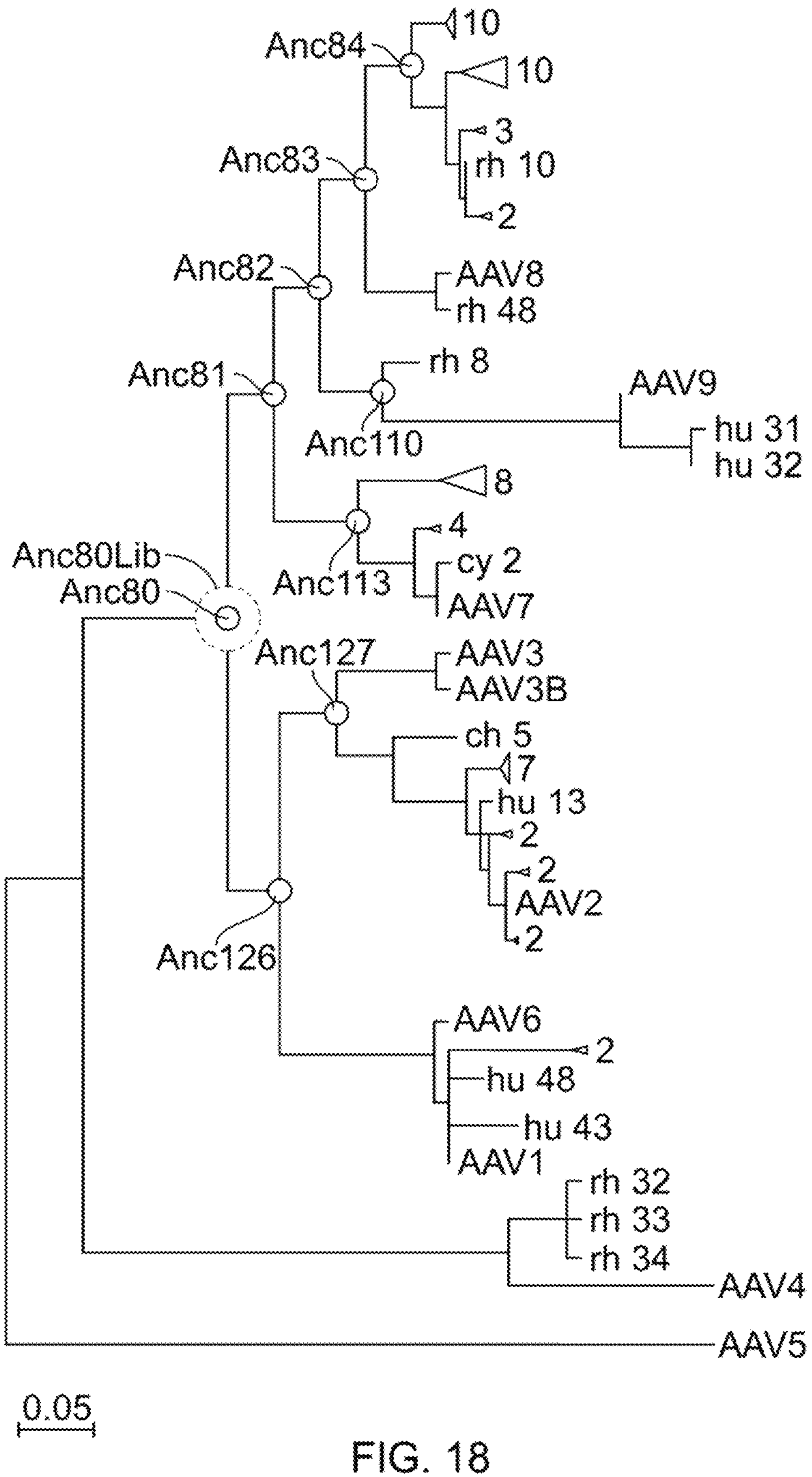
FIG. 18 is a phylogeny and ASR of the AAV evolutionary lineage created using maximum-likelihood phylogeny and 75 different isolates of AAV. Red circles represent evolutionary intermediates reconstructed through ASR. The blue circle represents a library of probabilistic space built around Anc80. Subclades are collapsed for clarity. The full phylogeny is presented in FIG. 24.
Figure 19A:
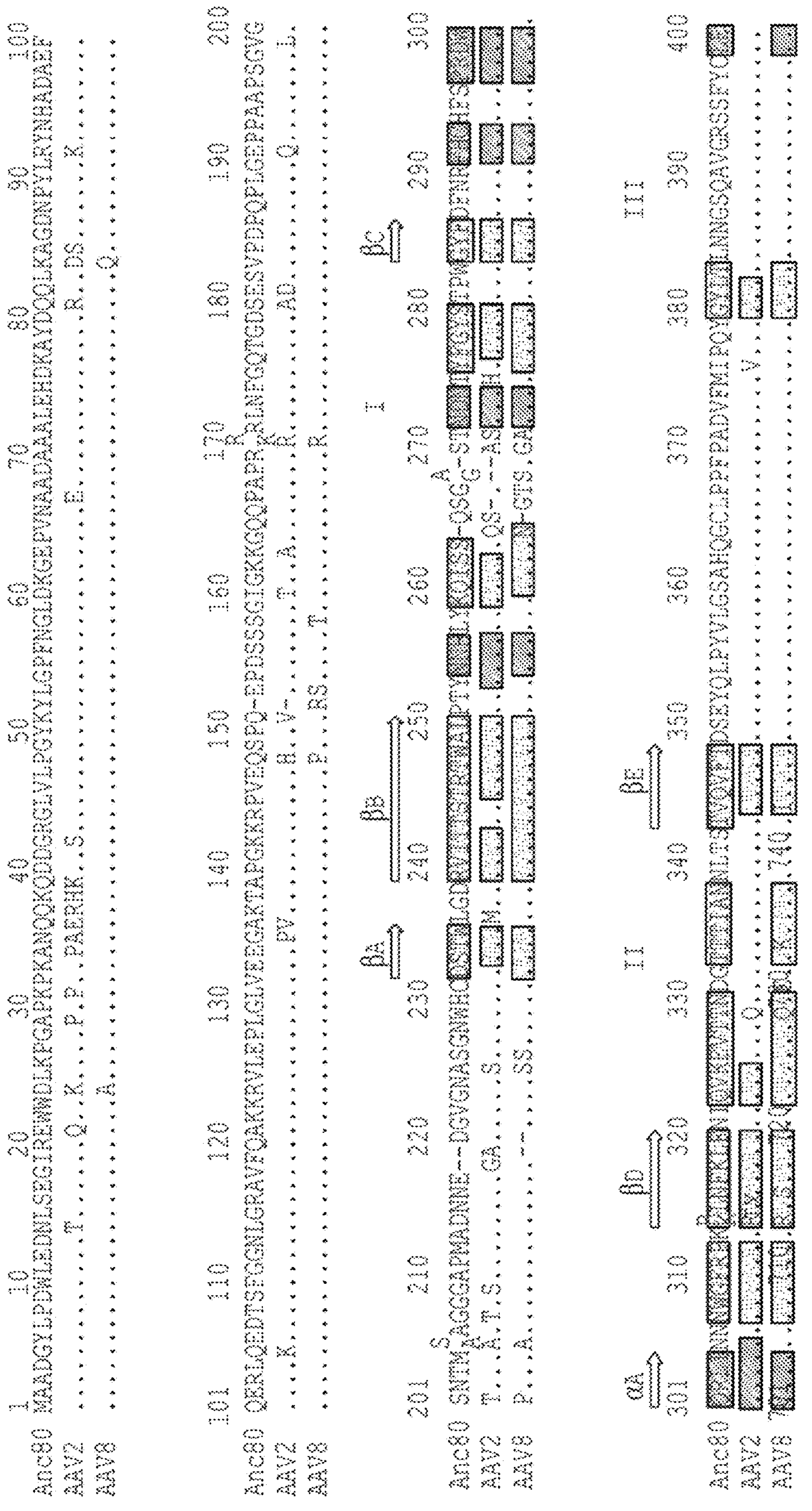
FIG. 19 shows the sequence and structural analysis of Anc80 vectors. Panel A is a sequence structure alignment of Anc80 (SEQ ID NO:37), AAV2 (SEQ ID NO:38) and AAV8 (SEQ ID NO:39) VP3 proteins. A structural alignment derived from the crystal structures of AAV2 (PDB 1LP3) and AAV8 (PDB 2QA0) VP3 and the predicted structure of Anc80L65 VP3, generated with UCSF Chimera (Pettersen et al., 2004, J. Comp. Chem., 25:1605-12) is shown in black print. The blue region is a non-structural alignment of the VP1/VP2 domains of AAV2, AAV8 and An80 (Notredame et al., 2000, J. Mol. Biol., 302:205-17). The ambiguous residues in the Anc80 library are represented in red, the lower position corresponding to Anc80L65 residues. Beta-strands and alpha-helices are represented in green and yellow, respectively. The positions of the nine beta-strands forming the AAV antiparallel beta-barrel are depicted with plain arrows, whereas the position of the conserved core alpha-helix is depicted with a dotted arrow. The approximate positions of variable regions (VR) I-IX are represented by the roman numerals above the sequence alignment. Panel B shows an AAV Cap sequence divergence matrix. Above the diagonal, the matrix represents the percent sequence divergence from selected AAV serotypes, as well as rh.10, the most homologous VP1 sequence as determined by BLAST. Below the diagonal, the number of amino-acid differences per position is presented. Panel C shows the superimposition of AAV2 and AAV8 VP3 crystal structures with Anc80L0065 VP3 predicted structure. The color code depicts the amino acid conservation between the 3 aligned sequences of panel A (red: highest conservation; blue: lowest conservation). Variables regions I-IX and C/M-termini are indicated in black. The approximate positions of the two, three and five-fold axis are represented by the black ellipse, triangle and pentagon, respectively. Panel D is the structural mapping of amino-acid changes as compared to AAV2 (left) and AAV8 (right) on VP1 trimer, visualizing the external (top) and internal (bottom) of the virion. Colored residues are divergent in Anc80. Red colored residues are ambiguous via ASR and, therefore, dimorphic in Anc80Lib.
Figure 19A:
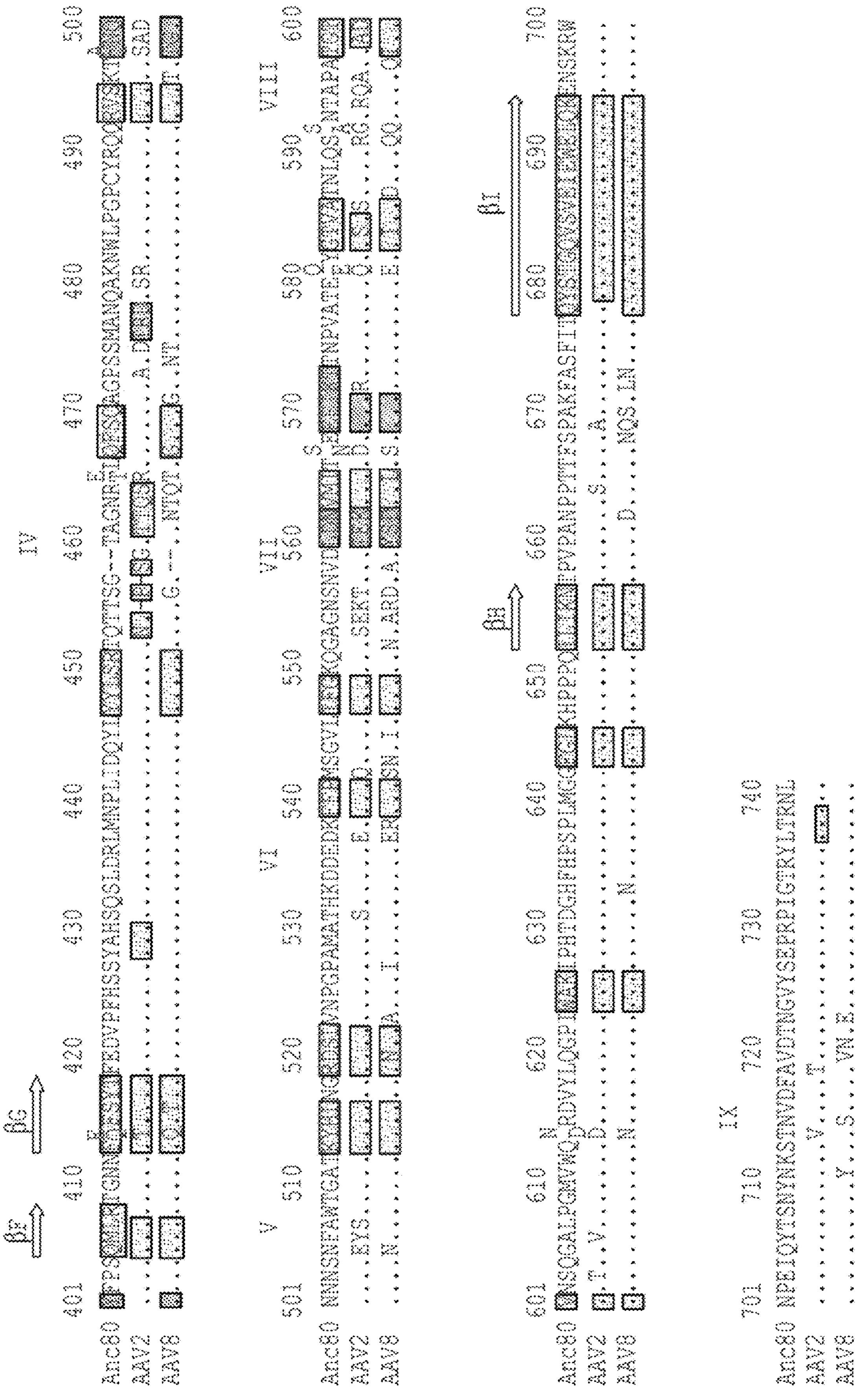

Anc80 was chosen in part because this reconstruction of this node was highly informed by the abundance of naturally occurring AAV clinically relevant descendants from this evolutionary intermediate. Furthermore, Anc80 is embedded in the phylogeny of the Dependoparvoviridae with known helper-dependent primate AAVs that arose prior to Anc80's speciation (FIG. 18) making it more likely that the ancestrally reconstructed particle retains the basic properties shared within this family. Using maximum-likelihood methods, a protein sequence prediction was derived for Anc80 based on calculated posterior probabilities for each residue in a particular position. In order to account for the uncertainty in selecting the appropriate amino-acid in each position, the aim was to generate all possible sequence permutations for positions with individual amino-acid posterior probabilities with $p>0.3$. A representation of this library, Anc80Lib, is illustrated in FIG. 19A in a part-structural alignment with an AAV2 and AAV8 reference capsid sequence. Practically, this led to a probabilistic sequence space as illustrated in FIG. 18: for all but 11 of the 736 Anc80 capsid amino-acid positions a unique residue prevailed in ASR, while for those 11 positions 2 amino-acid options were provided, resulting in a sequence space encompassing $2^{11}=2048$ permutations.

Figures 19B, 19C:
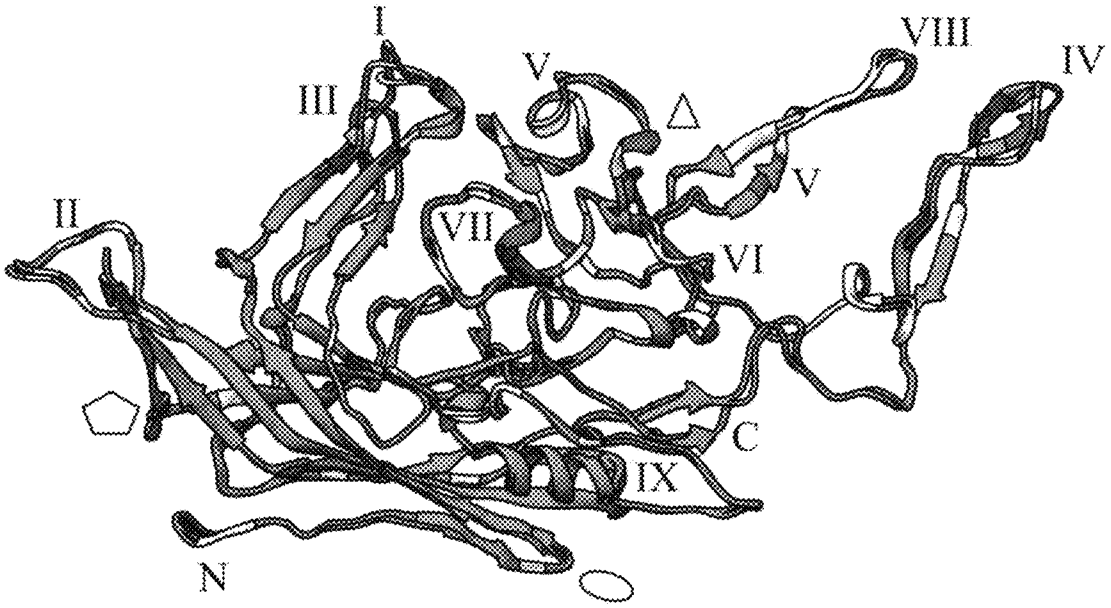
Figure 19D:
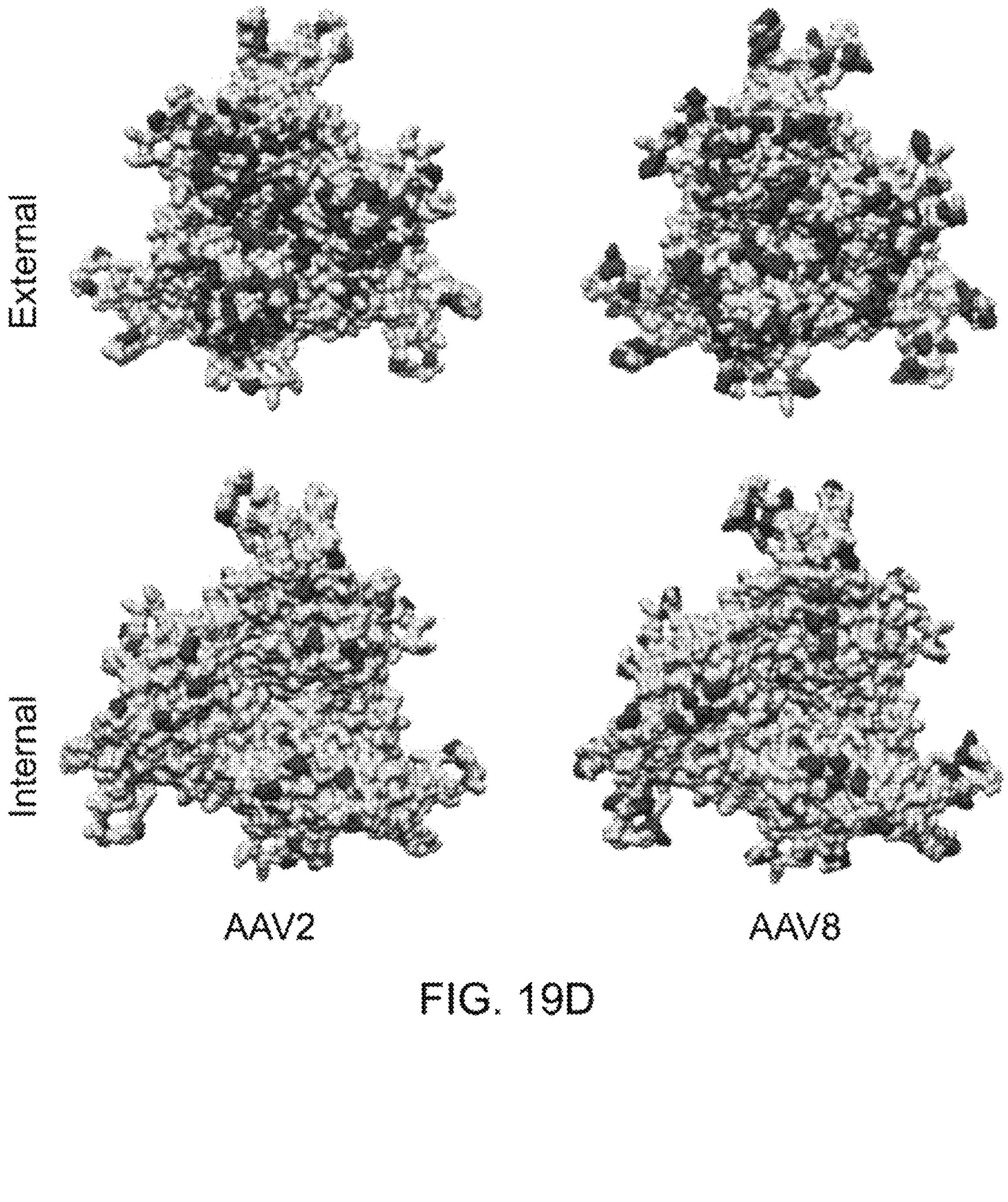

Structural and sequence alignment of Anc80Lib with extant AAVs and their X-ray crystallography data highlight significant divergence from currently known circulating AAV. The closest homologue as determined via BLAST search is rh.10, a rhesus macaque isolate within Clade E of the primate Dependoparvoviridae, which differs from Anc80Lib by minimally 8.0% which accounts for 59 divergent amino-acid positions (FIG. 19B). AAV8 and AAV2 differ 9.5% and 12.0%, respectively and those 70-87 variable sites are spread over the entire VP1 protein, including the VP1, 2 unique domains (FIG. 19A, 19B). Divergence is highest in the hypervariable domains I, IV, VII, and VIII, both in terms of sequence as well as based on structural modeling of Anc80Lib clones in overlay with AAV2 and 8 monomeric structures (FIG. 19A, 19C). Mapping of the variable Anc80 residues onto trimeric X-ray crystallography models of AAV2 and AAV8 in FIG. 19D highlight most changes to occur on peak and flanks of the protrusions around the 3-fold axis of symmetry on the external surface of the virion. However, a significant number of variable residues were also noted on the surface exposed domains outside of the 3-fold axis in addition to a smaller number of variations on the internal surface of the particle and on regions of Cap that are not resolved in the X ray structures.

Example 24—Anc80 Synthesis and Basic Characterization

Anc80Lib protein sequences were subsequently reverse translated and generated by gene synthesis in pooled library format. Capsid genes were cloned into an AAV packaging plasmid encoding AAV2 Rep into pAnc80Lib following which the library was deconvoluted clonally. Individual clones (named pAnc80LX, with X a consecutive number) were evaluated in isolation to avoid potentially interfering competitive interactions in a minimally divergent library population. A portion of individual Anc80 clones were Sanger sequenced verifying integrity and complexity requirements. Clonal Anc80 plasmids were co-transfected with a ΔF6 adenoviral helper plasmid, an expression construct for AAP derived from AAV2 (AAP2), and ITR flanked expression construct encoding luciferase. A total of 776 library clones were produced and inoculated at equal volume of producer cell lysate on HEK293 cells in a semi-high-throughput assay aiming to assess combined particle assembly and transduction efficiency. Approximately 50% of the Anc80 clones led to detectable signal over background in this rudimentary screening assay. Several lead candidates with highest luciferase signal progressed to sequencing confirmation and titration for DNase resistant genome particles (GC) and infectivity on HEK293 cells. Based on these results, Anc80L65, the $65^{th}$ Anc80Lib clone that was evaluated, was selected for further characterization. Anc80L65 vector yields from cell lysate are between 82-167% of AAV2 yields, yet were depressed compared to the high yielding AAV8 (3-5% relative AAV8 yields). In vitro infectivity on HEK293 is inferior to AAV2, however, superior to AAV8 on a particle per cell basis.

Figure 20A:
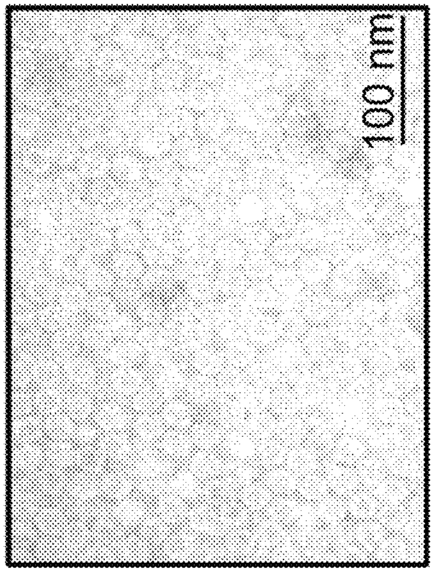
FIG. 20 are the results of biophysical and biochemical characterization of Anc80L65. Panel A shows negative staining Transmission Electron Microscopy (TEM) of Anc80L65, demonstrating that Anc80L65 forms particles of approximately 20-25 nm in diameter. Panel B is the Anc80L65 VP composition. Purified preps of Anc80L65 and three extant viruses were analyzed by SDS-PAGE. Anc80 demonstrates similar incorporation levels of monomers VP1, 2, and 3. Panel C shows an Empty:Full particle composition of purified AAV preparations. Sedimentation coefficient distributions were derived from the sedimentation profiles acquired with the refractive index optical measurement systems during analytical ultracentrifugation of preps of AAV8 and Anc80L65. Panel D shows the AAV thermostability. Intrinsic tryptophan fluorescence measurement of AAV particles under different temperatures illustrates distinct melting temperatures of AAV serotypes as compared to Anc80L65.
Figure 20B:
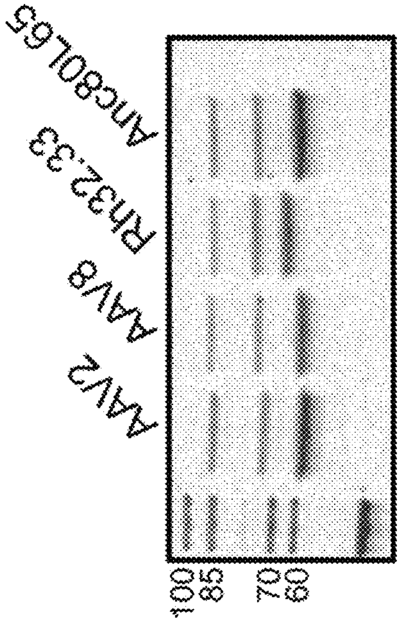
Figure 20C:
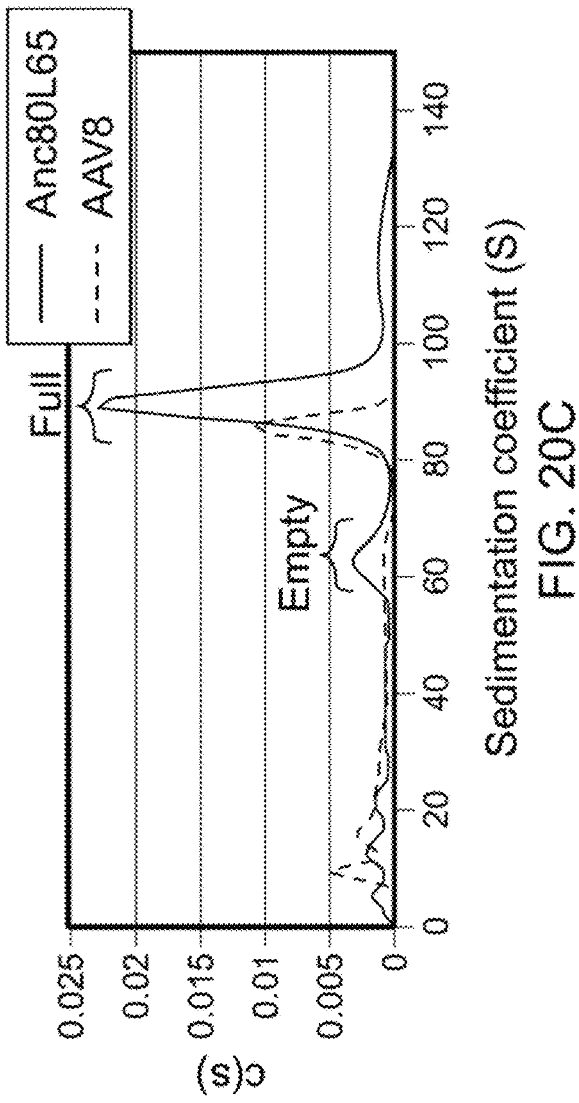
Figure 20D:
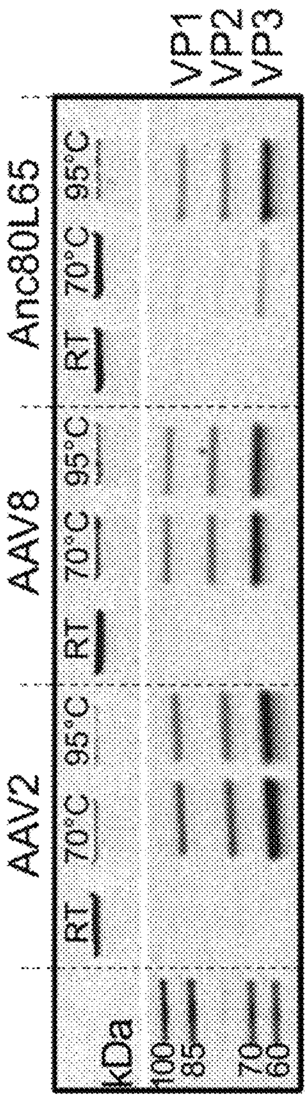

Anc80L65 vector preparations were produced and purified on an iodixanol gradient at scale following traditional protocols and subjected to a variety of biochemical, biophysical, and structural analyses. Particles within a purified preparation of Anc80L65 were visualized under negative staining by electron microscopy (EM) (FIG. 20A). Anc80L65 virions present as relatively uniform hexagonally shaped particles with a diameter of approximately 20-25 nm, not unlike other AAV capsomers. Denatured particles resolved under SDS electrophoresis into 3 bands of 60, 72, and 90 kDa, in an approximate ratio of 1:1:10 corresponding to the VP1-3 proteins from AAV2 and AAV8 particles (FIG. 20B). Analytical ultracentrifugation (AUC) allowed the determination of the sedimentation coefficient of genome containing or full Anc80L65 at 88.9 S, slightly increased from AAV8's (85.9 S) (FIG. 20C). This analysis permitted further determination of the relative abundance of empty or lower density assembled particles, presumed to be lacking a vector genome, as well as overall purity. One concern was that inaccurate modeling of the ancestral capsid sequence may have resulted in a structure deficient in its ability to package genomes and would result in a skewed empty versus:full ratio in Anc80L65 preparations. Results indicated approximately 16% empty versus 85% full particles in the preparation, in line with observations with AAV8 (FIG. 20C). Additionally, it was hypothesized that particle stability may be reduced due to suboptimal modeling of the ancestral capsid composition, and subjected the particle to heat stability assays which determined, against the indicated expectations, that Anc80L65 to be 15-30° C. more heat stable that its presumed AAV2 and AAV8 (FIG. 20D).

Figure 21B:
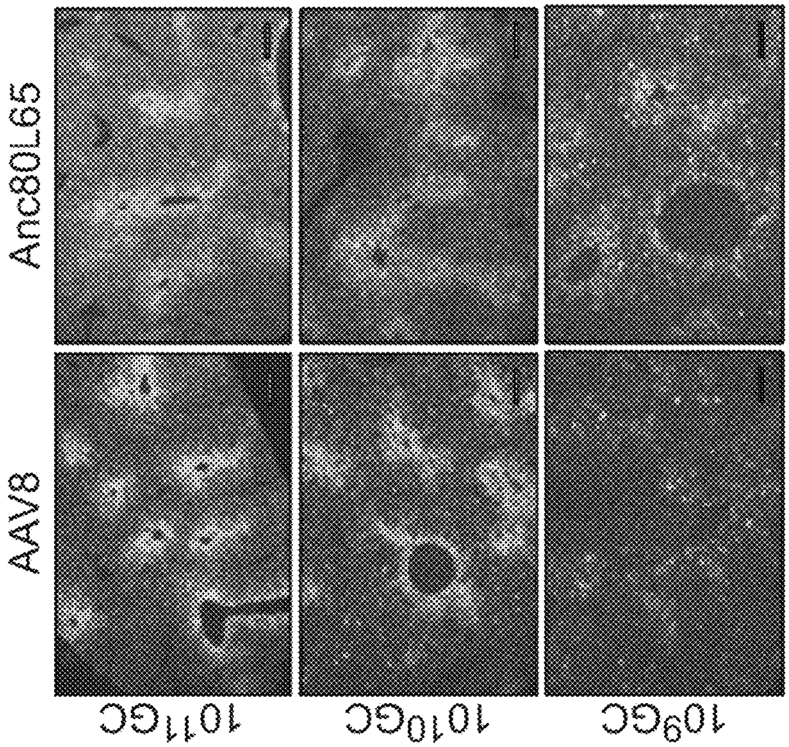
FIG. 21 are results from the in vivo evaluation of Anc80L65. Panel A, top panel, shows liver transduction and lacZ transgene expression comparison of AAV-2, AAV-8 and Anc80L65.TBG.nLacZ in liver 28 days after intraperitoneal delivery at a dose of $7.2\times10^{10}$ GC. Panel A, middle panel, shows muscle tropism of AAV2, AAV8 and Anc80L65 28 days following an intramuscular delivery at a dose of $1\times10^{10}$ GC to the rear-right thigh (gastrocnemius/biceps femoris muscle). Panel A, lower panel, shows a comparison of eGFP transgene expression between AAV2, AAV8, and Anc80L65 in the retina after subretinal delivery at a dose of $2\times10^{9}$ GC. AAV2 shows high affinity for RPE cells, while both RPE and photoreceptors are targeted using AAV8 and Anc80L65 vectors, with Anc80L65 showing higher transduction efficiency compared to AAV2 and AAV8. Panel B is a qualitative dose response eGFP-expression analysis at $10^{11}$ (top panel), $10^{10}$ (middle panel), and $10^{09}$ (bottom panel) GC comparing AAV-8 and Anc80L65 by retro-orbital sinus intravenous delivery. Both AAV8 and Anc80L65 show comparable eGFP expression at equal doses throughout the dose ranging. Panel C shows a quantitative AAV dose response analysis measuring mouse serum levels of recombinant human alpha 1-antitrypsin (hA1AT) transgene expression from AAV-8 (black symbols: square—$10^{11}$ GC, circle—$10^{10}$ GC, and four-square—$10^{9}$ GC) and Anc80L65 (grey symbols: diamond—$10^{11}$ GC, square—$10^{10}$ GC, and triangle—$10^{9}$ GC). Panel D is a graph of the Rhesus macaque liver gene transfer of AAV-8 and Anc80L65 expressing Rhesus chorionic-gonadotropin (rhCG) following saphenous vein injection of a dose of $1\times10^{12}$ GC/kg. Genomic DNA was harvested from macaque liver-lobes and viral genome (vg) per diploid genome (dpg) was measured by qPCR assay. One AAV8 and all three Anc80L65 animals successfully received ~1-3 vg per diploid cell of the caudal liver lobe, while 2 AAV8 animals likely had low level NAB resulting in vector neutralization and limited liver gene transfer. Panel E is a graph showing transgene mRNA expression of AAV8 and Anc80L65 in NHP caudal, right, left and middle liver-lobes by TaqMan probe-specific, quantitative reverse-transcriptase PCR (qRT-PCR). Quantitation of rhCG transcript was normalized with endogenous GAPDH mRNA levels.
Figure 21A:
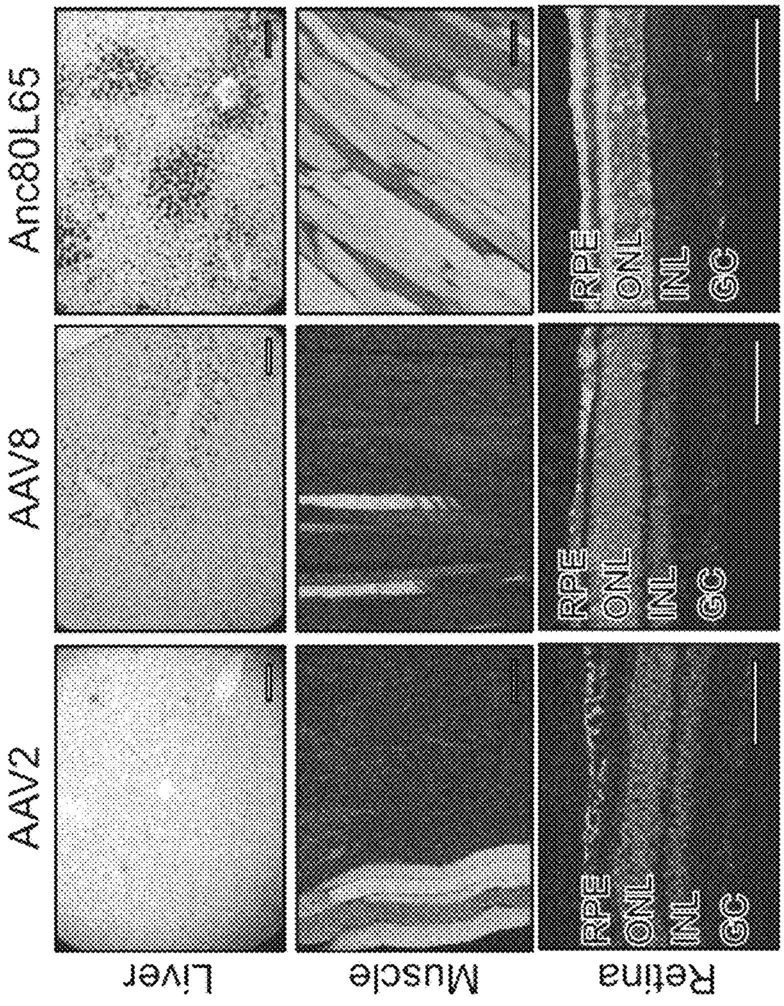
Figure 24:
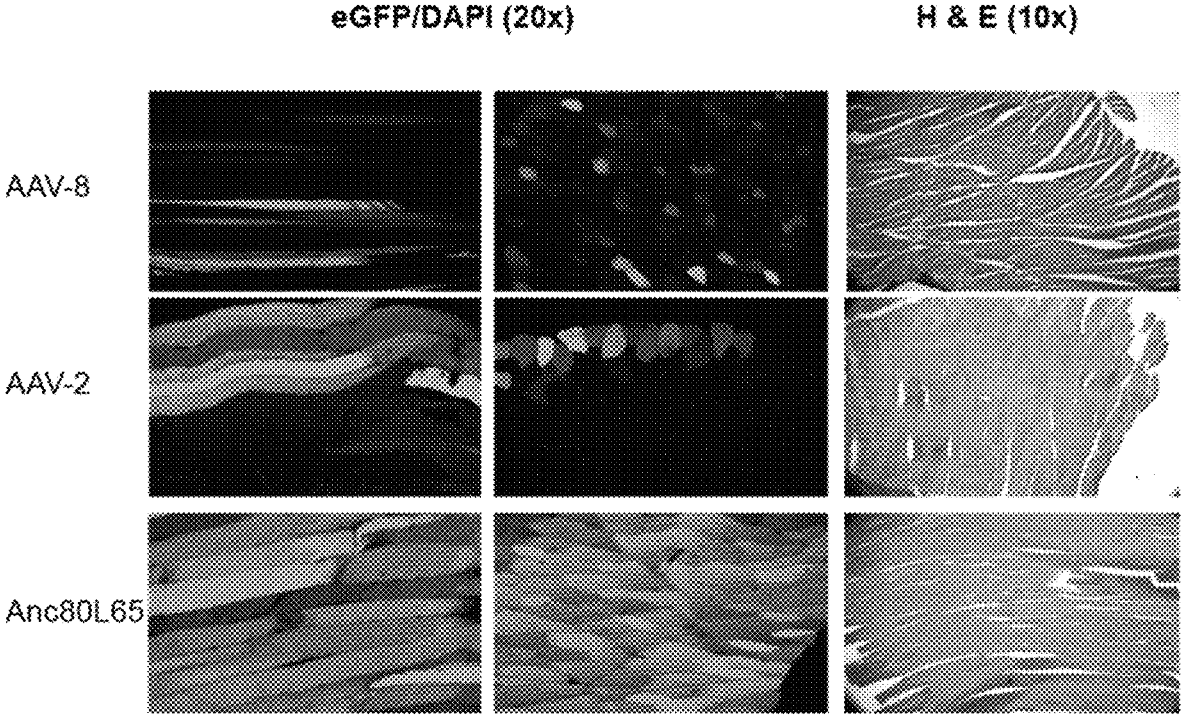
FIG. 24 shows eGFP expression after viral vector intramuscular injection (see, also, FIG. 21 above). For muscle-targeted eGFP experiments, mice received a single injection in the gastrocnemius muscle. eGFP expression was observed in transversal and longitudinal muscle sections (first and second columns). Blue staining marks nuclei (DAPI). The morphology of muscle was unchanged as seen in haematoxylin and eosin (H&E) stained sections (third column).

Example 25—In Vivo Gene Transfer and Transduction of Anc80L65 in Murine Model Next, the ability of Anc80L65-packaged transgenes to be delivered and expressed was evaluated from 3 clinically relevant target tissues and routes of administration (ROA) in the C57Bl/6 mouse: (a) liver following a systemic injection, (b) skeletal muscle following direct intramuscular injection, and (c) a subretinal injection for outer retina targeting. Large scale preparations of Anc80L65 were produced alongside with AAV2 and AAV8 controls with reporter genes and were injected at equal doses for liver, muscle and retina directed gene transfer in adult male C57Bl/6 mice. Expression, presented in FIG. 21, was monitored qualitatively (eGFP and/or LacZ) for all three target tissues and quantitatively via serum ELISA measurement of the secreted hA1AT (liver) at various time points. Liver-directed gene transfer was observed to be robust via two routes of administration and transgenes (FIG. 21A, 21B, 21C). Analogously to AAV8, hepatocytes were targeted efficiently as observed by LacZ and GFP staining surpassing the limited permissively described for AAV2 (Nakai et al., 2005, J. Virol., 79:214-24; Nakai et al., 2002, J. Virol., 76:11343-9). Quantitatively, Anc80 demonstrated similar efficiency of transduction to AAV8 by intracellular reporter and a secreted serum protein transgene product. Dose ranging studies demonstrated a linearity of gene transfer with dose above $10^{10}$ GC/mouse but a threshold below which linearity was not maintained for hA1AT (and less obvious by eGFP) (FIG. 21B, 21C). A bio-distribution study at the high dose of $5\times10^{11}$ GC/mouse was conducted at day 7 and 28 post-injection to evaluate tissue distribution of vector genomes in liver, heart, spleen, kidney, and lung of Anc80L65, alongside AAV8 as a control (Table 3). Results show similar ranges of gene transfer of Anc80 to AAV8 in the tissues tested, with moderate increases for Anc80L65 in spleen, heart, and lung. Via direct skeletal intramuscular injection, Anc80 efficiently targeted myofibers proximal to the injection site and longitudinally extending across the fiber (FIG. 21A and FIG. 24). Retinal transduction after subretinal injection is efficient in targeting the retina pigment epithelium (RPE), as was the case in AAV2 and AAV8 as previously noted. Photoreceptor targeting, a more difficult cell target, as is documented for AAV2, was observed with AAV8 and Anc80L65. While both AAV8 and Anc80L65 targeted the majority of photoreceptor cells, transduction with Anc80L65 leads consistently to higher expression levels per cell. A limited number of cells in the inner retina were also observed to be GFP positive by Anc80L65 transduction (FIG. 21A).

TABLE 3

Vector Genome Distribution in Mouse Liver, Heart, Spleen, Kidney, and Lung

| | 7 dpi | | 28 dpi | |
|---|---|---|---|---|
| | AAV8 | Anc80L65 | AAV8 | Anc80L65 |
| Liver | 31.04 ± 7.04 | 24.19 ± 0.51 | 8.59 ± 3.1 | 8.47 ± 1.35 |
| Lung | 0.77 ± 0.07 | 2.2 ± 0.46 | 0.16 ± 0.04 | 1.32 ± 0.78 |

TABLE 3-continued

Vector Genome Distribution in Mouse Liver, Heart, Spleen, Kidney, and Lung

| | 7 dpi | | 28 dpi | |
|---|---|---|---|---|
| | AAV8 | Anc80L65 | AAV8 | Anc80L65 |
| Kidney | 0.63 ± 0.06 | 1.2 ± 0.16 | 0.22 ± 0.06 | 0.86 ± 0.26 |
| Heart | 0.17 ± 0.06 | 0.53 ± 0.04 | 0.1 ± 0.04 | 0.7 ± 0.32 |
| Spleen | 0.02 ± 0 | 0.19 ± 0.12 | 0.02 ± 0.01 | 0.21 ± 0.15 |

Example 26—Anc80L65 Gene Transfer and Expression in Non-Human Primate Liver

Given the robust hepatotropism of Anc80L65 in mice, it was an aim to evaluate gene transfer of Anc80L65 in a large animal model. Six female rhesus macaques that were enrolled in prior studies unrelated to AAV were injected via saphenous vein with either AAV8 or Anc80L65 at a clinically relevant dose of $10^{12}$ GC/kg (Table 4). A rhCG reporter was used to express the rhesus cDNA for the β subunit of the chorionic gonadotropin, a transgene product that the animals are tolarized for in order to avoid a non-self transgene immune response. Animals enrolled in this experiment were prescreened for NAB to AAV8 and Anc80L65. NAB serum levels weeks prior to injection were below 1/4 titer to be enrolled in this study. Gene transfer was assessed by Taqman qPCR for vg of total liver DNA (caudal lobe) 70-71 days following injection (FIG. 21D). Surprisingly, 2 out of 3 control AAV8 injected animal had underwhelming gene transfer (<0.1 vg/dg) likely due to low level NAB at the time of injection undetectable by standard NAB assays as reported in previous studies. One AAV8 animal, presumably with no or minimal NAB to AAV8, demonstrated gene transfer levels for liver within the expected range of 0.81 vg/dg. Anc80L65 gene transfer apparently was unhindered by NAB (no Anc80L65 NAB detected pre-injection) and the 3 animals yielded hepatic transgene copy numbers ranging from 0.73-3.56 vg/dg. Liver expression was monitored via quantitative RT-PCR (FIG. 21E): Anc80L65 gave rise to expression superior to the AAV8, and achieved rhCG transcript levels between 13-26% of total GAPDH mRNA amounts in all liver lobes.

TABLE 4

Characteristic and Previous Clinical History of Rhesus Macaques Treated with Viral Vectors Injected Via Saphenous Vein

| Animal ID | Age | Sex | Weight (kg) | Experiment (days) | Previous History | Treatment |
|---|---|---|---|---|---|---|
| AP19 | 13.5 | F | 7.8 | 71 | Inoculated with MVA-HIV vaccine; in 2011, diagnosed with early endometriosis | IV Anc80 |
| AP18 | 9.5 | F | 7.2 | 71 | Inoculated with CMV; received anti-CD4 antibody | IV Anc80 |
| AP17 | 19.5 | F | 8.3 | 71 | Inoculated with MVA-HIV vaccine | IV Anc80 |
| AP16 | 15.5 | F | 6.3 | 70 | Inoculated with MVA-HIV vaccine | IV AAV8 |
| AP15 | 5 | F | 5 | 70 | Inoculated with CMV; received anti-CD4 antibody | IV AAV8 |
| AP14 | 5.5 | F | 5.2 | 70 | Inoculated with CMV; recent weight loss | IV AAV8 |

Example 27—Safety, Immunology, and Toxicology of Anc80L65

The consideration to use any efficient gene delivery vector system for therapeutic application requires extensive evaluation of its safety for clinical use. In addition, the use of a novel agent which may approximate an ancestral state of a Dependoparvovirus may further raise those concerns. Here, in a non-formal preclinical setting, several important aspects were examined that may limit Anc80L65 from a safety perspective. Animal expression studies (FIG. 21) were monitored for obvious signs of toxicity during the in-life phase of the study and, to the extent possible, for target tissue-specific toxicity. No notable adversity was found to be associated with the vector injection. Briefly, vector administration following intraperitoneal (maximum dose tested [mdt]: $3.9\times10^{10}$ GC/mouse), retro-orbital vein injection (mdt: $5\times10^{11}$ GC/mouse), subretinal (mbt: $2\times10^{9}$ GC/eye), intravitreal (mbt: $2\times10^{9}$ GC/eye), and direct intramuscular ($10^{10}$ GC/mouse) were not observed to have overt toxicity. A more direct assessment was performed in a high dose intravenous injection of $5\times10^{11}$ GC/mouse (approximately $2\times10^{13}$ GC/kg) of Anc80L65.TBG.eGFP alongside the following controls: (a) AAV8 with the same transgene cassette, and (b) an equal volume saline injection. Mice were phlebotomized pre-injection, 2 h, 1 d, 3 d, 7 d, 14 d, and 28 d post injection and blood was analyzed for Cell Blood Counts (CBC) and Serum Chemistry (Chem) (Tables 5 and 6), which were within range or comparable to controls for Anc80L65, and therefore, raised no significant concerns. Serum from the 2 h, 24 h, 3 d, and 7 d time points were further evaluated for cytokines as a measure of innate immune response to the vector antigens by multiplex 23 cytokine analysis (Table 7). Cytokines for Anc80L65 were overall concordant with those for saline and AAV8 control serum, and no major cytokine elevations or decreases were observed, however in some instances were moderately outside the ranges set by the saline control values in a manner that was more apparent for Anc80L65 than AAV8. Similar analyses were performed on the blood from the rhesus studies described in FIGS. 21D and 21E. Analogous to the mouse studies, from CBC and Chem values obtained, signs of toxicity related to the AAV8 or Anc80L65 test article were not identified (Tables 8 and 9).

Figure 22C:
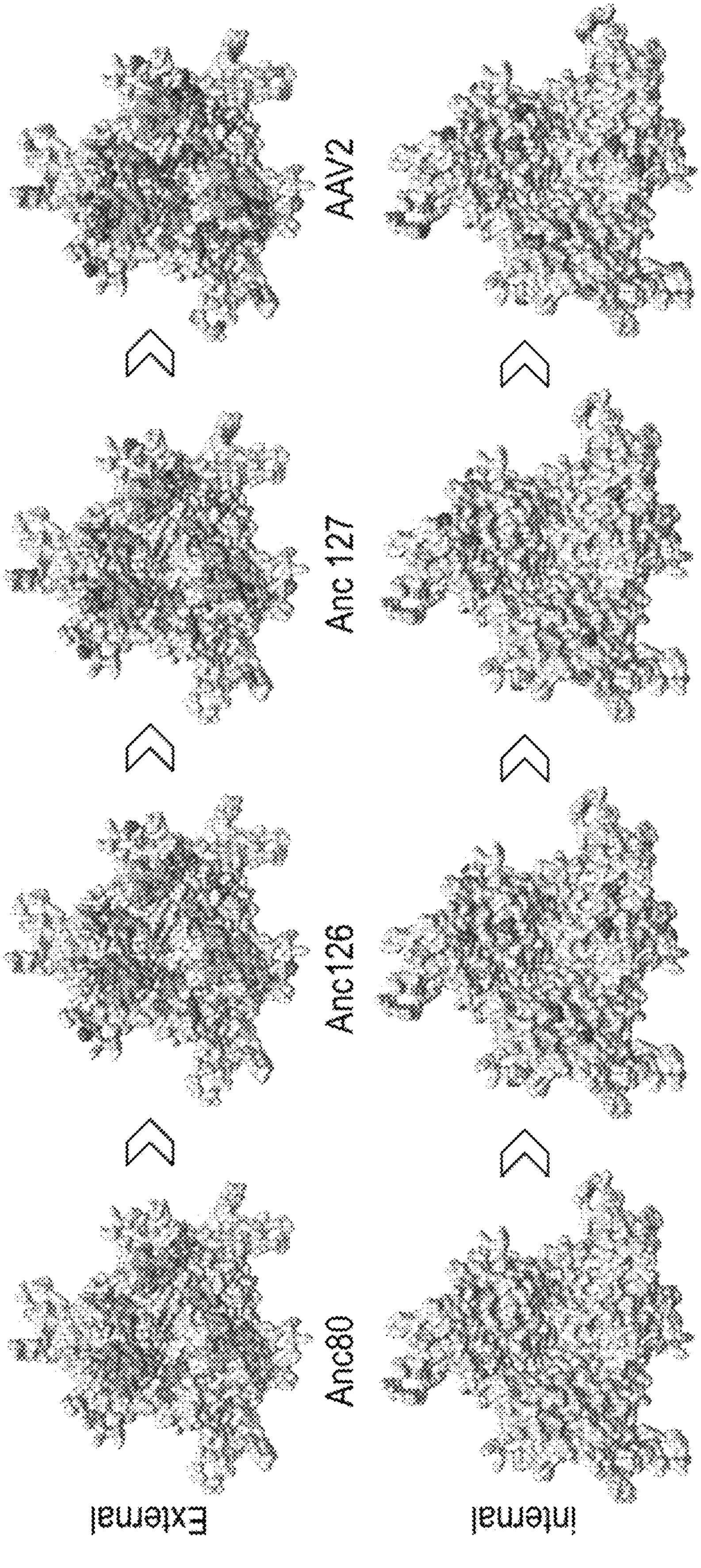
FIG. 22 are results from experiments in which Anc80L65 was immunologically characterized. Panel A is a graph showing rabbit anti-AAV serum cross-reactivity: rabbit antiserum raised against AAV serotypes (Y-axis) was tested for NAB to Anc80L65 versus the homologous AAV serotype in order to assess sero-cross-reactivity. Values (X-axis) represent smallest dilution at which 50% neutralization is achieved. The phylogenetic relationship between immunizing serotypes is depicted on the left. Panel B are Tables showing mouse in vivo gene transfer cross-neutralization: C57Bl/6 mice received an IV injection of AAV8 or Anc80L65.CASI.EGFP.2A.A1AT 25 days following an IM injection with either saline or AAV8.TBG.nLacZ. 14 days following the second injections, serum was titrated by ELISA for hA1AT expression. The Tables present the relative hA1AT levels of the pre-immunized mice versus the non-immunized for each vector (% control), and the NAB titer dilutions for AAV8 (NABS) and Anc80L65 (NAB80) 24 h prior to the second injection in the immunized group (n=5). Grey diverging arrow in Panels A and B schematically illustrate AAV2 and AAV8 lineage phenotypic evolution. Panel C is a non-structural multiple sequence alignment between Anc80, Anc126, Anc127 and AAV2 VP3 sequences was generated using the T-coffee alignment package. AAV2 trimer structure was generated using UCSF Chimera. The blue residues represent the variable residues relative to Anc80. The orange residues represent previously defined T and B-cell epitopes on AAV2. The green residues are overlaps between mutations relative to Anc80L65 and B/T-cell epitopes.

Pre-existing immunity to AAV serotypes is known to block gene transfer, and may put the patient at risk for adversity due to recall of memory T-cells toward vector antigens shared with the naturally occurring wild type virus involved in the primary infection. High titer rabbit antiserum raised against AAV serotypes 1, 2, 5, 6.2, 8, 9, and rh.32.33 was used. rh.10 also was included, as its sequence is most closely homologous to Anc80L65, differing in 8.0% of residues. In FIG. 22A, sera were tested for their ability to neutralize Anc80L65 versus the homologous vector capsid it was raised against. Results demonstrated no cross-reactivity to AAV5 and rh32.33, structurally highly divergent AAVs, while AAV2, 6.2, and 8, presumed descendants of Anc80L65, demonstrated low level cross-reactivity, albeit at levels that were 16-fold or lower than homologous antiserum titers. Among Anc80 lineage members, no cross-reactivity was observed above the limit of sensitivity for AAV9 and rh.10. Next, it was an aim to validate these results in an in vivo model for neutralization by pre-immunizing animals for AAV8 via intramuscular route, and assessing the neutralization of Anc80L65 following intravenous injection in comparison to AAV8, 25 days following the immunization (FIG. 22B). Neutralization was complete for AAV8 in the AAV8 pre-immunized animals. Anc80L65 was neutralized in 2/5 animals, yet demonstrated between 60-117% of transduction in 3/5 animals, notwithstanding demonstrated AAV8 NAB in those animals. These results demonstrate partial cross-reactivity of Anc80L65 with AAV8 in rabbit and mouse.

Example 28—AAV Lineage Analysis and Reconstruction

Figure 23A:
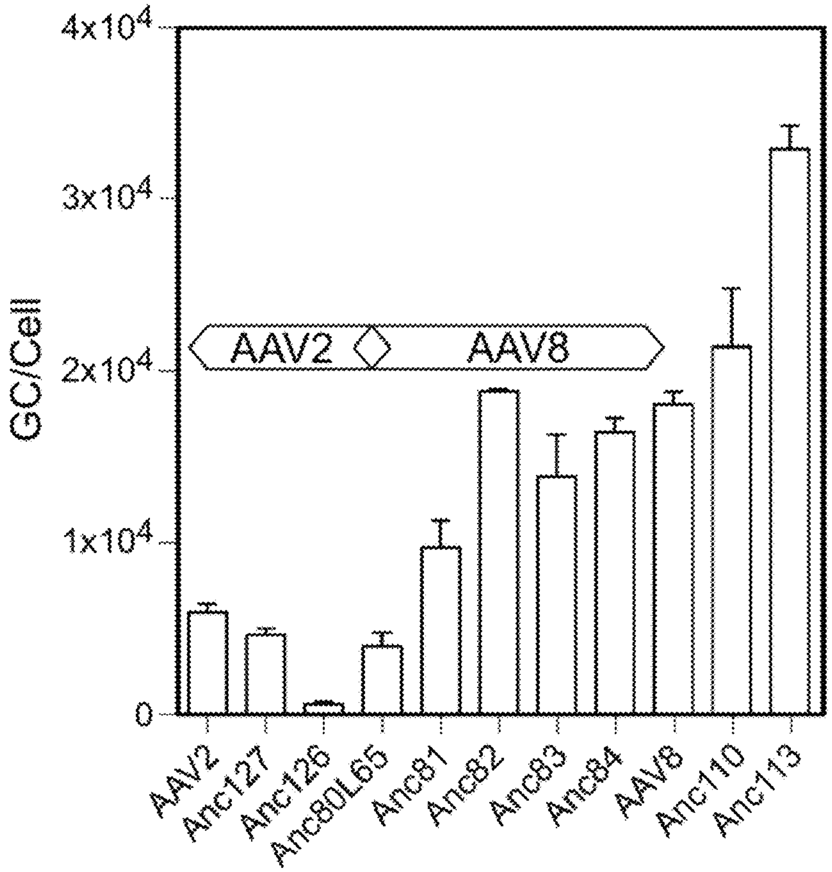
FIG. 23 is data showing that AAV lineage reconstruction modulates production, infectivity, and thermostability. Panel A is a graph showing the production of nine ancestral and two extant viral vectors containing a luciferase reporter gene driven by a CMV promoter, as determined by qPCR. Error bars represent standard deviation of three biological replicates. Panel B is a graph showing that ancestral and extant viral vectors were used to transduce HEK293 cells at a particle-to-cell ratio of $1.9\times10^{3}$. Error bars represent standard deviation of three distinct lots of vector. *Anc126 was added at ratios between $2.1\times10^{2}$ and $3.5\times10^{2}$ GC/cell due to low vector yield. Panel C shows a sypro-orange thermostability assay indicating denaturation temperatures of selected ancestral and extant AAV vectors.
Figure 23B:
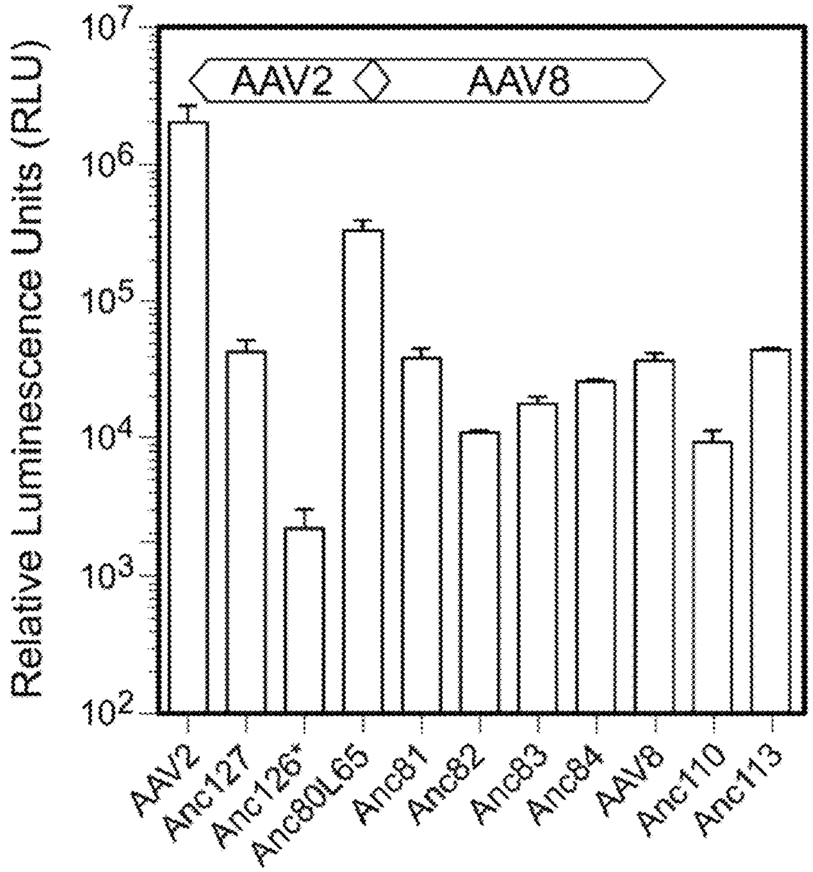
Figure 23C:
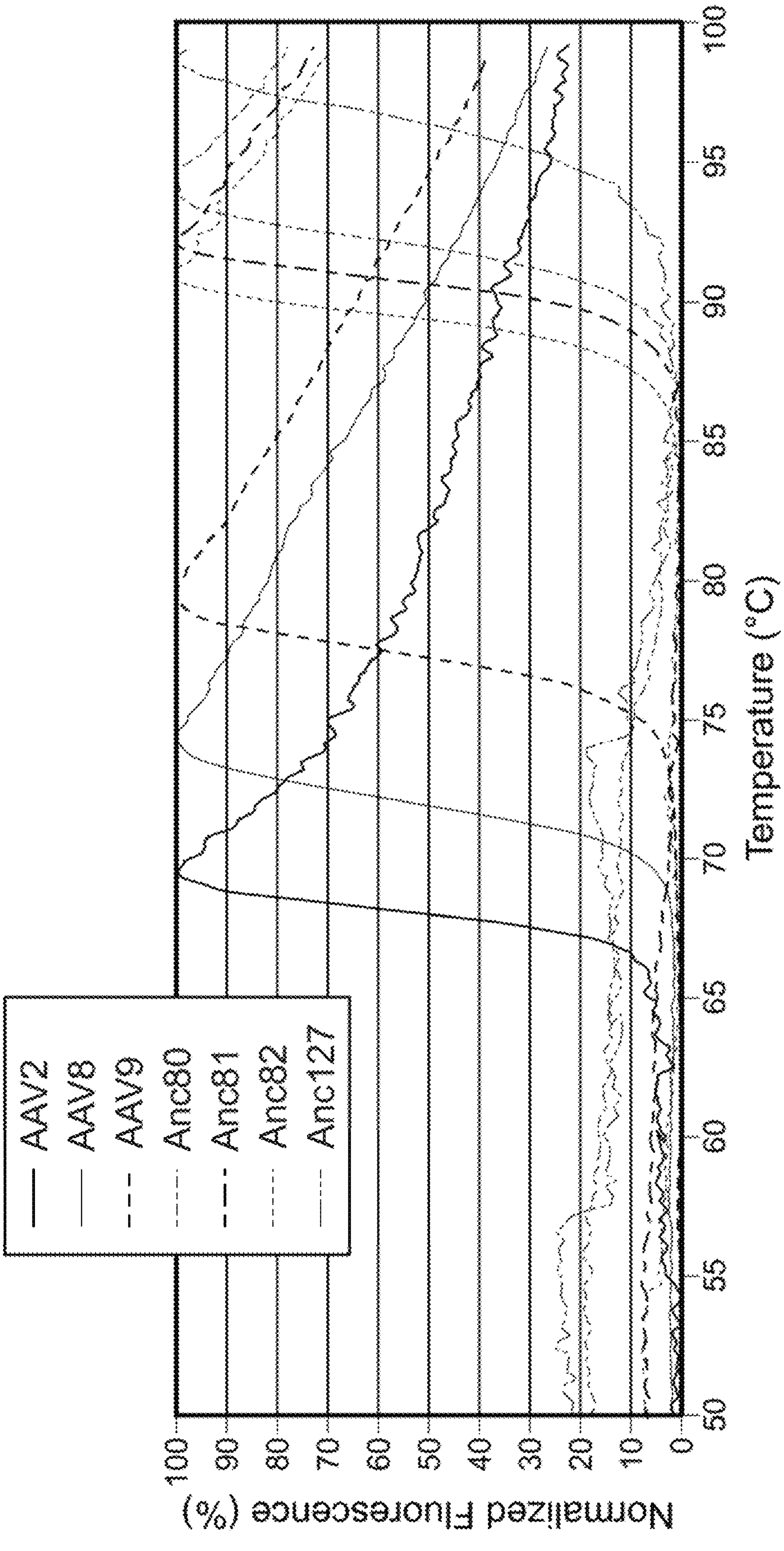

Strengthened by the successful synthesis of Anc80L65 based on ASR and its demonstration as producible, stable, and highly infectious agent for gene therapy, it was an aim to provide additional validation of the approach and modeling methodology by reconstructing the lineage of AAV further. The ambition with generating this additional set of reagents was to provide structural intermediates of Anc80 and extant AAVs that would enable empirical evaluation of the structure-function relationship within this viral family and highlight important epistatic couplings informative to future AAV rational design approaches. A total of 8 additional evolutionary intermediates of AAV were reconstructed by ASR and synthesized in the laboratory (FIG. 18): Anc81, Anc82, Anc83, Anc84, Anc110, and Anc113 were resolved in the branching leading toward AAV7, 8, and/or 9, while Anc126 and Anc127 are positioned in the natural history of AAV1, 2, and/or 3. For each of these, the sequence was determined by selecting the amino acid with the highest posterior probability per position. First, GC viral vector yields were determined in a HEK293 standard triple transfection of vector components and adenoviral help using Taqman qPCR for vector genomes. Results, shown in FIG. 23A, demonstrate increased productivity from Anc80 as the putative ancestor in the AAV7-9 lineage, in line with the higher production yields of those serotypes such as AAV8. The AAV1-3 branch did not present yield increases, and a very poor particle yield was observed for Anc126. It is possible that Anc126 yields can be improved upon through leveraging the statistical space, as was the case for Anc80, however, it is equally likely that Anc126 ASR is less informed due to undersampling of this branch of the AAV phylogeny. Infectivity of the produced particles at equal particle doses was further tested in vitro on HEK293 by GFP and luciferase. All newly synthesized Anc vectors demonstrated infectivity, however, at varying degrees (FIG. 23B). In the AAV7-9 lineage, infectious titers were overall depressed and more similar to the AAV8 phenotype than that of Anc80. Anc127, the only intermediate in the Anc80 to AAV2 lineage that could be tested at equal dose demonstrated declined transduction efficiency as compared to both Anc80 and AAV2. The heat stability profile of selected evolutionary intermediates in both branches of this lineage was further tested (FIG. 23C). Interestingly, Anc81 and Anc82 demonstrated high, yet moderately decreased melting temperature in a thermostability assay compared to Anc80L65, suggesting maybe a gradual reduction of thermostability with evolutionary age in this branch. In contrast, Anc127 demonstrated an even further increase from the already highly thermostable Anc80L65 vector.

Lastly, the ability of ASR to disrupt known epitopes to AAV2 was explored. Only few B or T-cell epitopes have been mapped on AAV2 to date, all of which were mapped onto Anc80L65, Anc126, Anc127, and AAV2, representing the AAV2 lineage. The introduction of the sequential mutations between these putative evolutionary intermediates highlights, in FIG. 22C, the overlap between the mutations and 2/4 human T-cell epitopes and 2/2 mouse B-cell epitopes. These data highlight the potential of ASR to be used as a method to eliminate or modulate antigenic regions onto the AAV capsid, and may suggest immunity was a major selective pressure in the natural history of AAV.

Example 29—In vivo Functionality of Anc110

Figure 27:
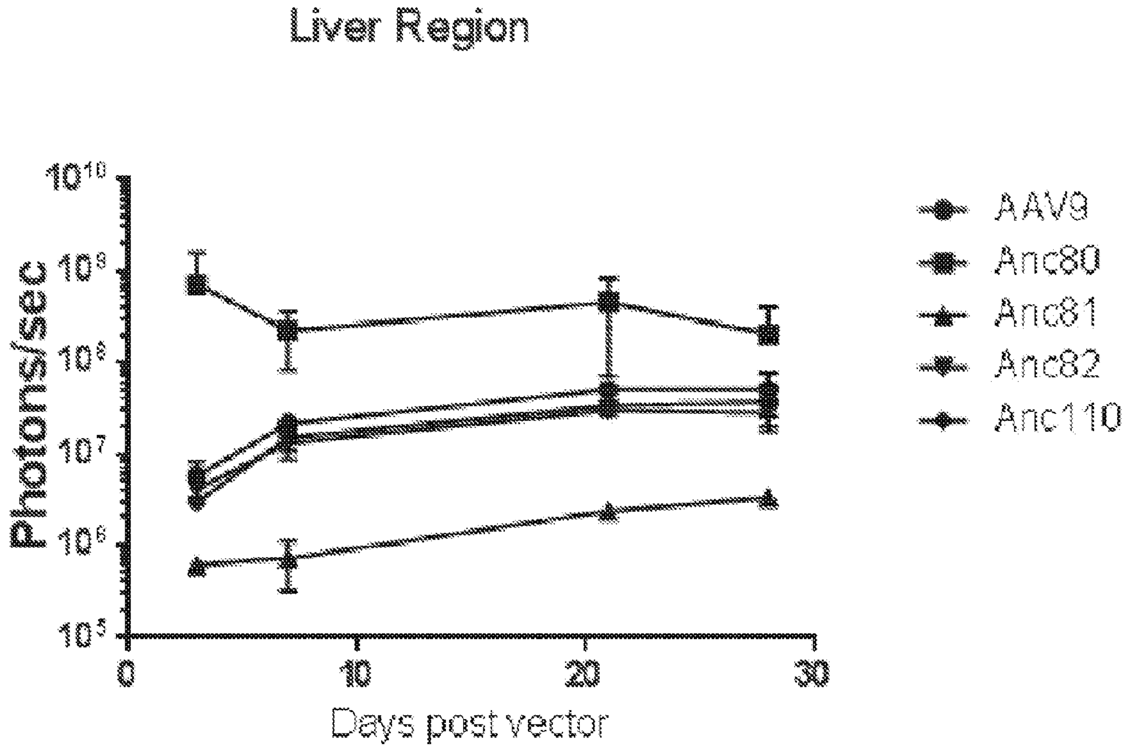
FIG. 27 is a graph showing luciferase liver transduction of Anc80, Anc81, Anc82, and Anc110 in comparison to AAV9 after IV administration in C57Bl/6 mice.

Experiments were performed to evaluate liver transduction of luciferase by Anc80, Anc81, Anc82, and Anc110 compared to AAV9 in in C57Bl/6 mice. The results in FIG. 27 demonstrate that, following intravenous injection of the indicated vector, Anc110 demonstrated equivalent levels of liver targeting as AAV9 in C57Bl/6 mice based on transgene expression of the luciferase reporter gene. Notably, AAV9 is currently in clinical studies.

TABLE 5

Complete Blood Count Values for Mice Injected with AAV8 and Anc80L65.

| Species | Test Name | Control 2 h | AAV2/8 2 h | AAV2/ Anc80L65 2 h | Control 24 h | AAV2/ 8 24 h | AAV2/ Anc80L65 24 h | Control 72 h | AAV2/ 8 72 h | AAV2/ Anc80L65 72 h | Control 7 d | AAV2/ 8 7 d |
|---|---|---|---|---|---|---|---|---|---|---|---|---|
| Mouse | WBC | 4.2 | 5.2 | 5.1 | 7.2 | 5.7 | 7.2 | 5.9 | 3.9 | 5 | 8.4 | 5.5 |
| Mouse | LYM | 3.3 | 3.8 | 3.9 | 6.2 | 5 | 6.2 | 5.3 | 3.4 | 4.4 | 7.4 | 4.9 |
| Mouse | MONO | 0.3 | 0.3 | 0.3 | 0.3 | 0.2 | 0.3 | 0.2 | 0.2 | 0.3 | 0.2 | 0.2 |
| Mouse | GRAN | 0.6 | 1.1 | 0.9 | 0.7 | 0.5 | 0.7 | 0.4 | 0.3 | 0.3 | 0.8 | 0.4 |
| Mouse | LYM % | 79.1 | 73.4 | 77.6 | 87 | 86.9 | 86 | 90 | 86.7 | 88.7 | 87.4 | 89.5 |
| Mouse | MONO % | 4.5 | 4.4 | 3.5 | 3.3 | 3.3 | 3.1 | 2.8 | 3.4 | 3.5 | 2.9 | 2.9 |
| Mouse | GRAN % | 16.4 | 22.2 | 18.9 | 9.7 | 9.8 | 10.9 | 7.2 | 9.9 | 7.8 | 9.7 | 7.6 |
| Mouse | HCT | 49.5 | 47.7 | 50.3 | 46.9 | 45.2 | 47.7 | 43 | 36.5 | 42.5 | 44.7 | 45.7 |
| Mouse | MCV | 44.6 | 44.9 | 44.8 | 44.3 | 44.2 | 44.2 | 44.7 | 45.3 | 44.9 | 44.7 | 45.3 |
| Mouse | RDWa | 30.7 | 32 | 31.2 | 30.8 | 30.4 | 30.6 | 31.2 | 31.9 | 30.9 | 31.1 | 32.5 |
| Mouse | RDW % | 16.8 | 17.8 | 17 | 17.2 | 17.2 | 17.1 | 17.5 | 17.8 | 17.1 | 17.4 | 17.8 |
| Mouse | HGB | 16.7 | 16 | 16.9 | 16.1 | 15.4 | 16.1 | 14.8 | 12.5 | 14.5 | 15 | 15.3 |
| Mouse | MCHC | 33.8 | 33.6 | 33.5 | 34.3 | 34.2 | 33.8 | 34.5 | 34.3 | 34.3 | 33.6 | 33.5 |
| Mouse | MCH | 15.1 | 15.1 | 15 | 15.2 | 15.1 | 14.9 | 15.4 | 15.5 | 15.4 | 15 | 15.2 |
| Mouse | RBC | 11.07 | 10.61 | 11.23 | 10.57 | 10.23 | 10.78 | 9.62 | 8.07 | 9.45 | 10.01 | 10.08 |
| Mouse | PLT | 216 | 423 | 364 | 410 | 208 | 430 | 498 | 205 | 334 | 407 | 175 |
| Mouse | MPV | 6 | 56 | 56 | 5.4 | 5.5 | 5.6 | 5.6 | 6 | 5.6 | 5.6 | 5.6 |

| Species | Test Name | AAV2/ Anc80L65 7 d | Control 14 d | AAV2/ 8 14 d | AAV2/ Anc80L65 14 d | Control 28 d | AAV2/ 8 28 d | AAV2/ Anc80L65 28 d | Test Units | Ref Range Low | Ref Range Low |
|---|---|---|---|---|---|---|---|---|---|---|---|
| Mouse | WBC | 5.8 | 7 | 8.2 | 7.3 | 6.5 | 5.5 | 8.1 | 10^3/μl | 2.6 | 12 |
| Mouse | LYM | 5.1 | 6.2 | 6.7 | 6.5 | 5.8 | 4.5 | 7.3 | 10^3/μl | 1.3 | 9 |
| Mouse | MONO | 0.2 | 0.3 | 0.5 | 0.3 | 0.2 | 0.3 | 0.3 | 10^3/μl | 0.1 | 0.5 |
| Mouse | GRAN | 0.5 | 0.5 | 1 | 0.5 | 0.5 | 0.7 | 0.5 | 10^3/μl | 0.4 | 2.5 |
| Mouse | LYM % | 87.5 | 88.2 | 82.6 | 88.9 | 89.4 | 81.8 | 90.6 | % | 0 | 99.9 |
| Mouse | MONO % | 3.5 | 3.5 | 4.2 | 3.4 | 2.9 | 4.8 | 2.4 | % | 0 | 99.9 |
| Mouse | GRAN % | 9 | 8.3 | 13.2 | 7.7 | 7.7 | 13.4 | 7 | % | 0 | 99.9 |
| Mouse | HCT | 44.6 | 46.1 | 45.2 | 47.3 | 47.2 | 47.3 | 46.9 | % | 32 | 48 |
| Mouse | MCV | 44.3 | 45.1 | 46.1 | 45.3 | 44.9 | 45.7 | 45 | fl | 42 | 55 |
| Mouse | RDWa | 30.6 | 31.6 | 32.4 | 31.7 | 30.9 | 32.1 | 30.8 | fl | 0 | 99.9 |
| Mouse | RDW % | 17.2 | 17.3 | 17.1 | 17.1 | 17 | 17.1 | 17 | % | 0 | 99.9 |
| Mouse | HGB | 15.1 | 15.6 | 15.1 | 15.7 | 15.7 | 16 | 15.8 | g/dl | 10.1 | 16.1 |
| Mouse | MCHC | 33.8 | 33.8 | 33.5 | 33.3 | 33.2 | 33.8 | 33.8 | g/dl | 29 | 35 |
| Mouse | MCH | 15 | 15.2 | 15.4 | 15.1 | 14.9 | 15.4 | 15.2 | pg | 13 | 18.1 |
| Mouse | RBC | 10.05 | 10.2 | 9.8 | 10.42 | 10.51 | 10.33 | 10.4 | 10^3/μl | 6.5 | 10.1 |
| Mouse | PLT | 216 | 333 | 342 | 283 | 367 | 476 | 620 | 10^3/μl | 300 | 1500 |
| Mouse | MPV | 5.4 | 5.9 | 5.5 | 5.7 | 5.7 | 5.7 | 5.6 | fl | 0 | 99.9 |

TABLE 6

Serum Biochemistry Values for Mice Injected with AAV8 and Anc80L65.

| Species | Test Name | Control 2 h | AAV2/ 8 2 h | AAV2/ Anc80L65 2 h | Control 24 h | AAV2/ 8 24 h | AAV2/ Anc80L65 24 h | Control 72 h | AAV2/ 8 72 h | AAV2/ Anc80L65 72 h | Control 7 d | AAV2/ 8 7 d |
|---|---|---|---|---|---|---|---|---|---|---|---|---|
| Mouse | Phosphorus | 10.4 | 8.9 | 9.9 | 7.1 | 7.5 | 8.5 | 8 | 7.2 | 7.2 | 6.7 | 7.2 |
| Mouse | ALT (GPT) | 24 | 28 | 20 | 16 | 21 | 20 | 21 | 18 | 21 | 24 | 17 |
| Mouse | Total Bilirubin | 0.8 | 0.5 | 0.4 | 0.4 | 0.6 | 0.3 | 0.3 | 0.5 | 0.8 | 0.4 | 0.8 |
| Mouse | ALP | 130 | 114 | 137 | 114 | 102 | 127 | 105 | 94 | 85 | 104 | 95 |
| Mouse | Albumin | 2.8 | 2.4 | 2.6 | 2.6 | 2.5 | 2.8 | 2.7 | 2.6 | 2.6 | 2.6 | 2.9 |
| Mouse | GGT | <10 | <10 | <10 | <10 | <10 | <10 | <10 | <10 | <10 | <10 | <10 |
| Mouse | Creatinine | 0.2 | 0.4 | 0.2 | 0.2 | 0.2 | 0.2 | 0.2 | 0.4 | 0.2 | 0.2 | 0.2 |
| Mouse | BUN | 24.5 | 21.4 | 23.7 | 27.8 | 26.8 | 23 | 33.3 | 24.8 | 26.2 | 26.4 | 32 |
| Mouse | Cholesterol | * | 116 | 119 | 113 | 75 | 124 | 104 | 71 | 64 | 111 | 110 |
| Mouse | Total Protein | * | 5.4 | 6 | 5.5 | 5.1 | 5.7 | 5.6 | 4.7 | 4.8 | 5.7 | 5.9 |
| Mouse | Glucose | * | 212 | 228 | 171 | 221 | 184 | 183 | 150 | 180 | 143 | 171 |

TABLE 6-continued

Serum Biochemistry Values for Mice Injected with AAV8 and Anc80L65.

| | | | | | | | | | | | | |
|---|---|---|---|---|---|---|---|---|---|---|---|---|
| Mouse | Calcium | * | 10.4 | 10.8 | 8.3 | 9.9 | 10.7 | 10 | 9.3 | 9.2 | 9.6 | * |
| Mouse | Hemolysis | mod | slight | slight | slight | mod | slight | slight | slight | slight | slight | slight |

| Species | Test Name | AAV2/ Anc80L65 7 d | Control 14 d | AAV2/ 8 14 d | AAV2/ Anc80L65 14 d | Control 28 d | AAV2/ 8 28 d | AAV2/ Anc80L65 28 d | Test Units | Ref Range Low | Ref Range High |
|---|---|---|---|---|---|---|---|---|---|---|---|
| Mouse | Phosphorus | 7.4 | 6.6 | 6.1 | 7.1 | 5.7 | 6.4 | 7.3 | mg/dl | 5.6 | 9.2 |
| Mouse | ALT (GPT) | 62 | 18 | 26 | 12 | 17 | 24 | 16 | U/l | 10 | 190 |
| Mouse | Total Bilirubin | 0.6 | 0.4 | 0.4 | 0.4 | 0.6 | 0.4 | 0.3 | mg/dl | 0.2 | 0.8 |
| Mouse | ALP | 90 | 69 | 95 | 101 | 75 | 76 | 93 | U/l | 0 | 260 |
| Mouse | Albumin | 2.7 | 2.2 | 2.3 | 2.3 | 1.7 | 2.2 | 2.2 | g/dl | 3 | 4 |
| Mouse | GGT | <10 | <10 | <10 | <10 | <10 | <10 | <10 | U/l | 0 | <10 |
| Mouse | Creatinine | | 0.2 | 0.2 | 0.4 | 0.2 | 0.2 | 0.2 | mg/dl | 0.5 | 1.6 |
| Mouse | BUN | 27.3 | 29.4 | 27.7 | 32.6 | 29.6 | 28.4 | 30.6 | mg/dl | 20 | 26 |
| Mouse | Cholesterol | 78 | 116 | 81 | 84 | 97 | 81 | 141 | mg/dl | 28 | 110 |
| Mouse | Total Protein | 5.4 | 5.3 | 5.3 | 5.4 | 5.7 | 5.2 | 5.4 | g/dl | 5 | 7 |
| Mouse | Glucose | 169 | 176 | 167 | 161 | 162 | 159 | 138 | mg/dl | 190 | 280 |
| Mouse | Calcium | 8.5 | 8.4 | 10 | 8.3 | 9.8 | 9.3 | 9.3 | mg/dl | 7.9 | 10.5 |
| Mouse | Hemolysis | slight | slight | slight | slight | slight | slight | slight | | | |

TABLE 7

Levels of Serum Cytokines Measured at Different Timepoints in Mice Injected with Saline, AAV8 and Anc80L65.

| Cytokines (control) | 2 h | 24 h | 3 d | 7 d | Cytokines (AAV8) | 2 h | 24 h | 3 d | 7 d | Cytokines (Anc80L65) | 2 h | 24 h | 3 d | 7 d |
|---|---|---|---|---|---|---|---|---|---|---|---|---|---|---|
| IL-1alpha | 215.5 | 226 | 135 | 176.5 | IL-1alpha | 255 | 227 | 248 | 188 | IL-1alpha | 206 | 172 | 271 | 214 |
| IL- 1beta | 244 | 213 | 228 | 222 | IL-1beta | 252 | 220 | 256 | 227 | IL-1beta | 247 | 200.5 | 253 | 204 |
| IL-2 | 152 | 73 | 143 | 100 | IL-2 | 265 | 106 | 216.5 | 149 | IL-2 | 280 | 218 | 212 | 143 |
| IL-3 | 119 | 142 | 115 | 124 | IL-3 | 161 | 120 | 132 | 127 | IL-3 | 149 | 158.5 | 133 | 111 |
| IL-4 | 198 | 218 | 189 | 200.5 | IL-4 | 257 | 198 | 217.5 | 204 | IL-4 | 232 | 216 | 218.5 | 190 |
| IL-5 | 94 | 126 | 99.5 | 107 | IL-5 | 153.5 | 108 | 122.5 | 121 | IL-5 | 130 | 130 | 129 | 105 |
| IL-6 | 228.5 | 146 | 125 | 130.5 | IL-6 | 198 | 144 | 141 | 161 | IL-6 | 204 | 134 | 154 | 112 |
| IL-9 | 239 | 264.5 | 277 | 225 | IL-9 | 278 | 200.5 | 275.5 | 239 | IL-9 | 287 | 259 | 283 | 236 |
| IL-10 | 175 | 234.5 | 135 | 156 | IL-10 | 226 | 203 | 182 | 210 | IL-10 | 211 | 206 | 196 | 174 |
| IL-12p40 | 764 | 707 | 671 | 641 | IL-12p40 | 772 | 794 | 726 | 708 | IL-12p40 | 716 | 765 | 685.5 | 697 |
| IL-12p70 | 280 | 331.5 | 284 | 271.5 | IL-12p70 | 380 | 286 | 280 | 289 | IL-12p70 | 364.5 | 320 | 316.5 | 255 |
| IL-13 | 97.5 | 117 | 109 | 102.5 | IL-13 | 144.5 | 117 | 126 | 121 | IL-13 | 127 | 125 | 125 | 91.5 |
| IL-17A | 813 | 729 | 606 | 660 | IL-17A | 1033 | 703 | 678 | 761 | IL-17A | 962 | 651 | 814 | 650 |
| Eotaxin | 171.5 | 193 | 177 | 178 | Eotaxin | 210 | 185 | 173 | 178 | Eotaxin | 183 | 188.5 | 193 | 167.5 |
| G-CSF | 339 | 186 | 171 | 303 | G-CSF | 331 | 184.5 | 191 | 177 | G-CSF | 205 | 212.5 | 219 | 153 |
| GM-CSF | 263 | 244 | 272 | 236 | GM-CSF | 284.5 | 234.5 | 207 | 258 | GM-CSF | 223 | 250 | 257 | 223 |
| IFN-gamma | 271 | 278 | 220 | 248 | IFN-gamma | 334 | 240 | 258 | 260 | IFN-gamma | 310 | 252 | 284 | 234.5 |
| KC | 594 | 293 | 288 | 243.5 | KC | 339 | 394 | 309 | 324.5 | KC | 321 | 290 | 337.5 | 280 |
| MCP-1 | 123 | 148 | 121 | 115 | MCP-1 | 175 | 131 | 137.5 | 141.5 | MCP-1 | 143.5 | 136 | 154 | 109 |
| MP-1alpha | 511.5 | 531.5 | 527 | 504 | MP-1alpha | 555 | 504.5 | 505 | 511 | MP-1alpha | 533.5 | 529 | 543 | 453.5 |
| MP-1beta | 121 | 144.5 | 130 | 126 | MP-1beta | 196 | 123 | 133.5 | 137 | MP-1beta | 173.5 | 160 | 134.5 | 115 |
| RANTES | 576.5 | 653 | 506 | 531 | RANTES | 602 | 690 | 571.5 | 638 | RANTES | 643 | 804 | 562 | 673 |
| TNF-alpha | 193 | 211 | 189 | 188 | TNF-alpha | 304 | 194 | 207 | 205 | TNF-alpha | 260.5 | 220 | 215 | 187 |

TABLE 8

Complete Blood Count Values for Non-Human Primates Injected with AAV8 and Anc80L65.

| | Baseline | 1 d | 3 d | 7 d | 15 d | 30 d | 60 d | Final | | Baseline | 1 d | 3 d | 7 d | 15 d | 30 d | 60 d | Final |
|---|---|---|---|---|---|---|---|---|---|---|---|---|---|---|---|---|---|
| | WBC (reference values 3.4-11.2 K/ul) | | | | | | | | | Neutrophils (reference values 40-68%) | | | | | | | |
| AP19 | 5.44 | 7.78 | 5.02 | 5.52 | 10.9 | 5.14 | 5.72 | 5.86 | AP19 | 63.23 | 56.42 | 56.28 | 51.31 | 37.85 | 55.71 | 44.64 | 46.82 |
| AP18 | 5.92 | 7.22 | 5.2 | 4.02 | 7.06 | 6.8 | 7.86 | 7.14 | AP18 | 79.98 | 72.41 | 67.16 | 56.11 | 58.26 | 61.49 | 0.22 | 59.89 |
| AP17 | 8.04 | 8.04 | 6.67 | 6.36 | 8.32 | 7.66 | 8.86 | 9.38 | AP17 | 74.45 | 68.29 | 57.87 | 61.93 | 73.13 | 67.32 | 57.06 | 73.59 |
| AP16 | 6.36 | 5.64 | 5 | 8.3 | 4.96 | 4.9 | 4.92 | 6.26 | AP16 | 80.42 | 64.45 | 58.41 | 70.9 | 58 | 57.49 | 45.03 | 51.27 |
| AP15 | 5.52 | 6.78 | 6.6 | 5.94 | 6.62 | 7.32 | 9.2 | 7.42 | AP15 | 68.37 | 57.44 | 57.53 | 57.43 | 57.84 | 53.19 | 32.26 | 60.72 |
| AP14 | 7.86 | 10.94 | 8.32 | 8.76 | 7.82 | 9.06 | 14.62 | 8.2 | AP14 | 72.63 | 78.34 | 72.48 | 72.35 | 60.34 | 64.01 | 59.89 | 55.86 |

TABLE 8-continued

Complete Blood Count Values for Non-Human Primates Injected with AAV8 and Anc80L65.

| | Baseline | 1 d | 3 d | 7 d | 15 d | 30 d | 60 d | Final | | Baseline | 1 d | 3 d | 7 d | 15 d | 30 d | 60 d | Final |
|---|---|---|---|---|---|---|---|---|---|---|---|---|---|---|---|---|---|
| Lymphocytes (reference values 31-64%) | | | | | | | | | Monocytes (reference values 1.4-4%) | | | | | | | | |
| AP19 | 29.4 | 29.79 | 35.48 | 42.86 | 55.27 | 39.68 | 48.99 | 46.69 | AP19 | 2.81 | 6.91 | 4.27 | 3.34 | 3.32 | 2.25 | 3.1 | 3.96 |
| AP18 | 17.28 | 19.62 | 27.05 | 34.33 | 35.82 | 31.97 | 97.6 | 34.84 | AP18 | 0.77 | 4.08 | 3.26 | 3.64 | 2.06 | 2.62 | 1.47 | 2.57 |
| AP17 | 17.52 | 16.51 | 33.76 | 28.17 | 23.65 | 28.59 | 35.94 | 21.43 | AP17 | 5.02 | 8.73 | 4.97 | 5.21 | 1.86 | 2.01 | 2.16 | 1.9 |
| AP16 | 15.38 | 27.71 | 37.5 | 21.39 | 30.16 | 33.34 | 39.13 | 35.63 | AP16 | 2.04 | 3.3 | 1.02 | 3.06 | 2.29 | 2.3 | 6.63 | 6.26 |
| API5 | 31.41 | 34.02 | 36.92 | 37.8 | 38.29 | 43.49 | 52.11 | 28.04 | AP15 | 2.15 | 4.31 | 2.85 | 2.43 | 1.88 | 1.47 | 6.23 | 3.26 |
| AP14 | 23.82 | 18.08 | 25.95 | 25.19 | 35.81 | 32.78 | 27.26 | 39.33 | AP14 | 1.77 | 1.94 | 0.37 | 1.52 | 1.42 | 0.79 | 3.84 | 2.39 |
| RBC (reference values 4.98-6.42 M/ul) | | | | | | | | | HGB (reference values 11.7-14.7 g/dl) | | | | | | | | |
| AP19 | 6.52 | 6.68 | 6.3 | 6.57 | 6.69 | 6.54 | 6.89 | 7.1 | AP19 | 15.7 | 16.9 | 15.7 | 15.9 | 16.1 | 16.1 | 17 | 16.8 |
| AP18 | 5.24 | 5.57 | 5.35 | 5.47 | 5.51 | 5.71 | 6.69 | 6.17 | API8 | 12.2 | 12.8 | 11.8 | 12.1 | 12.4 | 12.2 | 13.8 | 13.8 |
| AP17 | 6.46 | 6.94 | 6.34 | 5.39 | 6.28 | 6.62 | 7.01 | 6.69 | AP17 | 14.9 | 16.1 | 13.9 | 13.1 | 14.3 | 15.2 | 15.7 | 15.5 |
| AP16 | 5.35 | 5.9 | 5.37 | 5.18 | 4.94 | 5.45 | 5.7 | 5.91 | AP16 | 13.1 | 13.7 | 12.4 | 12.2 | 11.4 | 13.4 | 13.3 | 13.4 |
| AP15 | 5.78 | 5.51 | 5.35 | 4.89 | 4.84 | 5.81 | 5.53 | 5.03 | AP15 | 13.3 | 13.7 | 12.8 | 11.8 | 12.2 | 13.9 | 13.2 | 12.2 |
| AP14 | 4.92 | 5.69 | 5.21 | 5.5 | 5.17 | 5.13 | 5.47 | 5.78 | AP14 | 11.8 | 12.5 | 11.6 | 12.1 | 12.4 | 11.3 | 12.2 | 12.7 |
| HCT (reference values 37.2-47.1%) | | | | | | | | | MCV (reference values 69-79 fl) | | | | | | | | |
| AP19 | 48.3 | 49.3 | 47.2 | 48.7 | 49.4 | 49.2 | 51.7 | 53.2 | AP19 | 74.1 | 73.8 | 74.9 | 74.2 | 73.9 | 75.2 | 75.1 | 75 |
| AP18 | 35.5 | 37.7 | 35.9 | 36.5 | 37.2 | 39.3 | 41.9 | 41.3 | AP18 | 67.7 | 67.6 | 67.1 | 66.7 | 67.5 | 68.8 | 62.7 | 66.9 |
| AP17 | 44.4 | 47.6 | 43.5 | 36.9 | 43.7 | 46.1 | 49.1 | 47.4 | AP17 | 68.8 | 68.6 | 68.6 | 68.5 | 69.6 | 69.7 | 70 | 70.8 |
| AP16 | 38.2 | 42.4 | 38 | 36.6 | 35.1 | 38.3 | 40.3 | 42.1 | AP16 | 71.4 | 71.8 | 70.7 | 70.7 | 71 | 70.2 | 71.1 | 71.3 |
| AP15 | 42.1 | 39.8 | 38.9 | 35.8 | 35.2 | 42.8 | 40.4 | 36.4 | AP15 | 72.8 | 72.3 | 72.8 | 73.2 | 72.7 | 73.6 | 73 | 72.4 |
| AP14 | 33.3 | 38.6 | 35.5 | 36.8 | 34.8 | 34.6 | 36.9 | 38.6 | AP14 | 67.7 | 67.8 | 68.1 | 67 | 67.4 | 67.5 | 67.5 | 66.7 |
| PLT (reference values 190-536 K/u1) | | | | | | | | | MPV (reference values 8.9-16.1) | | | | | | | | |
| AP19 | 360 | 396 | 417 | 646 | 541 | 403 | 435 | 432 | AP19 | 14.1 | 12.9 | 12.8 | 12.2 | 13.6 | 13.1 | 12.2 | 12.2 |
| AP18 | 409 | 442 | 432 | 765 | 780 | 560 | 644 | 625 | AP18 | 9.6 | 10.9 | 8.4 | 9.7 | 8.1 | 9 | 8.7 | 10.2 |
| AP17 | 515 | 535 | 554 | 737 | 724 | 525 | 614 | 474 | AP17 | 8.4 | 8.7 | 8.9 | 9.9 | 9.7 | 7.7 | 8 | 11.4 |
| AP16 | 485 | 509 | 427 | 708 | 721 | 494 | 504 | 545 | AP16 | 9.3 | 10.4 | 8.8 | 10.1 | 10.4 | 9.5 | 9.6 | 11.1 |
| AP15 | 351 | 384 | 326 | 613 | 665 | 454 | 505 | 456 | AP15 | 13.7 | 15.4 | 15.1 | 11.6 | 9.7 | 12.4 | 11.3 | 11.3 |
| AP14 | 549 | 595 | 561 | 875 | 797 | 586 | 725 | 713 | AP14 | 10.8 | 11.1 | 10.7 | 10.2 | 8.9 | 9.3 | 9 | 10.1 |

TABLE 9

Serum Biochemistry Values for Non-Human Primates Injected with AAV8 and Anc80L65.

| | Baseline | 1 d | 3 d | 7 d | 15 d | 30 d | 60 d | Final | | Baseline | 1 d | 3 d | 7 d | 15 d | 30 d | 60 d | Final |
|---|---|---|---|---|---|---|---|---|---|---|---|---|---|---|---|---|---|
| ALT (reference values 0-59 U/1) | | | | | | | | | AST (reference values 0-46 U/1) | | | | | | | | |
| AP19 | 49 | 33 | 45 | 42 | 25 | 38 | 40 | 33 | AP19 | 59 | 24 | 36 | 31 | 27 | 28 | 24 | 24 |
| AP18 | 34 | | 34 | 23 | 22 | 16 | 22 | 17 | AP18 | 48 | | 26 | 19 | 21 | 10 | 17 | 14 |
| AP17 | 59 | 38 | 57 | 34 | 25 | 51 | 80 | 44 | AP17 | 62 | 33 | 38 | 28 | 29 | 38 | 31 | 22 |
| AP16 | 45 | 35 | 49 | 37 | 40 | 40 | 73 | 58 | AP16 | 55 | 31 | 38 | 22 | 22 | 34 | 24 | 20 |
| AP15 | 55 | 33 | 65 | 28 | 21 | 37 | 28 | 25 | AP15 | 72 | 30 | 40 | 18 | 21 | 20 | 21 | 25 |
| AP14 | 32 | 19 | 38 | 23 | 23 | 21 | 22 | 17 | AP14 | 47 | 26 | 24 | | | | | |
| GGT (reference values 0-69.9 U/1) | | | | | | | | | Total bilirubin (reference values 0-0.39 mg/dl) | | | | | | | | |
| AP19 | 40 | 41 | 40 | 39 | 38 | 43 | 43 | 48 | AP19 | 0.1 | 0.1 | 0.1 | 0.1 | 0.1 | 0.1 | 0.1 | 0.1 |
| AP18 | 35 | | 33 | 32 | 33 | 27 | 34 | 34 | AP18 | 0.2 | | | 0.1 | 0.1 | 0.1 | 0.1 | 0.1 |
| AP17 | 42 | 45 | 38 | 36 | 38 | 38 | 44 | 41 | AP17 | 0.1 | 0.1 | 0.1 | 0.2 | 0.1 | 0.2 | 0.2 | 0.1 |
| AP16 | 41 | 44 | 38 | 38 | 40 | 42 | 43 | 42 | AP16 | 0.1 | 0.1 | 0.1 | 0.1 | 0.1 | 0.1 | 0.1 | 0.1 |
| AP15 | 59 | 62 | 59 | 60 | 55 | 56 | 56 | 57 | AP15 | 0.1 | 0.1 | 0.1 | 0.1 | 0.1 | 0.1 | 0.1 | 0.2 |
| AP14 | 60 | 64 | 58 | 59 | 65 | 53 | 53 | 55 | AP14 | 0.1 | 0.1 | 0.1 | 0.2 | 0.1 | 0.1 | 0.1 | 0.1 |
| Albumin (reference values 3.3-4.7 g/dl) | | | | | | | | | BUN (reference values 9-23 mg/dl) | | | | | | | | |
| AP19 | 3.8 | 4.0 | 3.8 | 3.8 | 4.0 | 4.0 | 4.1 | 4.2 | AP19 | 11 | 17 | 11 | 11 | 11 | 10 | 10 | 10 |
| AP18 | 4.3 | | 4.2 | 4.1 | 4.1 | 2.3 | 4.2 | 3.9 | AP18 | 14 | | 12 | 14 | 13 | 7 | 13 | 11 |
| AP17 | 4.0 | 4.1 | 3.8 | 3.7 | 4.1 | 2.9 | 3.9 | 3.3 | AP17 | 15 | 12 | 14 | 10 | 11 | 10 | 12 | 8 |
| AP16 | 4.1 | 4.2 | 4.0 | 3.9 | 4.0 | 4.3 | 4.2 | 3.0 | AP16 | 20 | 15 | 12 | 12 | 12 | 13 | 15 | 10 |
| AP15 | 4.2 | 4.3 | 4.2 | 3.9 | 4.1 | 3.9 | 3.8 | 4.1 | AP15 | 21 | 21 | 15 | 19 | 16 | 24 | 10 | 13 |
| AP14 | 4.3 | 4.6 | 4.4 | 4.4 | 4.6 | 4.0 | 4.0 | 4.1 | AP14 | 18 | 22 | 15 | 17 | 20 | 13 | 13 | 15 |
| Total protein (reference values 6-7.8 g/dl) | | | | | | | | | Amylase (reference values 18-612 U/l) | | | | | | | | |
| AP19 | 6.8 | 7.0 | 7.0 | 6.8 | 6.8 | 6.8 | 6.8 | 7.2 | AP19 | 200 | 209 | 407 | 226 | 419 | 177 | 257 | 575 |
| AP18 | 6.9 | | 6.8 | 6.7 | 6.7 | 4.4 | 6.9 | 6.6 | AP18 | 228 | | 277 | 263 | 298 | 198 | 261 | 255 |
| AP17 | 6.9 | 7.0 | 6.5 | 6.3 | 6.7 | 5.8 | 6.7 | 6.1 | AP17 | 170 | 159 | 222 | 138 | 126 | 123 | 117 | 115 |
| AP16 | 7.3 | 7.4 | 7.0 | 6.8 | 7.0 | 7.2 | 7.2 | 5.8 | AP16 | 560 | 491 | 461 | 435 | 302 | 468 | 461 | 427 |

TABLE 9-continued

Serum Biochemistry Values for Non-Human Primates Injected with AAV8 and Anc80L65.

| | Baseline | 1 d | 3 d | 7 d | 15 d | 30 d | 60 d | Final | | Baseline | 1 d | 3 d | 7 d | 15 d | 30 d | 60 d | Final |
|---|---|---|---|---|---|---|---|---|---|---|---|---|---|---|---|---|---|
| AP15 | 6.8 | 7.0 | 6.9 | 6.3 | 6.5 | 6.4 | 6.2 | 6.7 | AP15 | 353 | 348 | 425 | 384 | 382 | 418 | 400 | 386 |
| AP14 | 6.7 | 7.1 | 6.7 | 6.9 | 6.9 | 6.1 | 6.5 | 6.6 | AP14 | 200 | 227 | 211 | 248 | 259 | 196 | 195 | 215 |
| CK (reference values 0-1596 U/l) | | | | | | | | | LDH (reference values 0-785 IU/l) | | | | | | | | |
| AP19 | 1807 | 534 | 1312 | 1727 | 643 | 1174 | 431 | 448 | AP19 | 430 | 176 | 326 | 249 | 326 | 405 | 181 | 197 |
| AP18 | 3660 | | 238 | 290 | 141 | 143 | 165 | 146 | AP18 | 508 | | 257 | 189 | 233 | 184 | 183 | 141 |
| AP17 | 4346 | 784 | 1180 | 796 | 1455 | 794 | 304 | 401 | AP17 | 560 | 259 | 277 | 211 | 479 | 307 | 204 | 228 |
| AP16 | 2231 | 496 | 940 | 601 | 386 | 770 | 600 | 237 | AP16 | 366 | 227 | 267 | 196 | 290 | 613 | 153 | 160 |
| AP15 | 1241 | 571 | 221 | 181 | 330 | 380 | 139 | 181 | AP15 | 329 | 297 | 375 | 174 | 189 | 308 | 203 | 164 |
| AP14 | 1099 | 779 | 292 | 71 | 176 | 239 | 198 | 566 | AP14 | 350 | 338 | 253 | 179 | 217 | 232 | 224 | 365 |
| ALP (reference values 0-704 U/l) | | | | | | | | | Creatinine (reference values 0.7-1.3 mg/dl) | | | | | | | | |
| AP19 | 177 | 195 | 174 | 196 | 108 | 173 | 176 | 153 | AP19 | 0.8 | 0.8 | 0.8 | 0.8 | 0.8 | 0.8 | 0.9 | 0.8 |
| AP18 | 116 | | 103 | 100 | 110 | 79 | 106 | 95 | AP18 | 0.8 | | 0.7 | 0.7 | 0.8 | 0.5 | 0.7 | 0.8 |
| AP17 | 205 | 194 | 184 | 248 | 193 | 215 | 219 | 156 | AP17 | 0.9 | 0.8 | 0.8 | 0.7 | 0.6 | 0.8 | 0.8 | 0.8 |
| AP16 | 100 | 107 | 104 | 96 | 175 | 89 | 117 | 92 | AP16 | 0.9 | 0.8 | 0.8 | 0.8 | 0.8 | 0.8 | 0.9 | 0.7 |
| AP15 | 140 | 148 | 151 | 141 | 163 | 155 | 150 | 154 | AP15 | 1.0 | 0.9 | 0.9 | 0.9 | 0.9 | 0.9 | 0.9 | 0.9 |
| AP14 | 97 | 111 | 101 | 105 | 111 | 89 | 110 | 97 | AP14 | 0.8 | 0.8 | 0.7 | 0.7 | 0.7 | 0.7 | 0.7 | 0.7 |
| Glucose (reference values 33-95 mg/dl) | | | | | | | | | Cholesterol (reference values 69-205 mg/dl) | | | | | | | | |
| AP19 | 80 | 87 | 78 | 63 | 63 | 67 | 77 | 88 | AP14 | 111 | 114 | 119 | 133 | 161 | 121 | 139 | 148 |
| AP18 | 68 | | 82 | 77 | 43 | 60 | 67 | 88 | AP18 | 143 | | 135 | 135 | 156 | 108 | 161 | 159 |
| AP17 | 92 | 96 | 71 | 93 | 64 | 79 | 106 | 69 | AP17 | 127 | 155 | 112 | 148 | 129 | 125 | 148 | 119 |
| AP16 | 80 | 36 | 74 | 84 | 76 | 53 | 72 | 66 | AP16 | 169 | 191 | 164 | 166 | 153 | 176 | 189 | 171 |
| AP15 | 79 | 35 | 53 | 58 | 83 | 55 | 55 | 67 | AP15 | 215 | 224 | 204 | 194 | 207 | 216 | 177 | 205 |
| AP14 | 71 | 61 | 73 | 75 | 68 | 56 | 83 | 66 | AP14 | 105 | 115 | 110 | 114 | 127 | 103 | 120 | 125 |

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

Sequence Listing

```
SEQ ID NO: 1: Anc80 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPAX1KRLNFGQTGDSESVPDPQPLGEP
PAAPSGVGSNTMX2AGGGAPMADNNEGADGVGNASGNWHCDSTWLGDRVITTSTRTWALPTYNN
HLYKQISSQSGX3STNDNTYFGYSTPWGYFDFNRFHCHFSPRDWQRLINNNWGFRPKX4LNFKL
FNIQVKEVTTNDGTTTIANNLTSTVQVFTDSEYQLPYVLGSAHQGCLPPFPADVFMIPQYGYLT
LNNGSQAVGRSSFYCLEYFPSQMLRTGNNFX5FSYTFEDVPFHSSYAHSQSLDRLMNPLIDQYL
YYLSRTQTTSGTAGNRX6LQFSQAGPSSMANQAKNWLPGPCYRQQRVSKTX7NQNNNSNFAWTG
ATKYHLNGRDSLVNPGPAMATHKDDEDKFFPMSGVLIFGKQGAGNSNVDLDNVMITX8EEEIKT
TNPVATEX9YGTVATNLQSX10NTAPATGTVNSQGALPGMVWQX11RDVYLQGPIWAKIPHTDG
HFHPSPLMGGFGLKHPPPQILIKNTPVPANPPTTFSPAKFASFITQYSTGQVSVEIEWELQKEN
SKRWNPEIQYTSNYNKSTNVDFAVDTNGVYSEPRPIGTRYLTRNL
X1 = K/R; X2 = A/S; X3 = A/G; X4 = R/K; X5 = E/Q; X6 = T/E; X7 =
A/T; X8 = S/N; X9 = Q/E; X10 = S/A; X11 = N/D

SEQ ID NO: 2: Anc80 VP1 DNA
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
```

-continued

Sequence Listing

CTCGGTCTGGTTGAGGAAGGCGCTAAGACGGCTCCTGGAAAGAAGAGACCGGTAGAGCAATCAC
CCCAGGAACCAGACTCCTCTTCGGGCATCGGCAAGAAAGGCCAGCAGCCCGCGXXX1AAGAGAC
TCAACTTTGGGCAGACAGGCGACTCAGAGTCAGTGCCCGACCCTCAACCACTCGGAGAACCCCC
CGCAGCCCCCTCTGGTGTGGGATCTAATACAATGXXX2GCAGGCGGTGGCGCTCCAATGGCAGA
CAATAACGAAGGCGCCGACGGAGTGGGTAACGCCTCAGGAAATTGGCATTGCGATTCCACATGG
CTGGGCGACAGAGTCATCACCACCAGCACCCGAACCTGGGCCCTCCCCACCTACAACAACCACC
TCTACAAGCAAATCTCCAGCCAATCGGGAXXX3AGCACCAACGACAACACCTACTTCGGCTACA
GCACCCCCTGGGGGTATTTTGACTTTAACAGATTCCACTGCCACTTCTCACCACGTGACTGGCA
GCGACTCATCAACAACAACTGGGGATTCCGGCCCAAGXXX4CTCAACTTCAAGCTCTTCAACAT
CCAGGTCAAGGAGGTCACGACGAATGATGGCACCACGACCATCGCCAATAACCTTACCAGCACG
GTTCAGGTCTTTACGGACTCGGAATACCAGCTCCCGTACGTCCTCGGCTCTGCGCACCAGGGCT
GCCTGCCTCCGTTCCCGGCGGACGTCTTCATGATTCCTCAGTACGGGTACCTGACTCTGAACAA
TGGCAGTCAGGCCGTGGGCCGTTCCTCCTTCTACTGCCTGGAGTACTTTCCTTCTCAAATGCTG
AGAACGGGCAACAACTTTXXX5TTCAGCTACACGTTTGAGGACGTGCCTTTTCACAGCAGCTAC
GCGCACAGCCAAAGCCTGGACCGGCTGATGAACCCCCTCATCGACCAGTACCTGTACTACCTGT
CTCGGACTCAGACCACGAGTGGTACCGCAGGAAATCGGXXX6TTGCAATTTTCTCAGGCCGGGC
CTAGTAGCATGGCGAATCAGGCCAAAAACTGGCTACCCGGGCCCTGCTACCGGCAGCAACGCGT
CTCCAAGACAXXX7AATCAAAATAACAACAGCAACTTTGCCTGGACCGGTGCCACCAAGTATCA
TCTGAATGGCAGAGACTCTCTGGTAAATCCCGGTCCCGCTATGGCAACCCACAAGGACGACGAA
GACAAATTTTTTCCGATGAGCGGAGTCTTAATATTTGGGAAACAGGGAGCTGGAAATAGCAACG
TGGACCTTGACAACGTTATGATAACCXXX8GAGGAAGAAATTAAAACCACCAACCCAGTGGCCA
CAGAAXXX9TACGGCACGGTGGCCACTAACCTGCAATCGXXX10AACACCGCTCCTGCTACAGG
GACCGTCAACAGTCAAGGAGCCTTACCTGGCATGGTCTGGCAGXXX11CGGGACGTGTACCTGC
AGGGTCCTATCTGGGCCAAGATTCCTCACACGGACGGACACTTTCATCCCTCGCCGCTGATGGG
AGGCTTTGGACTGAAACACCCGCCTCCTCAGATCCTGATTAAGAATACACCTGTTCCCGCGAAT
CCTCCAACTACCTTCAGTCCAGCTAAGTTTGCGTCGTTCATCACGCAGTACAGCACCGGACAGG
TCAGCGTGGAAATTGAATGGGAGCTGCAGAAAGAAAACAGCAAACGCTGGAACCCAGAGATTCA
ATACACTTCCAACTACAACAAATCTACAAATGTGGACTTTGCTGTTGACACAAATGGCGTTTAT
TCTGAGCCTCGCCCCATCGGCACCCGTTACCTCACCCGTAATCTG
XXX1 = AAG/AAA; XXX2 = GCA/AGC; XXX3 = GCA/GGC; XXX4 = AGA/AAG;
XXX5 = GAG/CAG; XXX6 = ACG/GAG; XXX7 = GCG/ACC; XXX8 = AGT/AAC;
XXX9 = CAG/GAG; XXX10 = TCA/GCC; XXX11 = AAC/GAC

SEQ ID NO: 3: Anc81 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSX1GIGKKGQQPAX2KRLNFGQTGDSESVPDPQPLGE
PPAAPSGVGSNTMAAGGGAPMADNNEGADGVGNASGNWHCDSTWLGDRVITTSTRTWALPTYNN
HLYKQISX3X4QSGGSTNDNTYFGYSTPWGYFDFNRFHCHFSPRDWQRLINNNWGFRPKX5LNF
KLFNIQVKEVTTNDGTTTIANNLTSTVQVFTDSEYQLPYVLGSAHQGCLPPFPADVFMIPQYGY
LTLNNGSQAVGRSSFYCLEYFPSQMLRTGNNFX6FSYTFEDVPFHSSYAHSQSLDRLMNPLIDQ
YLYYLSRTQTTGGTAGNX7X8LQFSQAGPSSMANQAKNWLPGPCYRQQRVSKTTNQNNNSNFAW
TGATKYHLNGRDSLVNPGVAMATHKDDEDRFFPSSGVLIFGKQGAGNX9NVDX10X11NVMITX
12EEEIKTTNPVATEEYGX13VATNLQSX14NTAPQTGTVNSQGALPGMVWQNRDVYLQGPIWA
KIPHTDGNFHPSPLMGGFGLKHPPPQILIKNTPVPANPPTTFX15PAKFASFITQYSTGQVSVE
IEWELQKENSKRWNPEIQYTSNYNKSTNVDFAVDTEGVYSEPRPIGTRYLTRNL
X1 = T/S; X2 = K/R; X3 = N/S; X4 = S/H; X5 = R/K; X6 = E/Q; X7 = R/Q;
X8 = T/E; X9 = D/S; X10 = L/Y; X11 = D/S; X12 = S/N; X13 = V/I; X14 = A/S;
X15 = S/T SEQ ID NO: 4: Anc81 VP1 DNA
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCAATCAC
CCCAGGAACCAGACTCCTCTXXX1GGCATCGGCAAGAAAGGCCAGCAGCCCGCGXXX2AAGAGA
CTCAACTTTGGGCAGACTGGCGACTCAGAGTCAGTGCCCGACCCTCAACCACTCGGAGAACCCC
CCGCAGCCCCCTCTGGTGTGGGATCTAATACAATGGCTGCAGGCGGTGGCGCTCCAATGGCAGA
CAATAACGAAGGCGCCGACGGAGTGGGTAATGCCTCAGGAAATTGGCATTGCGATTCCACATGG
CTGGGCGACAGAGTCATCACCACCAGCACCCGAACCTGGGCCCTCCCCACCTACAACAACCACC
TCTACAAGCAAATCTCCXXX3XXX4CAATCGGGAGGAAGCACCAACGACAACACCTACTTCGGC
TACAGCACCCCCTGGGGGTATTTTGACTTTAACAGATTCCACTGCCACTTCTCACCACGTGACT
GGCAGCGACTCATCAACAACAACTGGGGATTCCGGCCCAAGXXX5CTCAACTTCAAGCTCTTCA
ACATCCAGGTCAAGGAGGTCACGACGAATGATGGCACCACGACCATCGCCAATAACCTTACCAG
CACGGTTCAGGTCTTTACGGACTCGGAATACCAGCTCCCGTACGTCCTCGGCTCTGCGCACCAG
GGCTGCCTGCCTCCGTTCCCGGCGGACGTCTTCATGATTCCTCAGTACGGGTACCTGACTCTGA
ACAATGGCAGTCAGGCCGTGGGCCGTTCCTCCTTCTACTGCCTGGAGTACTTTCCTTCTCAAAT
GCTGAGAACGGGCAACAACTTTXXX6TTCAGCTACACGTTTGAGGACGTGCCTTTTCACAGCAG
CTACGCGCACAGCCAAAGCCTGGACCGGCTGATGAACCCCCTCATCGACCAGTACCTGTACTAC
CTGTCTCGGACTCAGACCACGGGAGGTACCGCAGGAAATXXX7XXX8TTGCAATTTTCTCAGGC
CGGGCCTAGTAGCATGGCGAATCAGGCCAAAAACTGGCTACCCGGGCCCTGCTACCGGCAGCAA
CGCGTCTCCAAGACAACGAATCAAAATAACAACAGCAACTTTGCCTGGACCGGTGCCACCAAGT
ATCATCTGAATGGCAGAGACTCTCTGGTAAATCCCGGTGTCGCTATGGCAACCCACAAGGACGA
CGAAGACCGATTTTTTCCGTCCAGCGGAGTCTTAATATTTGGGAAACAGGGAGCTGGAAATXXX -continued Sequence Listing 9AACGTGGACXXX10XXX11AACGTTATGATAACCXXX12GAGGAAGAAATTAAAACCACCAAC
CCAGTGGCCACAGAAGAGTACGGCXXX13GTGGCCACTAACCTGCAATCGXXX14AACACCGCT
CCTCAAACAGGGACCGTCAACAGTCAAGGAGCCTTACCTGGCATGGTCTGGCAGAACCGGGACG
TGTACCTGCAGGGTCCTATCTGGGCCAAGATTCCTCACACGGACGGAAACTTTCATCCCTCGCC
GCTGATGGGAGGCTTTGGACTGAAACACCCGCCTCCTCAGATCCTGATTAAGAATACACCTGTT
CCCGCGAATCCTCCAACTACCTTCXXX15CCAGCTAAGTTTGCGTCGTTCATCACGCAGTACAG
CACCGGACAGGTCAGCGTGGAAATTGAATGGGAGCTGCAGAAAGAAAACAGCAAACGCTGGAAC
CCAGAGATTCAATACACTTCCAACTACAACAAATCTACAAATGTGGACTTTGC7GTTGACACAG
AAGGCGTTTATTCTGAGCCTCGCCCCATCGGCACCCGTTACCTCACCCGTAATCTG
XXX1 = ACG/AGC; XXX2 = AAA/AAG; XXX3 = AAC/AGT; XXX4 = AGC/CAC;
XXX5 = AGA/AAG; XXX6 = GAG/CAG; XXX7 = CGG/CAG; XXX8 = ACG/GAG;
XXX9 = GAC/AGC; XXX10 = CTT/TAC; XXX11 = GAC/AGC; XXX12 =
AGT/AAC; XXX13 = GTG/ATC; XXX14 = GCA/AGC; XXX15 = AGT/ACC SEQ ID NO: 5: Anc82 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQREPDSSX1GIGKKGQQPAX2KRLNFGQTGDSESVPDPQPLG
EPPAAPSGVGSNTMAAGGGAPMADNNEGADGVGNSSGNWHCDSTWLGDRVITTSTRTWALPTYN
NHLYKQISNGTSGGSTNDNTYFGYSTPWGYFDFNRFHCHFSPRDWQRLINNNWGFRPKRLNFKL
FNIQVKEVTTNEGTKTIANNLTSTVQVFTDSEYQLPYVLGSAHQGCLPPFPADVFMIPQYGYLT
LNNGSQAVGRSSFYCLEYFPSQMLRTGNNFQFSYTFEDVPFHSSYAHSQSLDRLMNPLIDQYLY
YLSRTQTTGGTAGTQTLQFSQAGPSSMANQAKNWLPGPCYRQQRVSTTTNQNNNSNFAWTGATK
YHLNGRDSLVNPGVAMATHKDDEDRFFPSSGVLIFGKQGAGNDNVDYSNVMITX3EEEIKTTNP
VATEEYGWATNLQSANTAPQTGTVNSQGALPGMVWQNRDVYLQGPIWAKIPHTDGNFHPSPLM
GGFGLKHPPPQILIKNTPVPADPPTTFNQAKLNSFITQYSTGQVSVEIEWELQKENSKRWNPEI
QYTSNYYKSTNVDFAVNTEGVYSEPRPIGTRYLTRNL
X1 = T/S; X2 = K/R; X3 = S/N SEQ ID NO: 6: Anc82 VP1 DNA
ATGGCTGCCGATGGTTATCTTCCAGATTGGCTCGAGGACAACCTCTCTGAGGGCATTCGCGAGT
GGTGGGACCTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAATCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCAGTCAC
CACAGCGTGAGCCCGACTCCTCCXXX1GGCATCGGCAAGAAAGGCCAGCAGCCCGCCXXX2AAG
AGACTCAATTTCGGTCAGACTGGCGACTCAGAGTCAGTCCCCGACCCTCAACCTCTCGGAGAAC
CTCCAGCAGCGCCCTCTGGTGTGGGATCTAATACAATGGCTGCAGGCGGTGGCGCACCAATGGC
AGACAATAACGAAGGTGCCGACGGAGTGGGTAATTCCTCGGGAAATTGGCATTGCGATTCCACA
TGGCTGGGCGACAGAGTCATCACCACCAGCACCCGAACCTGGGCCCTGCCCACCTACAACAACC
ACCTCTACAAGCAAATCTCCAACGGGACCTCGGGAGGCAGCACCAACGACAACACCTACTTTGG
CTACAGCACCCCCTGGGGGTATTTTGACTTTAACAGATTCCACTGCCACTTCTCACCACGTGAC
TGGCAGCGACTCATCAACAACAACTGGGGATTCCGGCCCAAGAGACTCAACTTCAAGCTCTTCA
ACATCCAGGTCAAAGAGGTCACGACGAATGAAGGCACCAAGACCATCGCCAATAACCTCACCAG
CACCGTCCAGGTGTTTACGGACTCGGAATACCAGCTGCCGTACGTCCTCGGCTCTGCCCACCAG
GGCTGCCTGCCTCCGTTCCCGGCGGACGTCTTCATGATTCCTCAGTACGGCTACCTGACTCTCA
ACAACGGTAGTCAGGCCGTGGGACGTTCCTCCTTCTACTGCCTGGAGTACTTCCCCTCTCAGAT
GCTGAGAACGGGCAACAACTTTCAATTCAGCTACACTTTCGAGGACGTGCCTTTCCACAGCAGC
TACGCGCACAGCCAGAGTTTGGACAGGCTGATGAATCCTCTCATCGACCAGTACCTGTACTACC
TGTCAAGAACCCAGACTACGGGAGGCACAGCGGGAACCCAGACGTTGCAGTTTTCTCAGGCCGG
GCCTAGCAGCATGGCGAATCAGGCCAAAAACTGGCTGCCTGGACCCTGCTACAGACAGCAGCGC
GTCTCCACGACAACGAATCAAAACAACAACAGCAACTTTGCCTGGACTGGTGCCACCAAGTATC
ATCTGAACGGCAGAGACTCTCTGGTGAATCCGGGCGTCGCCATGGCAACCCACAAGGACGACGA
GGACCGCTTCTTCCCATCCAGCGGCGTCCTCATATTTGGCAAGCAGGGAGCTGGAAATGACAAC
GTGGACTATAGCAACGTGATGATAACCXXX3GAGGAAGAAATCAAGACCACCAACCCCGTGGCC
ACAGAAGAGTATGGCGTGGTGGCTACTAACCTACAGTCGGCAAACACCGCTCCTCAAACGGGGA
CCGTCAACAGCCAGGGAGCCTTACCTGGCATGGTCTGGCAGAACCGGGACGTGTACCTGCAGGG
TCCTATTTGGGCCAAGATTCCTCACACAGATGGCAACTTTCACCCGTCTCCTTTAATGGGCGGC
TTTGGACTTAAACATCCGCCTCCTCAGATCCTCATCAAAAACACTCCTGTTCCTGCGGATCCTC
CAACAACGTTCAACCAGGCCAAGCTGAATTCTTTCATCACGCAGTACAGCACCGGACAAGTCAG
CGTGGAGATCGAGTGGGAGCTGCAGAAGGAGAACAGCAAGCGCTGGAACCCAGAGATTCAGTAT
ACTTCCAACTACTACAAATCTACAAATGTGGACTTTGCTGTTAATACTGAGGGTGTTTACTCTG
AGCCTCGCCCCATTGGCACTCGTTACCTCACCCGTAATCTG
XXX1 = ACG/AGC; XXX2 = AAA/AGA; XXX¬3 = AGC/AAC SEQ ID NO: 7: Anc83 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQREPDSSX1GIGKKGQQPAX2KRLNFGQTGDSESVPDPQPLG
EPPAAPSGVGSNTMAAGGGAPMADNNEGADGVGSSSGNWHCDSTWLGDRVITTSTRTWALPTYN
NHLYKQISNGTSGGSTNDNTYFGYSTPWGYFDFNRFHCHFSPRDWQRLINNNWGFRPKRLX3FK
LFNIQVKEVTQNEGTKTIANNLTSTIQVFTDSEYQLPYVLGSAHQGCLPPFPADVFMIPQYGYL
TLNNGSQAVGRSSFYCLEYFPSQMLRTGNNFX4FSYTFEDVPFHSSYAHSQSLDRLMNPLIDQY
LYYLSRTQTTGGTAGTQTLQFSQAGPSX5MANQAKNWLPGPCYRQQRVSTTTSQNNNSNFAWTG
ATKYHLNGRDSLVNPGVAMATHKDDEX7RFFPSSGX7LIFGKQGAGKDNVDYSNVMLTSEEEIK -continued Sequence Listing TTNPVATEEYGVVADNLQQQNTAPQX8GTVNSQGALPGMVWQNRDVYLQGPIWAKIPHTDGNFH
PSPLMGGFGLKHPPPQILIKNTPVPADPPTTFNQAKLNSFITQYSTGQVSVEIEWELQKENSKR
WNPEIQYTSNYYKSTNVDFAVNTEGVYSEPRPIGTRYLTRNL
X1 = T/S; X2 = R/K; X3 = N/S; X4 = Q/E; X5 = N/T/S; X6 = D/E; X7 = I/V;
X8 = I/V SEQ ID NO: 8: Anc83 VP1 DNA
ATGGCTGCCGATGGTTATCTTCCAGATTGGCTCGAGGACAACCTCTCTGAGGGCATTCGCGAGT
GGTGGGACCTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAATCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCAGTCAC
CACAGCGTGAGCCCGACTCCTCCXXX1GGCATCGGCAAGAAAGGCCAGCAGCCCGCCXXX2AAG
AGACTCAATTTCGGTCAGACTGGCGACTCAGAGTCAGTCCCCGACCCTCAACCTCTCGGAGAAC
CTCCAGCAGCGCCCTCTGGTGTGGGATCTAATACAATGGCTGCAGGCGGTGGCGCACCAATGGC
AGACAATAACGAAGGTGCCGACGGAGTGGGTAGTTCCTCGGGAAATTGGCATTGCGATTCCACA
TGGCTGGGCGACAGAGTCATCACCACCAGCACCCGAACCTGGGCCCTGCCCACCTACAACAACC
ACCTCTACAAGCAAATCTCCAACGGGACCTCGGGAGGCAGCACCAACGACAACACCTACTTTGG
CTACAGCACCCCCTGGGGGTATTTTGACTTTAACAGATTCCACTGCCACTTCTCACCACGTGAC
TGGCAGCGACTCATCAACAACAACTGGGGATTCCGGCCCAAGAGACTCXXX3TTCAAGCTCTTC
AACATCCAGGTCAAAGAGGTCACGCAGAATGAAGGCACCAAGACCATCGCCAATAACCTCACCA
GCACCATCCAGGTGTTTACGGACTCGGAATACCAGCTGCCGTACGTCCTCGGCTCTGCCCACCA
GGGCTGCCTGCCTCCGTTCCCGGCGGACGTCTTCATGATTCCTCAGTACGGCTACCTGACTCTC
AACAACGGTAGTCAGGCCGTGGGACGTTCCTCCTTCTACTGCCTGGAGTACTTCCCCTCTCAGA
TGCTGAGAACGGGCAACAACTTTXXX4TTCAGCTACACTTTCGAGGACGTGCCTTTCCACAGCA
GCTACGCGCACAGCCAGAGTTTGGACAGGCTGATGAATCCTCTCATCGACCAGTACCTGTACTA
CCTGTCAAGAACCCAGACTACGGGAGGCACAGCGGGAACCCAGACGTTGCAGTTTTCTCAGGCC
GGGCCTAGCXXX5ATGGCGAATCAGGCCAAAAACTGGCTGCCTGGACCCTGCTACAGACAGCAG
CGCGTCTCCACGACAACGTCGCAAAACAACAACAGCAACTTTGCCTGGACTGGTGCCACCAAGT
ATCATCTGAACGGCAGAGACTCTCTGGTGAATCCGGGCGTCGCCATGGCAACCCACAAGGACGA
CGAGXXX6CGCTTCTTCCCATCCAGCGGCXXX7CTCATATTTGGCAAGCAGGGAGCTGGAAAAG
ACAACGTGGACTATAGCAACGTGATGCTAACCAGCGAGGAAGAAATCAAGACCACCAACCCCGT
GGCCACAGAAGAGTATGGCGTGGTGGCTGATAACCTACAGCAGCAAAACACCGCTCCTCAAXXX
8GGGACCGTCAACAGCCAGGGAGCCTTACCTGGCATGGTCTGGCAGAACCGGGACGTGTACCTG
CAGGGTCCTATTTGGGCCAAGATTCCTCACACAGATGGCAACTTTCACCCGTCTCCTTTAATGG
GCGGCTTTGGACTTAAACATCCGCCTCCTCAGATCCTCATCAAAAACACTCCTGTTCCTGCGGA
TCCTCCAACAACGTTCAACCAGGCCAAGCTGAATTCTTTCATCACGCAGTACAGCACCGGACAA
GTCAGCGTGGAGATCGAGTGGGAGCTGCAGAAGGAGAACAGCAAGCGCTGGAACCCAGAGATTC
AGTATACTTCCAACTACTACAAATCTACAAATGTGGACTTTGCTGTTAATACTGAGGGTGTTTA
CTCTGAGCCTCGCCCCATTGGCACTCGTTACCTCACCCGTAATCTG
XXX1 = ACG/AGC; XXX2 = AGA/AAG; XXX3 = AAC/AGC; XXX4 = CAA/GAA;
XXX5 = AAC/ACC/AGC; XXX6 = GAC/GAG; XXX7 = ATC/GTC; XXX8 =
ATA/GTA SEQ ID NO: 9: Anc84 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEPSPQRSPDSSTGIGKKGQQPAX1KRLNFGQTGDSESVPDPQPIGS
PPAAPSGVGSGTMAAGGGAPMADNNEGADGVGSSSGNWHCDSTWLGDRVITTSTRTWALPTYNN
HLYKQISNGTSGGSTNDNTYFGYSTPWGYFDFNRFHCHFSPRDWQRLINNNWGFRPKRLX2FKL
FNIQVKEVTQNEGTKTIANNLTSTIQVFTDSEYQLPYVLGSAHQGCLPPFPADVFMIPQYGYLT
LNNGSQAVGRSSFYCLEYFPSQMLRTGNNFEFSYTFEDVPFHSSYAHSQSLDRLMNPLIDQYLY
YLSRTQSTGGTAGTQQLLFSQAGPSNMSAQAKNWLPGPCYRQQRVSTTLSQNNNSNFAWTGATK
YHLNGRDSLVNPGVAMATHKDDEX3RFFPSSGX4LMFGKQGAGKDNVDYSNVMLTSEEEIKTTN
PVATEQYGVVADNLQQQNTAPIVGAVNSQGALPGMVWQNRDVYLQGPIWAKIPHTDGNFHPSPL
MGGFGLKHPPPQILIKNTPVPADPPTTFNQAKLNSFITQYSTGQVSVEIEWELQKENSKRWNPE
IQYTSNYYKSTNVDFAVNTEGVYSEPRPIGTRYLTRNL
X1 = R/K; X2 = N/S; X3 = D/E; X4 = I/V SEQ ID NO: 10: Anc84 VP1 DNA
ATGGCTGCCGATGGTTATCTTCCAGATTGGCTCGAGGACAACCTCTCTGAGGGCATTCGCGAGT
GGTGGGACCTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAATCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCCGTCAC
CACAGCGTTCCCCCGACTCCTCCACGGGCATCGGCAAGAAAGGCCAGCAGCCCGCCXXX1AAGA
GACTCAATTTCGGTCAGACTGGCGACTCAGAGTCAGTCCCCGACCCTCAACCTATCGGAGAACC
TCCAGCAGCGCCCTCTGGTGTGGGATCTGGTACAATGGCTGCAGGCGGTGGCGCACCAATGGCA
GACAATAACGAAGGTGCCGACGGAGTGGGTAGTTCCTCGGGAAATTGGCATTGCGATTCCACAT
GGCTGGGCGACAGAGTCATCACCACCAGCACCCGAACCTGGGCCCTGCCCACCTACAACAACCA
CCTCTACAAGCAAATCTCCAACGGGACCTCGGGAGGCAGCACCAACGACAACACCTACTTTGGC
TACAGCACCCCCTGGGGGTATTTTGACTTTAACAGATTCCACTGCCACTTCTCACCACGTGACT
GGCAGCGACTCATCAACAACAACTGGGGATTCCGGCCCAAGAGACTCXXX2TTCAAGCTCTTCA -continued Sequence Listing ACATCCAGGTCAAAGAGGTCACGCAGAATGAAGGCACCAAGACCATCGCCAATAACCTCACCAG
CACCATCCAGGTGTTTACGGACTCGGAATACCAGCTGCCGTACGTCCTCGGCTCTGCCCACCAG
GGCTGCCTGCCTCCGTTCCCGGCGGACGTCTTCATGATTCCTCAGTACGGCTACCTGACTCTCA
ACAACGGTAGTCAGGCCGTGGGACGTTCCTCCTTCTACTGCCTGGAGTACTTCCCCTCTCAGAT
GCTGAGAACGGGCAACAACTTTGAGTTCAGCTACACTTTCGAGGACGTGCCTTTCCACAGCAGC
TACGCGCACAGCCAGAGTTTGGACAGGCTGATGAATCCTCTCATCGACCAGTACCTGTACTACC
TGTCAAGAACCCAGTCTACGGGAGGCACAGCGGGAACCCAGCAGTTGCTGTTTTCTCAGGCCGG
GCCTAGCAACATGTCGGCTCAGGCCAAAAACTGGCTGCCTGGACCCTGCTACAGACAGCAGCGC
GTCTCCACGACACTGTCGCAAAACAACAACAGCAACTTTGCCTGGACTGGTGCCACCAAGTATC
ATCTGAACGGCAGAGACTCTCTGGTGAATCCGGGCGTCGCCATGGCAACCCACAAGGACGACGA
GXXX3CGCTTCTTCCCATCCAGCGGCXXX4CTCATGTTTGGCAAGCAGGGAGCTGGAAAAGACA
ACGTGGACTATAGCAACGTGATGCTAACCAGCGAGGAAGAAATCAAGACCACCAACCCCGTGGC
CACAGAACAGTATGGCGTGGTGGCTGATAACCTACAGCAGCAAAACACCGCTCCTATTGTGGGG
GCCGTCAACAGCCAGGGAGCCTTACCTGGCATGGTCTGGCAGAACCGGGACGTGTACCTGCAGG
GTCCTATTTGGGCCAAGATTCCTCACACAGATGGCAACTTTCACCCGTCTCCTTTAATGGGCGG
CTTTGGACTTAAACATCCGCCTCCTCAGATCCTCATCAAAAACACTCCTGTTCCTGCGGATCCT
CCAACAACGTTCAACCAGGCCAAGCTGAATTCTTTCATCACGCAGTACAGCACCGGACAAGTCA
GCGTGGAGATCGAGTGGGAGCTGCAGAAGGAGAACAGCAAGCGCTGGAACCCAGAGATTCAGTA
TACTTCCAACTACTACAAATCTACAAATGTGGACTTTGCTGTTAATACTGAGGGTGTTTACTCT
GAGCCTCGCCCCATTGGCACTCGTTACCTCACCCGTAATCTG
XXX1 = AGA/AAA; XXX2 = AAC/AGC; XXX3 = GAC/GAG; XXX4 = ATC/GTC SEQ ID NO: 11: Anc94 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEPSPQRSPDSSTGIGKKGQQPAKKRLNFGQTGDSESVPDPQPIGEP
PAGPSGLGSGTMAAGGGAPMADNNEGADGVGSSSGNWHCDSTWLGDRVITTSTRTWALPTYNNH
LYKQISNGTSGGSTNDNTYFGYSTPWGYFDFNRFHCHFSPRDWQRLINNNWGFRPKRLNFKLFN
IQVKEVTQNEGTKTIANNLTSTIQVFTDSEYQLPYVLGSAHQGCLPPFPADVFMIPQYGYLTLN
NGSQAVGRSSFYCLEYFPSQMLRTGNNFEFSYTFEDVPFHSSYAHSQSLDRLMNPLIDQYLYYL
SRTQSTGGTAGTQQLLFSQAGPX1NMSAQAKNWLPGPCYRQQRVSTTLSQNNNSNFAWTGATKY
HLNGRDSLVNPGVAMATHKDDEERFFPSSGVLMFGKQGAGKDNVDYSSVMLTSEEEIKTTNPVA
TEQYGVVADNLQQQNTAPIVGAVNSQGALPGMVWQNRDVYLQGPIWAKIPHTDGNFHPSPLMGG
FGLKHPPPQILIKNTPVPADPPTTFSQAKLASFITQYSTGQVSVEIEWELQKENSKRWNPEIQY
TSNYYKSTNVDFAVNTEGTYSEPRPIGTRYLTRNL
X1 = S/N SEQ ID NO: 12: Anc94 VP1 DNA
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCCATCAC
CCCAGCGTTCTCCAGACTCCTCTACGGGCATCGGCAAGAAAGGCCAGCAGCCCGCGAAAAAGAG
ACTCAACTTTGGGCAGACTGGCGACTCAGAGTCAGTGCCCGACCCTCAACCAATCGGAGAACCC
CCCGCAGGCCCCTCTGGTCTGGGATCTGGTACAATGGCTGCAGGCGGTGGCGCTCCAATGGCAG
ACAATAACGAAGGCGCCGACGGAGTGGGTAGTTCCTCAGGAAATTGGCATTGCGATTCCACATG
GCTGGGCGACAGAGTCATCACCACCAGCACCCGAACCTGGGCCCTCCCCACCTACAACAACCAC
CTCTACAAGCAAATCTCCAACGGGACTTCGGGAGGAAGCACCAACGACAACACCTACTTCGGCT
ACAGCACCCCCTGGGGGTATTTTGACTTTAACAGATTCCACTGCCACTTCTCACCACGTGACTG
GCAGCGACTCATCAACAACAACTGGGGATTCCGGCCCAAGAGACTCAACTTCAAGCTCTTCAAC
ATCCAGGTCAAGGAGGTCACGCAGAATGAAGGCACCAAGACCATCGCCAATAACCTTACCAGCA
CGATTCAGGTCTTTACGGACTCGGAATACCAGCTCCCGTACGTCCTCGGCTCTGCGCACCAGGG
CTGCCTGCCTCCGTTCCCGGCGGACGTCTTCATGATTCCTCAGTACGGGTACCTGACTCTGAAC
AATGGCAGTCAGGCCGTGGGCCGTTCCTCCTTCTACTGCCTGGAGTACTTTCCTTCTCAAATGC
TGAGAACGGGCAACAACTTTGAGTTCAGCTACACGTTTGAGGACGTGCCTTTTCACAGCAGCTA
CGCGCACAGCCAAAGCCTGGACCGGCTGATGAACCCCCTCATCGACCAGTACCTGTACTACCTG
TCTCGGACTCAGTCCACGGGAGGTACCGCAGGAACTCAGCAGTTGCTATTTTCTCAGGCCGGGC
CTXXXAACATGTCGGCTCAGGCCAAAAACTGGCTACCCGGGCCCTGCTACCGGCAGCAACGCGT
CTCCACGACACTGTCGCAAAATAACAACAGCAACTTTGCCTGGACCGGTGCCACCAAGTATCAT
CTGAATGGCAGAGACTCTCTGGTAAATCCCGGTGTCGCTATGGCAACCCACAAGGACGACGAAG
AGCGATTTTTTCCGTCCAGCGGAGTCTTAATGTTTGGGAAACAGGGAGCTGGAAAAGACAACGT
GGACTATAGCAGCGTTATGCTAACCAGTGAGGAAGAAATTAAAACCACCAACCCAGTGGCCACA
GAACAGTACGGCGTGGTGGCCGATAACCTGCAACAGCAAAACACCGCTCCTATTGTAGGGGCCG
TCAACAGTCAAGGAGCCTTACCTGGCATGGTCTGGCAGAACCGGGACGTGTACCTGCAGGGTCC
TATCTGGGCCAAGATTCCTCACACGGACGGAAACTTTCATCCCTCGCCGCTGATGGGAGGCTTT
GGACTGAAACACCCGCCTCCTCAGATCCTGATTAAGAATACACCTGTTCCCGCGGATCCTCCAA
CTACCTTCAGTCAAGCTAAGCTGGCGTCGTTCATCACGCAGTACAGCACCGGACAGGTCAGCGT
GGAAATTGAATGGGAGCTGCAGAAAGAAAACAGCAAACGCTGGAACCCAGAGATTCAATACACT
TCCAACTACTACAAATCTACAAATGTGGACTTTGCTGTTAACACAGAAGGCACTTATTCTGAGC
CTCGCCCCATCGGCACCCGTTACCTCACCCGTAATCTG
XXX1 = AGT/AAT -continued

| Sequence Listing |
| --- |

SEQ ID NO: 13: Anc113 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEX1SPQRSPDSSTGIGKKGQQPAX2KRLNFGQTGDSESVPDPQPLG
EPPAAPSGVGSGTMAAGGGAPMADNNEGADGVGNASGNWHCDSTWLGDRVITTSTRTWALPTYN
NHLYKQISSQSAGSTNDNTYFGYSTPWGYFDFNRFHCHFSPRDWQRLINNNWGFRPKKLX3FKL
FNIQVKEVTTNDGVTTIANNLTSTVQVFSDSEYQLPYVLGSAHQGCLPPFPADVFMIPQYGYLT
LNNGSQSVGRSSFYCLEYFPSQMLRTGNNFEFSYTFEDVPFHSSYAHSQSLDRLMNPLIDQYLY
YLARTQSTTGGTAGNRELQFX4QAGPSTMAEQAKNWLPGPCYRQQRVSKTLDQNNNSNFAWTGA
TKYHLNGRNSLVNPGVAMATHKDDEDRFFPSSGVLIFGKTGAANKTTLENVLMTX5EEEIKTTN
PVATEEYGX6VSSNLQSX7NTAPQTQTVNSQGALPGMVWQNRDVYLQGPIWAKIPHTDGNFHPS
PLMGGFGLKHPPPQILIKNTPVPANPPEVFTPAKFASFITQYSTGQVSVEIEWELQKENSKRWN
PEIQYTSNYDKSTNVDFAVDSEGVYSEPRPIGTRYLTRNL
X1 = P/Q; X2 = K/R; X3 = R/N; X4 = Y/H; X5 = N/S; X6 = V/I; X7 = A/S SEQ ID NO: 14: Anc113 VP1 DNA
ATGGCTGCCGATGGTTATCTTCCAGATTGGCTCGAGGACAACCTCTCTGAGGGCATTCGCGAGT
GGTGGGACCTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCATTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGXXX1TCA
CCTCAGCGTTCCCCCGACTCCTCCACGGGCATCGGCAAGAAAGGCCAGCAGCCCGCCXXX2AAG
AGACTCAATTTCGGTCAGACTGGCGACTCAGAGTCAGTCCCCGACCCTCAACCTCTCGGAGAAC
CTCCAGCAGCGCCCTCTGGTGTGGGATCTGGTACAATGGCTGCAGGCGGTGGCGCACCAATGGC
AGACAATAACGAAGGTGCCGACGGAGTGGGTAATGCCTCAGGAAATTGGCATTGCGATTCCACA
TGGCTGGGCGACAGAGTCATTACCACCAGCACCCGAACCTGGGCCCTGCCCACCTACAACAACC
ACCTCTACAAGCAAATCTCCAGTCAAAGTGCAGGTAGTACCAACGACAACACCTACTTCGGCTA
CAGCACCCCCTGGGGGTATTTTGACTTTAACAGATTCCACTGCCACTTCTCACCACGTGACTGG
CAGCGACTCATCAACAACAACTGGGGATTCCGGCCCAAGAAGCTGXXX3TTCAAGCTCTTCAAC
ATCCAGGTCAAGGAGGTCACGACGAATGACGGCGTTACGACCATCGCTAATAACCTTACCAGCA
CGGTTCAGGTATTCTCGGACTCGGAATACCAGCTGCCGTACGTCCTCGGCTCTGCGCACCAGGG
CTGCCTGCCTCCGTTCCCGGCGGACGTCTTCATGATTCCTCAGTACGGCTACCTGACTCTCAAC
AATGGCAGTCAGTCTGTGGGACGTTCCTCCTTCTACTGCCTGGAGTACTTCCCCTCTCAGATGC
TGAGAACGGGCAACAACTTTGAGTTCAGCTACACCTTCGAGGACGTGCCTTTCCACAGCAGCTA
CGCACACAGCCAGAGCCTGGACCGGCTGATGAATCCCCTCATCGACCAGTACTTGTACTACCTG
GCCAGAACACAGAGTACCACAGGAGGCACAGCTGGCAATCGGGAACTGCAGTTTXXX4CAGGCC
GGGCCTTCAACTATGGCCGAACAAGCCAAGAATTGGTTACCTGGACCTTGCTACCGGCAACAAA
GAGTCTCCAAAACGCTGGATCAAAACAACAACAGCAACTTTGCTTGGACTGGTGCCACCAAATA
TCACCTGAACGGCAGAAACTCGTTGGTTAATCCCGGCGTCGCCATGGCAACTCACAAGGACGAC
GAGGACCGCTTTTTCCCATCCAGCGGAGTCCTGATTTTTGGAAAAACTGGAGCAGCTAACAAAA
CTACATTGGAAAATGTGTTAATGACAXXX5GAAGAAGAAATTAAAACTACTAATCCTGTAGCCA
CGGAAGAATACGGGXXX6GTCAGCAGCAACTTACAATCGXXX7AATACTGCACCCCAGACACAA
ACTGTCAACAGCCAGGGAGCCTTACCTGGCATGGTCTGGCAGAACCGGGACGTGTACCTGCAGG
GTCCCATCTGGGCCAAGATTCCTCACACGGATGGCAACTTTCACCCGTCTCCTTTGATGGGCGG
CTTTGGACTTAAACATCCGCCTCCTCAGATCCTGATCAAGAACACTCCCGTTCCCGCTAATCCT
CCGGAGGTGTTTACTCCTGCCAAGTTTGCTTCGTTCATCACACAGTACAGCACCGGACAAGTCA
GCGTGGAAATCGAGTGGGAGCTGCAGAAGGAAAACAGCAAGCGCTGGAACCCGGAGATTCAGTA
CACCTCCAACTATGATAAGTCGACTAATGTGGACTTTGCCGTTGACAGCGAGGGTGTTTACTCT
GAGCCTCGCCCTATTGGCACTCGTTACCTCACCCGTAATCTG
XXX1 = CCG/CAG; XXX2 = AAA/AGA; XXX3 = CGG/AAC; XXX4 = TAC/CAC;
XXX5 = AAT/AGT; XXX6 = GTA/ATA; XXX7 = GCT/TCT SEQ ID NO: 15: Anc126 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGTGKX1GQQPAX2KRLNFGQTGDSESVPDPQPLGE
PPAAPSGVGSNTMASGGGAPMADNNEGADGVGNX3SGNWHCDSTWLGDRVITTSTRTWALPTYN
NHLYKQISSQSGASNDNHYFGYSTPWGYFDFNRFHCHFSPRDWQRLINNNWGFRPKX4LNFKLF
NIQVKEVTTNDGTTTIANNLTSTVQVFTDSEYQLPYVLGSAHQGCLPPFPADVFMIPQYGYLTL
NNGSQAVGRSSFYCLEYFPSQMLRTGNNFX5FSYTFEDVPFHSSYAHSQSLDRLMNPLIDQYLY
YLX6RTQTTSGTAQNRELX7FSQAGPSSMX8NQAKNWLPGPCYRQQRVSKTANDNNNSNFAWTG
ATKYHLNGRDSLVNPGPAMASHKDDEDKFFPMSGVLIFGKQGAGASNVDLDNVMITDEEEIKTT
NPVATEQYGTVATNLQSSNTAPATGTVNSQGALPGMVWQDRDVYLQGPIWAKIPHTDGHFHPSP
LMGGFGLKHPPPQILIKNTPVPANPPTTFSPAKFASFITQYSTGQVSVEIEWELQKENSKRWNP
EIQYTSNYNKSX9NVDFTVDTNGVYSEPRPIGTRYLTRNL
X1 = S/T; X2 = K/R; X3 = A/S; X4 = R/K; X5 = T/Q; X6 = S/N; X7 = Q/L;
X8=A/S; X9 = A/T SEQ ID NO: 16: Anc126 VP1 DNA
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGATGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGAGGGTTCTCGAACCT -continued Sequence Listing

```
CTTGGTCTGGTTGAGGAAGGTGCTAAGACGGCTCCTGGAAAGAAACGTCCGGTAGAGCAGTCGC
CACAAGAGCCAGACTCCTCCTCGGGCATTGGCAAGXXX1GGCCAGCAGCCCGCTXXX2AAGAGA
CTCAATTTTGGTCAGACTGGCGACTCAGAGTCAGTCCCCGACCCACAACCTCTCGGAGAACCTC
CAGCAGCCCCCTCTGGTGTGGGATCTAATACAATGGCTTCAGGCGGTGGCGCACCAATGGCAGA
CAATAACGAAGGCGCCGACGGAGTGGGTAATXXX3TCAGGAAATTGGCATTGCGATTCCACATG
GCTGGGCGACAGAGTCATCACCACCAGCACCCGAACATGGGCCTTGCCCACCTATAACAACCAC
CTCTACAAGCAAATCTCCAGTCAATCAGGGGCCAGCAACGACAACCACTACTTCGGCTACAGCA
CCCCCTGGGGGTATTTTGATTTCAACAGATTCCACTGCCATTTCTCACCACGTGACTGGCAGCG
ACTCATCAACAACAATTGGGGATTCCGGCCCAAGXXX4CTCAACTTCAAGCTCTTCAACATCCA
AGTCAAGGAGGTCACGACGAATGATGGCACCACGACCATCGCTAATAACCTTACCAGCACGGTT
CAAGTCTTCACGGACTCGGAGTACCAGTTGCCGTACGTCCTCGGCTCTGCGCACCAGGGCTGCC
TCCCTCCGTTCCCGGCGGACGTGTTCATGATTCCGCAGTACGGCTACCTAACGCTCAACAATGG
CAGCCAGGCAGTGGGACGGTCATCCTTTTACTGCCTGGAATATTTCCCATCGCAGATGCTGAGA
ACGGGCAATAACTTTXXX5TTCAGCTACACCTTCGAGGACGTGCCTTTCCACAGCAGCTACGCG
CACAGCCAGAGCCTGGACCGGCTGATGAATCCTCTCATCGACCAGTACCTGTATTACCTGXXX6
AGAACTCAGACTACGTCCGGAACTGCCCAAAACAGGGAGTTGXXX7TTTAGCCAGGCGGGTCCA
TCTAGCATGXXX8AATCAGGCCAAAAACTGGCTACCTGGACCCTGTTACCGGCAGCAGCGCGTT
TCTAAAACAGCAAATGACAACAACAACAGCAACTTTGCCTGGACTGGTGCTACAAAATATCACC
TTAATGGGCGTGATTCTTTAGTCAACCCTGGCCCTGCTATGGCCTCACACAAAGACGACGAAGA
CAAGTTCTTTCCCATGAGCGGTGTCTTGATTTTTGGAAAGCAGGGCGCCGGAGCTTCAAACGTT
GATTTGGACAATGTCATGATCACAGACGAAGAGGAAATCAAAACCACTAACCCCGTGGCCACCG
AACAATATGGGACTGTGGCAACCAATCTCCAGAGCAGCAACACAGCCCCTGCGACCGGAACTGT
GAATTCTCAGGGAGCCTTACCTGGAATGGTGTGGCAAGACAGAGACGTATACCTGCAGGGTCCT
ATTTGGGCCAAAATTCCTCACACGGATGGACACTTTCACCCGTCTCCTCTCATGGGCGGCTTTG
GACTTAAGCACCCGCCTCCTCAGATCCTCATCAAAAACACGCCTGTTCCTGCGAATCCTCCGAC
AACGTTTTCGCCTGCAAAGTTTGCTTCATTCATCACCCAGTATTCCACAGGACAAGTGAGCGTG
GAGATTGAATGGGAGCTGCAGAAAGAAAACAGCAAACGCTGGAATCCCGAAATACAGTATACAT
CTAACTATAATAAATCTXXX9AACGTTGATTTCACTGTGGACACCAATGGAGTTTATAGTGAGC
CTCGCCCCATTGGCACCCGTTACCTCACCCGTAACCTG
XXX1 = TCA/ACA; XXX2 = AAA/AGA; XXX3 = GCC/TCC; XXX4 = AGA/AAA;
XXX5 = ACC/CAG; XXX6 = AGC/AAC; XXX7 = CAG/CTG; XXX8 = GCT/TCT;
XXX9 = GCC/ACC

SEQ ID NO: 17: Anc127 VP1 polypeptide
MAADGYLPDWLEDNLSEGIREWWDLKPGAPQPKANQQHQDDX1RGLVLPGYKYLGPFNGLDKGE
PVNEADAAALEHDKAYDQQLKAGDNPYLKYNHADAEFQERLQEDTSFGGNLGRAVFQAKKRVLE
PLGLVEEAAKTAPGKKRPVEQSPQEPDSSSGIGKSGQQPAX2KRLNFGQTGDSESVPDPQPLGE
PPAAPSGVGSNTMASGGGAPMADNNEGADGVGNSSGNWHCDSTWLGDRVITTSTRTWALPTYNN
HLYKQISSQSGASNDNHYFGYSTPWGYFDFNRFHCHFSPRDWQRLINNNWGFRPKX3LNFKLFN
IQVKEVTQNDGTTTIANNLTSTVQVFTDSEYQLPYVLGSAHQGCLPPFPADVFMIPQYGYLTLN
NGSQAVGRSSFYCLEYFPSQMLRTGNNFX4FSYTFEDVPFHSSYAHSQSLDRLMNPLIDQYLYY
LX5RTQTTSGTTQQSRLX6FSQAGPSSMX7QQAX8NWLPGPCYRQQRVSKTANDNNNSNFAWTX
9ATKYHLNGRDSLVNPGPAMASHKDDEEKFFPMHGX10LIFGKQGTGASNVDLDNVMITDEEEI
RTTNPVATEQYGTVATNLQSSNTAPATGTVNSQGALPGMVWQDRDVYLQGPIWAKIPHTDGHFH
PSPLMGGFGLKHPPPQILIKNTPVPANPPTTFSPAKFASFITQYSTGQVSVEIEWELQKENSKR
WNPEIQYTSNYNKSVNVDFTVDTNGVYSEPRPIGTRYLTRNL
X1 = G/S; X2 = R/K; X3 = K/R; X4 = T/Q; X5 = S/R; X6 = Q/L; X7 = A/S;
X8=K/R; X9 = G/A; X10 = V/N

SEQ ID NO: 18: Anc127 VP1 DNA
ATGGCTGCTGACGGTTATCTTCCAGATTGGCTCGAGGACAACCTTTCTGAAGGCATTCGTGAGT
GGTGGGATCTGAAACCTGGAGCCCCTCAACCCAAAGCGAACCAACAACACCAGGACGACXXX1C
GGGGTCTTGTGCTTCCGGGTTACAAATACCTCGGACCCTTTAACGGACTCGACAAAGGAGAGCC
GGTCAACGAGGCGGACGCGGCAGCCCTCGAACACGACAAAGCTTACGACCAGCAGCTCAAGGCC
GGTGACAACCCGTACCTCAAGTACAACCACGCCGACGCCGAGTTTCAGGAGCGTCTTCAAGAAG
ATACGTCTTTTGGGGGCAACCTTGGCAGAGCAGTCTTCCAGGCCAAAAAGAGGGTCCTTGAGCC
TCTTGGTCTGGTTGAGGAAGCAGCTAAAACGGCTCCTGGAAAGAAGAGGCCTGTAGAACAGTCT
CCTCAGGAACCGGACTCATCATCTGGTATTGGCAAATCGGGCCAACAGCCTGCCXXX2AAAAGA
CTAAATTTCGGTCAGACTGGAGACTCAGAGTCAGTCCCAGACCCTCAACCTCTCGGAGAACCAC
CAGCAGCCCCCTCAGGTGTGGGATCTAATACAATGGCTTCAGGCGGTGGCGCACCAATGGCAGA
CAATAACGAGGGTGCCGATGGAGTGGGTAATTCCTCAGGAAATTGGCATTGCGATTCCACATGG
CTGGGCGACAGAGTCATCACCACCAGCACCAGAACCTGGGCCCTGCCCACTTACAACAACCATC
TCTACAAGCAAATCTCCAGCCAATCAGGAGCTTCAAACGACAACCACTACTTTGGCTACAGCAC
CCCTTGGGGGTATTTTGACTTTAACAGATTCCACTGCCACTTCTCACCACGTGACTGGCAGCGA
CTCATTAACAACAACTGGGGATTCCGGCCCAAGXXX3CTCAACTTCAAGCTCTTCAACATCCAA
GTTAAAGAGGTCACGCAGAACGATGGCACGACGACTATTGCCAATAACCTTACCAGCACGGTTC
AAGTGTTTACGGACTCGGAGTATCAGCTCCCGTACGTGCTCGGGTCGGCGCACCAAGGCTGTCT
CCCGCCGTTTCCAGCGGACGTCTTCATGATCCCTCAGTATGGATACCTCACCCTGAACAACGGA
AGTCAAGCGGTGGGACGCTCATCCTTTTACTGCCTGGAGTACTTCCCTTCGCAGATGCTAAGGA
CTGGAAATAACTTCXXX4TTCAGCTATACCTTCGAGGATGTACCTTTTCACAGCAGCTACGCTC
ACAGCCAGAGTTTGGATCGCTTGATGAATCCTCTTATTGATCAGTATCTGTACTACCTGXXX5A
GAACGCAAACAACCTCTGGAACAACCCAACAATCACGGCTGXXX6TTTAGCCAGGCTGGGCCTT
CGTCTATGXXX7CAGCAGGCCXXX8AATTGGCTACCTGGGCCCTGCTACCGGCAACAGAGAGTT
TCAAAGACTGCTAACGACAACAACAACAGTAACTTTGCTTGGACAXXX9GCCACCAAATATCAT
CTCAATGGCCGCGACTCGCTGGTGAATCCAGGACCAGCTATGGCCAGTCACAAGGACGATGAAG
AAAAATTTTTCCCTATGCACGGCXXX10CTAATATTTGGCAAACAAGGGACAGGGGCAAGTAAC
GTAGATTTAGATAATGTAATGATTACGGATGAAGAAGAGATTCGTACCACCAATCCTGTGGCAA
```

-continued

| Sequence Listing |
| --- |

CAGAGCAGTATGGAACTGTGGCAACTAACTTGCAGAGCTCAAATACAGCTCCCGCGACTGGAAC
TGTCAATAGTCAGGGGGCCTTACCTGGCATGGTGTGGCAAGATCGTGACGTGTACCTTCAAGGA
CCTATCTGGGCAAAGATTCCTCACACGGATGGACACTTTCATCCTTCTCCTCTGATGGGAGGCT
TTGGACTGAAACATCCGCCTCCTCAAATCTTGATCAAAAATACTCCGGTACCGGCAAATCCTCC
GACGACTTTCAGCCCGGCCAAGTTTGCTTCATTTATCACTCAGTACTCCACTGGACAGGTCAGC
GTGGAAATTGAGTGGGAGCTACAGAAAGAAAACAGCAAACGTTGGAATCCAGAGATTCAGTACA
CTTCCAACTACAACAAGTCTGTTAATGTGGACTTTACTGTAGACACTAATGGTGTTTATAGTGA
ACCTCGCCCTATTGGAACCCGGTATCTCACACGAAACTTG
XXX1 = GGT/AGT; XXX2 = AGA/AAA; XXX3 = AAA/AGA; XXX4 = ACA/CAG;
XXX5 = AGC/AGA; XXX6 = CAA/CTC; XXX7 = GCT/TCT; XXX8 = AAA/AGA;
XXX9 = GGG/GCG; XXX10 = GTT/GAC

SEQ ID NO: 19: Anc80L27 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPARKRLNFGQTGDSESVPDPQPLGEPP
AAPSGVGSNTMAAGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKRLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFEFSYTFEDVPFHSSYAHSQSLDRLMNPLIDQYLYYLSR
TQTTSGTAGNRTLQFSQAGPSSMANQAKNWLPGPCYRQQRVSKTANQNNNSNFAWTGATKYHLN
GRDSLVNPGPAMATHKDDEDKFFPMSGVLIFGKQGAGNSNVDLDNVMITNEEEIKTTNPVATEQ
YGTVATNLQSANTAPATGTVNSQGALPGMVWQDRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 20: Anc80L59 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPAKKRLNFGQTGDSESVPDPQPLGEPP
AAPSGVGSNTMASGGGAPMADNNEGADGVGNASGNWHCDSTWLGDRVITTSTRTWALPTYNNHL
YKQISSQSGASTNDNTYFGYSTPWGYFDFNRFHCHFSPRDWQRLINNNWGFRPKRLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFQFSYTFEDVPFHSSYAHSQSLDRLMNPLIDQYLYYLSR
TQTTSGTAGNRELQFSQAGPSSMANQAKNWLPGPCYRQQRVSKTTNQNNNSNFAWTGATKYHLN
GRDSLVNPGPAMATHKDDEDKFFPMSGVLIFGKQGAGNSNVDLDNVMITNEEEIKTTNPVATEE
YGTVATNLQSANTAPATGTVNSQGALPGMVWQNRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 21: Anc80L60 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPARKRLNFGQTGDSESVPDPQPLGEPP
AAPSGVGSNTMAAGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKRLNFKLFNIQ
VKEVTTMDGTTTIANNLTSTVQVFTDSEYQLPYVLGSAHQGCLPPFPADVFMIPQYGYLTLNNG
SQAVGRSSFYCLEYFPSQMLRTGNNFEFSYTFEDVPFHSSYAHSQSLDRLMNPLIDQYLYYLSR
TQTTSGTAGNRELQFSQAGPSSMANQAKNWLPGPCYRQQRVSKTTNQNNNSNFAWTGATKYHLN
GRDSLVNPGPAMATHKDDEDKFFPMSGVLIFGKQGAGNSNVDLDNVMITSEEEIKTTNPVATEE
YGTVATNLQSSNTAPATGTVNSQGALPGMVWQERDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVY SE PRPIGTRYLTRNL SEQ ID NO: 22: Anc80L62 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPARKRLNFGQTGDSESVPDPQPLGEPP
AAPSGVGSNTMASGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKKLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFEFSYTFEDVPFHSSYAHSQSLDRLMNPLIDQYLYYLSR
TQTTSGTAGNRELQFSQAGPSSMANQAKNWLPGPCYRQQRVSKTTNQNNNSNFAWTGATKYHLN
GRDSLVNPGPAMATHKDDEDKFFPMSGVLIFGKQGAGNSNVDLDNVMITSEEEIKTTNPVATEE
YGTVATNLQSANTAPATGTVNSQGALPGMVWQDRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 23: Anc80L65 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPARKRLNFGQTGDSESVPDPQPLGEPP
AAPSGVGSNTMAAGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKKLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFQFSYTFEDVPFHSSYAHSQSLDRLMNPLIDQYLYYLSR
TQTTSGTAGNRTLQFSQAGPSSMANQAKNWLPGPCYRQQRVSKTTNQNNNSNFAWTGATKYHLN -continued Sequence Listing GRDSLVNPGPAMATHKDDEDKFFPMSGVLIFGKQGAGNSNVDLDNVMITNEEEIKTTNPVATEE
YGTVATNLQSANTAPATGTVNSQGALPGMVWQDRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 24: Anc80L33 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPAKKRLNFGQTGDSESVPDPQPLGEPP
AAPSGVGSNTMAAGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKKLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFEFSYTFEDVPFHSSYAHSQSLDRLMNPLIDQYLYYLSR
TQTTSGTAGNRTLQFSQAGPSSMANQAKNWLPGPCYRQQRVSKTANQNNNSNFAWTGATKYHLN
GRDSLVNPGPAMATHKDDEDKFFPMSGVLIFGKQGAGNSNVDLDNVMITSEEEIKTTNPVATEQ
YGTVATNLQSSNTAPATGTVNSQGALPGMVWQNRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNCVYSEPRPIGTRYLTRNL SEQ ID NO: 25: Anc80L36 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPAKKRLNFGQTGDSESVPDPQPLGEPP
AAPSGVGSNTMASGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKKLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFEFSYTFSDVPFHSSYAHSQSLDRLMNPLIDQYLYYLSR
TQTTSGTAGNRTLQFSQAGPSSMANQAKNWLPGPCYRQQRVSKTANQNNNSNFAWTGATKYHLN
GRDSLVNPGPAMATHKDDEDKFFPMSGVLIFGKQGAGNSNVDLDNVMITSEEEIKTTNPVATEE
YGTVATNLQSSNTAPATGTVNSQGALPGMVWQNRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 26: Anc80L44 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKKGQQPAKKRLNFGQTGDSESVPDPQPLGEPP
AAPSGVGSNTMASGGGAPMADNNEGADGVGNASGNWHCDSTWLGDRVITTSTRTWALPTYNNHL
YKQISSQSGGSTNDNTYFGYSTPWGYFDFNRFHCHFSPRDWQRLINNNWGFRPKKLNFKLFNIQ
VKEVTTNDGTTTIANNLTSTVQVFTDSEYQLPYVLGSAHQGCLPPFPADVFMIPQYGYLTLNNG
SQAVGRSSFYCLEYFPSQMLRTGNNFQFSYTFEDVPFHSSYAHSQSLDRLMNPLIDQYLYYLSR
TQTTSGTAGNRELQFSQAGPSSMANQAKNWLPGPCYRQQRVSKTTNQNNNSNFAWTGATKYHLN
GRDSLVNPGPAMATHKDDEDKFFPMSGVLIFGKQGAGNSNVDLDNVMITNEEEIKTTNPVATEQ
YGTVATNLQSANTAPATGTVNSQGALPGMVWQDRDVYLQGPIWAKIPHTDGHFHPSPLMGGFGL
KHPPPQILIKNTPVPANPPTTFSPAKFASFITQYSTGQVSVEIEWELQKENSKRWNPEIQYTSN
YNKSTNVDFAVDTNGVYSEPRPIGTRYLTRNL SEQ ID NO: 27: AAV8 VP1 polypeptide (YP_077180.1)
MAADGYLPDWLEDNLSEGIREWWALKPGAPKPKANQQKQDDGRGLVLPGYKYLGPFNGLDKGEP
VNAADAAALEHDKAYDQQLQAGDNPYLRYNHADAEFQERLQEDTSFGGNLGRAVFQAKKRVLEP
LGLVEEGAKTAPGKKRPVEPSPQRSPDSSTGIGKKGQQPARKRLNFGQTGDSESVPDPQPLGEP
PAAPSGVGPNTMAAGGGAPMADNNEGADGVGSSSGNWHCDSTWLGDRVITTSTRTWALPTYNNH
LYKQISNGTSGGATNDNTYFGYSTPWGYFDFNRFHCHFSPRDWQRLINNNWGFRPKRLSFKLFN
IQVKEVTQNEGTKTIANNLTSTIQVFTDSEYQLPYVLGSAHQGCLPPFPADVFMIPQYGYLTLN
NGSQAVGRSSFYCLEYFPSQMLRTGNNFQFTYTFEDVPFHSSYAHSQSLDRLMNPLIDQYLYYL
SRTQTTGGTANTQTLGFSQGGPNTMANQAKNWLPGPCYRQQRVSTTTGQNNNSNFAWTAGTKYH
LNGRNSLANPGIAMATHKDDEERFFPSNGILIFGKQNAARDNADYSDVMLTSEEEIKTTNPVAT
EEYGIVADNLQQQNTAPQIGTVNSQGALPGMVWQNRDVYLQGPIWAKIPHTDGNFHPSPLMGGF
GLKHPPPQILIKNTPVPADPPTTFNQSKLNSFITQYSTGQVSVEIEWELQKENSKRWNPEIQYT
SNYYKSTSVDFAVNTEGVYSEPRPIGTRYLTRNL SEQ ID NO: 28: AAV9 VP1 polypeptide (AAS99264.1)
MAADGYLPDWLEDNLSEGIREWWALKPGAPQPKANQQHQDNARGLVLPGYKYLGPGNGLDKGEP
VNAADAAALEHDKAYDQQLKAGDNPYLKYNHADAEFQERLKEDTSFGGNLGRAVFQAKKRLLEP
LGLVEEAAKTAPGKKRPVEQSPQEPDSSAGIGKSGAQPAKKRLNFGQTGDTESVPDPQPIGEPP
AAPSGVGSLTMASGGGAPVADNNEGADGVGSSSGNWHCDSQWLGDRVITTSTRTWALPTYNNHL
YKQISNSTSGGSSNDNAYFGYSTPWGYFDFNRFHCHFSPRDWQRLINNNWGFRPKRLNFKLFNI
QVKEVTDNNGVKTIANNLTSTVQVFTDSDYQLPYVLGSAHEGCLPPFPADVFMIPQYGYLTLND
GSQAVGRSSFYCLEYFPSQMLRTGNNFQFSYEFENVPFHSSYAHSQSLDRLMNPLIDQYLYYLS
KTINGSGQNQQTLKFSVAGPSNMAVQGRNYIPGPSYRQQRVSTTVTQNNNSEFAWPGASSWALN
GRNSLMNPGPAMASHKEGEDRFFPLSGSLIFGKQGTGRDNVDADKVMITNEEEIKTTNPVATES
YGQVATNHQSAQAQAQTGWVQNQGILPGMVWQDRDVYLQGPIWAKIPHTDGNFHPSPLMGGFGM
KHPPPQILIKNTPVPADPPTAFNKDKLNSFITQYSTGQVSVEIEWELQKENSKRWNPEIQYTSN
YYKSNNVEFAVNTEGVYSEPRPIGTRYLTRNL -continued

| Sequence Listing |
|---|

SEQ ID NO: 29: AAV6 VP1 polypeptide (AAB95450.1)
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
FGLVEEGAKTAPGKKRPVEQSPQEPDSSSGIGKTGQQPAKKRLNFGQTGDSESVPDPQPLGEPP
ATPAAVGPTTMASGGGAPMADNNEGADGVGNASGNWHCDSTWLGDRVITTSTRTWALPTYNNHL
YKQISSASTGASNDNHYFGYSTPWGYFDFNRFHCHFSPRDWQRLINNNWGFRPKRLNFKLFNIQ
VKEVTTNDGVTTIANNLTSTVQVFSDSEYQLPYVLGSAHQGCLPPFPADVFMIPQYGYLTLNNG
SQAVGRSSFYCLEYFPSQMLRTGNNFTFSYTFEDVPFHSSYAHSQSLDRLMNPLIDQYLYYLNR
TQNQSGSAQNKDLLFSRGSPAGMSVQPKNWLPGPCYRQQRVSKTKTDNNNSNFTWTGASKYNLN
GRESIINPGTAMASHKDDKDKFFPMSGVMIFGKESAGASNTALDNVMITDEEEIKATNPVATER
FGTVAVNLQSSSTDPATGDVHVMGALPGMVWQDRDVYLQGPIWAKIPHTDGHFHPSPLMGGFGL
KHPPPQILIKNTPVPANPPAEFSATKFASFITQYSTGQVSVEIEWELQKENSKRWNPEVQYTSN
YAKSANVDFTVDNNGLYTEPRPIGTRYLTRPL SEQ ID NO: 30: AAV1 VP1 polypeptide (NP_049542.1)
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSSSGIGKTGQQPAKKRLNFGQTGDSESVPDPQPLGEPP
ATPAAVGPTTMASGGGAPMADNNEGADGVGNASGNWHCDSTWLGDRVITTSTRTWALPTYNNHL
YKQISSASTGASNDNHYFGYSTPWGYFDFNRFHCHFSPRDWQRLINNNWGFRPKRLNFKLFNIQ
VKEVTTNDGVTTIANNLTSTVQVFSDSEYQLPYVLGSAHQGCLPPFPADVFMIPQYGYLTLNNG
SQAVGRSSFYCLEYFPSQMLRTGNNFTFSYTFEEVPFHSSYAHSQSLDRLMNPLIDQYLYYLNR
TQNQSGSAQNKDLLFSRGSPAGMSVQPKNWLPGPGYRQQRVSKTKTDNNNSNFTWTGASKYNLN
GRESIINPGTAMASHKDDEDKFFPMSGVMIFGKESAGASNTALDNVMITDEEEIKATNPVATER
FGTVAVNFQSSSTDPATGDVHAMGALPGMVWQDRDVYLQGPIWAKIPHTDGHFHPSPLMGGFGL
KNPPPQILIKNTPVPANPPAEFSATKFASFITQYSTGQVSVEIEWELQKENSKRWNPEVQYTSN
YAKSANVDFTVDNNGLYTEPRPIGTRYLTRPL SEQ ID NO: 31: AAV2 VP1 polypeptide (YP_680426.1)
MAADGYLPDWLEDTLSEGIRQWWKLKPGPPPPKPAERHKDDSRGLVLPGYKYLGPFNGLDKGEP
VNEADAAALEHDKAYDRQLDSGDNPYLKYNHADAEFQERLKEDTSFGGNLGRAVFQAKKRVLEP
LGLVEEPVKTAPGKKRPVEHSPVEPDSSSGTGKAGQQPARKRLNFGQTGDADSVPDPQPLGQPP
AAPSGLGTNTMATGSGAPMADNNEGADGVGNSSGNWHCDSTWMGDRVITTSTRTWALPTYNNHL
YKQISSQSGASNDNHYFGYSTPWGYFDFNRFHCHFSPRDWQRLINNNWGFRPKRLNFKLFNIQV
KEVTQNDGTTTIANNLTSTVQVFTDSEYQLPYVLGSAHQGCLPPFPADVFMVPQYGYLTLNNGS
QAVGRSSFYCLEYFPSQMLRTGNNFTFSYTFEDVPFHSSYAHSQSLDRLMNPLIDQYLYYLSRT
NTPSGTTTQSRLQFSQAGASDIRDQSRNWLPGPCYRQQRVSKTSADNNNSEYSWTGATKYHLNG
RDSLVNPGPAMASHKDDEEKFFPQSGVLIFGKQGSEKTNVDIEKVMITDEEEIRTTNPVATEQY
GSVSTNLQRGNRQAATADVNTQGVLPGMVWQDRDVYLQGPIWAKIPHTDGHFHPSPLMGGFGLK
HPPPQILIKNTPVPANPSTTFSAAKFASFITQYSTGQVSVEIEWELQKENSKRWNPSIQYTSNY
NKSVNVDFTVDTNGVYSEPRPIGTRYLTRNL SEQ ID NO: 32: AAV3 VP1 polypeptide (NP_043941.1)
MAADGYLPDWLEDNLSEGIREWWALKPGVPQPKANQQHQDNRRGLVLPGYKYLGPGNGLDKGEP
VNEADAAALEHDKAYDQQLKAGDNPYLKYNHADAEFQERLQEDTSFGGNLGRAVFQAKKRILEP
LGLVEEAAKTAPGKKGAVDQSPQEPDSSSGVGKSGKQPARKRLNFGQTGDSESVPDPQPLGEPP
AAPTSLGSNTMASGGGAPMADNNEGADGVGNSSGNWHCDSQWLGDRVITTSTRTWALPTYNNHL
YKQISSQSGASNDNHYFGYSTPWGYFDFNRFHCHFSPRDWQRLINNNWGFRPKKLSFKLFNIQV
RGVTQNDGTTTIANNLTSTVQVFTDSEYQLPYVLGSAHQGCLPPFPADVFMVPQYGYLTLNNGS
QAVGRSSFYCLEYFPSQMLRTGNNFQFSYTFEDVPFHSSYAHSQSLDRLMNPLIDQYLYYLNRT
QGTTSGTTNQSRLLFSQAGPQSMSLQARNWLPGPCYRQQRLSKTANDNNNSNFPWTAASKYHLN
GRDSLVNPGPAMASHKDDEEKFFPMHGNLIFGKEGTTASNAELDNVMITDEEEIRTTNPVATEQ
YGTVANNLQSSNTAPTTGTVNHQGALPGMVWQDRDVYLQGPIWAKIPHTDGHFHPSPLMGGFGL
KHPPPQIMIKNTPVPANPPTTFSPAKFASFITQYSTGQVSVEIEWELQKENSKRWNPEIQYTSN
YNKSVNVDFTVDTNGVYSEPRPIGTRYLTRNL SEQ ID NO: 33: AAV3B VP1 polypeptide (3KIC A)
MAADGYLPDWLEDNLSEGIREWWALKPGVPQPKANQQHQDNRRGLVLPGYKYLGPGNGLDKGEP
VNEADAAALEHDKAYDQQLKAGDNPYLKYNHADAEFQERLQEDTSFGGNLGRAVFQAKKRILEP
LGLVEEAAKTAPGKKRPVDQSPQEPDSSSGVGKSGKQPARKRLNFGQTGDSESVPDPQPLGEPP
AAPTSLGSNTMASGGGAPMADNNEGADGVGNSSGNWHCDSQWLGDRVITTSTRTWALPTYNNHL
YKQISSQSGASNDNHYFGYSTPWGYFDFNRFHCHFSPRDWQRLINNNWGFRPKKLSFKLFNIQV
KEVTQNDGTTTIANNLTSTVQVFTDSEYQLPYVLGSAHQGCLPPFPADVFMVPQYGYLTLNNGS
QAVGRSSFYCLEYFPSQMLRTGNNFQFSYTFEDVPFHSSYAHSQSLPRLMNPLIDQYLYYLNRT
QGTTSGTTNQSRLLFSQAGPQSMSLQARNWLPGPCYRQQRLSKTANDNNNSNFPWTAASKYHLN
GRDSLVNPGPAMASHKDDEEKFFPMHGNLIFGKEGTTASNAELDNVMITDEEEIRTTNPVATEQ
YGTVANNLQSSNTAPTTRTVNDQGALPGMVWQDRDVYLQGPIWAKIPHTDGHFHPSPLMGGFGL
KHPPPQIMIKNTPVPANPPTTFSPAKFASFITQYSTGQVSVEIEWELQKENSKRWNPEIQYTSN
YNKSVNVDFTVDTNGVYSEPRPIGTRYLTRNL SEQ ID NO: 34: AAV7 VP1 polypeptide (YP_077178.1)
MAADGYLPDWLEDNLSEGIREWWDLKPGAPKPKANQQKQDNGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPAKKRPVEPSPQRSPDSSTGIGKKGQQPARKRLNFGQTGDSESVPDPQPLGEP
PAAPSSVGSGTVAAGGGAPMADNNEGADGVGNASGNWHCDSTWLGDRVITTSTRTWALPTYNNH
LYKQISSETAGSTNDNTYFGYSTPWGYFDFNRFHCHFSPRDWQRLINNNWGFRPKKLRFKLFNI
QVKEVTTNDGVTTIANNLTSTIQVFSDSEYQLPYVLGSAHQGCLPPFPADVFMIPQYGYLTLNN -continued Sequence Listing GSQSVGRSSFYCLEYFPSQMLRTGNNFEFSYSFEDVPFHSSYAHSQSLDRLMNPLIDQYLYYLA
RTQSNPGGTAGNRELQFYQGGPSTMAEQAKNWLPGPCFRQQRVSKTLDQNNNSNFAWTGATKYH
LNGRNSLVNPGVAMATHKDDEDRFFPSSGVLIFGKTGATNKTTLENVLMTNEEEIRPTNPVATE
EYGIVSSNLQAANTAAQTQVVNNQGALPGMVWQNRDVYLQGPIWAKIPHTDGNFHPSPLMGGFG
LKHPPPQILIKNTPVPANPPEVFTPAKFASFITQYSTGQVSVEIEWELQKENSKRWNPEIQYTS
NFEKQTGVDFAVDSQGVYSEPRPIGTRYLTRNL SEQ ID NO: 35: Anc80L1 VP1
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGACCGGTAGAGCAATCAC
CCCAGGAACCAGACTCCTCTTCGGGCATCGGCAAGAAAGGCCAGCAGCCCGCGAAAAAGAGACT
CAACTTTGGGCAGACAGGCGACTCAGAGTCAGTGCCCGACCCTCAACCACTCGGAGAACCCCCC
GCAGCCCCCTCTGGTGTGGGATCTAATACAATGGCTGCAGGCGGTGGCGCTCCAATGGCAGACA
ATAACGAAGGCGCCGACGGAGTGGGTAACGCCTCAGGAAATTGGCATTGCGATTCCACATGGCT
GGGCGACAGAGTCATCACCACCAGCACCCGAACCTGGGCCCTCCCCACCTACAACAACCACCTC
TACAAGCAAATCTCCAGCCAATCGGGAGCAAGCACCAACGACAACACCTACTTCGGCTACAGCA
CCCCCTGGGGGTATTTTGACTTTAACAGATTCCACTGCCACTTCTCACCACGTGACTGGCAGCG
ACTCATCAACAACAACTGGGGATTCCGGCCCAAGAGACTCAACTTCAAGCTCTTCAACATCCAG
GTCAAGGAGGTCACGACGAATGATGGCACCACGACCATCGCCAATAACCTTACCAGCACGGTTC
AGGTCTTTACGGACTCGGAATACCAGCTCCCGTACGTCCTCGGCTCTGCGCACCAGGGCTGCCT
GCCTCCGTTCCCGGCGGACGTCTTCATGATTCCTCAGTACGGGTACCTGACTCTGAACAATGGC
AGTCAGGCCGTGGGCCGTTCCTCCTTCTACTGCCTGGAGTACTTTCCTTCTCAAATGCTGAGAA
CGGGCAACAACTTTGAGTTCAGCTACACGTTTGAGGACGTGCCTTTTCACAGCAGCTACGCGCA
CAGCCAAAGCCTGGACCGGCTGATGAACCCCCTCATCGACCAGTACCTGTACTACCTGTCTCGG
ACTCAGACCACGAGTGGTACCGCAGGAAATCGGACGTTGCAATTTTCTCAGGCCGGGCCTAGTA
GCATGGCGAATCAGGCCAAAAACTGGCTACCCGGGCCCTGCTACCGGCAGCAACGCGTCTCCAA
GACAGCGAATCAAAATAACAACAGCAACTTTGCCTGGACCGGTGCCACCAAGTATCATCTGAAT
GGCAGAGACTCTCTGGTAAATCCCGGTCCCGCTATGGCAACCCACAAGGACGACGAAGACAAAT
TTTTTCCGATGAGCGGAGTCTTAATATTTGGGAAACAGGGAGCTGGAAATAGCAACGTGGACCT
TGACAACGTTATGATAACCAGTGAGGAAGAAATTAAAACCACCAACCCAGTGGCCACAGAACAG
TACGGCACGGTGGCCACTAACCTGCAATCGTCAAACACCGCTCCTGCTACAGGGACCGTCAACA
GTCAAGGAGCCTTACCTGGCATGGTCTGGCAGAACCGGGACGTGTACCTGCAGGGTCCTATCTG
GGCCAAGATTCCTCACACGGACGGACACTTTCATCCCTCGCCGCTGATGGGAGGCTTTGGACTG
AAACACCCGCCTCCTCAGATCCTGATTAAGAATACACCTGTTCCCGCGAATCCTCCAACTACCT
TCAGTCCAGCTAAGTTTGCGTCGTTCATCACGCAGTACAGCACCGGACAGGTCAGCGTGGAAAT
TGAATGGGAGCTGCAGAAAGAAAACAGCAAACGCTGGAACCCAGAGATTCAATACACTTCCAAC
TACAACAAATCTACAAATGTGGACTTTGCTGTTGACACAAATGGCGTTTATTCTGAGCCTCGCC
CCATCGGCACCCGTTACCTCACCCGTAATCTGTAA SEQ ID NO: 36: Anc80L1 VP1
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEPSPQRSPDSSTGIGKKGQQPAKKRLNFGQTGDSESVPDPQPIGEP
PAGPSGLGSGTMAAGGGAPMADNNEGADGVGSSSGNWHCDSTWLGDRVITTSTRTWALPTYNNH
LYKQISNGTSGGSTNDNTYFGYSTPWGYFDFNRFHCHFSPRDWQRLINNNWGFRPKRLNFKLFN
IQVKEVTQNEGTKTIANNLTSTIQVFTDSEYQLPYVLGSAHQGCLPPFPADVFMIPQYGYLTLN
NGSQAVGRSSFYCLEYFPSQMLRTGNNFEFSYQFEDVPFHSSYAHSQSLDRLMNPLIDQYLYYL
SRTQSTGGTAGTQQLLFSQAGPNNMSAQAKNWLPGPCYRQQRVSTTLSQNNNSNFAWTGATKYH
LNGRDSLVNPGVAMATHKDDEERFFPSSGVLMFGKQGAGKDNVDYSSVMLTSEEEIKTTNPVAT
EQYGVVADNLQQQNAAPIVGAVNSQGALPGMVWQNRDVYLQGPIWAKIPHTDGNFHPSPLMGGF
GLKHPPPQILIKNTPVPADPPTTFSQAKLASFITQYSTGQVSVEIEWELQKENSKRWNPEIQYT
SNYYKSTNVDFAVNTDGTYSEPRPIGTRYLTRNL SEQ ID NO: 37: Anc80 VP3 polypeptide
MAAGGGAPMADNNEGADGVGSSSGNWHCDSTWLGDRVITTSTRTWALPTYNNHLYKQISNGTSG
GSTNDNTYFGYSTPWGYFDFNRFHCHFSPRDWQRLINNNWGFRPKRLNFKLFNIQVKEVTQNEG
TKTIANNLTSTIQVFTDSEYQLPYVLGSAHQGCLPPFPADVFMIPQYGYLTLNNGSQAVGRSSF
YCLEYFPSQMLRTGNNFEFSYQFEDVPFHSSYAHSQSLDRLMNPLIDQYLYYLSRTQSTGGTAG
TQQLLFSQAGPNNMSAQAKNWLPGPCYRQQRVSTTLSQNNNSNFAWTGATKYHLNGRDSLVNPG
VAMATHKDDEERFFPSSGVLMFGKQGAGKDNVDYSSVMLTSEEEIKTTNPVATEQYGVVADNLQ
QQNAAPIVGAVNSQGALPGMVWQNRDVYLQGPIWAKIPHTDGNFHPSPLMGGFGLKHPPPQILI
KNTPVPADPPTTFSQAKLASFITQYSTGQVSVEIEWELQKENSKRWNPEIQYTSNYYKSTNVDF
AVNTDGTYSEPRPIGTRYLTRNL SEQ ID NO: 38: AAV2 VP3 polypeptide (GenBank Accession No. AAC03779.1
MATGSGAPMADNNEGADGVGNSSGNWHCDSTWMGDRVITTSTRTWALPTYNNHLYKQISSQSGA
SNDNHYFGYSTPWGYFDFNRFHCHFSPRDWQRLINNNWGFRPKRLNFKLFNIQVKEVTQNDGTT
TIANNLTSTVQVFTDSEYQLPYVLGSAHQGCLPPFPADVFMVPQYGYLTLNNGSQAVGRSSFYC
LEYFPSQMLRTGNNFTFSYTFEDVPFHSSYAHSQSLDRLMNPLIDQYLYYLSRTNTPSGTTTQS
RLQFSQAGASDIRDQSRNWLPGPCYRQQRVSKTSADNNNSEYSWTGATKYHLNGRDSLVNPGPA
MASHKDDEEKFFPQSGVLIFGKQGSEKTNVDIEKVMITDEEEIRTTNPVATEQYGSVSTNLQRG -continued Sequence Listing NRQAATADVNTQGVLPGMVWQDRDVYLQGPIWAKIPHTDGHFHPSPLMGGFGLKHPPPQILIKN
TPVPANPSTTFSAAKFASFITQYSTGQVSVEIEWELQKENSKRWNPEIQYTSNYNKSVNVDFTV
DTNGVYSEPRPIGTRYLTRNL SEQ ID NO: 39: AAV8 VP3 polypeptide
MAAGGGAPMADNNEGADGVGSSSGNWHCDSTWLGDRVITTSTRTWALPTYNNHLYKQISNGTSG
GATNDNTYFGYSTPWGYFDFNRFHCHFSPRDWQRLINNNWGFRPKRLSFKLFNIQVKEVTQNEG
TKTIANNLTSTIQVFTDSEYQLPYVLGSAHQGCLPPFPADVFMIPQYGYLTLNNGSQAVGRSSF
YCLEYFPSQMLRTGNNFQFTYTFEDVPFHSSYAHSQSLDRLMNPLIDQYLYYLSRTQTTGGTAN
TQTLGFSQGGPNTMANQAKNWLPGPCYRQQRVSTTTGQNNNSNFAWTAGTKYHLNGRNSLANPG
IAMATHKDDEERFFPSNGILIFGKQNAARDNADYSDVMLTSEEEIKTTNPVATEEYGIVADNLQ
QQNTAPQIGTVNSQGALPGMVWQNRDVYLQGPIWAKIPHTDGNFHPSPLMGGFGLKHPPPQILI
KNTPVPADPPTTFNQSKLNSFITQYSTGQVSVEIEWELQKENSKRWNPEIQYTSNYYKSTSVDF
AVNTEGVYSEPRPIGTRYLTRNL SEQ ID NO: 40: AAV5 VP1 polypeptide (GenBank Accession No.
AAD13756.1
MSFVDHPPDWLEEVGEGLREFLGLEAGPPKPKPNQQHQDQARGLVLPGYNYLGPGNGLDRGEPV
NRADEVAREHDISYNEQLEAGDNPYLKYNHADAEFQEKLADDTSFGGNLGKAVFQAKKRVLEPF
GLVEEGAKTAPTGKRIDDHFPKRKKARTEEDSKPSTSSDAEAGPSGSQQLQIPAQPASSLGADT
MSAGGGGPLGDNNQGADGVGNASGDWHCDSTWMGDRVVTKSTRTWVLPSYNNHQYREIKSGSVD
GSNANAYFGYSTPWGYFDFNRFHSHWSPRDWQRLINNYWGFRPRSLRVKIFNIQVKEVTVQDST
TTIANNLTSTVQVFTDDDYQLPYVVGNGTEGCLPAFPPQVFTLPQYGYATLNRDNTENPTERSS
FFCLEYFPSKMLRTGNNFEFTYNFEEVPFHSSFAPSQNLFKLANPLVDQYLYRFVSTNNTGGVQ
FNKNLAGRYANTYKNWFPGPMGRTQGWNLGSGVNRASVSAFATTNRMELEGASYQVPPQPNGMT
NNLQGSNTYALENTMIFNSQPANPGTTATYLEGNMLITSESETQPVNRVAYNVGGQMATNNQSS
TTAPATGTYNLQEIVPGSVWMERDVYLQGPIWAKIPETGAHFHPSPAMGGFGLKHPPPMMLIKN
TPVPGNITSFSDVPVSSFITQYSTGQVTVEMEWELKKENSKRWNPEIQYTNNYNDPQFVDFAPD
STGEYRTTRPIGTRYLTRPL SEQ ID NO: 41: rh10 VP1 polypeptide (GenBank Accession No.
AAQ88201.1
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEPSPQRSPDSSTGIGKKGQQPAKKRLNFGQTGDSESVPDPQPIGEP
PAGPSGLGSGTMAAGGGAPMADNNEGADGVGSSSGNWHCDSTWLGDRVITTSTRTWALPTYNNH
LYKQISNGTSGGSTNDNTYFGYSTPWGYFDFNRFHCHFSPRDWQRLINNNWGFRPKRLNFKLFN
IQVKEVTQNEGTKTIANNLTSTIQVFTDSEYQLPYVLGSAHQGCLPPFPADVFMIPQYGYLTLN
NGSQAVGRSSFYCLEYFPSQMLRTGNNFEFSYQFEDVPFHSSYAHSQSLDRLMNPLIDQYLYYL
SRTQSTGGTAGTQQLLFSQAGPNNMSAQAKNWLPGPCYRQQRVSTTLSQNNNSNFAWTGATKYH
LNGRDSLVNPGVAMATHKDDEERFFPSSGVLMFGKQGAGKDNVDYSSVMLTSEEEIKTTNPVAT
EQYGVVADNLQQQNAAPIVGAVNSQGALPGMVWQNRDVYLQGPIWAKIPHTDGNFHPSPLMGGF
GLKHPPPQILIKNTPVPADPPTTFSQAKLASFITQYSTGQVSVEIEWELQKENSKRWNPEIQYT
SNYYKSTNVDFAVNTDGTYSEPRPIGTRYLTRNL SEQ ID NO: 42: Anc110 VP1 polypeptide
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEQSPQEPDSS$X_1$GIGKTGQQPA$X_2$KRLNFGQTGDSESVPDPQPLGEP
PAAPSGVGSNTMASGGGAPMADNNEGADGVGNSSGNWHCDSTWLGDRVITTSTRTWALPTYNNH
LYKQISNGTSGGSTNDNTYFGYSTPWGYFDFNRFHCHFSPRDWQRLINNNWGFRPKRLNFKLFN
IQVKEVTTNEGTKTIANNLTSTVQVFTDSEYQLPYVLGSAHQGCLPPFPADVFMIPQYGYLTLN
NGSQAVGRSSFYCLEYFPSQMLRTGNNFQFSYTFEDVPFHSSYAHSQSLDRLMNPLIDQYLYYL
SRTQTTGT$X_3$GTQTL$X_4$FSQAGPSSMANQARNWVPGPCYRQQRVSTTTNQNNNSNFAWTGA$X_5$K$X_6$
$X_7$LNGRDSLMNPGVAMASHKDDEDRFFPSSGVLIFGKQGAGNDNVDYS$X_8$VMITNEEEIKTTNPV
ATEEYGAVATN$X_9$Q$X_{10}$ANTQAQTGLVHNQGVLPGMVWQNRDVYLQGPIWAKIPHTDGNFHPSPL
MGGFGLKHPPPQILIKNTPVPADPPTTFNQAKLNSFITQYSTGQVSVEIEWELQKENSKRWNPE
IQYTSNYYKSTNVDFAVNTEGVYSEPRPIGTRYLTRNL
X1 = S/T; X2 = K/R; X3 = A/G; X4 = Q/A; X5 = T/A; X6 = Y/F; X7 =
H/K; X8 = Q/N; X9 = N/H; X10 = S/A SEQ ID NO: 43: Anc110 VP1 DNA
ATGGCTGCCGATGGTTATCTTCCAGATTGGCTCGAGGACAACCTCTCTGAGGGCATTCGCGAGT
GGTGGGACTTGAAACCTGGAGCCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGACGCAGCGGCCCTCGAGCACGACAAAGCCTACGACCAGCAGCTCAAAGCGG
GTGACAATCCGTACCTGCGGTATAATCACGCCGACGCCGAGTTTCAGGAGCGTCTGCAAGAAGA
TACGTCTTTTGGGGGCAACCTCGGGCGAGCAGTCTTCCAGGCCAAGAAGCGGGTTCTCGAACCT
CTCGGTCTGGTTGAGGAAGGCGCTAAGACGGCTCCTGGAAAGAAGAGGCCGGTAGAGCAGTCGC
CACAAGAGCCAGACTCCTCCXXX1GGCATCGGCAAGACAGGCCAGCAGCCCGCTXXX2AAGAGA
CTCAATTTTGGTCAGACTGGCGACTCAGAGTCAGTCCCCGACCCACAACCTCTCGGAGAACCTC
CAGCAGCCCCCTCAGGTGTGGGATCTAATACAATGGCTTCAGGCGGTGGCGCTCCAATGGCAGA
CAATAACGAAGGCGCCGACGGAGTGGGTAATTCCTCGGGAAATTGGCATTGCGATTCCACATGG
CTGGGGGACAGAGTCATCACCACCAGCACCCGAACCTGGGCCCTGCCCACCTACAACAACCACC
TCTACAAGCAAATCTCCAACGGCACCTCGGGAGGAAGCACCAACGACAACACCTATTTTGGCTA
CAGCACCCCCTGGGGGTATTTTGACTTCAACAGATTCCACTGTCACTTTTCACCACGTGACTGG
CAACGACTCATCAACAACAATTGGGGATTCCGGCCCAAAAGACTCAACTTCAAGCTGTTCAACA -continued Sequence Listing TCCAGGTCAAGGAAGTCACGACGAACGAAGGCACCAAGACCATCGCCAATAATCTCACCAGCAC
CGTGCAGGTCTTTACGGACTCGGAGTACCAGTTACCGTACGTGCTAGGATCCGCTCACCAGGGA
TGTCTGCCTCCGTTCCCGGCGGACGTCTTCATGATTCCTCAGTACGGCTATTTAACTTTAAACA
ATGGAAGCCAAGCCGTGGGACGTTCCTCCTTCTACTGTCTGGAGTATTTCCCATCGCAGATGCT
GAGAACCGGCAACAACTTTCAGTTCAGCTACACCTTCGAGGACGTGCCTTTCCACAGCAGCTAC
GCGCACAGCCAGAGCCTGGACAGGCTGATGAATCCCCTCATCGACCAGTACCTGTACTACCTGT
CCAGAACGCAAACGACTGGAACTXXX3GGGACGCAGACTCTGXXX4TTCAGCCAAGCGGGTCCT
AGCTCAATGGCCAACCAGGCTAGAAATTGGGTGCCCGGACCTTGCTACCGGCAGCAGCGCGTCT
CCACGACAACCAACCAGAACAACAACAGCAACTTTGCCTGGACGGGAGCTXXX5AAGXXX6XXX
7CTGAACGGCCGAGACTCTCTAATGAATCCGGGCGTGGCAATGGCTTCCCACAAGGATGACGAG
GACCGCTTCTTCCCTTCGAGCGGGGTCCTGATTTTTGGCAAGCAAGGAGCCGGGAACGATAATG
TGGATTACAGCXXX8GTGATGATTACAAATGAGGAAGAAATCAAGACTACCAACCCCGTGGCCA
CAGAAGAATATGGAGCAGTGGCCACCAACXXXSCAGXXX10GCCAATACGCAGGCGCAGACCGG
ACTCGTGCACAACCAGGGGGTGCTTCCCGGCATGGTGTGGCAGAATAGAGACGTGTACCTGCAG
GGTCCCATCTGGGCCAAAATTCCTCACACGGACGGCAACTTTCACCCGTCTCCCCTGATGGGCG
GCTTTGGACTGAAGCACCCGCCTCCTCAAATTCTCATCAAGAACACACCGGTTCCAGCGGACCC
GCCGACTACCTTCAACCAGGCCAAGCTGAACTCTTTCATCACGCAGTACAGCACCGGACAGGTC
AGCGTGGAAATCGAGTGGGAGCTGCAGAAAGAAAACAGCAAACGCTGGAATCCAGAGATTCAAT
ACACTTCCAACTACTACAAATCTACAAATGTGGACTTTGCTGTCAACACGGAGGGGGTTTATAG
CGAGCCTCGCCCCATTGGCACCCGTTACCTCACCCGCAACCTGTAA
XXX1 = TCG/ACG; XXX2 = AAA/AGA; XXX3 = GCA/GGA; XXX4 = CAA/GCA;
XXX5 = ACC/GCC; XXX6 = TAT/TTT; XXX7 - CAC/AAA; XXX8 = CAA/AAC;
XXX9 = AAC/CAC; XXX10 = TCC/GCC SEQ ID NO: 44: AAV4 VP1 polypeptide (GenBank Accession No.
NP_044927.1)
MTDGYLPDWLEDNLSEGVREWWALQPGAPKPKANQQHQDNARGLVLPGYKYLGPGNGLDKGEPV
NAADAAALEHDKAYDQQLKAGDNPYLKYNHADAEFQQRLQGDTSFGGNLGRAVFQAKKRVLEPL
GLVEQAGETAPGKKRPLIESPQQPDSSTGIGKKGKQPAKKKLVFEDETGAGDGPPEGSTSGAMS
DDSEMRAAAGGAAVEGGQGADGVGNASGDWHCDSTWSEGHVTTTSTRTWVLPTYNNHLYKRLGE
SLQSNTYNGFSTPWGYFDFNRFHCHFSPRDWQRLINNNWGMRPKAMRVKIFNIQVKEVTTSNGE
TTVANNLTSTVQIFADSSYELPYVMDAGQEGSLPPFPNDVFMVPQYGYCGLVTGNTSQQQTDRN
AFYCLEYFPSQMLRTGNNFEITYSFEKVPFHSMYAHSQSLDRLMNPLIDQYLWGLQSTTTGTTL
NAGTATTNFTKLRPTNFSNFKKNWLPGPSIKQQGFSKTANQNYKIPATGSDSLIKYETHSTLDG
RWSALTPGPPMATAGPADSKFSNSQLIFAGPKQNGNTATVPGTLIFTSEEELAATNATDTDMWG
NLPGGDQSNSNLPTVDRLTALGAVPGMVWQNRDIYYQGPIWAKIPHTDGHFHPSPLIGGFGLKH
PPPQIFIKNTPVPANPATTFSSTPVNSFITQYSTGQVSVQIDWEIQKERSKRWNPEVQFTSNYG
QQNSLLWAPDAAGKYTEPRAIGTRYLTHHL SEQ ID NO: 45: rh32.33 VP1 polypeptide (GenBank Accession No.
EU368926
MAADGYLPDWLEDNLSEGIREWWDLKPGAPKPKANQQKQDDGRGLVLPGYKYLGPFNGLDKGEP
VNAADAAALEHDKAYDCQLKAGDNPYLRYNHADAEFQERLQEDTSFGGNLGRAVFQAKKRVLEP
LGLVEEGAKTAPGKKRPLESPQEPDSSSGIGKKGKQPAKKRLNFEEDTGAGDGPPEGSDTSAMS
SDIEMRAAPGGNAVDAGQGSDGVGNASGDWHCDSTWSEGKVTTTSTRTWVLPTYNNHLYLRLGT
TSNSNTYNGFSTPWGYFDFNRFHCHFSPRDWQRLINNNWGLRPKAMRVKIFNIQVKEVTTSNGE
TTVANNLTSTVQIFADSSYELPYVMDAGQEGSLPPFPNDVFMVPQYGYCGIVTGENQNQTDRNA
FYCLEYFPSQMLRTGNNFEMAYNFEKVPFHSMYAHSQSLDRLMNPLLDQYLWHLQSTTSGETLN
QGNAATTFGKIRSGDFAFYRKNWLPGPCVKQQRFSKTASQNYKIPASGGNALLKYDTHYTLNNR
WSNIAPGPPMATAGPSDGDFSNAQLIFPGPSVTGNTTTSANNLLFTSEEEIAATNPRDTDMFGQ
IADNNQNATTAPITGNVTAMGVLPGMVWQNRDIYYQGPIWAKIPHADGHFHPSPLIGGFGLKHP
PPQIFIKNTPVPANPATTFTAARVDSFITQYSTGQVAVQIEWEIEKERSKRWNPEVQFTSNYGN
QSSMLWAPDTTGKYTEPRVIGSRYLTNHL

What is claimed is:

1. An adeno-associated virus (AAV) capsid polypeptide having the amino acid sequence shown in SEQ ID NO: 42.

2. The AAV capsid polypeptide of claim 1, wherein the AAV capsid polypeptide is purified.

3. The AAV capsid polypeptide of claim 1 encoded by the nucleic acid sequence shown in SEQ ID NO: 43.

4. A nucleic acid molecule encoding an adeno-associated virus (AAV) capsid polypeptide having the nucleic acid sequence shown in SEQ ID NO: 43.

5. A vector comprising the nucleic acid molecule of claim 4.

6. A non-human host cell comprising the vector of claim 5.

7. A purified virus particle comprising the AAV capsid polypeptide of claim 1.

8. The purified virus particle of claim 7, further comprising a transgene.

9. A method of gene transfer and/or vaccination with a transgene, the method comprising administering a virus particle to a subject in need of gene transfer or vaccination, wherein the virus particle comprises an AAV capsid polypeptide having the amino acid sequence shown in SEQ ID NO:42.

10. A method of vaccinating a subject, the method comprising administering a target antigen operably linked to a AAV capsid polypeptide having the amino acid sequence shown in SEQ ID NO:42 to a subject in need of vaccination.

* * * * *

SEQUENCE LISTING

<160> NUMBER OF SEQ ID NOS: 53

<210> SEQ ID NO 1
<211> LENGTH: 736
<212> TYPE: PRT
<213> ORGANISM: Adeno-associated virus
<220> FEATURE:
<221> NAME/KEY: MOD_RES
<222> LOCATION: (168)..(168)
<223> OTHER INFORMATION: Lys or Arg
<220> FEATURE:
<221> NAME/KEY: MOD_RES
<222> LOCATION: (204)..(204)
<223> OTHER INFORMATION: Ala or Ser
<220> FEATURE:
<221> NAME/KEY: MOD_RES
<222> LOCATION: (266)..(266)
<223> OTHER INFORMATION: Ala or Gly
<220> FEATURE:
<221> NAME/KEY: MOD_RES
<222> LOCATION: (311)..(311)
<223> OTHER INFORMATION: Arg or Lys
<220> FEATURE:
<221> NAME/KEY: MOD_RES
<222> LOCATION: (411)..(411)
<223> OTHER INFORMATION: Glu or Gln
<220> FEATURE:
<221> NAME/KEY: MOD_RES
<222> LOCATION: (460)..(460)
<223> OTHER INFORMATION: Thr or Glu
<220> FEATURE:
<221> NAME/KEY: MOD_RES
<222> LOCATION: (493)..(493)
<223> OTHER INFORMATION: Ala or Thr
<220> FEATURE:
<221> NAME/KEY: MOD_RES
<222> LOCATION: (562)..(562)
<223> OTHER INFORMATION: Ser or Asn
<220> FEATURE:
<221> NAME/KEY: MOD_RES
<222> LOCATION: (576)..(576)
<223> OTHER INFORMATION: Gln or Glu
<220> FEATURE:
<221> NAME/KEY: MOD_RES
<222> LOCATION: (587)..(587)
<223> OTHER INFORMATION: Ser or Ala
<220> FEATURE:
<221> NAME/KEY: MOD_RES
<222> LOCATION: (609)..(609)
<223> OTHER INFORMATION: Asn or Asp

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Xaa Ala Gly Gly Gly
        195                 200                 205

Ala Pro Met Ala Asp Asn Asn Glu Gly Ala Asp Gly Val Gly Asn Ala
```

-continued

```
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Xaa Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Xaa Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Xaa Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Xaa Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Xaa Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Xaa Glu Glu Glu Ile Lys Thr Thr Asn Pro Val Ala Thr Glu Xaa
                565                 570                 575

Tyr Gly Thr Val Ala Thr Asn Leu Gln Ser Xaa Asn Thr Ala Pro Ala
            580                 585                 590

Thr Gly Thr Val Asn Ser Gln Gly Ala Leu Pro Gly Met Val Trp Gln
        595                 600                 605

Xaa Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640
```

Lys His Pro Pro Pro Gln Ile Leu Ile Lys Asn Thr Pro Val Pro Ala
645 650 655

Asn Pro Pro Thr Thr Phe Ser Pro Ala Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Asn Lys Ser Thr Asn Val Asp Phe Ala Val Asp Thr Asn Gly Val
705 710 715 720

Tyr Ser Glu Pro Arg Pro Ile Gly Thr Arg Tyr Leu Thr Arg Asn Leu
725 730 735

<210> SEQ ID NO 2
<211> LENGTH: 2208
<212> TYPE: DNA
<213> ORGANISM: Adeno-associated virus
<220> FEATURE:
<221> NAME/KEY: misc_feature
<222> LOCATION: (502)..(504)
<223> OTHER INFORMATION: This region may encompass “aag” or “aaa”
<220> FEATURE:
<221> NAME/KEY: misc_feature
<222> LOCATION: (610)..(612)
<223> OTHER INFORMATION: This region may encompass “gca” or “agc”
<220> FEATURE:
<221> NAME/KEY: misc_feature
<222> LOCATION: (796)..(798)
<223> OTHER INFORMATION: This region may encompass “gca” or “ggc”
<220> FEATURE:
<221> NAME/KEY: misc_feature
<222> LOCATION: (931)..(933)
<223> OTHER INFORMATION: This region may encompass “aga” or “aag”
<220> FEATURE:
<221> NAME/KEY: misc_feature
<222> LOCATION: (1231)..(1233)
<223> OTHER INFORMATION: This region may encompass “gag” or “cag”
<220> FEATURE:
<221> NAME/KEY: misc_feature
<222> LOCATION: (1378)..(1380)
<223> OTHER INFORMATION: This region may encompass “acg” or “gag”
<220> FEATURE:
<221> NAME/KEY: misc_feature
<222> LOCATION: (1477)..(1479)
<223> OTHER INFORMATION: This region may encompass “gcg” or “acc”
<220> FEATURE:
<221> NAME/KEY: misc_feature
<222> LOCATION: (1684)..(1686)
<223> OTHER INFORMATION: This region may encompass “agt” or “aac”
<220> FEATURE:
<221> NAME/KEY: misc_feature
<222> LOCATION: (1726)..(1728)
<223> OTHER INFORMATION: This region may encompass “cag” or “gag”
<220> FEATURE:
<221> NAME/KEY: misc_feature
<222> LOCATION: (1759)..(1761)
<223> OTHER INFORMATION: This region may encompass “tca” or “gcc”
<220> FEATURE:
<221> NAME/KEY: misc_feature
<222> LOCATION: (1825)..(1827)
<223> OTHER INFORMATION: This region may encompass “aac” or “gac”

<400> SEQUENCE: 2
atggctgccg atggttatct tccagattgg ctcgaggaca acctctctga gggcattcgc 60
gagtggtggg acttgaaacc tggagccccg aaacccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240

-continued

```
cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gcaatcaccc caggaaccag actcctcttc gggcatcggc    480

aagaaaggcc agcagcccgc gnnnaagaga ctcaactttg ggcagacagg cgactcagag    540

tcagtgcccg accctcaacc actcggagaa ccccccgcag ccccctctgg tgtgggatct    600

aatacaatgn nngcaggcgg tggcgctcca atggcagaca ataacgaagg cgccgacgga    660

gtgggtaacg cctcaggaaa ttggcattgc gattccacat ggctgggcga cagagtcatc    720

accaccagca cccgaacctg ggccctcccc acctacaaca accacctcta caagcaaatc    780

tccagccaat cgggannnag caccaacgac aacacctact tcggctacag caccccctgg    840

gggtattttg actttaacag attccactgc cacttctcac cacgtgactg gcagcgactc    900

atcaacaaca actggggatt ccggcccaag nnnctcaact tcaagctctt caacatccag    960

gtcaaggagg tcacgacgaa tgatggcacc acgaccatcg ccaataacct taccagcacg   1020

gttcaggtct ttacggactc ggaataccag ctcccgtacg tcctcggctc tgcgcaccag   1080

ggctgcctgc ctccgttccc ggcggacgtc ttcatgattc ctcagtacgg gtacctgact   1140

ctgaacaatg gcagtcaggc cgtgggccgt tcctccttct actgcctgga gtactttcct   1200

tctcaaatgc tgagaacggg caacaacttt nnnttcagct acacgtttga ggacgtgcct   1260

tttcacagca gctacgcgca cagccaaagc ctggaccggc tgatgaaccc cctcatcgac   1320

cagtacctgt actacctgtc tcggactcag accacgagtg gtaccgcagg aaatcggnnn   1380

ttgcaatttt ctcaggccgg gcctagtagc atggcgaatc aggccaaaaa ctggctaccc   1440

gggccctgct accggcagca acgcgtctcc aagacannna atcaaaataa caacagcaac   1500

tttgcctgga ccggtgccac caagtatcat ctgaatggca gagactctct ggtaaatccc   1560

ggtcccgcta tggcaaccca caaggacgac gaagacaaat tttttccgat gagcggagtc   1620

ttaatatttg ggaaacaggg agctggaaat agcaacgtgg accttgacaa cgttatgata   1680

accnnngagg aagaaattaa aaccaccaac ccagtggcca cagaannnta cggcacggtg   1740

gccactaacc tgcaatcgnn naacaccgct cctgctacag ggaccgtcaa cagtcaagga   1800

gccttacctg gcatggtctg gcagnnncgg gacgtgtacc tgcagggtcc tatctgggcc   1860

aagattcctc acacggacgg acactttcat ccctcgccgc tgatgggagg ctttggactg   1920

aaacacccgc ctcctcagat cctgattaag aatacacctg ttcccgcgaa tcctccaact   1980

accttcagtc cagctaagtt tgcgtcgttc atcacgcagt acagcaccgg acaggtcagc   2040

gtggaaattg aatgggagct gcagaaagaa aacagcaaac gctggaaccc agagattcaa   2100

tacacttcca actacaacaa atctacaaat gtggactttg ctgttgacac aaatggcgtt   2160

tattctgagc ctcgccccat cggcacccgt tacctcaccc gtaatctg                2208
```

<210> SEQ ID NO 3
<211> LENGTH: 737
<212> TYPE: PRT
<213> ORGANISM: Adeno-associated virus
<220> FEATURE:
<221> NAME/KEY: MOD_RES
<222> LOCATION: (157)..(157)
<223> OTHER INFORMATION: Thr or Ser
<220> FEATURE:
<221> NAME/KEY: MOD_RES
<222> LOCATION: (168)..(168)
<223> OTHER INFORMATION: Lys or Arg -continued
<220> FEATURE:
<221> NAME/KEY: MOD_RES
<222> LOCATION: (262)..(262)
<223> OTHER INFORMATION: Asn or Ser
<220> FEATURE:
<221> NAME/KEY: MOD_RES
<222> LOCATION: (263)..(263)
<223> OTHER INFORMATION: Ser or His
<220> FEATURE:
<221> NAME/KEY: MOD_RES
<222> LOCATION: (312)..(312)
<223> OTHER INFORMATION: Arg or Lys
<220> FEATURE:
<221> NAME/KEY: MOD_RES
<222> LOCATION: (412)..(412)
<223> OTHER INFORMATION: Glu or Gln
<220> FEATURE:
<221> NAME/KEY: MOD_RES
<222> LOCATION: (460)..(460)
<223> OTHER INFORMATION: Arg or Gln
<220> FEATURE:
<221> NAME/KEY: MOD_RES
<222> LOCATION: (461)..(461)
<223> OTHER INFORMATION: Thr or Glu
<220> FEATURE:
<221> NAME/KEY: MOD_RES
<222> LOCATION: (552)..(552)
<223> OTHER INFORMATION: Asp or Ser
<220> FEATURE:
<221> NAME/KEY: MOD_RES
<222> LOCATION: (556)..(556)
<223> OTHER INFORMATION: Leu or Tyr
<220> FEATURE:
<221> NAME/KEY: MOD_RES
<222> LOCATION: (557)..(557)
<223> OTHER INFORMATION: Asp or Ser
<220> FEATURE:
<221> NAME/KEY: MOD_RES
<222> LOCATION: (563)..(563)
<223> OTHER INFORMATION: Ser or Asn
<220> FEATURE:
<221> NAME/KEY: MOD_RES
<222> LOCATION: (580)..(580)
<223> OTHER INFORMATION: Val or Ile
<220> FEATURE:
<221> NAME/KEY: MOD_RES
<222> LOCATION: (588)..(588)
<223> OTHER INFORMATION: Asn or Ser
<220> FEATURE:
<221> NAME/KEY: MOD_RES
<222> LOCATION: (664)..(664)
<223> OTHER INFORMATION: Ser or Thr

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Xaa Gly Ile Gly
145                 150                 155                 160

Lys Lys Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Xaa Xaa Gln Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Xaa Leu Asn Phe Lys Leu Phe Asn Ile
305                 310                 315                 320

Gln Val Lys Glu Val Thr Thr Asn Asp Gly Thr Thr Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Xaa Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Gly Asn Xaa Xaa Leu Gln Phe
    450                 455                 460

Ser Gln Ala Gly Pro Ser Ser Met Ala Asn Gln Ala Lys Asn Trp Leu
465                 470                 475                 480

Pro Gly Pro Cys Tyr Arg Gln Gln Arg Val Ser Lys Thr Thr Asn Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
        515                 520                 525

Lys Asp Asp Glu Asp Arg Phe Phe Pro Ser Ser Gly Val Leu Ile Phe
    530                 535                 540

Gly Lys Gln Gly Ala Gly Asn Xaa Asn Val Asp Xaa Xaa Asn Val Met
```

-continued

```
545                 550                 555                 560

Ile Thr Xaa Glu Glu Glu Ile Lys Thr Thr Asn Pro Val Ala Thr Glu
                565                 570                 575

Glu Tyr Gly Xaa Val Ala Thr Asn Leu Gln Ser Xaa Asn Thr Ala Pro
            580                 585                 590

Gln Thr Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Thr Thr Phe Xaa Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Thr Asn Val Asp Phe Ala Val Asp Thr Glu Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 4
<211> LENGTH: 2211
<212> TYPE: DNA
<213> ORGANISM: Adeno-associated virus
<220> FEATURE:
<221> NAME/KEY: misc_feature
<222> LOCATION: (469)..(471)
<223> OTHER INFORMATION: This region may encompass "acg" or "agc"
<220> FEATURE:
<221> NAME/KEY: misc_feature
<222> LOCATION: (502)..(504)
<223> OTHER INFORMATION: This region may encompass "aaa" or "aag"
<220> FEATURE:
<221> NAME/KEY: misc_feature
<222> LOCATION: (784)..(786)
<223> OTHER INFORMATION: This region may encompass "aac" or "agt"
<220> FEATURE:
<221> NAME/KEY: misc_feature
<222> LOCATION: (787)..(789)
<223> OTHER INFORMATION: This region may encompass "agc" or "cac"
<220> FEATURE:
<221> NAME/KEY: misc_feature
<222> LOCATION: (934)..(936)
<223> OTHER INFORMATION: This region may encompass "aga" or "aag"
<220> FEATURE:
<221> NAME/KEY: misc_feature
<222> LOCATION: (1234)..(1236)
<223> OTHER INFORMATION: This region may encompass "gag" or "cag"
<220> FEATURE:
<221> NAME/KEY: misc_feature
<222> LOCATION: (1378)..(1380)
<223> OTHER INFORMATION: This region may encompass "cgg" or "cag"
<220> FEATURE:
<221> NAME/KEY: misc_feature
<222> LOCATION: (1381)..(1383)
<223> OTHER INFORMATION: This region may encompass "acg" or "gag"
<220> FEATURE:
<221> NAME/KEY: misc_feature
<222> LOCATION: (1654)..(1656)
<223> OTHER INFORMATION: This region may encompass "gac" or "agc"
<220> FEATURE:
```

<221> NAME/KEY: misc_feature
<222> LOCATION: (1666)..(1668)
<223> OTHER INFORMATION: This region may encompass “ctt” or “tac”
<220> FEATURE:
<221> NAME/KEY: misc_feature
<222> LOCATION: (1669)..(1671)
<223> OTHER INFORMATION: This region may encompass “gac” or “agc”
<220> FEATURE:
<221> NAME/KEY: misc_feature
<222> LOCATION: (1687)..(1689)
<223> OTHER INFORMATION: This region may encompass “agt” or “aac”
<220> FEATURE:
<221> NAME/KEY: misc_feature
<222> LOCATION: (1738)..(1740)
<223> OTHER INFORMATION: This region may encompass “gtg” or “atc”
<220> FEATURE:
<221> NAME/KEY: misc_feature
<222> LOCATION: (1762)..(1764)
<223> OTHER INFORMATION: This region may encompass “gca” or “agc”
<220> FEATURE:
<221> NAME/KEY: misc_feature
<222> LOCATION: (1990)..(1992)
<223> OTHER INFORMATION: This region may encompass “agt” or “acc”

<400> SEQUENCE: 4
atggctgccg atggttatct tccagattgg ctcgaggaca acctctctga gggcattcgc 60
gagtggtggg acttgaaacc tggagccccg aaacccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gcaatcaccc caggaaccag actcctctnn nggcatcggc 480
aagaaaggcc agcagcccgc gnnnaagaga ctcaactttg ggcagactgg cgactcagag 540
tcagtgcccg accctcaacc actcggagaa ccccccgcag ccccctctgg tgtgggatct 600
aatacaatgg ctgcaggcgg tggcgctcca atggcagaca ataacgaagg cgccgacgga 660
gtgggtaatg cctcaggaaa ttggcattgc gattccacat ggctgggcga cagagtcatc 720
accaccagca cccgaacctg ggccctcccc acctacaaca accacctcta caagcaaatc 780
tccnnnnnnc aatcgggagg aagcaccaac gacaacacct acttcggcta cagcaccccc 840
tgggggtatt ttgactttaa cagattccac tgccacttct caccacgtga ctggcagcga 900
ctcatcaaca acaactgggg attccggccc aagnnnctca acttcaagct cttcaacatc 960
caggtcaagg aggtcacgac gaatgatggc accacgacca tcgccaataa ccttaccagc 1020
acggttcagg tctttacgga ctcggaatac cagctcccgt acgtcctcgg ctctgcgcac 1080
cagggctgcc tgcctccgtt cccggcggac gtcttcatga ttcctcagta cgggtacctg 1140
actctgaaca atggcagtca ggccgtgggc cgttcctcct tctactgcct ggagtacttt 1200
ccttctcaaa tgctgagaac gggcaacaac tttnnnttca gctacacgtt tgaggacgtg 1260
ccttttcaca gcagctacgc gcacagccaa agcctggacc ggctgatgaa ccccctcatc 1320
gaccagtacc tgtactacct gtctcggact cagaccacgg gaggtaccgc aggaaatnnn 1380
nnnttgcaat tttctcaggc cgggcctagt agcatggcga atcaggccaa aaactggcta 1440
cccgggccct gctaccggca gcaacgcgtc tccaagacaa cgaatcaaaa taacaacagc 1500
aactttgcct ggaccggtgc caccaagtat catctgaatg gcagagactc tctggtaaat 1560
cccggtgtcg ctatggcaac ccacaaggac gacgaagacc gatttttttcc gtccagcgga 1620

```
gtcttaatat ttgggaaaca gggagctgga aatnnnaacg tggacnnnnn naacgttatg   1680

ataaccnnng aggaagaaat taaaaccacc aacccagtgg ccacagaaga gtacggcnnn   1740

gtggccacta acctgcaatc gnnnaacacc gctcctcaaa cagggaccgt caacagtcaa   1800

ggagccttac ctggcatggt ctggcagaac cgggacgtgt acctgcaggg tcctatctgg   1860

gccaagattc ctcacacgga cggaaacttt catccctcgc cgctgatggg aggctttgga   1920

ctgaaacacc cgcctcctca gatcctgatt aagaatacac ctgttcccgc gaatcctcca   1980

actaccttcn nnccagctaa gtttgcgtcg ttcatcacgc agtacagcac cggacaggtc   2040

agcgtggaaa ttgaatggga gctgcagaaa gaaaacagca aacgctggaa cccagagatt   2100

caatacactt ccaactacaa caaatctaca aatgtggact ttgctgttga cacagaaggc   2160

gtttattctg agcctcgccc catcggcacc cgttacctca cccgtaatct g            2211
```

<210> SEQ ID NO 5
<211> LENGTH: 738
<212> TYPE: PRT
<213> ORGANISM: Adeno-associated virus
<220> FEATURE:
<221> NAME/KEY: MOD_RES
<222> LOCATION: (158)..(158)
<223> OTHER INFORMATION: Thr or Ser
<220> FEATURE:
<221> NAME/KEY: MOD_RES
<222> LOCATION: (169)..(169)
<223> OTHER INFORMATION: Lys or Arg
<220> FEATURE:
<221> NAME/KEY: MOD_RES
<222> LOCATION: (564)..(564)
<223> OTHER INFORMATION: Ser or Asn

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Arg Glu Pro Asp Ser Ser Xaa Gly Ile
145                 150                 155                 160

Gly Lys Lys Gly Gln Gln Pro Ala Xaa Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205
```

-continued

```
Gly Ala Pro Met Ala Asp Asn Asn Glu Gly Ala Asp Gly Val Gly Asn
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Thr Asn Glu Gly Thr Lys Thr Ile Ala
                325                 330                 335

Asn Asn Leu Thr Ser Thr Val Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Gly Thr Gln Thr Leu Gln
    450                 455                 460

Phe Ser Gln Ala Gly Pro Ser Ser Met Ala Asn Gln Ala Lys Asn Trp
465                 470                 475                 480

Leu Pro Gly Pro Cys Tyr Arg Gln Gln Arg Val Ser Thr Thr Thr Asn
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Gln Gly Ala Gly Asn Asp Asn Val Asp Tyr Ser Asn Val
545                 550                 555                 560

Met Ile Thr Xaa Glu Glu Glu Ile Lys Thr Thr Asn Pro Val Ala Thr
                565                 570                 575

Glu Glu Tyr Gly Val Val Ala Thr Asn Leu Gln Ser Ala Asn Thr Ala
            580                 585                 590

Pro Gln Thr Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620
```

```
Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 6
<211> LENGTH: 2214
<212> TYPE: DNA
<213> ORGANISM: Adeno-associated virus
<220> FEATURE:
<221> NAME/KEY: misc_feature
<222> LOCATION: (472)..(474)
<223> OTHER INFORMATION: This region may encompass “acg” or “agc”
<220> FEATURE:
<221> NAME/KEY: misc_feature
<222> LOCATION: (505)..(507)
<223> OTHER INFORMATION: This region may encompass “aaa” or “aga”
<220> FEATURE:
<221> NAME/KEY: misc_feature
<222> LOCATION: (1690)..(1692)
<223> OTHER INFORMATION: This region may encompass “agc” or “aac”

<400> SEQUENCE: 6

atggctgccg atggttatct tccagattgg ctcgaggaca acctctctga gggcattcgc     60

gagtggtggg acctgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata atcacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gcagtcacca cagcgtgagc ccgactcctc cnnnggcatc    480

ggcaagaaag gccagcagcc cgccnnnaag agactcaatt tcggtcagac tggcgactca    540

gagtcagtcc ccgaccctca acctctcgga gaacctccag cagcgccctc tggtgtggga    600

tctaatacaa tggctgcagg cggtggcgca ccaatggcag acaataacga aggtgccgac    660

ggagtgggta attcctcggg aaattggcat tgcgattcca catggctggg cgacagagtc    720

atcaccacca gcacccgaac ctgggccctg cccacctaca acaaccacct ctacaagcaa    780

atctccaacg ggacctcggg aggcagcacc aacgacaaca cctactttgg ctacagcacc    840

ccctgggggt attttgactt taacagattc cactgccact tctcaccacg tgactggcag    900

cgactcatca acaacaactg gggattccgg cccaagagac tcaacttcaa gctcttcaac    960

atccaggtca aagaggtcac gacgaatgaa ggcaccaaga ccatcgccaa taacctcacc   1020

agcaccgtcc aggtgtttac ggactcggaa taccagctgc cgtacgtcct cggctctgcc   1080
```

```
caccagggct gcctgcctcc gttcccggcg gacgtcttca tgattcctca gtacggctac   1140

ctgactctca acaacggtag tcaggccgtg ggacgttcct ccttctactg cctggagtac   1200

ttcccctctc agatgctgag aacgggcaac aactttcaat tcagctacac tttcgaggac   1260

gtgcctttcc acagcagcta cgcgcacagc cagagtttgg acaggctgat gaatcctctc   1320

atcgaccagt acctgtacta cctgtcaaga acccagacta cgggaggcac agcgggaacc   1380

cagacgttgc agttttctca ggccgggcct agcagcatgg cgaatcaggc caaaaactgg   1440

ctgcctggac cctgctacag acagcagcgc gtctccacga caacgaatca aaacaacaac   1500

agcaactttg cctggactgg tgccaccaag tatcatctga acggcagaga ctctctggtg   1560

aatccgggcg tcgccatggc aacccacaag gacgacgagg accgcttctt cccatccagc   1620

ggcgtcctca tatttggcaa gcagggagct ggaaatgaca acgtggacta tagcaacgtg   1680

atgataaccn nngaggaaga aatcaagacc accaaccccg tggccacaga agagtatggc   1740

gtggtggcta ctaacctaca gtcggcaaac accgctcctc aaacggggac cgtcaacagc   1800

cagggagcct tacctggcat ggtctggcag aaccgggacg tgtacctgca gggtcctatt   1860

tgggccaaga ttcctcacac agatggcaac tttcacccgt ctcctttaat gggcggcttt   1920

ggacttaaac atccgcctcc tcagatcctc atcaaaaaca ctcctgttcc tgcggatcct   1980

ccaacaacgt tcaaccaggc caagctgaat tctttcatca cgcagtacag caccggacaa   2040

gtcagcgtgg agatcgagtg ggagctgcag aaggagaaca gcaagcgctg gaacccagag   2100

attcagtata cttccaacta ctacaaatct acaaatgtgg actttgctgt taatactgag   2160

ggtgtttact ctgagcctcg ccccattggc actcgttacc tcacccgtaa tctg         2214
```

```
<210> SEQ ID NO 7
<211> LENGTH: 738
<212> TYPE: PRT
<213> ORGANISM: Adeno-associated virus
<220> FEATURE:
<221> NAME/KEY: MOD_RES
<222> LOCATION: (158)..(158)
<223> OTHER INFORMATION: Thr or Ser
<220> FEATURE:
<221> NAME/KEY: MOD_RES
<222> LOCATION: (169)..(169)
<223> OTHER INFORMATION: Arg or Lys
<220> FEATURE:
<221> NAME/KEY: MOD_RES
<222> LOCATION: (315)..(315)
<223> OTHER INFORMATION: Asn or Ser
<220> FEATURE:
<221> NAME/KEY: MOD_RES
<222> LOCATION: (413)..(413)
<223> OTHER INFORMATION: Gln or Glu
<220> FEATURE:
<221> NAME/KEY: MOD_RES
<222> LOCATION: (472)..(472)
<223> OTHER INFORMATION: Asn, Thr or Ser
<220> FEATURE:
<221> NAME/KEY: MOD_RES
<222> LOCATION: (534)..(534)
<223> OTHER INFORMATION: Asp or Glu
<220> FEATURE:
<221> NAME/KEY: MOD_RES
<222> LOCATION: (542)..(542)
<223> OTHER INFORMATION: Ile or Val
<220> FEATURE:
<221> NAME/KEY: MOD_RES
<222> LOCATION: (595)..(595)
<223> OTHER INFORMATION: Ile or Val

<400> SEQUENCE: 7

Met Ala Ala Asp Gly Tyr Leu Pro Asp Trp Leu Glu Asp Asn Leu Ser
```

-continued

```
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Arg Glu Pro Asp Ser Ser Xaa Gly Ile
145                 150                 155                 160

Gly Lys Lys Gly Gln Gln Pro Ala Xaa Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Xaa Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Xaa Phe Ser Tyr
                405                 410                 415

Thr Phe Glu Asp Val Pro Phe His Ser Ser Tyr Ala His Ser Gln Ser
            420                 425                 430
```

```
Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Gly Thr Gln Thr Leu Gln
    450                 455                 460

Phe Ser Gln Ala Gly Pro Ser Xaa Met Ala Asn Gln Ala Lys Asn Trp
465                 470                 475                 480

Leu Pro Gly Pro Cys Tyr Arg Gln Gln Arg Val Ser Thr Thr Thr Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Xaa Arg Phe Phe Pro Ser Ser Gly Xaa Leu Ile
    530                 535                 540

Phe Gly Lys Gln Gly Ala Gly Lys Asp Asn Val Asp Tyr Ser Asn Val
545                 550                 555                 560

Met Leu Thr Ser Glu Glu Glu Ile Lys Thr Thr Asn Pro Val Ala Thr
                565                 570                 575

Glu Glu Tyr Gly Val Val Ala Asp Asn Leu Gln Gln Gln Asn Thr Ala
            580                 585                 590

Pro Gln Xaa Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 8
<211> LENGTH: 2214
<212> TYPE: DNA
<213> ORGANISM: Adeno-associated virus
<220> FEATURE:
<221> NAME/KEY: misc_feature
<222> LOCATION: (472)..(474)
<223> OTHER INFORMATION: This region may encompass “acg” or “agc”
<220> FEATURE:
<221> NAME/KEY: misc_feature
<222> LOCATION: (505)..(507)
<223> OTHER INFORMATION: This region may encompass “aga” or “aag”
<220> FEATURE:
<221> NAME/KEY: misc_feature
<222> LOCATION: (943)..(945)
<223> OTHER INFORMATION: This region may encompass “aac” or “agc”
<220> FEATURE:
<221> NAME/KEY: misc_feature
<222> LOCATION: (1237)..(1239)
<223> OTHER INFORMATION: This region may encompass "caa" or "gaa"
<220> FEATURE:
<221> NAME/KEY: misc_feature
<222> LOCATION: (1414)..(1416)
<223> OTHER INFORMATION: This region may encompass "aac" or "acc" or "agc"
<220> FEATURE:
<221> NAME/KEY: misc_feature
<222> LOCATION: (1600)..(1602)
<223> OTHER INFORMATION: This region may encompass "gac" or "gag"
<220> FEATURE:
<221> NAME/KEY: misc_feature
<222> LOCATION: (1624)..(1626)
<223> OTHER INFORMATION: This region may encompass "atc" or "gtc"
<220> FEATURE:
<221> NAME/KEY: misc_feature
<222> LOCATION: (1783)..(1785)
<223> OTHER INFORMATION: This region may encompass "ata" or "gta"

<400> SEQUENCE: 8
atggctgccg atggttatct tccagattgg ctcgaggaca acctctctga gggcattcgc 60
gagtggtggg acctgaaacc tggagccccg aaacccaaag ccaaccagca aaagcaggac 120
gacggccggg gtctggtgct tcctggctac aagtacctcg gacccttcaa cggactcgac 180
aagggggagc ccgtcaacgc ggcggacgca gcggccctcg agcacgacaa ggcctacgac 240
cagcagctca aagcgggtga caatccgtac ctgcggtata atcacgccga cgccgagttt 300
caggagcgtc tgcaagaaga tacgtctttt gggggcaacc tcgggcgagc agtcttccag 360
gccaagaagc gggttctcga acctctcggt ctggttgagg aaggcgctaa gacggctcct 420
ggaaagaaga gaccggtaga gcagtcacca cagcgtgagc ccgactcctc cnnnggcatc 480
ggcaagaaag gccagcagcc cgccnnnaag agactcaatt tcggtcagac tggcgactca 540
gagtcagtcc ccgaccctca acctctcgga gaacctccag cagcgccctc tggtgtggga 600
tctaatacaa tggctgcagg cggtggcgca ccaatggcag acaataacga aggtgccgac 660
ggagtgggta gttcctcggg aaattggcat tgcgattcca catggctggg cgacagagtc 720
atcaccacca gcacccgaac ctgggccctg cccacctaca acaaccacct ctacaagcaa 780
atctccaacg ggacctcggg aggcagcacc aacgacaaca cctactttgg ctacagcacc 840
ccctgggggt attttgactt taacagattc cactgccact tctcaccacg tgactggcag 900
cgactcatca acaacaactg gggattccgg cccaagagac tcnnnttcaa gctcttcaac 960
atccaggtca aagaggtcac gcagaatgaa ggcaccaaga ccatcgccaa taacctcacc 1020
agcaccatcc aggtgtttac ggactcggaa taccagctgc cgtacgtcct cggctctgcc 1080
caccagggct gcctgcctcc gttcccggcg gacgtcttca tgattcctca gtacggctac 1140
ctgactctca acaacggtag tcaggccgtg ggacgttcct ccttctactg cctggagtac 1200
ttcccctctc agatgctgag aacgggcaac aactttnnnt tcagctacac tttcgaggac 1260
gtgcctttcc acagcagcta cgcgcacagc cagagtttgg acaggctgat gaatcctctc 1320
atcgaccagt acctgtacta cctgtcaaga acccagacta cgggaggcac agcgggaacc 1380
cagacgttgc agttttctca ggccgggcct agcnnnatgg cgaatcaggc caaaaactgg 1440
ctgcctggac cctgctacag acagcagcgc gtctccacga caacgtcgca aaacaacaac 1500
agcaactttg cctggactgg tgccaccaag tatcatctga acggcagaga ctctctggtg 1560
aatccgggcg tcgccatggc aacccacaag gacgacgagn nncgcttctt cccatccagc 1620
ggcnnnctca tatttggcaa gcagggagct ggaaaagaca acgtggacta tagcaacgtg 1680
atgctaacca gcgaggaaga aatcaagacc accaaccccg tggccacaga agagtatggc 1740

```
gtggtggctg ataacctaca gcagcaaaac accgctcctc aannngggac cgtcaacagc   1800

cagggagcct tacctggcat ggtctggcag aaccgggacg tgtacctgca gggtcctatt   1860

tgggccaaga ttcctcacac agatggcaac tttcacccgt ctcctttaat gggcggcttt   1920

ggacttaaac atccgcctcc tcagatcctc atcaaaaaca ctcctgttcc tgcggatcct   1980

ccaacaacgt tcaaccaggc caagctgaat tctttcatca cgcagtacag caccggacaa   2040

gtcagcgtgg agatcgagtg ggagctgcag aaggagaaca gcaagcgctg gaacccagag   2100

attcagtata cttccaacta ctacaaatct acaaatgtgg actttgctgt taatactgag   2160

ggtgtttact ctgagcctcg ccccattggc actcgttacc tcacccgtaa tctg         2214
```

```
<210> SEQ ID NO 9
<211> LENGTH: 738
<212> TYPE: PRT
<213> ORGANISM: Adeno-associated virus
<220> FEATURE:
<221> NAME/KEY: MOD_RES
<222> LOCATION: (169)..(169)
<223> OTHER INFORMATION: Arg or Lys
<220> FEATURE:
<221> NAME/KEY: MOD_RES
<222> LOCATION: (315)..(315)
<223> OTHER INFORMATION: Asn or Ser
<220> FEATURE:
<221> NAME/KEY: MOD_RES
<222> LOCATION: (534)..(534)
<223> OTHER INFORMATION: Asp or Glu
<220> FEATURE:
<221> NAME/KEY: MOD_RES
<222> LOCATION: (542)..(542)
<223> OTHER INFORMATION: Ile or Val

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Xaa Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Ser Gly Thr Met Ala Ala Gly Gly
        195                 200                 205
```

-continued

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Xaa Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Xaa Arg Phe Phe Pro Ser Ser Gly Xaa Leu Met
    530                 535                 540

Phe Gly Lys Gln Gly Ala Gly Lys Asp Asn Val Asp Tyr Ser Asn Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Thr Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620
```

```
Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 10
<211> LENGTH: 2214
<212> TYPE: DNA
<213> ORGANISM: Adeno-associated virus
<220> FEATURE:
<221> NAME/KEY: misc_feature
<222> LOCATION: (505)..(507)
<223> OTHER INFORMATION: This region may encompass “aga” or “aaa”
<220> FEATURE:
<221> NAME/KEY: misc_feature
<222> LOCATION: (943)..(945)
<223> OTHER INFORMATION: This region may encompass “aac” or “agc”
<220> FEATURE:
<221> NAME/KEY: misc_feature
<222> LOCATION: (1600)..(1602)
<223> OTHER INFORMATION: This region may encompass “gac” or “gag”
<220> FEATURE:
<221> NAME/KEY: misc_feature
<222> LOCATION: (1624)..(1626)
<223> OTHER INFORMATION: This region may encompass “atc” or “gtc”

<400> SEQUENCE: 10

atggctgccg atggttatct tccagattgg ctcgaggaca acctctctga gggcattcgc     60

gagtggtggg acctgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata atcacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccgtcacca cagcgttccc ccgactcctc cacgggcatc    480

ggcaagaaag gccagcagcc cgccnnnaag agactcaatt tcggtcagac tggcgactca    540

gagtcagtcc ccgaccctca acctatcgga gaacctccag cagcgccctc tggtgtggga    600

tctggtacaa tggctgcagg cggtggcgca ccaatggcag acaataacga aggtgccgac    660

ggagtgggta gttcctcggg aaattggcat tgcgattcca catggctggg cgacagagtc    720

atcaccacca gcacccgaac ctgggccctg cccacctaca acaaccacct ctacaagcaa    780

atctccaacg ggacctcggg aggcagcacc aacgacaaca cctactttgg ctacagcacc    840

ccctgggggt attttgactt taacagattc cactgccact tctcaccacg tgactggcag    900

cgactcatca acaacaactg gggattccgg cccaagagac tcnnnttcaa gctcttcaac    960
```

```
atccaggtca aagaggtcac gcagaatgaa ggcaccaaga ccatcgccaa taacctcacc   1020

agcaccatcc aggtgtttac ggactcggaa taccagctgc cgtacgtcct cggctctgcc   1080

caccagggct gcctgcctcc gttcccggcg gacgtcttca tgattcctca gtacggctac   1140

ctgactctca acaacggtag tcaggccgtg ggacgttcct ccttctactg cctggagtac   1200

ttcccctctc agatgctgag aacgggcaac aactttgagt tcagctacac tttcgaggac   1260

gtgcctttcc acagcagcta cgcgcacagc cagagtttgg acaggctgat gaatcctctc   1320

atcgaccagt acctgtacta cctgtcaaga acccagtcta cgggaggcac agcgggaacc   1380

cagcagttgc tgtttctcca ggccgggcct agcaacatgt cggctcaggc caaaaactgg   1440

ctgcctggac cctgctacag acagcagcgc gtctccacga cactgtcgca aaacaacaac   1500

agcaactttg cctggactgg tgccaccaag tatcatctga acggcagaga ctctctggtg   1560

aatccgggcg tcgccatggc aacccacaag gacgacgagn nncgcttctt cccatccagc   1620

ggcnnnctca tgtttggcaa gcagggagct ggaaaagaca acgtggacta tagcaacgtg   1680

atgctaacca gcgaggaaga aatcaagacc accaaccccg tggccacaga acagtatggc   1740

gtggtggctg ataacctaca gcagcaaaac accgctccta ttgtgggggc cgtcaacagc   1800

cagggagcct tacctggcat ggtctggcag aaccgggacg tgtacctgca gggtcctatt   1860

tgggccaaga ttcctcacac agatggcaac tttcacccgt ctcctttaat gggcggcttt   1920

ggacttaaac atccgcctcc tcagatcctc atcaaaaaca ctcctgttcc tgcggatcct   1980

ccaacaacgt tcaaccaggc caagctgaat tctttcatca cgcagtacag caccggacaa   2040

gtcagcgtgg agatcgagtg ggagctgcag aaggagaaca gcaagcgctg gaacccagag   2100

attcagtata cttccaacta ctacaaatct acaaatgtgg actttgctgt taatactgag   2160

ggtgtttact ctgagcctcg ccccattggc actcgttacc tcacccgtaa tctg         2214
```

<210> SEQ ID NO 11
<211> LENGTH: 738
<212> TYPE: PRT
<213> ORGANISM: Adeno-associated virus
<220> FEATURE:
<221> NAME/KEY: MOD_RES
<222> LOCATION: (471)..(471)
<223> OTHER INFORMATION: Ser or Asn

<400> SEQUENCE: 11

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
```

-continued

```
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Xaa Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560
```

```
Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Thr Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 12
<211> LENGTH: 2214
<212> TYPE: DNA
<213> ORGANISM: Adeno-associated virus
<220> FEATURE:
<221> NAME/KEY: misc_feature
<222> LOCATION: (1411)..(1413)
<223> OTHER INFORMATION: This region may encompass "agt" or "aat"

<400> SEQUENCE: 12

atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata accacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga gaccggtaga gccatcaccc cagcgttctc cagactcctc tacgggcatc    480

ggcaagaaag gccagcagcc cgcgaaaaag agactcaact ttgggcagac tggcgactca    540

gagtcagtgc ccgaccctca accaatcgga gaaccccccg caggcccctc tggtctggga    600

tctggtacaa tggctgcagg cggtggcgct ccaatggcag acaataacga aggcgccgac    660

ggagtgggta gttcctcagg aaattggcat tgcgattcca catggctggg cgacagagtc    720

atcaccacca gcacccgaac ctgggccctc cccacctaca acaaccacct ctacaagcaa    780

atctccaacg ggacttcggg aggaagcacc aacgacaaca cctacttcgg ctacagcacc    840

ccctgggggt attttgactt taacagattc cactgccact tctcaccacg tgactggcag    900

cgactcatca acaacaactg gggattccgg cccaagagac tcaacttcaa gctcttcaac    960
```

atccaggtca aggaggtcac gcagaatgaa ggcaccaaga ccatcgccaa taaccttacc 1020
agcacgattc aggtctttac ggactcggaa taccagctcc cgtacgtcct cggctctgcg 1080
caccagggct gcctgcctcc gttcccggcg gacgtcttca tgattcctca gtacgggtac 1140
ctgactctga acaatggcag tcaggccgtg ggccgttcct ccttctactg cctggagtac 1200
tttccttctc aaatgctgag aacgggcaac aactttgagt tcagctacac gtttgaggac 1260
gtgccttttc acagcagcta cgcgcacagc caaagcctgg accggctgat gaacccccctc 1320 atcgaccagt acctgtacta cctgtctcgg actcagtcca cgggaggtac cgcaggaact 1380
cagcagttgc tattttctca ggccgggcct nnnaacatgt cggctcaggc caaaaactgg 1440
ctacccgggc cctgctaccg gcagcaacgc gtctccacga cactgtcgca aaataacaac 1500
agcaactttg cctggaccgg tgccaccaag tatcatctga atggcagaga ctctctggta 1560
aatcccggtg tcgctatggc aacccacaag gacgacgaag agcgattttt tccgtccagc 1620
ggagtcttaa tgtttgggaa acagggagct ggaaaagaca acgtggacta tagcagcgtt 1680
atgctaacca gtgaggaaga aattaaaacc accaacccag tggccacaga acagtacggc 1740
gtggtggccg ataacctgca acagcaaaac accgctccta ttgtaggggc cgtcaacagt 1800
caaggagcct tacctggcat ggtctggcag aaccgggacg tgtacctgca gggtcctatc 1860
tgggccaaga ttcctcacac ggacggaaac tttcatccct cgccgctgat gggaggcttt 1920
ggactgaaac acccgcctcc tcagatcctg attaagaata cacctgttcc cgcggatcct 1980
ccaactacct tcagtcaagc taagctggcg tcgttcatca cgcagtacag caccggacag 2040
gtcagcgtgg aaattgaatg ggagctgcag aaagaaaaca gcaaacgctg gaacccagag 2100
attcaataca cttccaacta ctacaaatct acaaatgtgg actttgctgt taacacagaa 2160
ggcacttatt ctgagcctcg ccccatcggc acccgttacc tcacccgtaa tctg 2214

<210> SEQ ID NO 13
<211> LENGTH: 737
<212> TYPE: PRT
<213> ORGANISM: Adeno-associated virus
<220> FEATURE:
<221> NAME/KEY: MOD_RES
<222> LOCATION: (148)..(148)
<223> OTHER INFORMATION: Pro or Gln
<220> FEATURE:
<221> NAME/KEY: MOD_RES
<222> LOCATION: (169)..(169)
<223> OTHER INFORMATION: Lys or Arg
<220> FEATURE:
<221> NAME/KEY: MOD_RES
<222> LOCATION: (314)..(314)
<223> OTHER INFORMATION: Arg or Asn
<220> FEATURE:
<221> NAME/KEY: MOD_RES
<222> LOCATION: (466)..(466)
<223> OTHER INFORMATION: Tyr or His
<220> FEATURE:
<221> NAME/KEY: MOD_RES
<222> LOCATION: (563)..(563)
<223> OTHER INFORMATION: Asn or Ser
<220> FEATURE:
<221> NAME/KEY: MOD_RES
<222> LOCATION: (580)..(580)
<223> OTHER INFORMATION: Val or Ile
<220> FEATURE:
<221> NAME/KEY: MOD_RES
<222> LOCATION: (588)..(588)
<223> OTHER INFORMATION: Ala or Ser

<400> SEQUENCE: 13

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Xaa Ser Pro Gln Arg Ser Pro Asp Ser Ser Thr Gly Ile
145                 150                 155                 160

Gly Lys Lys Gly Gln Gln Pro Ala Xaa Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Xaa Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Thr
                405                 410                 415

Phe Glu Asp Val Pro Phe His Ser Ser Tyr Ala His Ser Gln Ser Leu
```

-continued

```
            420                 425                 430

Asp Arg Leu Met Asn Pro Leu Ile Asp Gln Tyr Leu Tyr Tyr Leu Ala
        435                 440                 445

Arg Thr Gln Ser Thr Thr Gly Gly Thr Ala Gly Asn Arg Glu Leu Gln
    450                 455                 460

Phe Xaa Gln Ala Gly Pro Ser Thr Met Ala Glu Gln Ala Lys Asn Trp
465                 470                 475                 480

Leu Pro Gly Pro Cys Tyr Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Ala Asn Lys Thr Thr Leu Glu Asn Val Leu
545                 550                 555                 560

Met Thr Xaa Glu Glu Glu Ile Lys Thr Thr Asn Pro Val Ala Thr Glu
                565                 570                 575

Glu Tyr Gly Xaa Val Ser Ser Asn Leu Gln Ser Xaa Asn Thr Ala Pro
            580                 585                 590

Gln Thr Gln Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asp Lys Ser Thr Asn Val Asp Phe Ala Val Asp Ser Glu Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 14
<211> LENGTH: 2211
<212> TYPE: DNA
<213> ORGANISM: Adeno-associated virus
<220> FEATURE:
<221> NAME/KEY: misc_feature
<222> LOCATION: (442)..(444)
<223> OTHER INFORMATION: This region may encompass “ccg” or “cag”
<220> FEATURE:
<221> NAME/KEY: misc_feature
<222> LOCATION: (505)..(507)
<223> OTHER INFORMATION: This region may encompass “aaa” or “aga”
<220> FEATURE:
<221> NAME/KEY: misc_feature
<222> LOCATION: (940)..(942)
<223> OTHER INFORMATION: This region may encompass “cgg” or “aac”
<220> FEATURE:

<221> NAME/KEY: misc_feature
<222> LOCATION: (1396)..(1398)
<223> OTHER INFORMATION: This region may encompass “tac” or “cac”
<220> FEATURE:
<221> NAME/KEY: misc_feature
<222> LOCATION: (1687)..(1689)
<223> OTHER INFORMATION: This region may encompass “aat” or “agt”
<220> FEATURE:
<221> NAME/KEY: misc_feature
<222> LOCATION: (1738)..(1740)
<223> OTHER INFORMATION: This region may encompass “gta” or “ata”
<220> FEATURE:
<221> NAME/KEY: misc_feature
<222> LOCATION: (1762)..(1764)
<223> OTHER INFORMATION: This region may encompass “gct” or “tct”

<400> SEQUENCE: 14

```
atggctgccg atggttatct tccagattgg ctcgaggaca acctctctga gggcattcgc     60

gagtggtggg acctgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa ggcctacgac    240

cagcagctca aagcgggtga caatccgtac ctgcggtata accacgccga cgccgagttt    300

caggagcgtc tgcaagaaga tacgtcattt gggggcaacc tcgggcgagc agtcttccag    360

gccaagaagc gggttctcga acctctcggt ctggttgagg aaggcgctaa gacggctcct    420

ggaaagaaga gaccggtaga gnnntcacct cagcgttccc ccgactcctc cacgggcatc    480

ggcaagaaag gccagcagcc cgccnnnaag agactcaatt tcggtcagac tggcgactca    540

gagtcagtcc ccgaccctca acctctcgga gaacctccag cagcgccctc tggtgtggga    600

tctggtacaa tggctgcagg cggtggcgca ccaatggcag acaataacga aggtgccgac    660

ggagtgggta atgcctcagg aaattggcat tgcgattcca catggctggg cgacagagtc    720

attaccacca gcacccgaac ctgggccctg cccacctaca acaaccacct ctacaagcaa    780

atctccagtc aaagtgcagg tagtaccaac gacaacacct acttcggcta cagcaccccc    840

tgggggtatt ttgactttaa cagattccac tgccacttct caccacgtga ctggcagcga    900

ctcatcaaca acaactgggg attccggccc aagaagctgn nnttcaagct cttcaacatc    960

caggtcaagg aggtcacgac gaatgacggc gttacgacca tcgctaataa ccttaccagc   1020

acggttcagg tattctcgga ctcggaatac cagctgccgt acgtcctcgg ctctgcgcac   1080

cagggctgcc tgcctccgtt cccggcggac gtcttcatga ttcctcagta cggctacctg   1140

actctcaaca atggcagtca gtctgtggga cgttcctcct tctactgcct ggagtacttc   1200

ccctctcaga tgctgagaac gggcaacaac tttgagttca gctacacctt cgaggacgtg   1260

cctttccaca gcagctacgc acacagccag agcctggacc ggctgatgaa tcccctcatc   1320

gaccagtact tgtactacct ggccagaaca cagagtacca caggaggcac agctggcaat   1380

cgggaactgc agtttnnnca ggccgggcct tcaactatgg ccgaacaagc caagaattgg   1440

ttacctggac cttgctaccg gcaacaaaga gtctccaaaa cgctggatca aaacaacaac   1500

agcaactttg cttggactgg tgccaccaaa tatcacctga acggcagaaa ctcgttggtt   1560

aatcccggcg tcgccatggc aactcacaag gacgacgagg accgcttttt cccatccagc   1620

ggagtcctga tttttggaaa aactggagca gctaacaaaa ctacattgga aaatgtgtta   1680

atgacannng aagaagaaat taaaactact aatcctgtag ccacggaaga atacgggnnn   1740

gtcagcagca acttacaatc gnnnaatact gcaccccaga cacaaactgt caacagccag   1800

ggagccttac ctggcatggt ctggcagaac cgggacgtgt acctgcaggg tcccatctgg   1860
```

gccaagattc ctcacacgga tggcaacttt cacccgtctc ctttgatggg cggctttgga 1920
cttaaacatc cgcctcctca gatcctgatc aagaacactc ccgttcccgc taatcctccg 1980
gaggtgttta ctcctgccaa gtttgcttcg ttcatcacac agtacagcac cggacaagtc 2040
agcgtggaaa tcgagtggga gctgcagaag gaaaacagca agcgctggaa cccggagatt 2100
cagtacacct ccaactatga taagtcgact aatgtggact ttgccgttga cagcgagggt 2160
gtttactctg agcctcgccc tattggcact cgttacctca cccgtaatct g 2211

<210> SEQ ID NO 15
<211> LENGTH: 735
<212> TYPE: PRT
<213> ORGANISM: Adeno-associated virus
<220> FEATURE:
<221> NAME/KEY: MOD_RES
<222> LOCATION: (162)..(162)
<223> OTHER INFORMATION: Ser or Thr
<220> FEATURE:
<221> NAME/KEY: MOD_RES
<222> LOCATION: (168)..(168)
<223> OTHER INFORMATION: Lys or Arg
<220> FEATURE:
<221> NAME/KEY: MOD_RES
<222> LOCATION: (224)..(224)
<223> OTHER INFORMATION: Ala or Ser
<220> FEATURE:
<221> NAME/KEY: MOD_RES
<222> LOCATION: (310)..(310)
<223> OTHER INFORMATION: Arg or Lys
<220> FEATURE:
<221> NAME/KEY: MOD_RES
<222> LOCATION: (410)..(410)
<223> OTHER INFORMATION: Thr or Gln
<220> FEATURE:
<221> NAME/KEY: MOD_RES
<222> LOCATION: (446)..(446)
<223> OTHER INFORMATION: Ser or Asn
<220> FEATURE:
<221> NAME/KEY: MOD_RES
<222> LOCATION: (461)..(461)
<223> OTHER INFORMATION: Gln or Leu
<220> FEATURE:
<221> NAME/KEY: MOD_RES
<222> LOCATION: (471)..(471)
<223> OTHER INFORMATION: Ala or Ser
<220> FEATURE:
<221> NAME/KEY: MOD_RES
<222> LOCATION: (708)..(708)
<223> OTHER INFORMATION: Ala or Thr

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro

```
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Xaa Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Xaa
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Xaa Leu Asn Phe Lys Leu Phe Asn Ile Gln Val
305                 310                 315                 320

Lys Glu Val Thr Thr Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Xaa Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Xaa Arg Thr
        435                 440                 445

Gln Thr Thr Ser Gly Thr Ala Gln Asn Arg Glu Leu Xaa Phe Ser Gln
    450                 455                 460

Ala Gly Pro Ser Ser Met Xaa Asn Gln Ala Lys Asn Trp Leu Pro Gly
465                 470                 475                 480

Pro Cys Tyr Arg Gln Gln Arg Val Ser Lys Thr Ala Asn Asp Asn Asn
                485                 490                 495

Asn Ser Asn Phe Ala Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Asp Lys Phe Phe Pro Met Ser Gly Val Leu Ile Phe Gly Lys
    530                 535                 540
```

```
Gln Gly Ala Gly Ala Ser Asn Val Asp Leu Asp Asn Val Met Ile Thr
545                 550                 555                 560

Asp Glu Glu Glu Ile Lys Thr Thr Asn Pro Val Ala Thr Glu Gln Tyr
                565                 570                 575

Gly Thr Val Ala Thr Asn Leu Gln Ser Ser Asn Thr Ala Pro Ala Thr
            580                 585                 590

Gly Thr Val Asn Ser Gln Gly Ala Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Thr Thr Phe Ser Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Xaa Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 16
<211> LENGTH: 2205
<212> TYPE: DNA
<213> ORGANISM: Adeno-associated virus
<220> FEATURE:
<221> NAME/KEY: misc_feature
<222> LOCATION: (484)..(486)
<223> OTHER INFORMATION: This region may encompass “tca” or “aca”
<220> FEATURE:
<221> NAME/KEY: misc_feature
<222> LOCATION: (502)..(504)
<223> OTHER INFORMATION: This region may encompass “aaa” or “aga”
<220> FEATURE:
<221> NAME/KEY: misc_feature
<222> LOCATION: (670)..(672)
<223> OTHER INFORMATION: This region may encompass “gcc” or “tcc”
<220> FEATURE:
<221> NAME/KEY: misc_feature
<222> LOCATION: (928)..(930)
<223> OTHER INFORMATION: This region may encompass “aga” or “aaa”
<220> FEATURE:
<221> NAME/KEY: misc_feature
<222> LOCATION: (1228)..(1230)
<223> OTHER INFORMATION: This region may encompass “acc” or “cag”
<220> FEATURE:
<221> NAME/KEY: misc_feature
<222> LOCATION: (1336)..(1338)
<223> OTHER INFORMATION: This region may encompass “agc” or “aac”
<220> FEATURE:
<221> NAME/KEY: misc_feature
<222> LOCATION: (1381)..(1383)
<223> OTHER INFORMATION: This region may encompass “cag” or “ctg”
<220> FEATURE:
<221> NAME/KEY: misc_feature
<222> LOCATION: (1411)..(1413)
<223> OTHER INFORMATION: This region may encompass “gct” or “tct”
<220> FEATURE:
<221> NAME/KEY: misc_feature
<222> LOCATION: (2122)..(2124)
<223> OTHER INFORMATION: This region may encompass “gcc” or “acc”

<400> SEQUENCE: 16
atggctgccg atggttatct tccagattgg ctcgaggaca acctctctga gggcattcgc 60
gagtggtggg acttgaaacc tggagccccg aaacccaaag ccaaccagca aaagcaggac 120
gacggccggg gtctggtgct tcctggctac aagtacctcg gacccttcaa cggactcgac 180
aagggggagc ccgtcaacgc ggcggatgca gcggccctcg agcacgacaa ggcctacgac 240
cagcagctca aagcgggtga caatccgtac ctgcggtata accacgccga cgccgagttt 300
caggagcgtc tgcaagaaga tacgtctttt gggggcaacc tcgggcgagc agtcttccag 360
gccaagaaga gggttctcga acctcttggt ctggttgagg aaggtgctaa gacggctcct 420
ggaaagaaac gtccggtaga gcagtcgcca caagagccag actcctcctc gggcattggc 480
aagnnnggcc agcagcccgc tnnnaagaga ctcaattttg gtcagactgg cgactcagag 540
tcagtccccg acccacaacc tctcggagaa cctccagcag ccccctctgg tgtgggatct 600
aatacaatgg cttcaggcgg tggcgcacca atggcagaca ataacgaagg cgccgacgga 660
gtgggtaatn nntcaggaaa ttggcattgc gattccacat ggctgggcga cagagtcatc 720
accaccagca cccgaacatg ggccttgccc acctataaca accacctcta caagcaaatc 780
tccagtcaat caggggccag caacgacaac cactacttcg gctacagcac cccctggggg 840
tattttgatt tcaacagatt ccactgccat ttctcaccac gtgactggca gcgactcatc 900
aacaacaatt ggggattccg gcccaagnnn ctcaacttca agctcttcaa catccaagtc 960
aaggaggtca cgacgaatga tggcaccacg accatcgcta ataaccttac cagcacggtt 1020
caagtcttca cggactcgga gtaccagttg ccgtacgtcc tcggctctgc gcaccagggc 1080
tgcctccctc cgttcccggc ggacgtgttc atgattccgc agtacggcta cctaacgctc 1140
aacaatggca gccaggcagt gggacggtca tccttttact gcctggaata tttcccatcg 1200
cagatgctga gaacgggcaa taactttnnn ttcagctaca ccttcgagga cgtgcctttc 1260
cacagcagct acgcgcacag ccagagcctg gaccggctga tgaatcctct catcgaccag 1320
tacctgtatt acctgnnnag aactcagact acgtccggaa ctgcccaaaa cagggagttg 1380
nnntttagcc aggcgggtcc atctagcatg nnnaatcagg ccaaaaactg gctacctgga 1440
ccctgttacc ggcagcagcg cgtttctaaa acagcaaatg acaacaacaa cagcaacttt 1500
gcctggactg gtgctacaaa atatcacctt aatgggcgtg attctttagt caaccctggc 1560
cctgctatgg cctcacacaa agacgacgaa gacaagttct ttcccatgag cggtgtcttg 1620
atttttggaa agcagggcgc cggagcttca aacgttgatt tggacaatgt catgatcaca 1680
gacgaagagg aaatcaaaac cactaacccc gtggccaccg aacaatatgg gactgtggca 1740
accaatctcc agagcagcaa cacagcccct gcgaccggaa ctgtgaattc tcagggagcc 1800
ttacctggaa tggtgtggca agacagagac gtatacctgc agggtcctat ttgggccaaa 1860
attcctcaca cggatggaca ctttcacccg tctcctctca tgggcggctt tggacttaag 1920
cacccgcctc ctcagatcct catcaaaaac acgcctgttc ctgcgaatcc tccgacaacg 1980
ttttcgcctg caaagtttgc ttcattcatc acccagtatt ccacaggaca agtgagcgtg 2040
gagattgaat gggagctgca gaaagaaaac agcaaacgct ggaatcccga aatacagtat 2100
acatctaact ataataaatc tnnnaacgtt gatttcactg tggacaccaa tggagtttat 2160
agtgagcctc gccccattgg cacccgttac ctcacccgta acctg 2205

<210> SEQ ID NO 17
<211> LENGTH: 735

<212> TYPE: PRT
<213> ORGANISM: Adeno-associated virus
<220> FEATURE:
<221> NAME/KEY: MOD_RES
<222> LOCATION: (42)..(42)
<223> OTHER INFORMATION: Gly or Ser
<220> FEATURE:
<221> NAME/KEY: MOD_RES
<222> LOCATION: (168)..(168)
<223> OTHER INFORMATION: Arg or Lys
<220> FEATURE:
<221> NAME/KEY: MOD_RES
<222> LOCATION: (310)..(310)
<223> OTHER INFORMATION: Lys or Arg
<220> FEATURE:
<221> NAME/KEY: MOD_RES
<222> LOCATION: (410)..(410)
<223> OTHER INFORMATION: Thr or Gln
<220> FEATURE:
<221> NAME/KEY: MOD_RES
<222> LOCATION: (446)..(446)
<223> OTHER INFORMATION: Ser or Arg
<220> FEATURE:
<221> NAME/KEY: MOD_RES
<222> LOCATION: (461)..(461)
<223> OTHER INFORMATION: Gln or Leu
<220> FEATURE:
<221> NAME/KEY: MOD_RES
<222> LOCATION: (471)..(471)
<223> OTHER INFORMATION: Ala or Ser
<220> FEATURE:
<221> NAME/KEY: MOD_RES
<222> LOCATION: (475)..(475)
<223> OTHER INFORMATION: Lys or Arg
<220> FEATURE:
<221> NAME/KEY: MOD_RES
<222> LOCATION: (504)..(504)
<223> OTHER INFORMATION: Gly or Ala
<220> FEATURE:
<221> NAME/KEY: MOD_RES
<222> LOCATION: (539)..(539)
<223> OTHER INFORMATION: Val or Asn

<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Gln Pro
            20                  25                  30

Lys Ala Asn Gln Gln His Gln Asp Asp Xaa Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
```

-continued

```
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Xaa Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Xaa Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Xaa Arg Thr
        435                 440                 445

Gln Thr Thr Ser Gly Thr Thr Gln Gln Ser Arg Leu Xaa Phe Ser Gln
    450                 455                 460

Ala Gly Pro Ser Ser Met Xaa Gln Gln Ala Xaa Asn Trp Leu Pro Gly
465                 470                 475                 480

Pro Cys Tyr Arg Gln Gln Arg Val Ser Lys Thr Ala Asn Asp Asn Asn
                485                 490                 495

Asn Ser Asn Phe Ala Trp Thr Xaa Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Met His Gly Xaa Leu Ile Phe Gly Lys
    530                 535                 540

Gln Gly Thr Gly Ala Ser Asn Val Asp Leu Asp Asn Val Met Ile Thr
545                 550                 555                 560

Asp Glu Glu Glu Ile Arg Thr Thr Asn Pro Val Ala Thr Glu Gln Tyr
                565                 570                 575

Gly Thr Val Ala Thr Asn Leu Gln Ser Ser Asn Thr Ala Pro Ala Thr
            580                 585                 590

Gly Thr Val Asn Ser Gln Gly Ala Leu Pro Gly Met Val Trp Gln Asp
        595                 600                 605
```

```
Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Thr Thr Phe Ser Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 18
<211> LENGTH: 2205
<212> TYPE: DNA
<213> ORGANISM: Adeno-associated virus
<220> FEATURE:
<221> NAME/KEY: misc_feature
<222> LOCATION: (124)..(126)
<223> OTHER INFORMATION: This region may encompass “ggt” or “agt”
<220> FEATURE:
<221> NAME/KEY: misc_feature
<222> LOCATION: (502)..(504)
<223> OTHER INFORMATION: This region may encompass “aga” or “aaa”
<220> FEATURE:
<221> NAME/KEY: misc_feature
<222> LOCATION: (928)..(930)
<223> OTHER INFORMATION: This region may encompass “aaa” or “aga”
<220> FEATURE:
<221> NAME/KEY: misc_feature
<222> LOCATION: (1228)..(1230)
<223> OTHER INFORMATION: This region may encompass “aca” or “cag”
<220> FEATURE:
<221> NAME/KEY: misc_feature
<222> LOCATION: (1336)..(1338)
<223> OTHER INFORMATION: This region may encompass “agc” or “aga”
<220> FEATURE:
<221> NAME/KEY: misc_feature
<222> LOCATION: (1381)..(1383)
<223> OTHER INFORMATION: This region may encompass “caa” or “ctc”
<220> FEATURE:
<221> NAME/KEY: misc_feature
<222> LOCATION: (1411)..(1413)
<223> OTHER INFORMATION: This region may encompass “gct” or “tct”
<220> FEATURE:
<221> NAME/KEY: misc_feature
<222> LOCATION: (1423)..(1425)
<223> OTHER INFORMATION: This region may encompass “aaa” or “aga”
<220> FEATURE:
<221> NAME/KEY: misc_feature
<222> LOCATION: (1510)..(1512)
<223> OTHER INFORMATION: This region may encompass “ggg” or “gcg”
<220> FEATURE:
<221> NAME/KEY: misc_feature
<222> LOCATION: (1615)..(1617)
<223> OTHER INFORMATION: This region may encompass “gtt” or “gac”

<400> SEQUENCE: 18

```
atggctgctg acggttatct tccagattgg ctcgaggaca acctttctga aggcattcgt      60

gagtggtggg atctgaaacc tggagcccct caacccaaag cgaaccaaca acaccaggac     120

gacnnncggg gtcttgtgct tccgggttac aaatacctcg gacccttaa cggactcgac      180
```

```
aaaggagagc cggtcaacga ggcggacgcg gcagccctcg aacacgacaa agcttacgac    240
cagcagctca aggccggtga caacccgtac ctcaagtaca accacgccga cgccgagttt    300
caggagcgtc ttcaagaaga tacgtctttt gggggcaacc ttggcagagc agtcttccag    360
gccaaaaaga gggtccttga gcctcttggt ctggttgagg aagcagctaa aacggctcct    420
ggaaagaaga ggcctgtaga acagtctcct caggaaccgg actcatcatc tggtattggc    480
aaatcgggcc aacagcctgc cnnnaaaaga ctaaatttcg gtcagactgg agactcagag    540
tcagtcccag accctcaacc tctcggagaa ccaccagcag ccccctcagg tgtgggatct    600
aatacaatgg cttcaggcgg tggcgcacca atggcagaca ataacgaggg tgccgatgga    660
gtgggtaatt cctcaggaaa ttggcattgc gattccacat ggctgggcga cagagtcatc    720
accaccagca ccagaacctg ggccctgccc acttacaaca accatctcta caagcaaatc    780
tccagccaat caggagcttc aaacgacaac cactactttg gctacagcac cccttggggg    840
tattttgact ttaacagatt ccactgccac ttctcaccac gtgactggca gcgactcatt    900
aacaacaact ggggattccg gcccaagnnn ctcaacttca agctcttcaa catccaagtt    960
aaagaggtca cgcagaacga tggcacgacg actattgcca ataaccttac cagcacggtt   1020
caagtgttta cggactcgga gtatcagctc ccgtacgtgc tcgggtcggc gcaccaaggc   1080
tgtctcccgc cgtttccagc ggacgtcttc atgatccctc agtatggata cctcaccctg   1140
aacaacggaa gtcaagcggt gggacgctca tccttttact gcctggagta cttcccttcg   1200
cagatgctaa ggactggaaa taacttcnnn ttcagctata ccttcgagga tgtacctttt   1260
cacagcagct acgctcacag ccagagtttg gatcgcttga tgaatcctct tattgatcag   1320
tatctgtact acctgnnnag aacgcaaaca acctctggaa caacccaaca atcacggctg   1380
nnntttagcc aggctgggcc ttcgtctatg nnncagcagg ccnnnaattg gctacctggg   1440
ccctgctacc ggcaacagag agtttcaaag actgctaacg acaacaacaa cagtaacttt   1500
gcttggacan nngccaccaa atatcatctc aatggccgcg actcgctggt gaatccagga   1560
ccagctatgg ccagtcacaa ggacgatgaa gaaaaatttt tccctatgca cggcnnncta   1620
atatttggca aacaagggac aggggcaagt aacgtagatt tagataatgt aatgattacg   1680
gatgaagaag agattcgtac caccaatcct gtggcaacag agcagtatgg aactgtggca   1740
actaacttgc agagctcaaa tacagctccc gcgactggaa ctgtcaatag tcagggggcc   1800
ttacctggca tggtgtggca agatcgtgac gtgtaccttc aaggacctat ctgggcaaag   1860
attcctcaca cggatggaca ctttcatcct tctcctctga tgggaggctt tggactgaaa   1920
catccgcctc ctcaaatctt gatcaaaaat actccggtac cggcaaatcc tccgacgact   1980
ttcagcccgg ccaagtttgc ttcatttatc actcagtact ccactggaca ggtcagcgtg   2040
gaaattgagt gggagctaca gaaagaaaac agcaaacgtt ggaatccaga gattcagtac   2100
acttccaact acaacaagtc tgttaatgtg gactttactg tagacactaa tggtgtttat   2160
agtgaacctc gccctattgg aacccggtat ctcacacgaa acttg                   2205
```

```
<210> SEQ ID NO 19
<211> LENGTH: 736
<212> TYPE: PRT
<213> ORGANISM: Adeno-associated virus

<400> SEQUENCE: 19

Met Ala Ala Asp Gly Tyr Leu Pro Asp Trp Leu Glu Asp Asn Leu Ser
1               5                   10                  15
```

-continued

```
Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
```

```
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Ala Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Gln
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735


<210> SEQ ID NO 20
<211> LENGTH: 736
<212> TYPE: PRT
<213> ORGANISM: Adeno-associated virus

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
```

500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 736
<212> TYPE: PRT
<213> ORGANISM: Adeno-associated virus

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

-continued

```
Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
```

-continued

```
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Glu Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735


<210> SEQ ID NO 22
<211> LENGTH: 736
<212> TYPE: PRT
<213> ORGANISM: Adeno-associated virus

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205
```

-continued

```
Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
```

625 630 635 640

Lys His Pro Pro Pro Gln Ile Leu Ile Lys Asn Thr Pro Val Pro Ala
645 650 655

Asn Pro Pro Thr Thr Phe Ser Pro Ala Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Asn Lys Ser Thr Asn Val Asp Phe Ala Val Asp Thr Asn Gly Val
705 710 715 720

Tyr Ser Glu Pro Arg Pro Ile Gly Thr Arg Tyr Leu Thr Arg Asn Leu
725 730 735

<210> SEQ ID NO 23
<211> LENGTH: 736
<212> TYPE: PRT
<213> ORGANISM: Adeno-associated virus

<400> SEQUENCE: 23

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Lys Gly Gln Gln Pro Ala Arg Lys Arg Leu Asn Phe Gly Gln Thr
165 170 175

Gly Asp Ser Glu Ser Val Pro Asp Pro Gln Pro Leu Gly Glu Pro Pro
180 185 190

Ala Ala Pro Ser Gly Val Gly Ser Asn Thr Met Ala Ala Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Gln Ser Gly Gly Ser Thr Asn Asp Asn Thr
260 265 270

```
Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
```

-continued

```
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735


<210> SEQ ID NO 24
<211> LENGTH: 736
<212> TYPE: PRT
<213> ORGANISM: Adeno-associated virus

<400> SEQUENCE: 24

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335
```

-continued

```
Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Ala Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Gln
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 25
<211> LENGTH: 736
<212> TYPE: PRT

<213> ORGANISM: Adeno-associated virus

<400> SEQUENCE: 25

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Gln Ser Pro Gln Glu Pro Asp Ser Ser Ser Gly Ile Gly
145 150 155 160

Lys Lys Gly Gln Gln Pro Ala Lys Lys Arg Leu Asn Phe Gly Gln Thr
165 170 175

Gly Asp Ser Glu Ser Val Pro Asp Pro Gln Pro Leu Gly Glu Pro Pro
180 185 190

Ala Ala Pro Ser Gly Val Gly Ser Asn Thr Met Ala Ser Gly Gly Gly
195 200 205

Ala Pro Met Ala Asp Asn Asn Glu Gly Ala Asp Gly Val Gly Asn Ala
210 215 220

Ser Gly Asn Trp His Cys Asp Ser Thr Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Gln Ser Gly Gly Ser Thr Asn Asp Asn Thr
260 265 270

Tyr Phe Gly Tyr Ser Thr Pro Trp Gly Tyr Phe Asp Phe Asn Arg Phe
275 280 285

His Cys His Phe Ser Pro Arg Asp Trp Gln Arg Leu Ile Asn Asn Asn
290 295 300

Trp Gly Phe Arg Pro Lys Lys Leu Asn Phe Lys Leu Phe Asn Ile Gln
305 310 315 320

Val Lys Glu Val Thr Thr Asn Asp Gly Thr Thr Thr Ile Ala Asn Asn
325 330 335

Leu Thr Ser Thr Val Gln Val Phe Thr Asp Ser Glu Tyr Gln Leu Pro
340 345 350

Tyr Val Leu Gly Ser Ala His Gln Gly Cys Leu Pro Pro Phe Pro Ala
355 360 365

Asp Val Phe Met Ile Pro Gln Tyr Gly Tyr Leu Thr Leu Asn Asn Gly
370 375 380

Ser Gln Ala Val Gly Arg Ser Ser Phe Tyr Cys Leu Glu Tyr Phe Pro
385 390 395 400

-continued

```
Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Ala Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735


<210> SEQ ID NO 26
<211> LENGTH: 736
<212> TYPE: PRT
<213> ORGANISM: Adeno-associated virus

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

-continued

```
Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
    450                 455                 460
```

```
Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Gln
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 27
<211> LENGTH: 738
<212> TYPE: PRT
<213> ORGANISM: Adeno-associated virus

<400> SEQUENCE: 27

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525
```

-continued

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 28
<211> LENGTH: 736
<212> TYPE: PRT
<213> ORGANISM: Adeno-associated virus

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

-continued

```
Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
```

-continued

```
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 29
<211> LENGTH: 736
<212> TYPE: PRT
<213> ORGANISM: Adeno-associated virus

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220
```

-continued

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
```

```
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 30
<211> LENGTH: 736
<212> TYPE: PRT
<213> ORGANISM: Adeno-associated virus

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

-continued

```
His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
```

```
705                 710                 715                 720

Tyr Thr Glu Pro Arg Pro Ile Gly Thr Arg Tyr Leu Thr Arg Pro Leu
                725                 730                 735


<210> SEQ ID NO 31
<211> LENGTH: 735
<212> TYPE: PRT
<213> ORGANISM: Adeno-associated virus

<400> SEQUENCE: 31

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350
```

-continued

```
Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 32
<211> LENGTH: 736
<212> TYPE: PRT
<213> ORGANISM: Adeno-associated virus

<400> SEQUENCE: 32

-continued

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415
```

-continued

```
Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 33
<211> LENGTH: 736
<212> TYPE: PRT
<213> ORGANISM: Adeno-associated virus

<400> SEQUENCE: 33

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60
```

-continued

```
Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480
```

```
Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 34
<211> LENGTH: 737
<212> TYPE: PRT
<213> ORGANISM: Adeno-associated virus

<400> SEQUENCE: 34

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

-continued

```
Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540
```

```
Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu


<210> SEQ ID NO 35
<211> LENGTH: 2211
<212> TYPE: DNA
<213> ORGANISM: Adeno-associated virus

<400> SEQUENCE: 35

atggctgccg atggttatct tccagattgg ctcgaggaca acctctctga gggcattcgc      60

gagtggtggg acttgaaacc tggagccccg aaacccaaag ccaaccagca aaagcaggac     120

gacggccggg gtctggtgct tcctggctac aagtacctcg gacccttcaa cggactcgac     180

aagggggagc ccgtcaacgc ggcggacgca gcggccctcg agcacgacaa ggcctacgac     240

cagcagctca aagcgggtga caatccgtac ctgcggtata accacgccga cgccgagttt     300

caggagcgtc tgcaagaaga tacgtctttt gggggcaacc tcgggcgagc agtcttccag     360

gccaagaagc gggttctcga acctctcggt ctggttgagg aaggcgctaa gacggctcct     420

ggaaagaaga gaccggtaga gcaatcaccc caggaaccag actcctcttc gggcatcggc     480

aagaaaggcc agcagcccgc gaaaaagaga ctcaactttg ggcagacagg cgactcagag     540

tcagtgcccg accctcaacc actcggagaa ccccccgcag cccctctggg tgtgggatct     600

aatacaatgg ctgcaggcgg tggcgctcca atggcagaca ataacgaagg cgccgacgga     660

gtgggtaacg cctcaggaaa ttggcattgc gattccacat ggctgggcga cagagtcatc     720

accaccagca cccgaacctg ggccctcccc acctacaaca accacctcta caagcaaatc     780

tccagccaat cgggagcaag caccaacgac aacacctact tcggctacag caccccctgg     840

gggtattttg actttaacag attccactgc cacttctcac cacgtgactg gcagcgactc     900

atcaacaaca actggggatt ccggcccaag agactcaact tcaagctctt caacatccag     960

gtcaaggagg tcacgacgaa tgatggcacc acgaccatcg ccaataacct taccagcacg    1020
```

```
gttcaggtct ttacggactc ggaataccag ctcccgtacg tcctcggctc tgcgcaccag   1080

ggctgcctgc ctccgttccc ggcggacgtc ttcatgattc ctcagtacgg gtacctgact   1140

ctgaacaatg gcagtcaggc cgtgggccgt tcctccttct actgcctgga gtactttcct   1200

tctcaaatgc tgagaacggg caacaacttt gagttcagct acacgtttga ggacgtgcct   1260

tttcacagca gctacgcgca cagccaaagc ctggaccggc tgatgaaccc cctcatcgac   1320

cagtacctgt actacctgtc tcggactcag accacgagtg gtaccgcagg aaatcggacg   1380

ttgcaatttt ctcaggccgg gcctagtagc atggcgaatc aggccaaaaa ctggctaccc   1440

gggccctgct accggcagca acgcgtctcc aagacagcga atcaaaataa caacagcaac   1500

tttgcctgga ccggtgccac caagtatcat ctgaatggca gagactctct ggtaaatccc   1560

ggtcccgcta tggcaaccca caaggacgac gaagacaaat tttttccgat gagcggagtc   1620

ttaatatttg ggaaacaggg agctggaaat agcaacgtgg accttgacaa cgttatgata   1680

accagtgagg aagaaattaa aaccaccaac ccagtggcca cagaacagta cggcacggtg   1740

gccactaacc tgcaatcgtc aaacaccgct cctgctacag ggaccgtcaa cagtcaagga   1800

gccttacctg gcatggtctg gcagaaccgg gacgtgtacc tgcagggtcc tatctgggcc   1860

aagattcctc acacggacgg acactttcat ccctcgccgc tgatgggagg ctttggactg   1920

aaacacccgc ctcctcagat cctgattaag aatacacctg ttcccgcgaa tcctccaact   1980

accttcagtc cagctaagtt tgcgtcgttc atcacgcagt acagcaccgg acaggtcagc   2040

gtggaaattg aatgggagct gcagaaagaa aacagcaaac gctggaaccc agagattcaa   2100

tacacttcca actacaacaa atctacaaat gtggactttg ctgttgacac aaatggcgtt   2160

tattctgagc ctcgccccat cggcacccgt tacctcaccc gtaatctgta a            2211
```

```
<210> SEQ ID NO 36
<211> LENGTH: 738
<212> TYPE: PRT
<213> ORGANISM: Adeno-associated virus

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
```

```
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 37
<211> LENGTH: 535
<212> TYPE: PRT
<213> ORGANISM: Adeno-associated virus

<400> SEQUENCE: 37

Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Glu Phe Ser Tyr Gln Phe Glu Asp Val Pro Phe His Ser Ser Tyr
```

-continued

```
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
        275                 280                 285

Ser Thr Thr Leu Ser Gln Asn Asn Asn Ser Asn Phe Ala Trp Thr Gly
    290                 295                 300

Ala Thr Lys Tyr His Leu Asn Gly Arg Asp Ser Leu Val Asn Pro Gly
305                 310                 315                 320

Val Ala Met Ala Thr His Lys Asp Asp Glu Glu Arg Phe Phe Pro Ser
                325                 330                 335

Ser Gly Val Leu Met Phe Gly Lys Gln Gly Ala Gly Lys Asp Asn Val
            340                 345                 350

Asp Tyr Ser Ser Val Met Leu Thr Ser Glu Glu Glu Ile Lys Thr Thr
        355                 360                 365

Asn Pro Val Ala Thr Glu Gln Tyr Gly Val Val Ala Asp Asn Leu Gln
    370                 375                 380

Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Ser Gln Ala
    450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Asp Gly Thr Tyr Ser Glu Pro Arg Pro Ile Gly Thr
        515                 520                 525

Arg Tyr Leu Thr Arg Asn Leu
    530                 535


<210> SEQ ID NO 38
<211> LENGTH: 533
<212> TYPE: PRT
<213> ORGANISM: Adeno-associated virus

<400> SEQUENCE: 38

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45
```

-continued

```
Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Asn Ser Glu Tyr Ser Trp Thr Gly Ala Thr
    290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Glu Ile Arg Thr Thr Asn Pro
        355                 360                 365

Val Ala Thr Glu Gln Tyr Gly Ser Val Ser Thr Asn Leu Gln Arg Gly
    370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Pro Gln Ile Leu Ile Lys Asn
        435                 440                 445

Thr Pro Val Pro Ala Asn Pro Ser Thr Thr Phe Ser Ala Ala Lys Phe
    450                 455                 460

Ala Ser Phe Ile Thr Gln Tyr Ser Thr Gly Gln Val Ser Val Glu Ile
```

```
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
        515                 520                 525

Leu Thr Arg Asn Leu
    530


<210> SEQ ID NO 39
<211> LENGTH: 535
<212> TYPE: PRT
<213> ORGANISM: Adeno-associated virus

<400> SEQUENCE: 39

Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ala Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Ser
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Thr Tyr Thr Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Thr Thr Gly Gly Thr Ala Asn
                245                 250                 255

Thr Gln Thr Leu Gly Phe Ser Gln Gly Gly Pro Asn Thr Met Ala Asn
            260                 265                 270

Gln Ala Lys Asn Trp Leu Pro Gly Pro Cys Tyr Arg Gln Gln Arg Val
        275                 280                 285

Ser Thr Thr Thr Gly Gln Asn Asn Asn Ser Asn Phe Ala Trp Thr Ala
    290                 295                 300
```

```
Gly Thr Lys Tyr His Leu Asn Gly Arg Asn Ser Leu Ala Asn Pro Gly
305                 310                 315                 320

Ile Ala Met Ala Thr His Lys Asp Asp Glu Glu Arg Phe Phe Pro Ser
                325                 330                 335

Asn Gly Ile Leu Ile Phe Gly Lys Gln Asn Ala Ala Arg Asp Asn Ala
            340                 345                 350

Asp Tyr Ser Asp Val Met Leu Thr Ser Glu Glu Glu Ile Lys Thr Thr
        355                 360                 365

Asn Pro Val Ala Thr Glu Glu Tyr Gly Ile Val Ala Asp Asn Leu Gln
    370                 375                 380

Gln Gln Asn Thr Ala Pro Gln Ile Gly Thr Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Asn Gln Ser
    450                 455                 460

Lys Leu Asn Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Ser Val Asp Phe
            500                 505                 510

Ala Val Asn Thr Glu Gly Val Tyr Ser Glu Pro Arg Pro Ile Gly Thr
        515                 520                 525

Arg Tyr Leu Thr Arg Asn Leu
    530                 535


<210> SEQ ID NO 40
<211> LENGTH: 724
<212> TYPE: PRT
<213> ORGANISM: Adeno-associated virus

<400> SEQUENCE: 40

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140
```

-continued

```
Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560
```

Val Ala Tyr Asn Val Gly Gly Gln Met Ala Thr Asn Asn Gln Ser Ser
565 570 575

Thr Thr Ala Pro Ala Thr Gly Thr Tyr Asn Leu Gln Glu Ile Val Pro
580 585 590

Gly Ser Val Trp Met Glu Arg Asp Val Tyr Leu Gln Gly Pro Ile Trp
595 600 605

Ala Lys Ile Pro Glu Thr Gly Ala His Phe His Pro Ser Pro Ala Met
610 615 620

Gly Gly Phe Gly Leu Lys His Pro Pro Pro Met Met Leu Ile Lys Asn
625 630 635 640

Thr Pro Val Pro Gly Asn Ile Thr Ser Phe Ser Asp Val Pro Val Ser
645 650 655

Ser Phe Ile Thr Gln Tyr Ser Thr Gly Gln Val Thr Val Glu Met Glu
660 665 670

Trp Glu Leu Lys Lys Glu Asn Ser Lys Arg Trp Asn Pro Glu Ile Gln
675 680 685

Tyr Thr Asn Asn Tyr Asn Asp Pro Gln Phe Val Asp Phe Ala Pro Asp
690 695 700

Ser Thr Gly Glu Tyr Arg Thr Thr Arg Pro Ile Gly Thr Arg Tyr Leu
705 710 715 720

Thr Arg Pro Leu

<210> SEQ ID NO 41
<211> LENGTH: 738
<212> TYPE: PRT
<213> ORGANISM: Adeno-associated virus

<400> SEQUENCE: 41

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Gly Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Lys Lys Arg Leu Asn Phe Gly Gln
165 170 175

Thr Gly Asp Ser Glu Ser Val Pro Asp Pro Gln Pro Ile Gly Glu Pro
180 185 190

Pro Ala Gly Pro Ser Gly Leu Gly Ser Gly Thr Met Ala Ala Gly Gly
195 200 205

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620
```

-continued

```
Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 42
<211> LENGTH: 738
<212> TYPE: PRT
<213> ORGANISM: Adeno-associated virus
<220> FEATURE:
<221> NAME/KEY: MOD_RES
<222> LOCATION: (157)..(157)
<223> OTHER INFORMATION: Ser or Thr
<220> FEATURE:
<221> NAME/KEY: MOD_RES
<222> LOCATION: (169)..(169)
<223> OTHER INFORMATION: Lys or Arg
<220> FEATURE:
<221> NAME/KEY: MOD_RES
<222> LOCATION: (457)..(457)
<223> OTHER INFORMATION: Ala or Gly
<220> FEATURE:
<221> NAME/KEY: MOD_RES
<222> LOCATION: (463)..(463)
<223> OTHER INFORMATION: Gln or Ala
<220> FEATURE:
<221> NAME/KEY: MOD_RES
<222> LOCATION: (508)..(508)
<223> OTHER INFORMATION: Thr or Ala
<220> FEATURE:
<221> NAME/KEY: MOD_RES
<222> LOCATION: (510)..(510)
<223> OTHER INFORMATION: Tyr or Phe
<220> FEATURE:
<221> NAME/KEY: MOD_RES
<222> LOCATION: (511)..(511)
<223> OTHER INFORMATION: His or Lys
<220> FEATURE:
<221> NAME/KEY: MOD_RES
<222> LOCATION: (558)..(558)
<223> OTHER INFORMATION: Gln or Asn
<220> FEATURE:
<221> NAME/KEY: MOD_RES
<222> LOCATION: (585)..(585)
<223> OTHER INFORMATION: Asn or His
<220> FEATURE:
<221> NAME/KEY: MOD_RES
<222> LOCATION: (587)..(587)
<223> OTHER INFORMATION: Ser or Ala

<400> SEQUENCE: 42

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

-continued

```
Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Xaa Leu Gly Ile
145                 150                 155                 160

Gly Lys Thr Gly Gln Gln Pro Ala Xaa Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ser Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Thr Asn Glu Gly Thr Lys Thr Ile Ala
                325                 330                 335

Asn Asn Leu Thr Ser Thr Val Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Thr Xaa Gly Thr Gln Thr Leu Xaa Phe
    450                 455                 460
```

```
Ser Gln Ala Gly Pro Ser Ser Met Ala Asn Gln Ala Arg Asn Trp Val
465                 470                 475                 480

Pro Gly Pro Cys Tyr Arg Gln Gln Arg Val Ser Thr Thr Thr Asn Gln
                485                 490                 495

Asn Asn Asn Ser Asn Phe Ala Trp Thr Gly Ala Xaa Lys Xaa Xaa Leu
            500                 505                 510

Asn Gly Arg Asp Ser Leu Met Asn Pro Gly Val Ala Met Ala Ser His
        515                 520                 525

Lys Asp Asp Glu Asp Arg Phe Phe Pro Ser Ser Gly Val Leu Ile Phe
    530                 535                 540

Gly Lys Gln Gly Ala Gly Asn Asp Asn Val Asp Tyr Ser Xaa Val Met
545                 550                 555                 560

Ile Thr Asn Glu Glu Glu Ile Lys Thr Thr Asn Pro Val Ala Thr Glu
                565                 570                 575

Glu Tyr Gly Ala Val Ala Thr Asn Xaa Gln Xaa Leu Ala Asn Thr Gln
            580                 585                 590

Ala Gln Thr Gly Leu Val His Asn Gln Gly Val Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

```
<210> SEQ ID NO 43
<211> LENGTH: 2211
<212> TYPE: DNA
<213> ORGANISM: Adeno-associated virus
<220> FEATURE:
<221> NAME/KEY: misc_feature
<222> LOCATION: (469)..(471)
<223> OTHER INFORMATION: This region may encompass “tcg” or “acg”
<220> FEATURE:
<221> NAME/KEY: misc_feature
<222> LOCATION: (502)..(504)
<223> OTHER INFORMATION: This region may encompass “aaa” or “aga”
<220> FEATURE:
<221> NAME/KEY: misc_feature
<222> LOCATION: (1366)..(1368)
<223> OTHER INFORMATION: This region may encompass “gca” or “gga”
<220> FEATURE:
<221> NAME/KEY: misc_feature
<222> LOCATION: (1384)..(1386)
<223> OTHER INFORMATION: This region may encompass “caa” or “gca”
<220> FEATURE:
<221> NAME/KEY: misc_feature
<222> LOCATION: (1519)..(1521)
<223> OTHER INFORMATION: This region may encompass “acc” or “gcc”
```

<220> FEATURE:
<221> NAME/KEY: misc_feature
<222> LOCATION: (1525)..(1527)
<223> OTHER INFORMATION: This region may encompass “tat” or “ttt”
<220> FEATURE:
<221> NAME/KEY: misc_feature
<222> LOCATION: (1528)..(1530)
<223> OTHER INFORMATION: This region may encompass “cac” or “aaa”
<220> FEATURE:
<221> NAME/KEY: misc_feature
<222> LOCATION: (1669)..(1671)
<223> OTHER INFORMATION: This region may encompass “caa” or “aac”
<220> FEATURE:
<221> NAME/KEY: misc_feature
<222> LOCATION: (1750)..(1752)
<223> OTHER INFORMATION: This region may encompass “aac” or “cac”
<220> FEATURE:
<221> NAME/KEY: misc_feature
<222> LOCATION: (1756)..(1758)
<223> OTHER INFORMATION: This region may encompass “tcc” or “gcc”

<400> SEQUENCE: 43

```
atggctgccg atggttatct tccagattgg ctcgaggaca acctctctga gggcattcgc     60

gagtggtggg acttgaaacc tggagccccg aaacccaaag ccaaccagca aaagcaggac    120

gacggccggg gtctggtgct tcctggctac aagtacctcg gacccttcaa cggactcgac    180

aagggggagc ccgtcaacgc ggcggacgca gcggccctcg agcacgacaa agcctacgac    240

cagcagctca aagcgggtga caatccgtac ctgcggtata atcacgccga cgccgagttt    300

caggagcgtc tgcaagaaga tacgtctttt gggggcaacc tcgggcgagc agtcttccag    360

gccaagaagc gggttctcga acctctcggt ctggttgagg aaggcgctaa gacggctcct    420

ggaaagaaga ggccggtaga gcagtcgcca caagagccag actcctccnn nggcatcggc    480

aagacaggcc agcagcccgc tnnnaagaga ctcaattttg gtcagactgg cgactcagag    540

tcagtccccg acccacaacc tctcggagaa cctccagcag ccccctcagg tgtgggatct    600

aatacaatgg cttcaggcgg tggcgctcca atggcagaca ataacgaagg cgccgacgga    660

gtgggtaatt cctcgggaaa ttggcattgc gattccacat ggctgggga cagagtcatc    720

accaccagca cccgaacctg ggccctgccc acctacaaca accacctcta caagcaaatc    780

tccaacggca cctcgggagg aagcaccaac gacaacacct attttggcta cagcaccccc    840

tgggggtatt ttgacttcaa cagattccac tgtcactttt caccacgtga ctggcaacga    900

ctcatcaaca acaattgggg attccggccc aaaagactca acttcaagct gttcaacatc    960

caggtcaagg aagtcacgac gaacgaaggc accaagacca tcgccaataa tctcaccagc   1020

accgtgcagg tctttacgga ctcggagtac cagttaccgt acgtgctagg atccgctcac   1080

cagggatgtc tgcctccgtt cccggcggac gtcttcatga ttcctcagta cggctattta   1140

actttaaaca atggaagcca agccgtggga cgttcctcct tctactgtct ggagtatttc   1200

ccatcgcaga tgctgagaac cggcaacaac tttcagttca gctacacctt cgaggacgtg   1260

cctttccaca gcagctacgc gcacagccag agcctggaca ggctgatgaa tcccctcatc   1320

gaccagtacc tgtactacct gtccagaacg caaacgactg gaactnnngg gacgcagact   1380

ctgnnnttca gccaagcggg tcctagctca atggccaacc aggctagaaa ttgggtgccc   1440

ggaccttgct accggcagca gcgcgtctcc acgacaacca accagaacaa caacagcaac   1500

tttgcctgga cgggagctnn naagnnnnnn ctgaacggcc gagactctct aatgaatccg   1560

ggcgtggcaa tggcttccca caaggatgac gaggaccgct tcttcccttc gagcggggtc   1620

ctgatttttg gcaagcaagg agccgggaac gataatgtgg attacagcnn ngtgatgatt   1680
```

acaaatgagg aagaaatcaa gactaccaac cccgtggcca cagaagaata tggagcagtg 1740
gccaccaacn nncagnnngc caatacgcag gcgcagaccg gactcgtgca caaccagggg 1800
gtgcttcccg gcatggtgtg gcagaataga gacgtgtacc tgcagggtcc catctgggcc 1860
aaaattcctc acacggacgg caactttcac ccgtctcccc tgatgggcgg ctttggactg 1920
aagcacccgc ctcctcaaat tctcatcaag aacacaccgg ttccagcgga cccgccgact 1980
accttcaacc aggccaagct gaactctttc atcacgcagt acagcaccgg acaggtcagc 2040
gtggaaatcg agtgggagct gcagaaagaa aacagcaaac gctggaatcc agagattcaa 2100
tacacttcca actactacaa atctacaaat gtggactttg ctgtcaacac ggagggggtt 2160
tatagcgagc ctcgccccat tggcacccgt tacctcaccc gcaacctgta a 2211

<210> SEQ ID NO 44
<211> LENGTH: 734
<212> TYPE: PRT
<213> ORGANISM: Adeno-associated virus

<400> SEQUENCE: 44

Met Thr Asp Gly Tyr Leu Pro Asp Trp Leu Glu Asp Asn Leu Ser Glu
1 5 10 15

Gly Val Arg Glu Trp Trp Ala Leu Gln Pro Gly Ala Pro Lys Pro Lys
20 25 30

Ala Asn Gln Gln His Gln Asp Asn Ala Arg Gly Leu Val Leu Pro Gly
35 40 45

Tyr Lys Tyr Leu Gly Pro Gly Asn Gly Leu Asp Lys Gly Glu Pro Val
50 55 60

Asn Ala Ala Asp Ala Ala Ala Leu Glu His Asp Lys Ala Tyr Asp Gln
65 70 75 80

Gln Leu Lys Ala Gly Asp Asn Pro Tyr Leu Lys Tyr Asn His Ala Asp
85 90 95

Ala Glu Phe Gln Gln Arg Leu Gln Gly Asp Thr Ser Phe Gly Gly Asn
100 105 110

Leu Gly Arg Ala Val Phe Gln Ala Lys Lys Arg Val Leu Glu Pro Leu
115 120 125

Gly Leu Val Glu Gln Ala Gly Glu Thr Ala Pro Gly Lys Lys Arg Pro
130 135 140

Leu Ile Glu Ser Pro Gln Gln Pro Asp Ser Ser Thr Gly Ile Gly Lys
145 150 155 160

Lys Gly Lys Gln Pro Ala Lys Lys Lys Leu Val Phe Glu Asp Glu Thr
165 170 175

Gly Ala Gly Asp Gly Pro Pro Glu Gly Ser Thr Ser Gly Ala Met Ser
180 185 190

Asp Asp Ser Glu Met Arg Ala Ala Ala Gly Gly Ala Ala Val Glu Gly
195 200 205

Gly Gln Gly Ala Asp Gly Val Gly Asn Ala Ser Gly Asp Trp His Cys
210 215 220

Asp Ser Thr Trp Ser Glu Gly His Val Thr Thr Thr Ser Thr Arg Thr
225 230 235 240

Trp Val Leu Pro Thr Tyr Asn Asn His Leu Tyr Lys Arg Leu Gly Glu
245 250 255

Ser Leu Gln Ser Asn Thr Tyr Asn Gly Phe Ser Thr Pro Trp Gly Tyr
260 265 270

Phe Asp Phe Asn Arg Phe His Cys His Phe Ser Pro Arg Asp Trp Gln
275 280 285

-continued

```
Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
    690                 695                 700
```

```
Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730


<210> SEQ ID NO 45
<211> LENGTH: 733
<212> TYPE: PRT
<213> ORGANISM: Adeno-associated virus

<400> SEQUENCE: 45

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350
```

-continued

```
Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730
```

<210> SEQ ID NO 46
<211> LENGTH: 21
<212> TYPE: PRT
<213> ORGANISM: Adeno-associated virus

<400> SEQUENCE: 46

```
Glu Ile Lys Ala Thr Asn Pro Val Ala Thr Glu Arg Phe Gly Thr Val
1               5                   10                  15

Ala Val Asn Phe Gln
            20
```

<210> SEQ ID NO 47
<211> LENGTH: 21
<212> TYPE: PRT
<213> ORGANISM: Adeno-associated virus

<400> SEQUENCE: 47

```
Glu Ile Lys Ala Thr Asn Pro Val Ala Thr Glu Arg Phe Gly Thr Val
1               5                   10                  15

Ala Val Asn Leu Gln
            20
```

<210> SEQ ID NO 48
<211> LENGTH: 21
<212> TYPE: PRT
<213> ORGANISM: Adeno-associated virus

<400> SEQUENCE: 48

```
Glu Ile Arg Thr Thr Asn Pro Val Ala Thr Glu Gln Tyr Gly Ser Val
1               5                   10                  15

Ser Thr Asn Leu Gln
            20
```

<210> SEQ ID NO 49
<211> LENGTH: 21
<212> TYPE: PRT
<213> ORGANISM: Adeno-associated virus

<400> SEQUENCE: 49

```
Glu Ile Arg Thr Thr Asn Pro Val Ala Thr Glu Gln Tyr Gly Thr Val
1               5                   10                  15

Ala Asn Asn Leu Gln
            20
```

<210> SEQ ID NO 50
<211> LENGTH: 21
<212> TYPE: PRT
<213> ORGANISM: Adeno-associated virus

<400> SEQUENCE: 50

```
Glu Ile Arg Thr Thr Asn Pro Val Ala Thr Glu Gln Tyr Gly Thr Val
1               5                   10                  15

Ala Thr Asn Leu Gln
            20
```

<210> SEQ ID NO 51
<211> LENGTH: 21
<212> TYPE: PRT
<213> ORGANISM: Adeno-associated virus

<400> SEQUENCE: 51

```
Glu Ile Lys Thr Thr Asn Pro Val Ala Thr Glu Gln Tyr Gly Thr Val
1               5                   10                  15

Ala Thr Asn Leu Gln
            20
```

-continued

```
<210> SEQ ID NO 52
<211> LENGTH: 21
<212> TYPE: PRT
<213> ORGANISM: Adeno-associated virus
<220> FEATURE:
<221> NAME/KEY: MOD_RES
<222> LOCATION: (12)..(12)
<223> OTHER INFORMATION: Gln or Glu

<400> SEQUENCE: 52

Glu Ile Lys Thr Thr Asn Pro Val Ala Thr Glu Xaa Tyr Gly Thr Val
1               5                   10                  15

Ala Thr Asn Leu Gln
            20


<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 53

His His His His His His
1               5
```